United States Patent
Liu et al.

(10) Patent No.: US 12,134,771 B2
(45) Date of Patent: Nov. 5, 2024

(54) FUSION PROTEIN AND USE THEREOF IN BASE EDITING

(71) Applicant: ShanghaiTech University, Shanghai (CN)

(72) Inventors: Yajing Liu, Shanghai (CN); Shisheng Huang, Shanghai (CN); Xingxu Huang, Shanghai (CN)

(73) Assignee: ShanghaiTech University, Shanghai (CN)

( * ) Notice: Subject to any disclaimer, the term of this patent is extended or adjusted under 35 U.S.C. 154(b) by 0 days.

(21) Appl. No.: 18/150,778

(22) Filed: Jan. 5, 2023

(65) Prior Publication Data
US 2023/0313205 A1    Oct. 5, 2023

Related U.S. Application Data

(62) Division of application No. 17/323,603, filed on May 18, 2021.

(51) Int. Cl.
*C12N 15/62* (2006.01)
*C07K 14/775* (2006.01)
*C12N 9/22* (2006.01)

(52) U.S. Cl.
CPC .......... *C12N 15/625* (2013.01); *C07K 14/775* (2013.01); *C12N 9/22* (2013.01); *C07K 2319/09* (2013.01)

(58) Field of Classification Search
CPC ...... C12N 15/625; C12N 9/22; C07K 14/775; C07K 2319/09; C07K 2319/00
See application file for complete search history.

(56) References Cited

U.S. PATENT DOCUMENTS

2017/0121693 A1* 5/2017 Liu .................... A61P 21/00
2018/0127780 A1* 5/2018 Liu .................... C12N 7/00

FOREIGN PATENT DOCUMENTS

CN         111172133 A  *  5/2020  .......... C12N 15/113
WO    WO-2018176009 A1 *  9/2018  .......... C12N 15/102

OTHER PUBLICATIONS

Luo et al., CRISPR/Cas9-deaminase enables robust base editing in Rhodobacter sphaeroides 2.4.1, Apr. 2020, Microbial Cell Factories, vol. 19, Issue 93, pp. 1-14 (Year: 2020).*
Tufts, CRISPR/Cas9, 2019, pp. 1-3, retrieved from: https://sites.tufts.edu/crispr/genome-editing/nickases/ (Year: 2019) (Year: 2019).*
Caval et al., Mouse APOBEC1 cytidine deaminase can induce somatic mutations in chromosomal DNA, 2019, BMC Genomics, pp. 1-12 (Year: 2019).*
Bhattacharya et al., Impact of genetic variation on three dimensional structure and function of proteins, 2017, PLOS One, vol. 12, Issue 3, pp. 1-22 (Year: 2017).*
Fenton et al., Rheostat positions: A new classification of protein positions relevant to pharmacogenomics, 2020, Medicinal Chemistry Research, vol. 29, pp. 1133-1146 (Year: 2020).*
Guo et al., Protein tolerance to random amino acid change, 2004, PNAS, vol. 101, No. 25, pp. 9205-9210 (Year: 2004).*

* cited by examiner

*Primary Examiner* — Jeffrey Stucker
*Assistant Examiner* — Brittney E Donoghue
(74) *Attorney, Agent, or Firm* — IPRTOP LLC

(57) ABSTRACT

A fusion protein which may comprise a first nCas9 fragment, a chimeric insertion fragment, a second nCas9 fragment and two UGI fragments from N-terminus to C-terminus, wherein the chimeric insertion fragment is selected from APOBEC1 fragment or APOBEC3A fragment for cytosine deamination at the target site. The fusion protein may comprise a first nCas9 fragment, a chimeric insertion fragment and a second nCas9 fragment from N-terminus to C-terminus, wherein the chimeric insertion fragment is TadA-TadA* for cytosine deamination at the target site. The present disclosure provides a novel base editing tool that is compatible with insertion of various deaminases on the chimeric sites of nCas9. Compared with nCas9 terminal fusion base editor, the base editing tool of the present invention significantly reduce off-targeting on both DNA and RNA, while maintaining specific targeted base editing efficiency, with higher specificity and favorable industrialization prospects.

16 Claims, 6 Drawing Sheets
Specification includes a Sequence Listing.

FUSION PROTEIN AND USE THEREOF IN BASE EDITING

CROSS REFERENCE TO RELATED APPLICATION

This application is a divisional of U.S. patent application Ser. No. 17/323,603 filed May 18, 2021, which is incorporated herein by reference in its entirety.

FIELD

The present disclosure relates to the field of biotechnology, in particular to a base editing tool and use thereof.

BACKGROUND

Since CRISPR/Cas9 was published in 2013 for its application in gene editing in eukaryotic cells, gene editing technology based on CRISPR/Cas9 system has been greatly developed. This system merely consists of two parts: a guide RNA (gRNA) responsible for locating the target site sequence, and a Cas9 protein as an endonuclease. The combination of two parts can cleave target sites of interest with high efficacy and specificity, resulting in DNA double-strain break (DSB), which allows people to use non-homologous end joining (NHEJ) pathway of the cell itself to produce DNA fragment deletions or induce frameshift mutation, thereby resulting in gene knock-out. People can also use homology directed repair (HDR) pathway of a cell to perform precise substitution or knock-in of DNA fragment at target sites.

With the gradual deepening of research on CRISPR system, researchers have discovered that there are various problems with the gene editing based on DSBs. Firstly, the product of editing is uncontrollable. The repair product of NHEJ pathway at DSB sites on cellular DNA is random, sometimes only very small fragments are lost and no frameshift mutation is caused. Therefore, although DSBs can be produced, high knockout efficiency cannot be guaranteed. Secondly, the editing efficiency based on HDR repair pathway is always low, which is difficult to achieve high efficiency of gene editing in vivo. Finally, the off-target effects of CRISPR/Cas9 system can also result in irreversible sequence alteration on other sites in genome during editing process. The vast majority of human genetic diseases are caused by single base mutation. Therefore, the development of technologies that can edit single base precisely to address the above issues would be of great benefits to basic research and clinical disease treatment.

In 2017, a Cas9-based single base editing (BE) tool was reported in Nature by David R Liu's lab at Harvard. This system utilizes the fusion of nCas9, APOBEC1 and UGI to efficiently achieve targeted single base editing from cytosine (C) to thymine (T). The single base editing technology has attracted wide attention and application once published, and researchers have achieved efficient editing in different cell lines as well as in plants and animals.

With the wide application of cleavage editing technology, researchers have been developing an off-target detection technology with higher precision and sensitivity, for detecting BE with more strict requirements. In 2019, Yang Hui's lab and Gao Caixia's lab independently reported the gRNA-independent DNA off-target produced by CBE in Science respectively. In cultured cell line, the random off-target produced in each cell is different, and the off-target sites will be diluted in a cell population, making them undetectable. Yang Hui's team has developed a more sensitive unbiased off-target assay, GOTI, to detect the off-target effects of BE3. The method amplifies off-target sites by using mouse embryonic development cleverly, thus facilitating detection. Considering that the random off-targets on DNA are unpredictable and irreversible, this off-target phenomenon attracts public worry about the future of CBE in clinical therapeutic application. In the same year, Keith Joung's lab and Yang Hui's lab reported in Nature that CBE is severely off-target on the transcriptome, and BE3 can induce hundreds of gene mutations such as proto-oncogene and tumor suppressor genes, and may also result in other mutations that seriously harm health. Although RNAs in eukaryotic cells will not be inherited, theoretically all RNAs will involve in the regulations of cellular functions directly or by expressing proteins. Therefore, the production of off-target mutations also has a direct impact on cells.

The off-target editing of BE on RNA can be partially eliminated by amino acid mutation of deaminase. However, this method cannot guarantee success completely, for elimination of off-target editing may be accompanied by loss of efficiency on target editing. In addition, de novo evolution and verification are required for each deaminase, thus the workload of this method is great. Moreover, the random off-targeting caused by BE3 on DNA remains a problem. Therefore, it is urgent to develop a general, convenient and cost-effective evolutionary technology or strategy to reduce RNA or DNA off-targeting caused by BE3.

SUMMARY

The present disclosure provides a base editing tool and use thereof.

One aspect of the present disclosure is to provide a fusion protein comprising a first nCas9 fragment, a chimeric insertion fragment, a second nCas9 fragment and two UGI fragments from N-terminus to C-terminus, wherein the chimeric insertion fragment is selected from an APOBEC1 fragment or an APOBEC3A fragment.

In some embodiments of the present disclosure, the first nCas9 fragment has an amino acid sequence comprising:
 a) an amino acid sequence of SEQ ID NO: 1; or,
 b) an amino acid sequence having at least 80% sequence identity to SEQ ID NO: 1 and retaining the function of the amino acid sequence defined in a), preferably retaining on-target activity of nCas9;
 and/or, the second nCas9 fragment has an amino acid sequence comprising:
 c) an amino acid sequence of SEQ ID NO: 2; or,
 d) an amino acid sequence having at least 80% sequence identity to SEQ ID NO: 2 and retaining the function of the amino acid sequence defined in c), preferably retaining nCas9 on-target activity.

In some embodiments of the present disclosure, the APOBEC1 fragment has an amino acid sequence comprising:
 e) an amino acid sequence of SEQ ID NO: 3; or,
 f) an amino acid sequence having at least 80% sequence identity to SEQ ID NO: 3 and retaining the function of the amino acid sequence defined in e), preferably retaining cytosine deaminase activity.

In some embodiments of the present disclosure, the APOBEC3A fragment has an amino acid sequence comprising:
 i) an amino acid sequence of SEQ ID NO: 4; or,
 j) an amino acid sequence having at least 80% sequence identity to SEQ ID NO: 4 and retaining the function of the amino acid sequence defined in i), preferably retaining cytosine deaminase activity.

In some embodiments of the present disclosure, the UGI fragment has an amino acid sequence comprising:

k) an amino acid sequence of SEQ ID NO: 5; or,
l) an amino acid sequence having at least 80% sequence identity to SEQ ID NO: 4 and retaining the function of the amino acid sequence defined in k), preferably retaining the activity of inhibiting the glycosylation of uracil DNA.

In some embodiments of the present disclosure, the fusion protein further comprises a nuclear localization signal fragment; preferably, the nuclear localization signal fragment comprises an amino acid sequence of SEQ ID NO: 6.

In some embodiments of the present disclosure, the fusion protein further comprises a flexible linker peptide fragment; preferably, the flexible linker peptide fragment comprises an amino acid sequence of SEQ ID NO: 7 or SEQ ID NO.8.

In some embodiments of the present disclosure, the fusion protein has an amino acid sequence as shown in SEQ ID NO: 9 or 10.

Another aspect of the present disclosure is to provide an isolated polynucleotide encoding the fusion protein described herein.

Another aspect of the present disclosure is to provide a construct comprising the isolated polynucleotide described above.

Another aspect of the present disclosure is to provide an expression system comprising the construct described above or having the polynucleotide described above integrated into its genome.

In some embodiments of the present disclosure, the host cell of the expression system is selected from eukaryotic cells or prokaryotic cells, preferably selected from mouse cells or human cells; more preferably selected from mouse brain neuroma cells, human embryonic kidney cells, human cervical cancer cells, human colon cancer cells, or human osteosarcoma cells; more preferably selected from N2a cells, HEK293FT cells, Hela cells, HCT116 cells or U2OS cells.

Another aspect of the present disclosure is to provide a use of the fusion protein, the isolated polynucleotide, the construct or the expression system described above in gene editing.

In some embodiments of the present disclosure, the use is specifically a use in gene editing in eukaryotes.

Another aspect of the present disclosure is to provide a base editing system comprising the fusion protein described herein, wherein the base editing system further comprises sgRNA.

Another aspect of the present disclosure is to provide a method for gene editing comprising performing gene editing by the fusion protein described above, or the base editing system described above.

DETAILED DESCRIPTION

Figure 1:
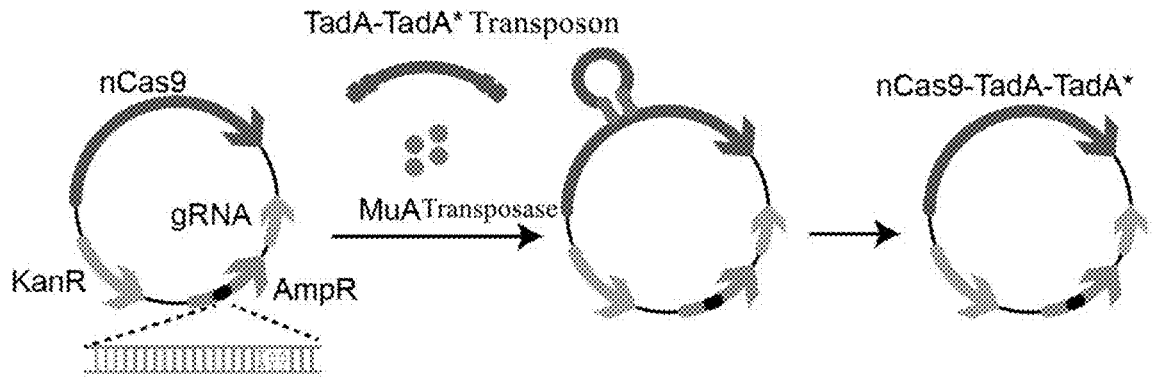
FIG. 1 is a schematic diagram of the present disclosure showing the construction of an nCas9 random insertion library based on Mu transposase.

After considerable exploratory research, the inventors of the present disclosure find that having a fusion functional fragment chimerized at proper locations within the nCas9 protein can extremely reduce the off-targeting caused by BE on both RNA and DNA at the same time, without affecting the on-target editing efficiency of BE, and on this basis, the present disclosure has been completed.

The first aspect of the present disclosure is to provide a fusion protein comprising a first nCas9 fragment, a chimeric insertion fragment, a second nCas9 fragment and two UGI fragments from N-terminus to C-terminus, and the chimeric insertion fragment is selected from an APOBEC1 fragment or an APOBEC3A fragment. The fusion protein substitutes 1048Thr-1063Ile of nCas9 (GenBank: MK048158.1) with a chimeric insertion fragment, and performs base editing at target sites in the guidance of sgRNA, which can extremely reduce the off-targeting caused by BE on RNA and DNA at the same time, without affecting the on-target editing efficiency of BE.

In the fusion protein provided by the present disclosure, the first nCas9 fragment may have an amino acid sequence comprising: a) an amino acid sequence of SEQ ID NO: 1; or, b) an amino acid sequence having at least 80% sequence identity to SEQ ID NO: 1 and retaining the function of the amino acid sequence defined in a). In particular, the amino acid sequence in b) refers to a polypeptide fragment obtained by substituting, deleting or adding one or more (specifically can be 1-50, 1-30, 1-20, 1-10, 1-5, 1-3, 1, 2, or 3) amino acids of the amino acid sequence shown in SEQ ID NO: 1, or obtained by addition of one or more (specifically can be 1-50, 1-30, 1-20, 1-10, 1-5, 1-3, 1, 2, or 3) amino acids at N-terminus or C-terminus, and having the function of a polypeptide fragment comprising the amino acid of SEQ ID NO: 1. For example, the first nCas9 fragment and the second nCas9 fragment still have the on-target activity of nCas9 after being combined, and specifically may have the activity of being able to target DNA under the guidance of a suitable gRNA. The amino acid sequence in b) may have at least 80%, 85%, 90%, 93%, 95%, 97% or 99% identity to SEQ ID NO: 1. Generally, the first nCas9 fragment is derived from *Streptococcus pyogenes*.

The term "sequence identity" in the present disclosure generally refers to the percentage of identical amino acid residues in sequences which may be aligned for purposes of comparison, and the identity of two or more target sequences can be calculated by calculation software known in the art, e.g., a software from NCBI.

In the fusion protein provided by the present disclosure, the second nCas9 fragment may have an amino acid sequence comprising: c) an amino acid sequence of SEQ ID NO: 2; or, d) an amino acid sequence having at least 80% sequence identity to SEQ ID NO: 2 and retaining the function of the amino acid sequence defined in c). In particular, the amino acid sequence in d) refers to a polypeptide fragment obtained by substituting, deleting or adding one or more (specifically can be 1-50, 1-30, 1-20, 1-10, 1-5, 1-3, 1, 2, or 3) amino acids of the amino acid sequence shown in SEQ ID NO: 2, or obtained by addition of one or more (specifically can be 1-50, 1-30, 1-20, 1-10, 1-5, 1-3, 1, 2, or 3) amino acids at N-terminus or C-terminus, and having the function of a polypeptide fragment comprising the amino acid of SEQ ID NO: 2. For example, the first nCas9 fragment and the second nCas9 fragment still have the on-target activity of nCas9 after being combined, and specifically may have the activity of being able to target DNA under the guidance of a suitable gRNA. The amino acid sequence in d) may have at least 80%, 85%, 90%, 93%, 95%, 97% or 99% identity to SEQ ID NO: 2. Generally, the second nCas9 fragment is derived from *E. coli* (*Streptococcus pyogenes*).

In the fusion protein provided by the present disclosure, the APOBEC1 fragment may have an amino acid sequence comprising: e) an amino acid sequence of SEQ ID NO: 3; or, f) an amino acid sequence having at least 80% sequence identity to SEQ ID NO: 3 and retaining the function of the amino acid sequence defined in e). In particular, the amino acid sequence in d) refers to a polypeptide fragment obtained by substituting, deleting or adding one or more (specifically can be 1-50, 1-30, 1-20, 1-10, 1-5, 1-3, 1, 2, or 3) amino acids of the amino acid sequence shown in SEQ ID NO: 3, or obtained by addition of one or more (specifically can be 1-50, 1-30, 1-20, 1-10, 1-5, 1-3, 1, 2, or 3) amino acids at N-terminus or C-terminus, and having the function of a polypeptide fragment comprising the amino acid of SEQ ID NO: 3. For example, the APOBEC1 fragment may have cytosine deaminase activity, and specifically may have the function of deaminating cytosine (C) to uracil (U). The amino acid sequence in f) may have at least 80%, 85%, 90%, 93%, 95%, 97% or 99% identity to SEQ ID NO: 3. Generally, the APOBEC1 fragment is derived from rat.

In the fusion protein provided by the present disclosure, the APOBEC3A fragment may have an amino acid sequence comprising: g) an amino acid sequence of SEQ ID NO: 4; or, h) an amino acid sequence having at least 80% sequence identity to SEQ ID NO: 4 and retaining the function of the amino acid sequence defined in g). In particular, the amino acid sequence in the h) refers to a polypeptide fragment obtained by substituting, deleting or adding one or more (specifically can be 1-50, 1-30, 1-20, 1-10, 1-5, 1-3, 1, 2, or 3) amino acids of the amino acid sequence shown in SEQ ID NO: 4, or obtained by addition of one or more (specifically can be 1-50, 1-30, 1-20, 1-10, 1-5, 1-3, 1, 2, or 3) amino acids at N-terminus or C-terminus, and having the function of a polypeptide fragment comprising the amino acid of SEQ ID NO: 4. For example, the APOBEC3A may have cytosine deaminase activity, and specifically may have the function of deaminating cytosine (C) to uracil (U). The amino acid sequence in h) has at least 80%, 85%, 90%, 93%, 95%, 97% or 99% identity to SEQ ID NO: 4. Generally, the APOBEC3A fragment is derived from human.

The fusion protein provided by the present disclosure may comprise two independent UGI fragments. The two UGI fragments may each independently have an amino acid sequence comprising: i) an amino acid sequence of SEQ ID NO: 5; or, j) an amino acid sequence having at least 80% sequence identity to SEQ ID NO: 5 and retaining the function of the amino acid sequence defined in i). In particular, the amino acid sequence in the j) refers to a polypeptide fragment obtained by substituting, deleting or adding one or more (specifically can be 1-50, 1-30, 1-20, 1-10, 1-5, 1-3, 1, 2, or 3) amino acids of the amino acid sequence shown in SEQ ID NO: 5, or obtained by addition of one or more (specifically can be 1-50, 1-30, 1-20, 1-10, 1-5, 1-3, 1, 2, or 3) amino acids at N-terminus or C-terminus, and having the function of a polypeptide fragment comprising the amino acid of SEQ ID NO: 5. For example, the two UGI fragments may have the activity of inhibiting glycosylation of uracil DNA. The amino acid sequence in j) may have at least 80%, 85%, 90%, 93%, 95%, 97% or 99% identity to SEQ ID NO: 5. Generally, the UGI fragments are derived from *Bacillus subtilis* bacteriophage.

In the fusion protein provided by the present disclosure, the substitution, deletion or addition can be the substitution of conservative amino acid. The "substitution of conservative amino acid" refers to the substitution of an amino acid residue by another amino acid residue having a similar side chain. Families of amino acid residues having similar side chains have been known to person skilled in the art, e.g. including but not limited to basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan) isoleucine), and aromatic side chains (e.g., tyrosine, phenylalanine, tryptophan, histidine). Non-limiting specific cases of conservative amino acid substitutions are provided in the Table below. The numbers in Table 1 (Amino Acid Similarity Matrix) indicate the similarity between two amino acids, when the number is 0 or higher, it is considered a conservative amino acid substitution, and Table 2 shows a scheme of exemplary conservative amino acid substitution.

TABLE 1

| | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | -8 | -7 | -6 | -2 | -6 | -5 | -7 | -7 | -4 | -5 | -3 | -3 | 2 | -6 | -4 | -5 | -2 | 0 | 0 | 17 |
| Y | 0 | -5 | -5 | -3 | -3 | -3 | -4 | -4 | -2 | -4 | 0 | -4 | -5 | -2 | -2 | -1 | -1 | 7 | 10 | |
| F | -4 | -5 | -5 | -3 | -4 | -3 | -6 | -5 | -4 | -5 | -2 | -5 | -4 | -1 | 0 | 1 | 2 | 9 | | |
| L | -6 | -4 | -3 | -3 | -2 | -2 | -4 | -3 | -3 | -2 | -2 | -3 | -3 | 2 | 4 | 2 | 6 | | | |
| I | -2 | -3 | -2 | -1 | -1 | 0 | -2 | -2 | -2 | -2 | -2 | -2 | -2 | 4 | 2 | 5 | | | | |
| M | -5 | -3 | -2 | -2 | -1 | -1 | -3 | -2 | 0 | -1 | -2 | 0 | 0 | 2 | 6 | | | | | |
| V | -2 | -1 | -1 | -1 | 0 | 0 | -2 | -2 | -2 | -2 | -2 | -2 | -2 | 4 | | | | | | |
| R | -4 | -3 | 0 | 0 | -2 | -1 | -1 | -1 | 0 | 1 | 2 | 3 | 6 | | | | | | | |
| K | -5 | -2 | -1 | 0 | -1 | 0 | 0 | 0 | 1 | 1 | 0 | 5 | | | | | | | | |
| H | -3 | -2 | 0 | -1 | -1 | -1 | 1 | 1 | 2 | 3 | 6 | | | | | | | | | |
| Q | -5 | -1 | 0 | -1 | 0 | -1 | 2 | 2 | 1 | 4 | | | | | | | | | | |
| N | -4 | 0 | -1 | 1 | 0 | 0 | 2 | 1 | 2 | | | | | | | | | | | |
| E | -5 | 0 | -1 | 0 | 0 | 0 | 3 | 4 | | | | | | | | | | | | |
| D | -5 | 1 | -1 | 0 | 0 | 0 | 4 | | | | | | | | | | | | | |
| T | -2 | 0 | 0 | 1 | 1 | 3 | | | | | | | | | | | | | | |
| A | -2 | 1 | 1 | 1 | 2 | | | | | | | | | | | | | | | |
| S | 0 | 1 | 1 | 1 | | | | | | | | | | | | | | | | |
| P | -3 | -1 | 6 | | | | | | | | | | | | | | | | | |
| G | -3 | 5 | | | | | | | | | | | | | | | | | | |
| C | 12 | | | | | | | | | | | | | | | | | | | |

TABLE 2

| Amino Acid Residue | Conservative substitution |
|---|---|
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

The fusion protein provided by the present disclosure may further comprise a nuclear localization signal fragment (BPNLS fragment), and the nuclear localization signal fragment generally can interact with nuclear import carrier, so that the protein can be transported into nucleus. The nuclear localization signal fragment can be located at the N-terminus of the first nCas9 fragment, and at the C-terminus of the second UGI fragment of the two UGI fragments, i.e., there is a BPNLS fragment at each end of the intact fusion protein. The BPNLS fragment can comprise an amino acid sequence of SEQ ID NO: 6.

The fusion protein provided by the present disclosure may further comprise a flexible linker peptide fragment. The flexible linker peptide fragment is generally a kind of flexible, linear and bendable amino acid fragment, which generally make a certain activity space between two proteins linked. For example, the flexible linker peptide fragment can be an XTEN peptide fragment, etc. The flexible linker peptide fragment (e.g., XTEN peptide fragment) can be located between the first nCas9 fragment and the chimeric fragment (ABOBEC1 or APOBEC3A), or between the chimeric fragment (ABOBEC1 or APOBEC3A) and the second nCas9 fragment. The XTEN peptide fragment can comprise an amino acid sequence of SEQ ID NO: 7. Another example of the flexible linker peptide fragment can be a GS peptide fragment, etc. The flexible linker peptide fragment (e.g., GS peptide fragment) can be located between the second nCas9 fragment and the first UGI of the two UGI fragments, or between the two UGI fragments. The flexible linker peptide fragment can comprise an amino acid sequence of SEQ ID NO: 8.

The fusion protein provided by the present disclosure can comprise a BPNLS peptide fragment, a first nCas9 fragment, a XTEN peptide fragment, APOBEC1, XTEN peptide fragment, a second nCas9 fragment, a GS peptide fragment and two UGI fragments from N-terminus to C-terminus. In a specific example of the present disclosure, the fusion protein can comprise a BPNLS peptide fragment, a first nCas9 fragment, a XTEN peptide fragment, APOBEC1, a XTEN peptide fragment, a second nCas9 fragment, a GS peptide fragment and two UGI fragments from N-terminus to C-terminus, and the fusion protein has an amino acid sequence of SEQ ID NO: 9.

The fusion protein provided by the present disclosure can comprise a BPNLS peptide fragment, a first nCas9 fragment, a XTEN peptide fragment, APOBEC3A, a XTEN peptide fragment, a second nCas9 fragment, a GS peptide fragment and two UGI fragments from N-terminus to C-terminus. In a specific example of the present disclosure, the fusion protein can comprise a BPNLS peptide fragment, a first nCas9 fragment, a XTEN peptide fragment, APOBEC3A, a XTEN peptide fragment, a second nCas9 fragment, a GS peptide fragment and two UGI fragments from N-terminus to C-terminus, and the fusion protein has an amino acid sequence of SEQ ID NO: 10.

The second aspect of the present disclosure is to provide an isolated polynucleotide encoding the fusion protein as provided by the first aspect of the present disclosure.

The third aspect of the present disclosure is to provide a construct containing the isolated polynucleotide as provided in the second aspect of the present disclosure. The construct can generally be obtained by inserting the isolated polynucleotide into proper expression vectors, and person skilled in the art can select proper expression vectors, e.g., the expression vector can include, but not limited to, pCMV expression vector, pSV2 expression vector, etc.

The fourth aspect of the present disclosure is to provide an expression system comprising the construct provided in the third aspect of the present disclosure or having the polynucleotide provided in the second aspect of the present disclosure integrated into its genome. The expression system can be a host cell expressing the fusion protein mentioned above, and the fusion protein can cooperate with sgRNA so that the fusion protein can be localized to target region, and base editing of the target region can be realized. In another specific example, the host cells can be eukaryotic cells and/or prokaryotic cells, specifically cells from mice or human; more specifically mouse brain neuroma cells, human embryonic kidney cells, human cervical cancer cells, human colon cancer cells, or human osteosarcoma cells, etc.; more specifically N2a cells, HEK293FT cells, Hela cells, HCT116 cells or U2OS cells.

The fifth aspect of the present disclosure is to provide a use of the fusion protein as provided in the first aspect of the present disclosure, the isolated polynucleotide as provided in the second aspect of the present disclosure, the construct as provided in the third aspect of the present disclosure, or the expression system as provided in the fourth aspect of the present disclosure in gene editing, preferably a use in gene editing in eukaryotes; the eukaryotes can specifically be metazoa, specifically including but not limited to human, mice, etc. The use can specifically include, but not limited to, C-to-T base editing-, etc. These base editing can be applied to edit splice acceptor/donor sites to regulate RNA splicing, or applied in model (e.g. disease model, cell model, animal model, etc.) construction or in treatment of human diseases, etc. In one specific example of the present disclosure, the edited object can be an embryo, a cell, etc.

The sixth aspect of the present disclosure is to provide a base editing system comprising the fusion protein as provided in the first aspect of the present disclosure, wherein the base editing system further comprises sgRNA. A person skilled in the art can choose appropriate sgRNA targeting specific sites according to target editing region of a gene. For example, the sequence of a sgRNA can generally be at least partially complementary to the target region, and thereby can cooperate with the fusion protein, so that the fusion protein can be localized to target region to realize base editing in target region, e.g., it can be a cytosine deaminase reaction in which cytosine (C) is deaminated to thymine (T).

The seventh aspect of the present disclosure is to provide a method for base editing comprising: performing gene editing by the fusion protein as provided in the first aspect of the present disclosure, or the base editing system as provided in the sixth aspect of the present disclosure. For example, the method for base editing can comprise: culturing the expression system provided in the fourth aspect of the present disclosure under appropriate conditions, thus expressing the fusion protein, and the fusion protein can perform base editing on target region in the presence of sgRNA which cooperated with the fusion protein and targeting target region. The method for providing the presence of the sgRNA is known to a person skilled in the art, e.g., it can be culturing an expression system which can express the sgRNA under appropriate conditions, and the expression system can include a host cell containing the expression vector comprising the polynucleotide encoding the sgRNA, or a host cell having the polynucleotide encoding the sgRNA integrated into its genome. In one specific example of the present disclosure, the sgRNA and the fusion protein can be expressed in the same host cell, and the host cell can be a target cell. In another specific example of the present disclosure, the gene editing is gene editing in vitro.

The present disclosure provides a novel base editing tool, which can be compatible with insertion of various deaminases by the chimeric sites on nCas9. The tool shows significant decrease in off-target cases on DNA and RNA compared with nCas9 terminus fusion base editor while maintaining specific target base editing efficiency, which has higher specificity and good industrialization prospect.

The following specific examples illustrate the embodiments of the present disclosure, and a person skilled in the art can easily understand other advantages and effects of the present disclosure according to the content disclosed in the present specification. The present disclosure can also be carried out or applied by other different specific embodiments, and various details in the present specification can be based on different opinions and applications, and various modifications or changes can be made without departing from the spirit of the present disclosure.

Before further describing the specific embodiments of the present disclosure, it can be understood that the protection scope of the present disclosure is not limited to the following specific particular embodiments; it can also be understood that the terms used in the embodiments of the present disclosure are used for describing the specific particular embodiments, rather than limiting the scope of protection of the present disclosure. In the specification and claims of the present disclosure, unless specified otherwise in the content, the term "a", "an" or "this" in singular form cover the plural form thereof.

When numerical ranges are given in the embodiments, it can be understood that the two endpoints of each numerical range and any value between the two endpoints can be selected, unless specified otherwise in the present disclosure. Unless defined otherwise, all technical and scientific terms used in the present disclosure have the same meanings commonly understood by those of skill in the art. In addition to the specific methods, devices, and materials used in the embodiments, according to the knowledge in the prior art and the description of the present disclosure, those of skill in the art can also use any prior art methods, devices, and materials which are similar or equal to the methods, devices, and materials described in the embodiments of the present disclosure to realize the present disclosure.

Unless specified otherwise, the experimental methods, detection methods, and preparation methods disclosed in the present disclosure all use conventional molecular biological, biochemical, chromatin structure and analysis, analytical chemical, cell culture, and recombinant DNA technology in the art, and other conventional technology in related fields. The technologies have been completely described in existing documents. For details, please refer to: Sambrook et al., MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, Chromatin (P. M. Wassarman and A. P. Wolffe, eds.), Academic Press, San Diego, 1999; and METHODS IN MOLECULAR BIOLOGY, Vol. 119, Chromatin Protocols (P. B. Becker, ed) Humana Press, Totowa, 1999, etc.

EXAMPLE 1

1. Construction of TadA-TadA* Transposon Based on MuA Transposase

The sequence of TadA-TadA* transposon (SEQ ID NO: 11) was synthesized by Shanghai Biosune Biotechnology Co., Ltd., and amplified by PCR using high-fidelity enzyme kit (Vazyme, P501-d2). The forward primer was: GGTCTCTGATCCGGCGCACGAA (SEQ ID NO: 71); the reverse primer was: GGTCTCTGATCCGGCGCACGAA (SEQ ID NO: 72);

The amplification system used is as follows:

TABLE 3

| Water | Add water to 20 μL |
|---|---|
| 2× buffer | 25 μL |
| dNTP | 1 μL |
| Forward primer (10 μM) | 2 μL |
| Reverse primer (10 μM) | 2 μL |
| Synthesized template of TadA-TadA* transposon | 1 ng |
| High-fidelity enzyme | 1 μL |

The PCR procedure used are as follows:

TABLE 4

| 1 cycle | 98° C. | 3 min |
|---|---|---|
| 35 cycles | 95° C. | 20 s |
| | 68° C. | 30 s |
| | 72° C. | set with (an extension of) 30 s/kb |
| 1 cycle | 72° C. | 5 min |
| 1 cycle | 4° C. | ∞ |

The PCR amplification product was purified and recovered by AxyPrep PCR Clean-up kit (Axygen, AP-PCR-500G) for later use.

2. Construction of sgRNA

The sgRNA used in detecting on-target editing efficiency of ABE (Adenine base editing) in eukaryote was ABE-site1. The sgRNAs used for subsequent detection of ABE and CE-ABE (centrally encapsulate ABE) at eight endogenous loci in HEK293T cells were site 2-site 9. The sgRNAs used for subsequent detection of ABE and CE-ABE at twelve endogenous loci in N2a cells were site10-site 21. The sequences of the loci are of SEQ ID NO: 12-32. The sgRNAs used in detecting CE-CBE and CE-A3A, namely site 22-site 32, are all endogenous gene loci in targeting HEK293T cells. The sequences of the loci are of SEQ ID NO: 57-67. The forward primers and reverse primers with 20 bases complementarily paired to target site sequences, and dissolve them to 100 μM with sterile water. The primers were ligated to a pGL3-U6-sgRNA (Addgene #51133) vector after annealing to construct target specific sgRNAs.

The annealing system used is as follows:

TABLE 5

| Forward primer | 4.5 μL |
|---|---|
| Reverse primer | 4.5 μL |
| 10× NEB buffer2 | 1 μL |

The annealing procedure used is as follows:

TABLE 6

| 95° C. | 5 min |
|---|---|
| 95-85° C. | −2° C./s |
| 85-25° C. | −0.1° C./s |
| 4° C. | ∞ |

The pGL3-U6-sgRNA (Addgene #51133) plasmid was digested with BsaI (NEB, R0535S) to obtain a linearized sgRNA vector. The enzymatic digestion system used is as follows:

TABLE 7

| Water | Add water to 50 μL |
|---|---|
| PGL3-U6 plasmid | 10 μg |
| 10× cutsmart buffer | 5 μL |
| BsaI Enzyme | 5 μL |

The above reaction system was prepared, and then subjected to reaction for 5 h at 37° C., the digested product was subjected to gel recovery with AxyPrep DNA gel recovery kit (Axygen, AP-GX-250G) to obtain a linearized vector. 50 ng of the linearized vector was ligated to 3 μL of the annealing product with T4 ligase (NEB, M0202S), and incubated for 2 h at 16° C., after transformation and plating, and correct target-specific sgRNA was verified by Sanger sequencing. The ligation system was as follows:

TABLE 8

| Water | Add water to 10 μL |
|---|---|
| Linear fragment of PGL3-U6-BsaI digestion | 20 ng |
| Annealing product | 1 μL |
| Solution I | 5 μL |

The ligation product was subjected to transfection subsequently, and recovered for 30 min, then plated on a LB agar plate with ampicillin resistance and incubated overnight at 37° C. Single clones were selected and sequenced to validate the sgRNA site1-site21 used for the detection of ABE.

3. Construction of a Recipient Plasmid for Random Insertion of MuA Transposase

The primers used for plasmid construction were all synthesized by Shanghai Biosune Biotechnology Co., Ltd.

Firstly, the pCMV-ABEmax (Addgene, #112095) plasmid was used as a template, with the forward primer: GACAAGAAGTACAGCATCGGCC (SEQ ID NO: 73); and the reverse primer: GCTGTACTTCTTGT-CACTGCTGACTTTCCGCTTCTTC (SEQ ID NO: 74) to obtain a fragment of 7629 bp in length. The PCR amplification product was purified and recovered by AxyPrep PCR Clean-up kit (Axygen, AP-PCR-500G), and the fragment was subjected to recombination with Gibson Assembly Master Mix recombinant kit (NEB, E2611S). The reaction system used is as follows:

TABLE 9

| Gibson Assembly Master Mix (2×) | 5 μL |
|---|---|
| 7629 bp PCR fragment | 200 ng |
| Sterile water | Add water to 10 μL |

The reaction solutions were mixed and incubated for 1 h at 50° C., subjected to transfection subsequently, recovered for 30 min, and plated on a LB agar plate with ampicillin resistance, incubated overnight at 37° C. Single clones were selected for verification by sequencing to obtain a pCMV-nCas9 plasmid (SEQ ID NO: 33). The successfully constructed plasmid (SEQ ID NO: 33) was subjected to plasmid extraction with AxyPrep plasmids miniprep kit (Axygen, AP-MN-P-250G).

SEQ ID NO: 33 was used as a template, the forward primer is: GAAGAAGCGGAAAGTCGACAAGAAGTACAG-CATCGG (SEQ ID NO: 75), the reverse primer is: CTGAGCTAGCTGT-CAACGAGCCCCAGCTGGTTCTTT (SEQ ID NO: 76);

PCR amplification was carried out to obtained a nCas9 fragment with length of 4507 bp;

The PET30 plasmid was used as a template, the forward primer is: CTCACTGATTAAGCATTGGTAAGCGCGGAACCCCTATTTGTT (SEQ ID NO: 77), the reverse primer is: CCGTTTCATGGTGGCATGTATATCTCCTTCTTAAAGTTAAACAAAATT (SEQ ID NO: 78); PCR amplification was carried out to obtained a KanR fragment with length of 4620 bp;

The pGL3-U6-sgRNA plasmid was used as a template, the forward primer was: GTATAATACTAGTGCTCTTGCCCGGCGTCAATACGTTTTAGAGCTAGAAATAGCAAGTT (SEQ ID NO: 79), the reverse primer is: gttagcagccggatcaaaaaaagcaccgactcgg (SEQ ID NO: 80); PCR amplification was carried out to obtain a U6-sgRNA fragment with length of 132 bp; Then the U6-sgRNA fragment was used as a template, the forward primer is: TTGACAGCTAGCTCAGTCCTAGGTATAATACTAGTGCTCTTGCC (SEQ ID NO: 81), the reverse primer is: GTTAGCAGCCGGATCAAAAAAAGCACCGACTCGG (SEQ ID NO: 82); PCR amplification was carried out to obtain a J23119promoter-gRNA fragment with length of 154 bp;

The pCMV-ABEmax (Addgene, #112095) plasmid was used as a template, the forward primer is: CTTTTCGGGGAAATGTGGGAAATGTGCGCGGAACC (SEQ ID NO: 83), the reverse primer is: CCCGGCGTCAATACGGGATA (SEQ ID NO: 84); PCR amplification was carried out to obtain an AmpR-1 fragment with length of 386 bp;

The pCMV-ABEmax (Addgene, #112095) plasmid was used as a template, the forward primer is: GTATTGACGCCGGGTAAGAGCAACTCGGTCGCCGC (SEQ ID NO: 85), the reverse primer is: TTACCAATGCTTAATCAGTGAGGCACC (SEQ ID NO: 86); PCR amplification was carried out to obtain an AmpR-2 fragment with length of 620 bp.

The PCR above was all carried out with Vazyme high-fidelity enzyme kit (Vazyme, P501-d2), and the reaction system used is as follows:

TABLE 10

| Water | Add to 50 μL |
|---|---|
| 2× buffer | 25 μL |
| dNTP | 1 μL |
| Forward primer (10 μM) | 2 μL |
| Reverse primer (10 μM) | 2 μL |
| High-fidelity enzyme | 1 μL |
| Template | 1 ng |

The PCR procedure is used as follows:

TABLE 11

| 1 cycle | 98° C. | 3 min |
|---|---|---|
| 35 cycles | 95° C. | 20 s |
| | 68° C. | 30 s |
| | 72° C. | set with (an extension of) 30 s/kb |
| 1 cycle | 72° C. | 5 min |
| 1 cycle | 4° C. | ∞ |

All the PCR amplification products above were purified and recovered by AxyPrep PCR Clean-up kit (Axygen, AP-PCR-500G), and the fragments were subjected to recombination with Gibson Assembly Master Mix recombinant kit (NEB, E2611S), and the reaction system used is as follows:

TABLE 12

| Gibson Assembly Master Mix (2×) | 10 μL |
|---|---|
| nCas9 fragment (4507 bp) | 80 ng |
| KanR fragment (4620 bp) | 80 ng |
| J23119 promoter-gRNA fragment (154 bp) | 10 ng |
| AmpR-1 fragment (386 bp) | 20 ng |
| AmpR-2 fragment (620 bp) | 30 ng |
| Sterile water | Add water to 20 μL |

The reaction solutions were mixed and incubated for 1 h at 50° C., subjected to transfection subsequently, recovered for 30 min, and plated on a LB agar plate with kanamycin resistance, incubated overnight at 37° C. Single clones were selected for sequencing verification to obtain a pET-nCas9-gRNA-AmpR (A118X)-KanR plasmid (SEQ ID NO: 34). The successfully constructed plasmid (SEQ ID NO: 34) was subjected to plasmid extraction with AxyPrep plasmids miniprep kit (Axygen, AP-MN-P-250G).

4. Construction of In Vitro Random Insertion Library

The fragment of TadA-TadA* transposon, pET-nCas9-gRNA-AmpR (A118X)-KanR plasmid (SEQ ID NO: 34) and MuA transposase (Thermo Fisher, F-701) obtained by PCR were reacted in vitro to form an insertion plasmid library having random insertion of the fragment of TadA-TadA* transposon in a plasmid, and the detailed process is shown in FIG. 1.

The detailed reaction system used is as follows:

TABLE 13

| TadA-TadA* fragment | 250 ng |
|---|---|
| plasmid (SEQ ID NO. 34) | 500 ng |
| MuA transposase | 1 μL |
| 5× Reaction Buffer for MuA Transposase | 4 μL |
| Water | Add water to 20 μL |

The reaction solution was incubated for 1 h at 30° C. to achieve random insertion, then incubated for 10 min at 75° C. to inactivate MuA transposase. Then DNA was purified by precipitation with isopropanol, and resuspended in 5 μL of deionized water, and electro-transfected into 100 μL of BL21 (DE3) Electro (Shanghai Weidi Biotechnology, EE1002) competent cells. Then 1 mL of SOC medium was added, and the bacteria was cultured for 1 h at 37° C. The bacteria mentioned above was recovered for 1 h in SOC medium after transformation, followed by spreading on several LB agar plates containing 10 μg/mL of kanamycin, and incubating for 16 h at 37° C. Then the bacterial colonies were scraped from the plates, followed by plasmid extraction with AxyPrep plasmids miniprep kit (Axygen, AP-MN-P-250G). The extracted MuA random insertion plasmid library was sequenced by Novogene Bioinformation Institution (Beijing, China), using Illumina HiSeq X Ten (2×150PE) to sequence the constructed transposon library. Firstly, all data readers were mapped to the main chain sequence by BWA v0.7.16 with default parameters. Broken reads were extracted, followed by mapping to the insertion sequence. All mapped reads were checked, and the breakpoints were recorded as insert loci. The final random insertion of the insertion library was obtained, in particular, the insert loci on nCas9 was calculated in terms of the C-terminus of the amino acid (e.g., the insertion occurs at the 5th Aspartic acid at C-terminus, and this insert loci is 5). After statistics, it was found that the coverage rate of the random insertion library based on MuA is very high, at least one insertion was occurred at 99.99% of amino acid sites on nCas9, and the insertion frequency (F) and insert loci (L) was ordering from small to large as follows:

TABLE 14

| | | | | | | | | | | | | | | | |
|---|---|---|---|---|---|---|---|---|---|---|---|---|---|---|---|
| L | 202 | 234 | 255 | 281 | 382 | 393 | 429 | 559 | 625 | 639 | 750 | 793 | 887 | 955 | 965 |
| F | 0 | 0 | 0 | 0 | 0 | 0 | 0 | 0 | 0 | 0 | 0 | 0 | 0 | 0 | 0 |
| L | 1062 | 1192 | 1317 | 103 | 184 | 228 | 233 | 235 | 431 | 472 | 529 | 535 | 586 | 588 | 678 |
| F | 0 | 0 | 0 | 1 | 1 | 1 | 1 | 1 | 1 | 1 | 1 | 1 | 1 | 1 | 1 |
| L | 794 | 1055 | 1064 | 1157 | 1280 | 12 | 37 | 55 | 96 | 268 | 546 | 554 | 568 | 609 | 850 |
| F | 1 | 1 | 1 | 1 | 1 | 2 | 2 | 2 | 2 | 2 | 2 | 2 | 2 | 2 | 2 |
| L | 933 | 1136 | 1194 | 1208 | 1232 | 1324 | 15 | 67 | 248 | 262 | 291 | 337 | 460 | 574 | 662 |
| F | 2 | 2 | 2 | 2 | 2 | 2 | 3 | 3 | 3 | 3 | 3 | 3 | 3 | 3 | 3 |
| L | 708 | 718 | 781 | 928 | 935 | 1037 | 1060 | 1067 | 1347 | 58 | 78 | 224 | 396 | 428 | 481 |
| F | 3 | 3 | 3 | 3 | 3 | 3 | 3 | 3 | 3 | 4 | 4 | 4 | 4 | 4 | 4 |
| L | 497 | 636 | 650 | 661 | 668 | 680 | 695 | 726 | 729 | 730 | 763 | 826 | 846 | 1000 | 1007 |
| F | 4 | 4 | 4 | 4 | 4 | 4 | 4 | 4 | 4 | 4 | 4 | 4 | 4 | 4 | 4 |
| L | 1124 | 1216 | 163 | 289 | 332 | 349 | 487 | 527 | 563 | 664 | 733 | 791 | 798 | 835 | 911 |
| F | 4 | 4 | 5 | 5 | 5 | 5 | 5 | 5 | 5 | 5 | 5 | 5 | 5 | 5 | 5 |
| L | 941 | 1006 | 1054 | 1080 | 1149 | 1359 | 26 | 63 | 169 | 225 | 277 | 279 | 290 | 351 | 389 |
| F | 5 | 5 | 5 | 5 | 5 | 5 | 6 | 6 | 6 | 6 | 6 | 6 | 6 | 6 | 6 |
| L | 410 | 462 | 491 | 566 | 571 | 572 | 673 | 741 | 868 | 920 | 948 | 971 | 1058 | 1066 | 1089 |
| F | 6 | 6 | 6 | 6 | 6 | 6 | 6 | 6 | 6 | 6 | 6 | 6 | 6 | 6 | 6 |
| L | 1141 | 1173 | 1321 | 1362 | 194 | 226 | 286 | 288 | 356 | 371 | 455 | 492 | 530 | 570 | 633 |
| F | 6 | 6 | 6 | 6 | 7 | 7 | 7 | 7 | 7 | 7 | 7 | 7 | 7 | 7 | 7 |
| L | 666 | 701 | 704 | 724 | 862 | 907 | 973 | 1029 | 1078 | 1097 | 1176 | 1303 | 1323 | 1357 | 49 |
| F | 7 | 7 | 7 | 7 | 7 | 7 | 7 | 7 | 7 | 7 | 7 | 7 | 7 | 7 | 8 |
| L | 60 | 97 | 160 | 218 | 295 | 457 | 638 | 641 | 706 | 840 | 866 | 896 | 1045 | 1233 | 1290 |
| F | 8 | 8 | 8 | 8 | 8 | 8 | 8 | 8 | 8 | 8 | 8 | 8 | 8 | 8 | 8 |
| L | 20 | 40 | 122 | 141 | 155 | 206 | 221 | 253 | 296 | 329 | 415 | 424 | 439 | 542 | 548 |
| F | 9 | 9 | 9 | 9 | 9 | 9 | 9 | 9 | 9 | 9 | 9 | 9 | 9 | 9 | 9 |
| L | 600 | 618 | 696 | 768 | 777 | 854 | 857 | 892 | 918 | 999 | 1228 | 1256 | 1284 | 1298 | 1325 |
| F | 9 | 9 | 9 | 9 | 9 | 9 | 9 | 9 | 9 | 9 | 9 | 9 | 9 | 9 | 9 |
| L | 1364 | 153 | 254 | 287 | 314 | 342 | 391 | 828 | 869 | 886 | 990 | 1021 | 1101 | 1226 | 1244 |
| F | 9 | 10 | 10 | 10 | 10 | 10 | 10 | 10 | 10 | 10 | 10 | 10 | 10 | 10 | 10 |
| L | 1270 | 1272 | 1274 | 1286 | 1289 | 1318 | 172 | 176 | 250 | 273 | 350 | 358 | 377 | 536 | 557 |
| F | 10 | 10 | 10 | 10 | 10 | 10 | 11 | 11 | 11 | 11 | 11 | 11 | 11 | 11 | 11 |
| L | 610 | 674 | 746 | 762 | 770 | 788 | 848 | 861 | 906 | 934 | 953 | 32 | 101 | 128 | 212 |
| F | 11 | 11 | 11 | 11 | 11 | 11 | 11 | 11 | 11 | 11 | 11 | 12 | 12 | 12 | 12 |
| L | 310 | 340 | 495 | 499 | 510 | 621 | 627 | 648 | 651 | 681 | 789 | 899 | 905 | 949 | 1001 |
| F | 12 | 12 | 12 | 12 | 12 | 12 | 12 | 12 | 12 | 12 | 12 | 12 | 12 | 12 | 12 |
| L | 1031 | 1044 | 1172 | 1212 | 1240 | 1241 | 1257 | 11 | 31 | 237 | 246 | 258 | 297 | 526 | 539 |
| F | 12 | 12 | 12 | 12 | 12 | 12 | 12 | 13 | 13 | 13 | 13 | 13 | 13 | 13 | 13 |
| L | 573 | 580 | 604 | 753 | 878 | 891 | 1065 | 1238 | 1252 | 1326 | 1327 | 22 | 45 | 95 | 118 |
| F | 13 | 13 | 13 | 13 | 13 | 13 | 13 | 13 | 13 | 13 | 13 | 14 | 14 | 14 | 14 |
| L | 140 | 168 | 241 | 247 | 256 | 275 | 308 | 325 | 419 | 430 | 433 | 613 | 647 | 692 | 702 |
| F | 14 | 14 | 14 | 14 | 14 | 14 | 14 | 14 | 14 | 14 | 14 | 14 | 14 | 14 | 14 |
| L | 735 | 751 | 811 | 859 | 951 | 969 | 1015 | 1069 | 1119 | 1180 | 1191 | 1245 | 1319 | 1361 | 88 |
| F | 14 | 14 | 14 | 14 | 14 | 14 | 14 | 14 | 14 | 14 | 14 | 14 | 14 | 14 | 15 |
| L | 98 | 147 | 173 | 240 | 283 | 338 | 406 | 422 | 534 | 544 | 593 | 659 | 685 | 691 | 774 |
| F | 15 | 15 | 15 | 15 | 15 | 15 | 15 | 15 | 15 | 15 | 15 | 15 | 15 | 15 | 15 |
| L | 804 | 853 | 923 | 947 | 1014 | 1036 | 1177 | 1182 | 1224 | 1333 | 1345 | 1363 | 9 | 47 | 92 |
| F | 15 | 15 | 15 | 15 | 15 | 15 | 15 | 15 | 15 | 15 | 15 | 15 | 16 | 16 | 16 |
| L | 94 | 104 | 106 | 109 | 236 | 244 | 305 | 402 | 441 | 464 | 494 | 635 | 667 | 679 | 698 |
| F | 16 | 16 | 16 | 16 | 16 | 16 | 16 | 16 | 16 | 16 | 16 | 16 | 16 | 16 | 16 |
| L | 709 | 759 | 832 | 836 | 964 | 1009 | 1086 | 1087 | 1236 | 14 | 43 | 72 | 179 | 197 | 276 |
| F | 16 | 16 | 16 | 16 | 16 | 16 | 16 | 16 | 16 | 17 | 17 | 17 | 17 | 17 | 17 |
| L | 284 | 327 | 335 | 482 | 484 | 502 | 602 | 737 | 749 | 809 | 813 | 942 | 981 | 986 | 1046 |
| F | 17 | 17 | 17 | 17 | 17 | 17 | 17 | 17 | 17 | 17 | 17 | 17 | 17 | 17 | 17 |
| L | 1107 | 1151 | 1158 | 1190 | 1210 | 1243 | 1300 | 2 | 16 | 18 | 66 | 130 | 171 | 209 | 242 |
| F | 17 | 17 | 17 | 17 | 17 | 17 | 17 | 18 | 18 | 18 | 18 | 18 | 18 | 18 | 18 |
| L | 313 | 359 | 409 | 442 | 486 | 682 | 712 | 748 | 796 | 898 | 957 | 979 | 995 | 1134 | 1264 |
| F | 18 | 18 | 18 | 18 | 18 | 18 | 18 | 18 | 18 | 18 | 18 | 18 | 18 | 18 | 18 |
| L | 1366 | 24 | 52 | 56 | 71 | 162 | 229 | 293 | 298 | 369 | 414 | 470 | 500 | 504 | 676 |
| F | 18 | 19 | 19 | 19 | 19 | 19 | 19 | 19 | 19 | 19 | 19 | 19 | 19 | 19 | 19 |
| L | 677 | 874 | 888 | 925 | 961 | 1104 | 1126 | 1132 | 1188 | 1193 | 1329 | 1368 | 13 | 89 | 186 |
| F | 19 | 19 | 19 | 19 | 19 | 19 | 19 | 19 | 19 | 19 | 19 | 19 | 20 | 20 | 20 |
| L | 207 | 208 | 261 | 274 | 278 | 292 | 317 | 318 | 352 | 420 | 473 | 537 | 612 | 637 | 755 |
| F | 20 | 20 | 20 | 20 | 20 | 20 | 20 | 20 | 20 | 20 | 20 | 20 | 20 | 20 | 20 |
| L | 775 | 803 | 837 | 849 | 871 | 880 | 897 | 921 | 938 | 1049 | 1072 | 1111 | 1147 | 1171 | 1205 |
| F | 20 | 20 | 20 | 20 | 20 | 20 | 20 | 20 | 20 | 20 | 20 | 20 | 20 | 20 | 20 |
| L | 1213 | 1305 | 1367 | 178 | 195 | 213 | 220 | 243 | 263 | 270 | 363 | 461 | 478 | 547 | 619 |
| F | 20 | 20 | 20 | 21 | 21 | 21 | 21 | 21 | 21 | 21 | 21 | 21 | 21 | 21 | 21 |
| L | 645 | 683 | 783 | 858 | 867 | 875 | 963 | 993 | 998 | 1108 | 1343 | 3 | 59 | 112 | 174 |
| F | 21 | 21 | 21 | 21 | 21 | 21 | 21 | 21 | 21 | 21 | 21 | 22 | 22 | 22 | 22 |
| L | 196 | 198 | 239 | 339 | 421 | 444 | 513 | 543 | 551 | 587 | 594 | 611 | 687 | 760 | 844 |
| F | 22 | 22 | 22 | 22 | 22 | 22 | 22 | 22 | 22 | 22 | 22 | 22 | 22 | 22 | 22 |
| L | 913 | 985 | 992 | 1002 | 1076 | 1109 | 1123 | 1125 | 1153 | 1156 | 1184 | 1230 | 1291 | 143 | 177 |
| F | 22 | 22 | 22 | 22 | 22 | 22 | 22 | 22 | 22 | 22 | 22 | 22 | 22 | 23 | 23 |
| L | 187 | 271 | 323 | 334 | 368 | 468 | 516 | 552 | 556 | 584 | 711 | 715 | 806 | 927 | 1030 |
| F | 23 | 23 | 23 | 23 | 23 | 23 | 23 | 23 | 23 | 23 | 23 | 23 | 23 | 23 | 23 |
| L | 1130 | 1159 | 1282 | 1315 | 1320 | 75 | 85 | 125 | 211 | 227 | 265 | 266 | 282 | 285 | 294 |
| F | 23 | 23 | 23 | 23 | 23 | 24 | 24 | 24 | 24 | 24 | 24 | 24 | 24 | 24 | 24 |
| L | 304 | 331 | 398 | 407 | 427 | 459 | 479 | 560 | 576 | 595 | 656 | 671 | 870 | 902 | 936 |
| F | 24 | 24 | 24 | 24 | 24 | 24 | 24 | 24 | 24 | 24 | 24 | 24 | 24 | 24 | 24 |

TABLE 14-continued

| | | | | | | | | | | | | | | | |
|---|---|---|---|---|---|---|---|---|---|---|---|---|---|---|---|
| L | 1027 | 33 | 81 | 117 | 215 | 357 | 426 | 545 | 663 | 689 | 890 | 974 | 980 | 1034 | 1063 |
| F | 24 | 25 | 25 | 25 | 25 | 25 | 25 | 25 | 25 | 25 | 25 | 25 | 25 | 25 | 25 |
| L | 1081 | 1114 | 1122 | 1295 | 1322 | 1342 | 7 | 44 | 126 | 148 | 452 | 498 | 585 | 653 | 684 |
| F | 25 | 25 | 25 | 25 | 25 | 25 | 26 | 26 | 26 | 26 | 26 | 26 | 26 | 26 | 26 |
| L | 717 | 864 | 960 | 988 | 1071 | 1084 | 1185 | 1247 | 1294 | 1335 | 27 | 121 | 167 | 183 | 364 |
| F | 26 | 26 | 26 | 26 | 26 | 26 | 26 | 26 | 26 | 26 | 27 | 27 | 27 | 27 | 27 |
| L | 489 | 507 | 883 | 908 | 929 | 962 | 997 | 1079 | 1133 | 1148 | 1152 | 1206 | 1304 | 1341 | 1344 |
| F | 27 | 27 | 27 | 27 | 27 | 27 | 27 | 27 | 27 | 27 | 27 | 27 | 27 | 27 | 27 |
| L | 158 | 190 | 192 | 249 | 343 | 365 | 564 | 620 | 743 | 785 | 945 | 954 | 967 | 1047 | 1116 |
| F | 28 | 28 | 28 | 28 | 28 | 28 | 28 | 28 | 28 | 28 | 28 | 28 | 28 | 28 | 28 |
| L | 1117 | 1131 | 1195 | 1214 | 46 | 64 | 170 | 180 | 257 | 260 | 280 | 354 | 390 | 477 | 688 |
| F | 28 | 28 | 28 | 28 | 29 | 29 | 29 | 29 | 29 | 29 | 29 | 29 | 29 | 29 | 29 |
| L | 700 | 705 | 722 | 773 | 881 | 912 | 989 | 1056 | 1118 | 1203 | 1223 | 1253 | 21 | 25 | 135 |
| F | 29 | 29 | 29 | 29 | 29 | 29 | 29 | 29 | 29 | 29 | 29 | 29 | 30 | 30 | 30 |
| L | 149 | 152 | 175 | 383 | 404 | 418 | 569 | 623 | 742 | 771 | 830 | 860 | 1033 | 1189 | 6 |
| F | 30 | 30 | 30 | 30 | 30 | 30 | 30 | 30 | 30 | 30 | 30 | 30 | 30 | 30 | 31 |
| L | 69 | 150 | 193 | 264 | 437 | 480 | 512 | 643 | 744 | 761 | 847 | 885 | 904 | 922 | 1025 |
| F | 31 | 31 | 31 | 31 | 31 | 31 | 31 | 31 | 31 | 31 | 31 | 31 | 31 | 31 | 31 |
| L | 1074 | 5 | 205 | 219 | 222 | 223 | 272 | 385 | 397 | 423 | 454 | 517 | 626 | 675 | 690 |
| F | 31 | 32 | 32 | 32 | 32 | 32 | 32 | 32 | 32 | 32 | 32 | 32 | 32 | 32 | 32 |
| L | 728 | 855 | 956 | 1022 | 1094 | 1181 | 1225 | 1246 | 1269 | 1275 | 54 | 61 | 165 | 311 | 596 |
| F | 32 | 32 | 32 | 32 | 32 | 32 | 32 | 32 | 32 | 32 | 33 | 33 | 33 | 33 | 33 |
| L | 657 | 727 | 807 | 818 | 824 | 842 | 910 | 983 | 1251 | 4 | 34 | 111 | 251 | 321 | 330 |
| F | 33 | 33 | 33 | 33 | 33 | 33 | 33 | 33 | 33 | 34 | 34 | 34 | 34 | 34 | 34 |
| L | 367 | 408 | 603 | 831 | 991 | 1023 | 1106 | 1242 | 1268 | 99 | 132 | 299 | 326 | 384 | 405 |
| F | 34 | 34 | 34 | 34 | 34 | 34 | 34 | 34 | 34 | 35 | 35 | 35 | 35 | 35 | 35 |
| L | 425 | 467 | 508 | 528 | 605 | 716 | 786 | 808 | 1161 | 1365 | 90 | 105 | 376 | 447 | 501 |
| F | 35 | 35 | 35 | 35 | 35 | 35 | 35 | 35 | 35 | 35 | 36 | 36 | 36 | 36 | 36 |
| L | 632 | 738 | 745 | 970 | 1016 | 1073 | 1120 | 1121 | 1221 | 1261 | 1346 | 93 | 145 | 400 | 413 |
| F | 36 | 36 | 36 | 36 | 36 | 36 | 36 | 36 | 36 | 36 | 36 | 37 | 37 | 37 | 37 |
| L | 453 | 505 | 523 | 561 | 606 | 823 | 838 | 882 | 42 | 48 | 379 | 440 | 541 | 601 | 740 |
| F | 37 | 37 | 37 | 37 | 37 | 37 | 37 | 37 | 38 | 38 | 38 | 38 | 38 | 38 | 38 |
| L | 889 | 994 | 1035 | 1052 | 1102 | 1135 | 1150 | 1174 | 1196 | 1207 | 1262 | 30 | 57 | 91 | 110 |
| F | 38 | 38 | 38 | 38 | 38 | 38 | 38 | 38 | 38 | 38 | 38 | 39 | 39 | 39 | 39 |
| L | 133 | 395 | 399 | 403 | 655 | 686 | 829 | 856 | 876 | 1050 | 1139 | 1146 | 1179 | 1254 | 137 |
| F | 39 | 39 | 39 | 39 | 39 | 39 | 39 | 39 | 39 | 39 | 39 | 39 | 39 | 39 | 40 |
| L | 216 | 232 | 252 | 301 | 589 | 614 | 644 | 903 | 917 | 919 | 982 | 1128 | 1263 | 1296 | 1297 |
| F | 40 | 40 | 40 | 40 | 40 | 40 | 40 | 40 | 40 | 40 | 40 | 40 | 40 | 40 | 40 |
| L | 1328 | 107 | 119 | 312 | 316 | 319 | 362 | 370 | 411 | 412 | 506 | 629 | 703 | 787 | 792 |
| F | 40 | 41 | 41 | 41 | 41 | 41 | 41 | 41 | 41 | 41 | 41 | 41 | 41 | 41 | 41 |
| L | 795 | 1012 | 1276 | 51 | 302 | 320 | 322 | 336 | 540 | 579 | 713 | 810 | 909 | 1088 | 448 |
| F | 41 | 41 | 41 | 42 | 42 | 42 | 42 | 42 | 42 | 42 | 42 | 42 | 42 | 42 | 43 |
| L | 463 | 465 | 483 | 575 | 720 | 725 | 966 | 975 | 987 | 1003 | 1160 | 1197 | 1285 | 1337 | 146 |
| F | 43 | 43 | 43 | 43 | 43 | 43 | 43 | 43 | 43 | 43 | 43 | 43 | 43 | 43 | 44 |
| L | 309 | 341 | 386 | 493 | 558 | 615 | 631 | 790 | 879 | 894 | 1011 | 1175 | 80 | 245 | 344 |
| F | 44 | 44 | 44 | 44 | 44 | 44 | 44 | 44 | 44 | 44 | 44 | 44 | 45 | 45 | 45 |
| L | 734 | 747 | 766 | 805 | 819 | 901 | 930 | 946 | 1008 | 1043 | 1234 | 1310 | 1312 | 432 | 665 |
| F | 45 | 45 | 45 | 45 | 45 | 45 | 45 | 45 | 45 | 45 | 45 | 45 | 45 | 46 | 46 |
| L | 1024 | 1155 | 1167 | 50 | 114 | 115 | 204 | 328 | 348 | 378 | 654 | 714 | 778 | 834 | 839 |
| F | 46 | 46 | 46 | 47 | 47 | 47 | 47 | 47 | 47 | 47 | 47 | 47 | 47 | 47 | 47 |
| L | 852 | 877 | 915 | 939 | 1013 | 1017 | 1162 | 1231 | 1281 | 116 | 345 | 347 | 469 | 496 | 515 |
| F | 47 | 47 | 47 | 47 | 47 | 47 | 47 | 47 | 47 | 48 | 48 | 48 | 48 | 48 | 48 |
| L | 555 | 591 | 799 | 1095 | 1178 | 1202 | 1248 | 1255 | 70 | 123 | 333 | 731 | 772 | 1096 | 1113 |
| F | 48 | 48 | 48 | 48 | 48 | 48 | 48 | 48 | 49 | 49 | 49 | 49 | 49 | 49 | 49 |
| L | 1154 | 1186 | 1215 | 23 | 324 | 374 | 475 | 598 | 769 | 780 | 958 | 1028 | 1140 | 1301 | 29 |
| F | 49 | 49 | 49 | 50 | 50 | 50 | 50 | 50 | 50 | 50 | 50 | 50 | 50 | 50 | 51 |
| L | 138 | 142 | 191 | 446 | 522 | 524 | 767 | 1115 | 1235 | 120 | 458 | 567 | 607 | 900 | 1100 |
| F | 51 | 51 | 51 | 51 | 51 | 51 | 51 | 51 | 51 | 52 | 52 | 52 | 52 | 52 | 52 |
| L | 1129 | 1143 | 1199 | 1200 | 87 | 161 | 200 | 693 | 699 | 719 | 1059 | 1082 | 8 | 83 | 217 |
| F | 52 | 52 | 52 | 52 | 53 | 53 | 53 | 53 | 53 | 53 | 53 | 53 | 54 | 54 | 54 |
| L | 392 | 474 | 490 | 549 | 1110 | 1187 | 1340 | 231 | 372 | 375 | 466 | 503 | 597 | 776 | 833 |
| F | 54 | 54 | 54 | 54 | 54 | 54 | 54 | 55 | 55 | 55 | 55 | 55 | 55 | 55 | 55 |
| L | 841 | 943 | 1227 | 1302 | 1360 | 35 | 210 | 388 | 434 | 642 | 723 | 916 | 972 | 1103 | 1201 |
| F | 55 | 55 | 55 | 55 | 55 | 56 | 56 | 56 | 56 | 56 | 56 | 56 | 56 | 56 | 56 |
| L | 1258 | 1309 | 1356 | 79 | 124 | 182 | 355 | 394 | 825 | 1349 | 346 | 387 | 660 | 843 | 931 |
| F | 56 | 56 | 56 | 57 | 57 | 57 | 57 | 57 | 57 | 57 | 58 | 58 | 58 | 58 | 58 |
| L | 1032 | 1099 | 1145 | 1355 | 102 | 181 | 185 | 199 | 373 | 435 | 779 | 872 | 1019 | 1026 | 1075 |
| F | 58 | 58 | 58 | 58 | 59 | 59 | 59 | 59 | 59 | 59 | 59 | 59 | 59 | 59 | 59 |
| L | 1311 | 1336 | 315 | 538 | 820 | 822 | 865 | 932 | 978 | 1204 | 1239 | 1271 | 136 | 139 | 154 |
| F | 59 | 59 | 60 | 60 | 60 | 60 | 60 | 60 | 60 | 60 | 60 | 60 | 61 | 61 | 61 |
| L | 485 | 697 | 959 | 984 | 1048 | 1068 | 86 | 156 | 366 | 509 | 863 | 1070 | 1091 | 1142 | 1220 |
| F | 61 | 61 | 61 | 61 | 61 | 61 | 62 | 62 | 62 | 62 | 62 | 62 | 62 | 62 | 62 |
| L | 1292 | 1313 | 1354 | 53 | 113 | 189 | 646 | 827 | 851 | 873 | 977 | 1004 | 1198 | 259 | 471 |
| F | 62 | 62 | 62 | 63 | 63 | 63 | 63 | 63 | 63 | 63 | 63 | 63 | 63 | 64 | 64 |
| L | 488 | 707 | 976 | 84 | 640 | 669 | 797 | 996 | 1083 | 1183 | 1338 | 514 | 582 | 732 | 1085 |
| F | 64 | 64 | 64 | 65 | 65 | 65 | 65 | 65 | 65 | 65 | 65 | 66 | 66 | 66 | 66 |
| L | 1265 | 38 | 736 | 739 | 801 | 884 | 1042 | 1127 | 201 | 443 | 511 | 710 | 1331 | 36 | 353 |
| F | 66 | 67 | 67 | 67 | 67 | 67 | 67 | 67 | 68 | 68 | 68 | 68 | 68 | 69 | 69 |
| L | 361 | 670 | 968 | 1229 | 1259 | 73 | 238 | 562 | 694 | 782 | 815 | 1163 | 1273 | 10 | 306 |
| F | 69 | 69 | 69 | 69 | 69 | 70 | 70 | 70 | 70 | 70 | 70 | 70 | 70 | 71 | 71 |

TABLE 14-continued

| | | | | | | | | | | | | | | | |
|---|---|---|---|---|---|---|---|---|---|---|---|---|---|---|---|
| L | 307 | 634 | 1005 | 1353 | 65 | 131 | 134 | 151 | 214 | 816 | 1010 | 1098 | 1237 | 144 | 1144 |
| F | 71 | 71 | 71 | 71 | 72 | 72 | 72 | 72 | 72 | 72 | 72 | 72 | 72 | 73 | 73 |
| L | 127 | 436 | 592 | 77 | 401 | 758 | 765 | 1350 | 590 | 658 | 754 | 1057 | 1314 | 578 | 649 |
| F | 74 | 74 | 74 | 75 | 75 | 75 | 75 | 75 | 76 | 76 | 76 | 76 | 76 | 77 | 77 |
| L | 1330 | 1211 | 1219 | 450 | 802 | 944 | 1278 | 1339 | 62 | 100 | 445 | 553 | 41 | 476 | 599 |
| F | 77 | 78 | 78 | 79 | 79 | 79 | 79 | 79 | 80 | 80 | 80 | 80 | 81 | 81 | 81 |
| L | 1169 | 1358 | 230 | 300 | 303 | 518 | 1166 | 1209 | 1348 | 1112 | 1283 | 1250 | 17 | 68 | 203 |
| F | 81 | 81 | 82 | 82 | 82 | 82 | 82 | 82 | 82 | 83 | 83 | 84 | 85 | 85 | 85 |
| L | 565 | 577 | 1170 | 1287 | 28 | 784 | 1222 | 1293 | 19 | 800 | 821 | 1351 | 108 | 416 | 845 |
| F | 86 | 86 | 86 | 86 | 87 | 87 | 87 | 87 | 88 | 88 | 88 | 88 | 89 | 90 | 90 |
| L | 1051 | 1061 | 1288 | 914 | 1077 | 752 | 757 | 1105 | 360 | 451 | 1352 | 74 | 817 | 940 | 1249 |
| F | 90 | 90 | 90 | 91 | 91 | 92 | 92 | 92 | 93 | 93 | 94 | 96 | 97 | 97 | 97 |
| L | 159 | 721 | 924 | 164 | 380 | 76 | 438 | 926 | 1299 | 1316 | 188 | 616 | 1307 | 521 | 583 |
| F | 98 | 98 | 99 | 101 | 101 | 102 | 102 | 102 | 102 | 102 | 103 | 103 | 103 | 104 | 105 |
| L | 129 | 630 | 1041 | 1164 | 1260 | 157 | 1093 | 1138 | 1334 | 624 | 1277 | 1308 | 764 | 456 | 1218 |
| F | 106 | 106 | 107 | 107 | 107 | 108 | 111 | 113 | 113 | 114 | 114 | 114 | 116 | 117 | 117 |
| L | 950 | 1279 | 937 | 1137 | 449 | 532 | 82 | 608 | 1168 | 1332 | 417 | 622 | 652 | 269 | 1266 |
| F | 118 | 118 | 119 | 119 | 120 | 121 | 122 | 122 | 123 | 124 | 125 | 126 | 126 | 128 | 128 |
| L | 581 | 628 | 672 | 525 | 550 | 812 | 39 | 381 | 756 | 166 | 267 | 1092 | 1020 | 952 | 617 |
| F | 131 | 132 | 132 | 133 | 133 | 133 | 134 | 136 | 137 | 138 | 138 | 138 | 141 | 144 | 146 |
| L | 1039 | 1165 | 1038 | 1053 | 519 | 814 | 1217 | 1018 | 893 | 1040 | 520 | 531 | 1306 | 533 | 1267 |
| F | 149 | 151 | 162 | 162 | 163 | 168 | 172 | 179 | 182 | 182 | 189 | 190 | 211 | 213 | 218 |
| L | 895 | 1090 | | | | | | | | | | | | | |
| F | 228 | 280 | | | | | | | | | | | | | |

5. Screening for Expression Plasmids with Functional Chimerized Fusion ABE Protein in *E. coli*.

Figure 2:
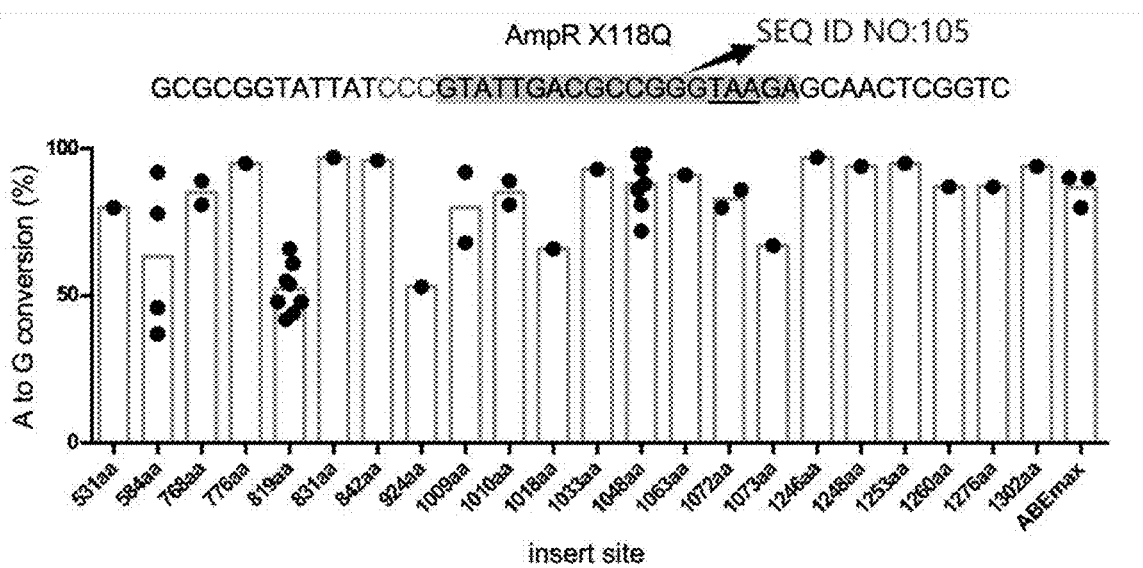
FIG. 2 is a schematic diagram of the present disclosure showing the screened nCas9 effective insertion sites and their base editing efficiency.

The bacteria was spread on several LB agar plates containing 10 µg/mL of kanamycin, and incubated for 16 h at 37° C. after above-mentioned transformation and 1 h of recovery in SOC medium. Then the bacterial colonies were scraped from the plates, resuspended in 100 mL of LLB containing 500 µM of IPTG. The culture was incubated for 10-12 h to induce the expression of nCas9 and repair the mutation on AmpR (A118X). Then cells with a reduced amount (5 mL, 1 mL, 500 µL, 100 µL) were seeded into 15 cm LB agar plates containing 10 µg/mL of ampicillin and 10 µg/mL of kanamycin. The plates were incubated overnight at 37° C., and then bacteria colonies were selected and subjected to Sanger sequencing for estimating the base editing on AmpR (A118X) and determining the insert loci of TadA-TadA*. Loci were selected as follows, and the specific positions were 51, 62, 63, 249, 531, 584, 719, 768, 770, 776, 782, 790, 808, 819, 831, 832, 842, 893, 924, 1009, 1010, 1018, 1033, 1050, 1051, 1063, 1072, 1073, 1090, 1227, 1246, 1248, 1253, 1260, 1263, 1276, 1290, 1302 and 1346, and the fragment of TadA-TadA* was inserted at the C-terminus of these loci. After ampicillin-resistance screening, and sequencing analysis of AmpR (A118X) site repair, it was found that the loci mentioned above with insertion of TadA-TadA* could form the chimeric fusion version of ABE with the function of base editing, and the corresponding insertion sites and efficiency of base editing are shown in FIG. 2.

6. Detection of Mutation Efficiency in *E. coli*

Figure 3:
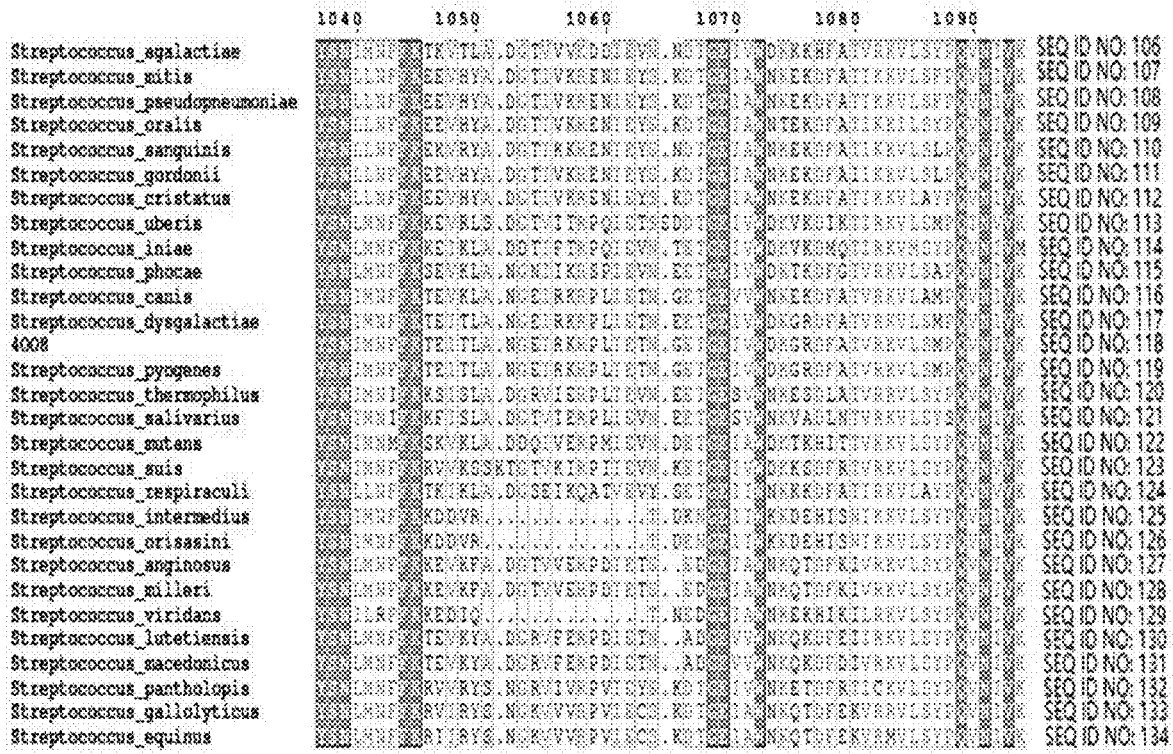
FIG. 3 is a schematic diagram of the present disclosure showing the comparison of non-conservative regions of the homologs of SpCas9.

Firstly, *E. coli* of the electro-transfected random insertion library was well spread on agarose plates containing antibiotic ampicillin, and incubated overnight in an incubator. Positive colonies were selected, and subjected to Sanger sequencing analysis with primer (cttttcggggaaatgtgg-gaaatgtgcgcggaacc) (SEQ ID NO: 87) and primer (cg-gatgcctagacaggtgttcaa) (SEQ ID NO: 88) for the determination of the mutation efficiency of adenine at the A118X locus and the corresponding insertion position of the fragment of TadA-TadA* on nCas9 (FIG. 2). In the 43 insertion sites recovered from the screening library, 9 sites are clustered in the short fragment (16-aa), which are located in 1048Thr, 1050Ile, 1051Thr, 1052Leu, 1054Asn, 1056Glu, 1057Ile, 1059Lys and 1063Ile. The accumulation of these sites in the screening library is specific, because in the unscreened library, these sites were inserted only 61, 39, 90, 38, 5, 29, 76, 53 and 25 times respectively, much less than some positions, such as other sites unrecovered after screening (e.g., 1090Pro insert 280 times). Therefore, a fragment of 16 amino acids has great tolerance to exogenous fragment insertion, and can be unnecessary to the function of nCas9. This fragment is non-conservation in 28 SpCas9 orthologs (FIG. 3). Thus, during the following construction of eukaryotic expression vectors, 1048Thr-1063Ile region was substituted with TadA-TadA* to generate CE-ABE[1048-1063]

7. Comparison of On-Target Editing Efficiency of ABEmax and Various CE-ABE in Human Cells After functional CE-ABE was obtained by screening in prokaryocytes, the on-target base editing efficiency of CE-ABE in HEK293T cells were further detected, and the process is used as follows:

Firstly, eukaryotic expression vectors of CE-ABE were constructed respectively:

After being successfully inserted into the 43 fragments of TadA-TadA* mentioned above, the editors with the function of adenine deamination were subjected to PCR amplification using the forward primer (agggagagccgccaccat-gaaacggacagccgac) (SEQ ID NO: 89) and the reverse primer (tcctcttcttcttgggctcgaattcgctgccgtcggc) (SEQ ID NO: 90), to obtain 20 fragments of CE-ABE.

The pCMV-ABEmax plasmid was amplified using the forward primer (ggtggcggctctccctatagtgagtc) (SEQ ID NO: 91) and the reverse primer (cccaagaagaaggaaagtctaacc) (SEQ ID NO: 92) to obtain the fragment of SEQ ID NO: 35.

The fragments were amplified by PCR with Vazyme high-fidelity enzyme kit (Vazyme, P501-d2). The PCR reaction system used as follows:

TABLE 15

| Water | Add to 50 µL |
|---|---|
| 2× buffer | 25 µL |
| dNTP | 1 µL |
| Forward primer (10 µM) | 2 µL |
| Reverse primer (10 µM) | 2 µL |

TABLE 15-continued

| High-fidelity enzyme | 1 μL |
| Cell lysates | 3-5 μL |

The PCR procedure used is as follows:

TABLE 16

| 1 cycle | 98° C. | 3 min |
| 10 cycles | 95° C. | 20 s |
| | 68° C. | 30 s, −1° C./cycle |
| | 72° C. | 4 min |
| 25 cycles | 95° C. | 20 s |
| | 58° C. | 30 s |
| | 72° C. | 4 min |
| 1 cycle | 72° C. | 5 min |
| 1 cycle | 4° C. | ∞ |

The PCR amplification products were purified and recovered by AxyPrep PCR Clean-up kit (Axygen, AP-PCR-500G), and subjected to recombination reaction, then the fragments were recombinated by Gibson Assembly Master Mix recombinant kit (NEB, E2611S), and the reaction system used is as follows:

TABLE 17

| Gibson Assembly Master Mix (2×) | 5 μL |
| PCR fragment of CE-ABE | 150 ng |
| PCR fragment of pCMV-ABE (SEQ ID NO: 35) | 50 ng |
| Sterile water | Add water to 10 μL |

The reaction solutions were mixed and incubated for 1 h at 50° C., and subjected to transformation subsequently, recovered for 30 min, and spread on a LB agar plate with ampicillin resistance, incubated overnight at 37° C. Single clones were selected for verification by sequencing to obtain a pCMV-CE-ABE plasmid (SEQ ID NO: 36-55). Plasmid extraction was carried out with AxyPrep plasmids miniprep kit (Axygen, AP-MN-P-250G). Sanger sequencing was carried out.

HEK293FT cells (from ATCC) were recovered and cultured in a 10 cm Petri dish (Corning, 430167), where the medium was DMEM (HyClone, SH30243.01) containing 10% (v/v) fetal bovine serum (HyClone, SV30087). The culture temperature was 37° C., and the concentration of CO2 was 5%. When the cell density was about 80% after subculture, the cells were distributed into 12-well plates. The 12-well plates were subjected to the treatment of coating with a 1:10 diluted polylysine solution (Sigma, P4707-50 mL) before use.

1) Cell transfection was carried out when the cell density was about 80% after seeded for 12-14 h. The amount of plasmids transfected was 700 ng of CE-ABE (SEQ ID NO: 36-55) plasmid, and 300 ng of sgRNA of 1ABE-site 1 (SEQ ID NO: 12) per well. The plasmids were mixed in 100 μL of Opti-MEM (Gibco, 11058021) medium. The pCMV-ABEmax plasmid was taken as a positive control group, 700 ng of plasmids (Addgene, #112095) and 300 ng of sgRNA of ABEmax-site1 (SEQ ID NO: 12) were added into each well.

2) In addition, 3 μL of transfection reagent Lipofectamine 2000 (Thermo, 11668019) was mixed into 100 μL of Opti-MEM medium, and let stand for 5 min.

3) Opti-MEM mixed with plasmids were added to Opti-MEM mixed with Lipofectamine 2000, pipetted slowly to mix well, let stand for 20 min.

4) The transfection solution after mixing and standing mentioned above were added to culturing cells respectively.

5) The solution was changed with DMEM containing 10% FBS after transfection for 6 h.

6) After transfection for 48 h, the medium was discarded, and the cells were washed once with PBS, then the cells were digested with TE (Thermo Fisher, R001100), and DMEM containing 10% FBS was used to terminate digestion. Cells were centrifuged and collected, and finally resuspended with the medium.

7) The resuspended cells were sorted by FACS (Fluorescence activated cell sorting), and cells with the top 5% of GFP fluorescent intensity were collected, at least 5,000 cells were collected for each sample.

⅙ of the cells collected above were lysed directly, and the fragments of target sites were amplified by PCR, with the forward primer: aaagatcttcacaggctaccccc (SEQ ID NO: 103) and the reverse primer: aatccacagcaacaccctctcc (SEQ ID NO: 104). The fragments of target sites of each genome were amplified by PCR with Vazyme high-fidelity enzyme kit (Vazyme, P501-d2). The PCR reaction system used is as follows:

TABLE 18

| Water | Add to 50 μL |
| 2× buffer | 25 μL |
| dNTP | 1 μL |
| Forward primer (10 μM) | 2 μL |
| Reverse primer (10 μM) | 2 μL |
| High-fidelity enzyme | 1 μL |
| Cell lysate solution | 3-5 μL |

The PCR procedure used is as follows:

TABLE 19

| 1 cycle | 98° C. | 3 min |
| 10 cycles | 95° C. | 20 s |
| | 68° C. | 30 s, −1° C./cycle |
| | 72° C. | 30 s |
| 25 cycles | 95° C. | 20 s |
| | 58° C. | 30 s |
| | 72° C. | 30 s |
| 1 cycle | 72° C. | 5 min |
| 1 cycle | 4° C. | ∞ |

The PCR amplification products were purified and recovered by AxyPrep PCR

Figure 4:
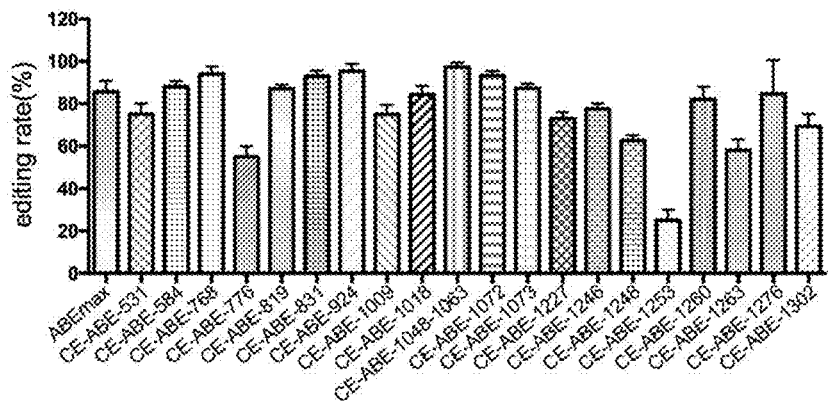
FIG. 4 is a schematic diagram of the present disclosure showing the results of base editing of screened CE-ABE on the human cell genome.

Clean-up kit (Axygen, AP-PCR-500G), and were subjected to Sanger sequencing. The sequencing result of corresponding insertion sites are shown in FIG. 4.

8. Comparison of Off-Targeting Caused by ABEmax and CE-ABE in Human Cells 30,000 of 5% GFP-positive cells mentioned above were collected, centrifuged and the supernatant was discarded, then TRIzol (Thermo Fisher, 15596018) reagent was added, and total RNA was extracted according to the instructions. Thereafter, part of the RNA was taken to reverse transcription, and the detailed steps are as follows:

1) Total RNA extraction: 1 mL of TRIzol reagent was added, pipetted for several times to homogenize the cells. TRIzol was pipetted into nuclease-free microtubes. Then 200 μL of chloroform was added and mixed well, centrifuged for 15 min at 12,000 rpm in pre-cooled centrifuge at 4° C.; 400 μL of the supernatant was carefully pipetted into a new nuclease-free microtube, and 400 μL of isopropanol was added and mixed well at room temperature, let stand for 10 min; after centrifuged for 15 min at 12,000 rpm in pre-cooled centrifuge at 4° C., the supernatant was discarded; 1 mL of 75% ethanol was added, mixed and centrifuged for 15 min at 12,000 rpm in pre-cooled centrifuge at 4° C., and the supernatant was discarded, the precipitate was dried naturally, and 20-30 μL of nuclease-free water was added, and the concentration of RNA was determined by NanoDrop.

2) Reverse transcription of total RNA to cDNA: HiScript@ II Q RT SuperMix for qPCR (+g DNA wiper) kit was used. Firstly, genomic DNA was discarded from total RNA, 500 ng of total RNA, 2 μL of 4×gDNA wiper Mix (Vazyme, R223-01), added with water to 8 μL, incubated for 5 min at 42° C. Then the reverse transcription reaction was started, 2 μL of 5×HiScript® II qRT SuperMix IIa (Vazyme, R223-01) was added into 8 μL of the reaction solution mentioned above. The mixture was incubated for 20 min at 50° C., then reacted at 85° C. for 2 min to inactivate the activity of reverse transcriptase, then cDNA was obtained for later detection.

Figure 5:
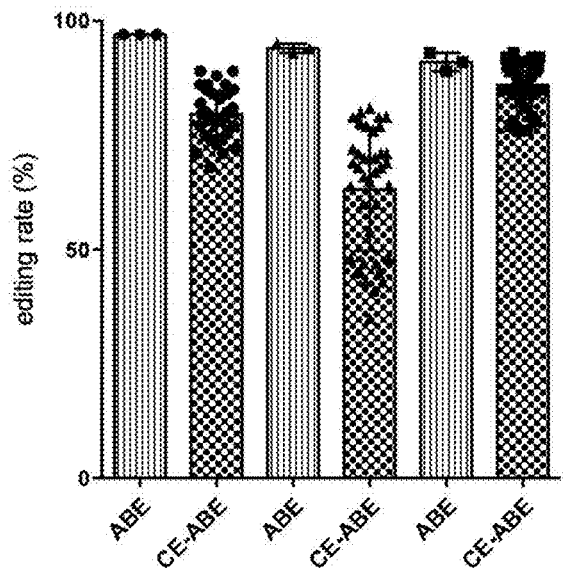
FIG. 5 is a schematic diagram of the present disclosure showing the off-target editing results of CE-ABE on the predicted RNA loci.
Figure 6:
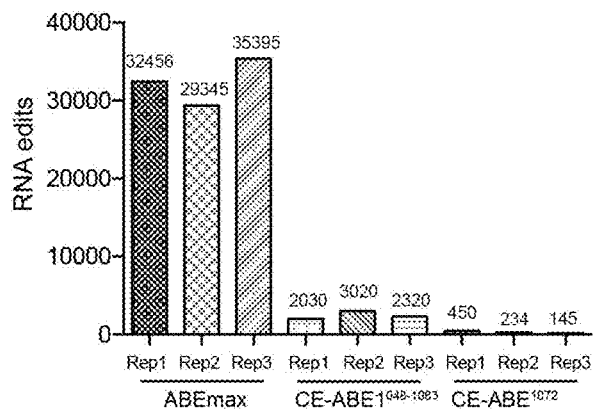
FIG. 6 is a schematic diagram of the present disclosure showing the off-target editing results caused by CE-ABE at the transcriptome level.

Three RNA off-target loci (chr19 (14518195), chr11 (62594034) and chr16 (25164711)) with high off-target rate were obtained from the previous RNA-seq data of cells transfected with ABEmax. Primers were designed for these three loci, and cDNA samples of CE-ABE were amplified for these three loci, followed by Sanger sequencing analysis, the results are shown in FIG. 5. It can be found by analysis that compared to ABEmax, all CE-ABEs have a significant decrease at the three RNA off-target loci. It is indicated that the chimeric deaminase inside nCas9 can effectively reduce the off-target editing of TadA-TadA* on part of RNA sites (FIG. 6).

Thereafter, whole transcriptome sequencing was applied to the RNA of cells transfected with CE-ABE$^{1048-1063}$ CE-ABE$^{1072}$ (the number after numbering refers to the insertion sites of the TadA-TadA* fragment inside nCas9) and ABEmax. All RNA samples were sequenced using Illumina HiSeq X Ten (2×150PE) of Novogene Bioinformation Institution (Beijing, China), with a read depth of about 20 million per sample. The readers were mapped to human reference genome (hg38) by STAR software (version 2.5.1), annotated with GENCODE v30. After deleting duplications, variants were recognized by GATK HaplotypeCaller (version 4.1.2), then filtered by QD (quality by depth), and all variants were verified by bam-readcount and quantified, with the parameter-q 20-b 30. The given editing should be at least ten folds, and it was required that at least 99% of the reads in these editing support the reference allele in wild-type samples. Finally, only A to G (for ABE) editing in transcript chain was considered to involve in downstream analysis. The detailed results are shown in FIG. 6, indicating that the CE-ABE chimerized at the loci 1048Thr-1063Ile and 1072 Val can significantly reduce the off-target editing of TadA-TadA* on RNA at the whole transcriptome level.

Figure 7:
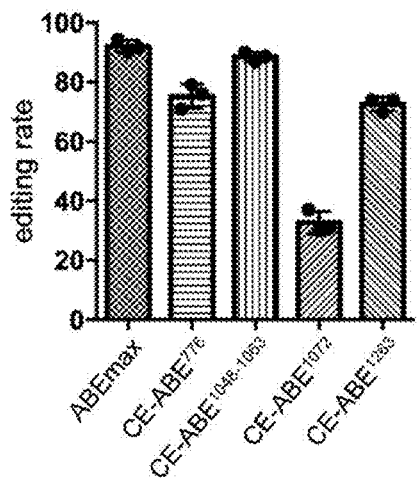
FIG. 7 is a schematic diagram of the present disclosure showing the results of on-target editing efficiency of CE-ABE in off-target assay samples.

Meanwhile, the on-target editing efficiency of three editors, ABEmax, CE-ABE$^{1048-1063}$ and CE-ABE$^{1072}$ was detected. The results show that although the on-target editing efficiency of CE-ABE-1072 was significantly lower than ABEmax, there was no significant difference between the on-target editing efficiency of CE-ABE$^{1048-1063}$ and ABEmax, and the detailed results are shown in FIG. 7.

9. The Base Editing Results of CE-ABE$^{1048-1063}$ at Various Endogenous Gene Loci The on-target base editing efficiency and editing windows of CE-ABE$^{1048-1063}$ in HEK293T cells and N2a cells were further determined, and the process was as follows:

HEK293FT and N2a cells (from ATCC) were recovered and cultured in 10 cm petri dishes (Corning, 430167), and the culture medium was DMEM (HyClone, SH30243.01) containing 10% (v/v) fetal bovine serum (HyClone, SV30087). The culture temperature was 37° C. and the concentration of CO2 was 5%. When the cell density was 80% after subculture, the cells were distributed into 12-well plates. The 12-well plates were subjected to the treatment of coating with a 1:10 diluted polylysine solution (Sigma, P4707-50ML) before use.

2) After the cells were seeded for 12-14 h with the cell density was about 80%, the cells were subjected to transfection. The amount of plasmids for transfection was 700 ng of CE-ABE$^{1048-1063}$ (SEQ ID NO: 45) per well, and for HEK293FT cells, 300 ng of plasmids containing gRNA was used for each loci (SEQ ID NO: 21-32); for N2a cells, 300 ng of plasmids containing gRNA was used for each loci (SEQ ID NO: 21-32). The plasmids were mixed in 100 μL of Opti-MEM (Gibco, 11058021) medium. The pCMV-AncBE4 max was set as control, 700 ng of pCMV-ABEmax plasmids and 300 ng of plasmids containing gRNA for each loci were added into each well.

3) In addition, 3 μL of Lipofectamine 2000 transfection reagent (Thermo, 11668019) was mixed into 100 μL of Opti-MEM medium, and let stand for 5 min.

4) The Opti-MEM mixed with plasmids was added into the Opti-MEM mixed with Lipofectamine 2000, and the mixture was pipetted slowly and mixed well, let stand for 20 min.

5) The transfection solution after mixing and standing was added into culture cells respectively.

6) After transfection for 6 h, the solution was changed with DMEM containing 10% FBS. After transfection for 48 h, the medium was discarded, and the cells were washed with PBS once, digested with TE (Thermo Fisher, R001100) then, followed by terminating the digestion with DMEM containing 10% FBS. The cells were centrifuged and collected, and finally resuspended with the medium.

7) The resuspended cells were sorted by FACS (Fluorescence activated Cell Sorting), and since the GFP signal was on a plasmid containing gRNA, all GFP positive cells were sorted directly, and at least 5000 cells were collected for each sample.

The cells collected above were subjected to lysis and fragments of target sites were amplified with PCR. The fragments of target sites of each genome were amplified with PCR by Vazyme high-fidelity enzyme kit (Vazyme, P501-d2). The PCR reaction system used is as follows:

TABLE 20

| | |
|---|---|
| Water | Add to 50 μL |
| 2× buffer | 25 μL |
| dNTP | 1 μL |
| Forward primer (10 μM) | 2 μL |
| Reverse primer (10 μM) | 2 μL |
| High-fidelity enzyme | 1 μL |
| Cell lysate solution | 3-5 μL |

The PCR procedure used is as follows:

TABLE 21

| | | |
|---|---|---|
| 1 cycle | 98° C. | 3 min |
| 10 cycles | 95° C. | 20 s |
| | 68° C. | 30 s, −1° C./cycle |
| | 72° C. | 30 s |

TABLE 21-continued

| 25 cycles | 95° C. | 20 s |
| | 58° C. | 30 s |
| | 72° C. | 30 s |
| 1 cycle | 72° C. | 5 min |
| 1 cycle | 4° C. | ∞ |

Figure 8:
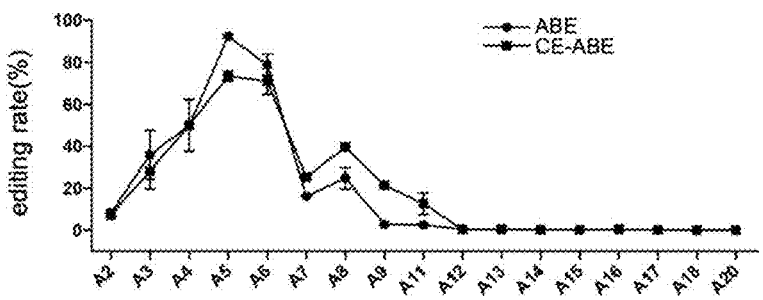
FIG. 8 is a schematic diagram of the present disclosure showing comparable editing efficiency of CE-ABE$^{1048-1063}$ and ABEmax in 293T cells.
Figure 9:
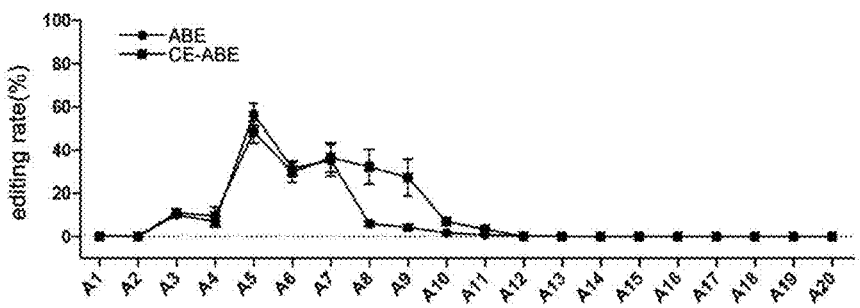
FIG. 9 is a schematic diagram of the present disclosure showing comparable editing efficiency of CE-ABE$^{1048-1063}$ and ABEmax in N2a cells.

The PCR amplification product was purified and recovered by AxyPrep PCR Clean-up kit (Axygen, AP-PCR-500G). PCR products with different barcodes were gathered and subjected to deep sequencing on the Illumina HiSeq X Ten (2×150PE) platform of Novogene Bioinformation Institution (Beijing, China). The adapter pairs of paired-end reads were removed, and paired-end reads of 11 bp or more of bases were combined into a single common read using AdaptorRemoval (version 2.2.2). Next, all processed reads were mapped to a target sequence by BWA-MEM algorithm (BWA v0.7.16). For each loci, the mutation rate was calculated by counting the bam reads with parameters -q 20-b 30. The indel (insertion or deletion) was calculated based on the reads of at least one nucleotide insertion or deletion in a protospacer. The frequency of indel was calculated as readers containing indels/total mapped readers. The results of sequencing are shown in FIGS. 8 and 9. The results indicate that the on-target base editing efficiency of CE-ABE$^{1048-1063}$ at multiple endogenous sites in HEK293T cells is comparable to that of ABEmax. Besides, the editing window of CE-ABE$^{1048-1063}$ shows no significant change, the detailed results are shown in FIGS. 8 and 9.

9. The Base Editing Results of CE-ABE$^{1048-1063}$ at Multiple Endogenous Gene Loci It has been found in above experiments that the on-target efficiency of CE-ABE with replacement of the fragment between 1048Thr-1063Ile with TadA-TadA* in nCas9 is the highest, while the low off-target efficiency is low. Furthermore, the 1048Thr-1063Ile peptide of nCas9 was replaced with APOBEC1 (SEQ ID NO: 68) and APOBEC3A (SEQ ID NO: 69) respectively, and the on-target base editing efficiency and editing windows of CE-ABE$^{1048-1063}$ were characterized in HEK293T cells. The procedure was as follows:

1) Firstly, the eukaryotic expression vectors of CE-ABE$^{1048-1063}$ and CE-A3A$^{1048-1063}$ were constructed respectively:

```
The APOBEC1 fragment was amplified by PCR
using the forward primer:
                                      (SEQ ID NO: 93)
catgaacttttttcaagtccggaTCCgagaccccaggc and the reverse primer:
                                      (SEQ ID NO: 94)
tttcgccgtttgtctcgctctctggtgttgctgac.

The APOBEC3A fragment was amplified by PCR
using the forward primer:
                                      (SEQ ID NO: 95)
catgaacttttttcaagtccggaTCCgagaccccaggc and the reverse primer:
                                      SEQ ID NO: 96)
tttcgccgtttgtctcgctctctggtgttgctgac(.

The pCMV-AncBE4max was used as the template in
PCR amplification with the forward primer:
                                      (SEQ ID NO: 97)
gagacaaacggcgaaaccggggagatc and the reverse primer:
                                      (SEQ ID NO: 98)
cttgaaaaagttcatgatgttgc.
```

The fragments were amplified by PCR with Vazyme high-fidelity enzyme kit (Vazyme, P501-d2). The PCR reaction system used is as follows:

TABLE 22

| Water | Add to 50 μL |
| 2× buffer | 25 μL |
| dNTP | 1 μL |
| Forward primer (10 μM) | 2 μL |
| Reverse primer (10 μM) | 2 μL |
| High-fidelity enzyme | 1 μL |
| Template DNA | 1 μL |

The PCR procedure used is as follows:

TABLE 23

| 1 cycle | 98° C. | 3 min |
| 10 cycles | 95° C. | 20 s |
| | 68° C. | 30 s, -1° C./cycle |
| | 72° C. | 4 min |
| 25 cycles | 95° C. | 20 s |
| | 58° C. | 30 s |
| | 72° C. | 4 min |
| 1 cycle | 72° C. | 5 min |
| 1 cycle | 4° C. | ∞ |

The PCR amplification product was purified and recovered by AxyPrep PCR Clean-up kit (Axygen, AP-PCR-500G), and subjected to recombination; the fragments were recombinated with Gibson Assembly Master Mix recombinant kit (NEB, E2611S), and the reaction system used is as follows:

TABLE 24

| Gibson Assembly Master Mix (2×) | 5 μL |
| PCR fragments of APOBEC1 and APOBEC3A | 150 ng |
| PCR fragment of pCMV-AncBE4max | 50 ng |
| Sterile water | Add water to 10 μL |

The reaction solutions were mixed and incubated for 1 h at 50° C., subjected to transformation subsequently, recovered for 30 min, and spread on a LB agar plate with ampicillin resistance, incubated overnight at 37° C. Single clones were selected for verification by sequencing to obtain a pCMV-CE-CBE$^{1048-1063}$ plasmid (SEQ ID NO: 56) and pCMV-CE-A3A$^{1048-1063}$ plasmid (SEQ ID NO: 70). Plasmid extraction was carried out with AxyPrep plasmids miniprep kit (Axygen, AP-MN-P-250G). Sanger sequencing was carried out.

HEK293FT cells (from ATCC) were recovered and cultured in 10 cm Petri dish (Corning, 430167), and the medium was DMEM (HyClone, SH30243.01) containing 10% (v/v) fetal bovine serum (HyClone, SV30087). The culture temperature was 37° C., and the concentration of CO2 was 5%. When the cell density was about 80% after subculture, the cells were distributed into 12-well plates. The 12-well plates were subjected to the treatment of coating with a 1:10 diluted polylysine solution (Sigma, P4707-50 mL) before use.

2) Cell transfection was carried out when the cell density was about 80% after seeded for 12-14 h. The amount of plasmids used to transfect was 700 ng of CE-ABE (SEQ ID NO: 56) and CE-A3A (SEQ ID NO: 70) per well, and 300 ng plasmids containing gRNA for each loci (SEQ ID NO: 57-67). The plasmids were mixed in 100 μL of Opti-MEM (Gibco, 11058021) medium. The pCMV-AncBE4 max plasmid was taken as a positive control group, 700 ng of pCMV-AncBE4 max plasmids and 300 ng of plasmids containing sgRNA for each loci were added into each well.

3) In addition, 3 μL of transfection reagent Lipofectamine 2000 (Thermo, 11668019) was mixed into 100 μL of Opti-MEM medium, and let stand for 5 min.

4) Opti-MEM mixed with plasmids were added to Opti-MEM mixed with Lipofectamine 2000, and pipetted slowly to mix well, let stand for 20 min.

5) The transfection solution after mixing and standing mentioned above were added to culturing cells respectively.

6) The solution was changed with DMEM containing 10% FBS after transfection for 6 h. After transfection for 48 h, the medium was discarded, and the cells were washed once with PBS, then the cells were digested with TE (Thermo Fisher, R001100), and DMEM containing 10% FBS was used to terminate digestion. Cells were centrifuged and collected, and finally resuspended with the medium.

7) The resuspended cells were sorted by FACS (Fluorescence activated cell sorting), and since the GFP signal is on gRNA plasmids, we directly sorted all GFP positive cells, and at least 5,000 cells were collected for each sample.

The cells collected above were lysed directly, and the fragments of target sites were amplified by PCR. The fragments of target sites of each genome were amplified by PCR with Vazyme high-fidelity enzyme kit (Vazyme, P501-d2). The PCR reaction system used is as follows:

TABLE 25

| Water | Add to 50 μL |
|---|---|
| 2× buffer | 25 μL |
| dNTP | 1 μL |
| Forward primer (10 μM) | 2 μL |
| Reverse primer (10 μM) | 2 μL |
| High-fidelity enzyme | 1 μL |
| Cell lysate | 3-5 μL |

The PCR procedure used is as follows:

TABLE 26

| 1 cycle | 98° C. | 3 min |
|---|---|---|
| 10 cycles | 95° C. | 20 s |
| | 68° C. | 30 s, −1° C./cycle |
| | 72° C. | 30 s |
| 25 cycles | 95° C. | 20 s |
| | 58° C. | 30 s |
| | 72° C. | 30 s |
| 1 cycle | 72° C. | 5 min |
| 1 cycle | 4° C. | ∞ |

Figure 10:
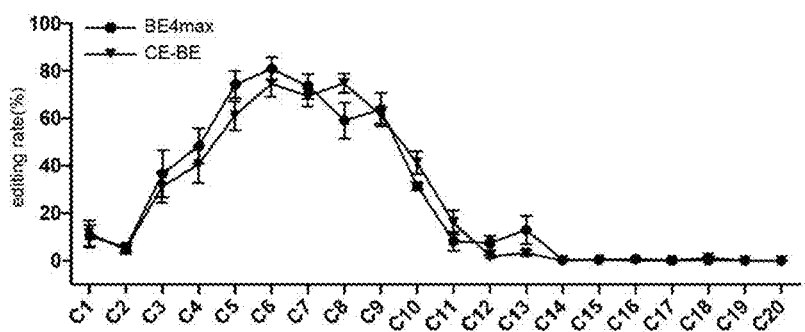
FIG. 10 is a schematic diagram of the present disclosure showing comparable editing efficiency of CE-BE$^{1048-1063}$ and AncBE4 max in 293T cells.
Figure 11:
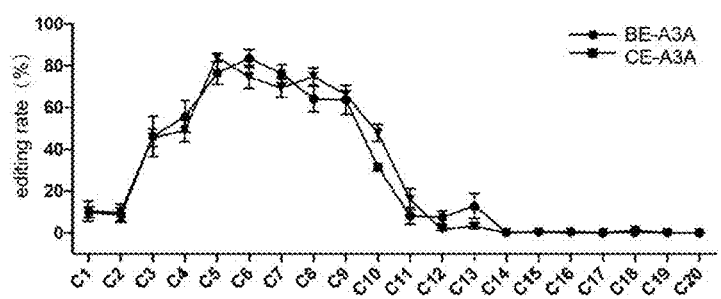
FIG. 11 is a schematic diagram of the present disclosure showing comparable editing efficiency of CE-A3A$^{1048-1063}$ and BE-A3A in 293T cells.

The PCR amplification product was purified and recovered by AxyPrep PCR Clean-up kit (Axygen, AP-PCR-500G). PCR products with different barcodes were gathered and subjected to deep sequencing on the Illumina HiSeq X Ten (2×150PE) platform of Novogene Bioinformation Institution (Beijing, China). The adapter pairs of a paired-end reads were removed, and paired-end reads of 11 bp or more of bases were combined into a single common read using AdaptorRemoval (version 2.2.2). Next, all processed reads were mapped to a target sequence by BWA-MEM algorithm (BWA v0.7.16). For each loci, the mutation rate was calculated by counting the bam reads with parameters −q 20 -b 30. The indel was calculated based on the reads of at least one nucleotide insertion or deletion in a protospacer. The frequency of an indel was calculated as readers containing indels/total mapped readers. The results of sequencing are shown in FIGS. 10 and 11. The results indicate that the on-target base editing efficiency of CE-BE at multiple endogenous sites in HEK293T cells is comparable to that of original BE. Besides, the editing window of CE-ABE shows no significant change, the detailed results are shown in FIG. 8, and FIGS. 10 and 11.

11. The Off-Target Editing Results of CE-ABE and CE-A3A on RNA in Human Cells 300000 of 5% of GFP positive cells described above were sorted by FACS, centrifuged and the supernatant was discarded, the TRIzol (Thermo Fisher, 15596018) reagent was added. Extraction of total RNA was carried out according to instructions. Next, part of total RNA was taken for reverse transcription, and the detailed steps are as follows:

Total RNA extraction: 1 mL of TRIzol reagent was added, and pipetted for several times to homogenize the cells. TRIzol was pipetted into a nuclease-free centrifuge microtube. Then, 200 μL of chloroform was added, mixed well, and centrifuged for 15 min at 12000 rpm in a pre-cooled centrifuge at 4° C.; 400 μL of the supernatant was pipetted carefully into a new nuclease-free centrifuge microtube, 400 μL of isopropanol was added, mixed well at room temperature and let stand for 10 min; after centrifuged for 15 min at 12000 rpm in a 4° C. pre-cool centrifuge, the supernatant was discarded; 1 mL of 75% ethanol was added, mixed well and centrifuged for 15 min at 12000 rpm in a pre-cooled centrifuge at 4° C., then the supernatant was discarded, the precipitate was dried naturally; 20-30 μL of nuclease-free water was added, and the RNA concentration test was carried out by NanoDrop.

Figure 12:
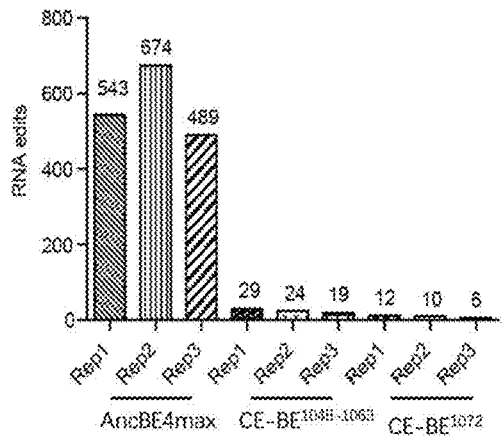
FIG. 12 is a schematic diagram of the present disclosure showing the off-target editing on RNA caused by CE-BE and AncBE4 max in 293T cells.
Figure 13:
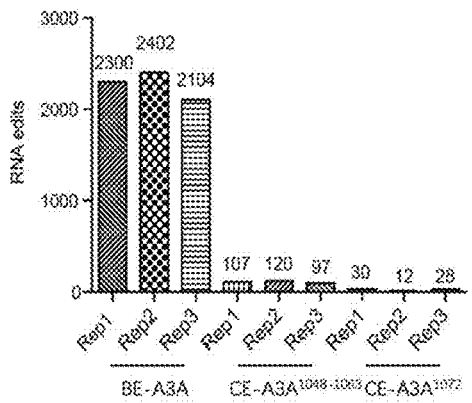
FIG. 13 is a schematic diagram of the present disclosure showing the off-target editing on RNA caused by CE-A3A and BE-A3A in 293T cells.

Subsequently, whole transcriptome sequencing was performed for BE4 max, CE-CBE$^{1048-1063}$ CE-CBE$^{1072}$, BE-A3A, CE-A3A$^{1048-1063}$, CE-A3A$^{1072}$, and all RNA samples were subjected to sequencing using Illumina HiSeq X Ten (2×150PE) of Novogene Bioinformation Institution (Beijing, China), with a read depth of about 20 million per sample. The readers were mapped to human reference genome (hg38) by STAR software (version 2.5.1), annotated with GENCODE v30. After deleting duplicates, variants were recognized by GATK HaplotypeCaller (version 4.1.2), then filtered by QD (quality by depth), and all variants were verified by bam-readcount and quantified, with the parameter −q20-b30. The given editing should be at least ten folds, and it was required that at least 99% of the reads in these editing support reference allele in wild-type samples. Finally, only C to T editing in transcript chain was considered to involve in downstream analysis. FIGS. 12 and 13 indicate that CE-CBE$^{1048-1063}$, CE-CBE$^{1072}$, CE-A3A$^{1048-1063}$ and CE-A3A$^{1072}$ chimerized at the loci 1048Thr-1063Ile and 1072 Val can significantly reduce the off-target editing of APOBEC1 and APOBEC3A on RNA at whole transcriptome level.

12. The Off-Target DNA Editing Results of CE-CBE$^{1048-1063}$ and CE-A3A$^{1048-1063}$ in Mouse Embryos CE-CBE$^{1048-1063}$ and CE-A3A$^{1048-1063}$ were transcribed to mRNA in vitro, and at first, CE-CBE$^{1048-1063}$ and CE-A3A$^{1048-1063}$ were amplified respectively by PCR using the forward primer: ATGCCTGCTATTGTCTTCCCAA (SEQ ID NO: 99) and the reverse primer: AACGGGGACTTTCCAAAATGTC (SEQ ID NO: 100) to obtain linearized fragments of CE-CBE$^{1048-1063}$ and CE-A3A$^{1048-1063}$. For sgRNA transcription, oligonucleotide chain was synthesized first, and linked to a linearized PUC57-Sp sgRNA plasmid after annealing. The PUC57 plasmid constructed was verified by Sanger sequencing, sgRNA was amplified by PCR using the forward primer: TCTCGCGCGTTTCGGTGATGACGG (SEQ ID NO: 101) and the reverse primer: AAAAAAATCTCGC-CAACAAGTTGAC (SEQ ID NO: 102):

The detailed steps are as follows:

TABLE 27

| | |
|---|---|
| Water | Add to 50 μL |
| 2× buffer | 25 μL |
| dNTP | 1 μL |
| Forward primer (10 μM) | 2 μL |
| Reverse primer (10 μM) | 2 μL |
| High-fidelity enzyme | 1 μL |
| CE-CBE/CE-A3A/sgRNA | 1 ng |

The PCR procedure used is as follows:

TABLE 28

| | | |
|---|---|---|
| 1 cycle | 98° C. | 3 min |
| 10 cycles | 95° C. | 20 s |
| | 68° C. | 30 s, −1° C./cycle |
| | 72° C. | 4 min |
| 25 cycles | 95° C. | 20 s |
| | 58° C. | 30 s |
| | 72° C. | 4 min |
| 1 cycle | 72° C. | 5 min |
| 1 cycle | 4° C. | ∞ |

The following operation was conducted under nuclease-free condition: Firstly, RNAsecureTMRNase Inactivation Reagent (Invitrogen™, AM7005) was added into the PCR product at a ratio of 1:25, set to dry bath at 60° C. for 10 min; next, the PCR fragments were recovered with MinElute PCR Purification Kit (QIAGEN, 28004).

(1) In Vitro Transcription of nCas9

In vitro transcription of Cas9 was carried out according to the instructions of mMESSAGE mMACHINE™ T7 ULTRA Transcription Kit (Invitrogen™, AM1345), and the reaction solution was added as follows:

10 μL T7 2×NTP/ARCA
2 μL 10×T7Reaction Buffer
600 ng template PCR fragment of Cas9
2 μL T7 Enzyme Mix
Add Nuclease-free water to 20 μL The reaction solution was reacted on a PCR thermal cycler after well mixed, and cover-heating temperature was set as 50° C., the system temperature was set as 37° C.; 1 μL of TURBO DNase digested template DNA was added after reacted for 2 h, and reacted at 37° C. for 15 min. Thereafter, poly-A was added for subsequent reaction, and the system was as follows:

20 μL the transcription product described above
20 μL 5×E-PAP Buffer
10 μL 25 mM $MnCl_2$
10 μL ATP Solution
36 μL Nuclease-free water Before the addition of E-PAP enzyme, 2.5 μL of the mixed reaction solution was pipetted for subsequent gel electrophoresis, then 4 μL of E-PAP enzyme was added into 96 μL of the reaction solution, reacted for 30 min at 37° C. 2.5 μL of the reaction solution after tailing was pipetted, and subjected to electrophoresis in 0.8% agarose gel with the reaction solution before tailing at 180 V for 10 min. After the bands were confirmed right, Cas9 mRNA was recovered with Rnasy Mini Kit (QIAGEN, 74104).

(2) In Vitro Transcription of sgRNA

The purified product obtained above was subjected to subsequent steps. In vitro transcription of sgRNA was conducted according to instructions of kit MEGA Shortscript™ T7 Transcription Kit (Invitrogen™, AM1354), 600 ng of template DNA was used for reaction, and the reaction solution was mixed as follows:

2 μL T7 10×Reaction Buffer
2 μL T7 ATP Solution (75 mM)
2 μL T7 CTP Solution (75 mM)
2 μL T7 GTP Solution (75 mM)
2 μL T7 UTP Solution (75 mM)
2 μL T7 Enzyme Mix
600 ng template PCR fragment of sgRNA
Add Nuclease-free water to 20 μL The reaction solution was reacted on a PCR thermal cycler after well mixed, and the cover-heating temperature was set as 50° C., the system temperature was set as 37° C. 1 μL of TURBO DNase digested template DNA was added after reacted for 6 h for digestion at 37° C. for 15 min. 1 μL of the mixed reaction solution was pipetted and subjected to electrophoresis in 0.8% agarose gel with a voltage of 180 V for 10 min. After the bands were confirmed right, mRNA of sgRNA was recovered with MEGAclear Kit (Invitrogen™, AM1908).

(3) Fertilized Eggs Injection and Embryo Transplantation

C57 female mice of 6-8 weeks old were taken for intraperitoneal injection of human chorionic gonadotropin, HCG (Ningbo Sansheng Pharm, B141002), and after 48 h, pregnant mare serum gonadotropin PMSG (Ningbo Sansheng Pharm, S141004) was injected intraperitoneally. The mice were caged together with C57 male mice of 7-8 weeks old. After 12 h, the mice were killed under anesthesia, and eggs were taken. The cells were separated when the fertilized eggs were developed to 2-cell stage, one of which was transferred to a zona pellucida of the other, and directly transferred to oviducts of pseudopregnant ICR female mice with other 20-25 fertilized eggs of ICR mice without injection.

CBE4 max/CE-CBE$^{1048-1063}$/CE-A3A$^{1048-1063}$ (100 ng/μL) were mixed with mRNA of sgRNA (50 ng/μL) respectively, and centrifuged for 5 min at 12000 rpm. The mRNA supernatant was pipetted into droplets of HEPES-CZB medium containing 5 μg/mL of cytochalasin B and injected into the remaining cell cytoplasm using a FemtoJect micropipette. Next, the injected fertilized eggs were cultured to 2-cell stage, and transferred to oviducts of pseudopregnant ICR female mice with other 20-25 fertilized eggs of ICR mice.

Figure 14:
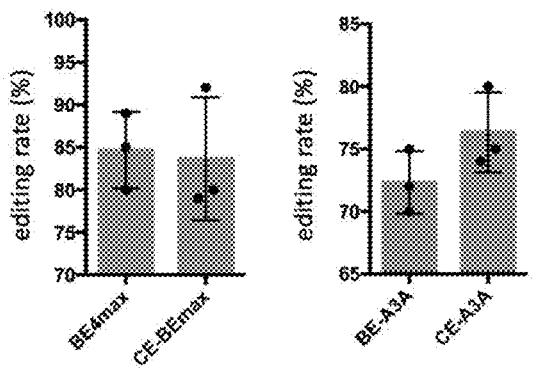
FIG. 14 is a schematic diagram of the present disclosure showing the results of on-target editing on DNA generated by BE4 max, BE-A3A, CE-BE$^{1048-1063}$ and CE-A3A$^{1048-1063}$.
Figure 15:
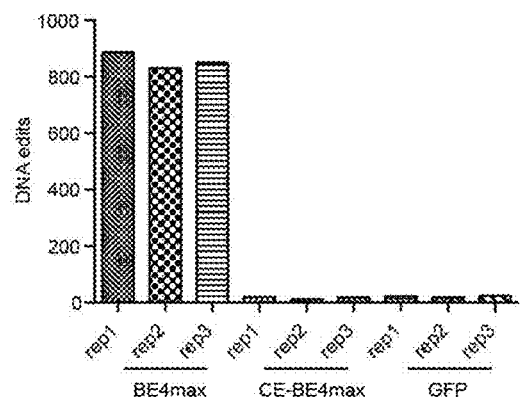
FIG. 15 is a schematic diagram of the present disclosure showing the results of off-target editing on DNA caused by BE4 max and CE-BE$^{1048-1063}$ (CE-BE4 max).
Figure 16:
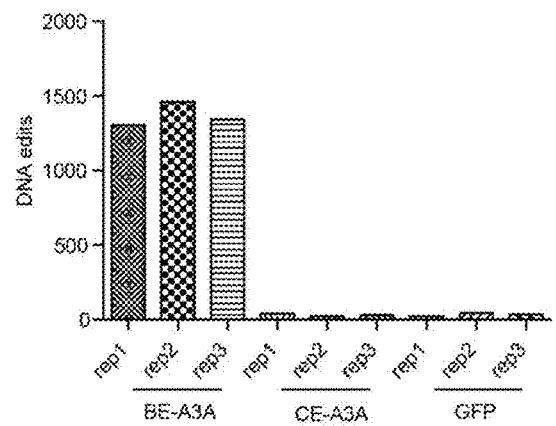
FIG. 16 is a schematic diagram of the present disclosure showing the results of off-target editing on DNA caused by BE-A3A and CE-A3A$^{1048-1063}$ (CE-A3A).

On day 13.5, the female mice were dissected, and the eye color of the mice was observed. C57 mice embryos were selected, lysed, and genomic DNA was extracted for subsequent detection. On-target efficiency of sgRNA was detected at first, and the editing efficiency was verified, the detailed results are shown in FIG. 14. Subsequently, WGS sequencing was conducted on genomic DNA respectively for analyzing the off-targeting of the editor on DNA, and the detailed results are shown in FIG. 15 and FIG. 16. It can be seen that CE-CBE$^{1048-1063}$ and CE-A3A$^{1048-1063}$ have better editing efficiency and lower off-target rate in mice embryos.

In conclusion, the present disclosure overcomes various shortcomings in the prior art, thereby has a high industrial value.

The present disclosure is not to be limited by the examples described which are intended as an example illustration of the principle and efficacy of the present disclosure. It will be apparent to those skilled in the art that various modifications and variations can be made to the examples described above in the present disclosure without departing from the spirit or scope of the disclosure. Therefore, all equivalent modifications or changes made by those with ordinary knowledge in the art without departing from the spirit and technical ideas disclosed in the present invention should still be covered by the claims of the present invention.

REFERENCE TO SEQUENCE LISTING SUBMITTED ELECTRONICALLY

This application incorporates by reference a Sequence Listing with this application as an XML file entitled "seq-220824.xml" created on Feb. 6, 2024 and having a size of 344 KB.

What is claimed is:

1. A fusion protein comprising a first fragment of a nCas9 protein, a chimeric insertion polypetide and a second fragment of the nCas9 protein from N-terminus to C-terminus, wherein the chimeric insertion polypetide is TadA-TadA*, wherein the TadA-TadA* is a polypeptide encoded by the nucleotide sequence shown in SEQ ID NO: 11; wherein
the first fragment of the nCas9 protein has an amino acid sequence as set forth in SEQ ID NO: 1; and
the second fragment of the nCas9 protein has an amino acid sequence as set forth in SEQ ID NO: 2.

2. The fusion protein of claim 1, wherein the fusion protein further comprises a nuclear localization signal.

3. The fusion protein of claim 2, wherein the nuclear localization signal comprises an amino acid sequence of SEQ ID NO: 6.

4. The fusion protein of claim 1, wherein the fusion protein further comprises a flexible linker peptide.

5. The fusion protein of claim 4, wherein the flexible linker peptide comprises an amino acid sequence of SEQ ID NO: 7 or SEQ ID NO: 8.

6. The fusion protein of claim 1, wherein the fusion protein is expressed by a plasmid as shown in SEQ ID NO: 45.

7. The fusion protein of claim 1, wherein the fusion protein is a protein encoded by a nucleotide sequence at positions 472-5811 of the plasmid shown in SEQ ID NO: 45.

8. An isolated polynucleotide encoding the fusion protein of claim 1.

9. A construct comprising the isolated polynucleotide of claim 8.

10. The construct of claim 9, wherein the construct is a plasmid as shown in SEQ ID NO. 45.

11. An expression system, wherein the expression system has the isolated polynucleotide of claim 8 integrated into its genome, or comprises a construct including the isolated polynucleotide.

12. W The expression system of claim 11, wherein a host cell of the expression system is selected from eukaryotic cells.

13. The expression system of claim 12, wherein the eukaryotic cells are selected from mouse cells and human cells.

14. The expression system of claim 13, wherein the eukaryotic cells are selected from mouse brain neuroma cells, human embryonic kidney cells, human cervical cancer cells, human colon cancer cells, and human osteosarcoma cells.

15. The expression system of claim 14, wherein the eukaryotic cells are selected from N2a cells, HEK293FT cells, Hela cells, HCT116 cells, and U2OS cells.

16. A base editing system comprising the fusion protein of claim 1, wherein the base editing system further comprises sgRNA.

* * * * *

SEQUENCE LISTING

```
Sequence total quantity: 134
SEQ ID NO: 1            moltype = AA   length = 1046
FEATURE                 Location/Qualifiers
source                  1..1046
                        mol_type = protein
                        organism = Synthetic construct
SEQUENCE: 1
DKKYSIGLAI GTNSVGWAVI TDEYKVPSKK FKVLGNTDRH SIKKNLIGAL LFDSGETAEA   60
TRLKRTARRR YTRRKNRICY LQEIFSNEMA KVDDSFFHRL EESFLVEEDK KHERHPIFGN  120
IVDEVAYHEK YPTIYHLRKK LVDSTDKADL RLIYLALAHM IKFRGHFLIE GDLNPDNSDV  180
DKLFIQLVQT YNQLFEENPI NASGVDAKAI LSARLSKSRR LENLIAQLPG EKKNGLFGNL  240
IALSLGLTPN FKSNFDLAED AKLQLSKDTY DDDLDNLLAQ IGDQYADLFL AAKNLSDAIL  300
LSDILRVNTE ITKAPLSASM IKRYDEHHQD LTLLKALVRQ QLPEKYKEIF FDQSKNGYAG  360
YIDGGASQEE FYKFIKPILE KMDGTEELLV KLNREDLLRK QRTFDNGSIP HQIHLGELHA  420
ILRRQEDFYP FLKDNREKIE KILTFRIPYY VGPLARGNSR FAWMTRKSEE TITPWNFEEV  480
VDKGASAQSF IERMTNFDKN LPNEKVLPKH SLLYEYFTVY NELTKVKYVT EGMRKPAFLS  540
GEQKKAIVDL LFKTNRKVTV KQLKEDYFKK IECFDSVEIS GVEDRFNASL GTYHDLLKII  600
KDKDFLDNEE NEDILEDIVL TLTLFEDREM IEERLKTYAH LFDDKVMKQL KRRRYTGWGR  660
LSRKLINGIR DKQSGKTILD FLKSDGFANR NFMQLIHDDS LTFKEDIQKA QVSGQQDSLH  720
EHIANLAGSP AIKKGILQTV KVVDELVKVM GRHKPENIVI EMARENQTTQ KGQKNSRERM  780
KRIEEGIKEL GSQILKEHPV ENTQLQNEKL YLYYLQNGRD MYVDQELDIN RLSDYDVDHI  840
VPQSFLKDDS IDNKVLTRSD KNRGKSDNVP SEEVVKKMKN YWRQLLNAKL ITQRKFDNLT  900
KAERGGLSEL DKAGFIKRQL VETRQITKHV AQILDSRMNT KYDENDKLIR EVKVITLKSK  960
LVSDFRKDFQ FYKVREINNY HHAHDAYLNA VVGTALIKKY PKLESEFVYG DYKVYDVRKM 1020
IAKSEQEIGK ATAKYFFYSN IMNFFK                                    1046

SEQ ID NO: 2            moltype = AA   length = 305
FEATURE                 Location/Qualifiers
source                  1..305
                        mol_type = protein
                        organism = Synthetic construct
SEQUENCE: 2
ETNGETGEIV WDKGRDFATV RKVLSMPQVN IVKKTEVQTG GFSKESILPK RNSDKLIARK   60
KDWDPKKYGG FDSPTVAYSV LVVAKVEKGK SKKLKSVKEL LGITIMERSS FEKNPIDFLE  120
AKGYKEVKKD LIIKLPKYSL FELENGRKRM LASAGELQKG NELALPSKYV NFLYLASHYE  180
KLKGSPEDNE QKQLFVEQHK HYLDEIIEQI SEFSKRVILA DANLDKVLSA YNKHRDKPIR  240
EQAENIIHLF TLTNLGAPAA FKYFDTTIDR KRYTSTKEVL DATLIHQSIT GLYETRIDLS  300
QLGGD                                                              305

SEQ ID NO: 3            moltype = AA   length = 262
FEATURE                 Location/Qualifiers
source                  1..262
                        mol_type = protein
                        organism = Synthetic construct
SEQUENCE: 3
SGSETPGTSE SATPESGSET GPVAVDPTLR RRIEPHEFEV FFDPRELRKE TCLLYEIKWG   60
TSHKIWRHSS KNTTKHVEVN FIEKFTSERH FCPSTSCSIT WFLSWSPCGE CSKAITEFLS  120
QHPNVTLVIY VARLYHHMDQ QNRQGLRDLV NSGVTIQIMT APEYDYCWRN FVNYPPGKEA  180
HWPRYPPLWM KLYALELHAG ILGLPPCLNI LRRKQPQLTF FTIALQSCHY QRLPPHILWA  240
TGLKSGSGSE TPGTSESATP ES                                          262

SEQ ID NO: 4            moltype = AA   length = 239
FEATURE                 Location/Qualifiers
source                  1..239
                        mol_type = protein
                        organism = Synthetic construct
SEQUENCE: 4
SGSETPGTSE SATPESGSME ASPASGPRHL MDPHIFTSNF NNGIGRHKTY LCYEVERLDN   60
GTSVKMDQHR GFLHNQAKNL LCGFYGRHAE LRFLDLVPSL QLDPAQIYRV TWFISWSPCF  120
SWGCAGEVRA FLQENTHVRL RIFAARIYYY DPLYKEALQM LRDAGAQVSI MTYDEFKHCW  180
DTFVDHQGCP FQPWDGLDEH SQALSGRLRA ILQNQGNSGS ESGSGSETPG TSESATPES  239

SEQ ID NO: 5            moltype = AA   length = 83
```

```
FEATURE                 Location/Qualifiers
source                  1..83
                        mol_type = protein
                        organism = Synthetic construct
SEQUENCE: 5
TNLSDIIEKE TGKQLVIQES ILMLPEEVEE VIGNKPESDI LVHTAYDEST DENVMLLTSD    60
APEYKPWALV IQDSNGENKI KML                                           83

SEQ ID NO: 6            moltype = AA   length = 18
FEATURE                 Location/Qualifiers
source                  1..18
                        mol_type = protein
                        organism = Synthetic construct
SEQUENCE: 6
KRTADGSEFE SPKKKRKV                                                 18

SEQ ID NO: 7            moltype = AA   length = 16
FEATURE                 Location/Qualifiers
source                  1..16
                        mol_type = protein
                        organism = Synthetic construct
SEQUENCE: 7
SGSETPGTSE SATPES                                                   16

SEQ ID NO: 8            moltype = AA   length = 10
FEATURE                 Location/Qualifiers
source                  1..10
                        mol_type = protein
                        organism = Synthetic construct
SEQUENCE: 8
SGGSGGSGGS                                                          10

SEQ ID NO: 9            moltype = AA   length = 1840
FEATURE                 Location/Qualifiers
source                  1..1840
                        mol_type = protein
                        organism = Synthetic construct
SEQUENCE: 9
KRTADGSEFE SPKKKRKVSS DKKYSIGLAI GTNSVGWAVI TDEYKVPSKK FKVLGNTDRH    60
SIKKNLIGAL LFDSGETAEA TRLKRTARRR YTRRKNRICY LQEIFSNEMA KVDDSFFHRL   120
EESFLVEEDK KHERHPIFGN IVDEVAYHEK YPTIYHLRKK LVDSTDKADL RLIYLALAHM   180
IKFRGHFLIE GDLNPDNSDV DKLFIQLVQT YNQLFEENPI NASGVDAKAI LSARLSKSRR   240
LENLIAQLPG EKKNGLFGNL IALSLGLTPN FKSNFDLAED AKLQLSKDTY DDDLDNLLAQ   300
IGDQYADLFL AAKNLSDAIL LSDILRVNTE ITKAPLSASM IKRYDEHHQD LTLLKALVRQ   360
QLPEKYKEIF FDQSKNGYAG YIDGGASQEE FYKFIKPILE KMDGTEELLV KLNREDLLRK   420
QRTFDNGSIP HQIHLGELHA ILRRQEDFYP FLKDNREKIE KILTFRIPYY VGPLARGNSR   480
FAWMTRKSEE TITPWNFEEV VDKGASAQSF IERMTNFDKN LPNEKVLPKH SLLYEYFTVY   540
NELTKVKYVT EGMRKPAFLS GEQKKAIVDL LFKTNRKVTV KQLKEDYFKK IECFDSVEIS   600
GVEDRFNASL GTYHDLLKII KDKDFLDNEE NEDILEDIVL TLTLFEDREM IEERLKTYAH   660
LFDDKVMKQL KRRRYTGWGR LSRKLINGIR DKQSGKTILD FLKSDGFANR NFMQLIHDDS   720
LTFKEDIQKA QVSGQGDSLH EHIANLAGSP AIKKGILQTV KVVDELVKVM GRHKPENIVI   780
EMARENQTTQ KGQKNSRERM KRIEEGIKEL GSQILKEHPV ENTQLQNEKL YLYYLQNGRD   840
MYVDQELDIN RLSDYDVDHI VPQSFLKDDS IDNKVLTRSD KNRGKSDNVP SEEVVKKMKN   900
YWRQLLNAKL ITQRKFDNLT KAERGGLSEL DKAGFIKRQL VETRQITKHV AQILDSRMNT   960
KYDENDKLIR EVKVITLKSK LVSDFRKDFQ FYKVREINNY HHAHDAYLNA VVGTALIKKY  1020
PKLESEFVYG DYKVYDVRKM IAKSEQEIGK ATAKYFFYSN IMNFFKSGSE TPGTSESATP  1080
ESGSETGPVA VDPTLRRRIE PHEFEVFFDP RELRKETCLL YEIKWGTSHK IWRHSSKNTT  1140
KHVEVNFIEK FTSERHFCPS TSCSITWFLS WSPCGECSKA ITEFLSQHPN VTLVIYVARL  1200
YHHMDQQNRQ GLRDLVNSGV TIQIMTAPEY DYCWRNFVNY PPGKEAHWPR YPPLWMKLYA  1260
LELHAGILGL PPCLNILRRK QPQLTFFTIA LQSCHYQRLP PHILWATGLK SGSGSETPGT  1320
SESATPESET NGETGEIVWD KGRDFATVRK VLSMPQVNIV KKTEVQTGGF SKESILPKRN  1380
SDKLIARKKD WDPKKYGGFD SPTVAYSVLV VAKVEKGKSK KLKSVKELLG ITIMERSSFE  1440
KNPIDFLEAK GYKEVKKDLI IKLPKYSLFE LENGRKRMLA SAGELQKGNE LALPSKYVNF  1500
LYLASHYEKL KGSPEDNEQK QLFVEQHKHY LDEIIEQISE FSKRVILADA NLDKVLSAYN  1560
KHRDKPIREQ AENIIHLFTL TNLGAPAAFK YFDTTIDRKR YTSTKEVLDA TLIHQSITGL  1620
YETRIDLSQL GGDSGGSGGS GGSTNLSDII EKETGKQLVI QESILMLPEE VEEVIGNKPE  1680
SDILVHTAYD ESTDENVMLL TSDAPEYKPW ALVIQDSNGE NKIKMLSGGS GGSGGSTNLS  1740
DIIEKETGKQ LVIQESILML PEEVEEVIGN KPESDILVHT AYDESTDENV MLLTSDAPEY  1800
KPWALVIQDS NGENKIKMLS GGSKRTADGS EFEPKKKRKV                        1840

SEQ ID NO: 10           moltype = AA   length = 1817
FEATURE                 Location/Qualifiers
source                  1..1817
                        mol_type = protein
                        organism = Synthetic construct
SEQUENCE: 10
KRTADGSEFE SPKKKRKVSS DKKYSIGLAI GTNSVGWAVI TDEYKVPSKK FKVLGNTDRH    60
SIKKNLIGAL LFDSGETAEA TRLKRTARRR YTRRKNRICY LQEIFSNEMA KVDDSFFHRL   120
EESFLVEEDK KHERHPIFGN IVDEVAYHEK YPTIYHLRKK LVDSTDKADL RLIYLALAHM   180
```

```
IKFRGHFLIE GDLNPDNSDV DKLFIQLVQT YNQLFEENPI NASGVDAKAI LSARLSKSRR   240
LENLIAQLPG EKKNGLFGNL IALSLGLTPN FKSNFDLAED AKLQLSKDTY DDDLDNLLAQ   300
IGDQYADLFL AAKNLSDAIL LSDILRVNTE ITKAPLSASM IKRYDEHHQD LTLLKALVRQ   360
QLPEKYKEIF FDQSKNGYAG YIDGGASQEE FYKFIKPILE KMDGTEELLV KLNREDLLRK   420
QRTFDNGSIP HQIHLGELHA ILRRQEDFYP FLKDNREIKA KILTFRIPYY VGPLARGNSR   480
FAWMTRKSEE TITPWNFEEV VDKGASAQSF IERMTNFDKN LPNEKVLPKH SLLYEYFTVY   540
NELTKVKYVT EGMRKPAFLS GEQKKAIVDL LFKTNRKVTV KQLKEDYFKK IECFDSVEIS   600
GVEDRFNASL GTYHDLLKII KDKDFLDNEE NEDILEDIVL TLTLFEDREM IEERLKTYAH   660
LFDDKVMKQL KRRRYTGWGR LSRKLINGIR DKQSGKTILD FLKSDGFANR NFMQLIHDDS   720
LTFKEDIQKA QVSGQGDSLH EHIANLAGSP AIKKGILQTV KVVDELVKVM GRHKPENIVI   780
EMARENQTTQ KGQKNSRERM KRIEEGIKEL GSQILKEHPV ENTQLQNEKL YLYYLQNGRD   840
MYVDQELDIN RLSDYDVDHI VPQSFLKDDS IDNKVLTRSD KNRGKSDNVP SEEVVKKMKN   900
YWRQLLNAKL ITQRKFDNLT KAERGGLSEL DKAGFIKRQL VETRQITKHV AQILDSRMNT   960
KYDENDKLIR EVKVITLKSK LVSDFRKDFQ FYKVREINNY HHAHDAYLNA VVGTALIKKY  1020
PKLESEFVYG DYKVYDVRKM IAKSEQEIGK ATAKYFFYSN IMNFFKSGSE TPGTSESATP  1080
ESGSMEASPA SGPRHLMDPH IFTSNFNNGI GRHKTYLCYE VERLDNGTSV KMDQHRGFLH  1140
NQAKNLLCGF YGRHAELRFL DLVPSLQLDP AQIYRVTWFI SWSPCFSWGC AGEVRAFLQE  1200
NTHVRLRIFA ARIYYYDPLY KEALQMLRDA GAQVSIMTYD EFKHCWDTFV DHQGCPFQPW  1260
DGLDEHSQAL SGRLRAILQN QGNSGSESGS GSETPGTSES ATPESETNGE TGEIVWDKGR  1320
DFATVRKVLS MPQVNIVKKT EVQTGGFSKE SILPKRNSDK LIARKKDWDP KKYGGFDSPT  1380
VAYSVLVVAK VEKGKSKKLK SVKELLGITI MERSSFEKNP IDFLEAKGYK EVKKDLIIKL  1440
PKYSLFELEN GRKRMLASAG ELQKGNELAL PSKYVNFLYL ASHYEKLKGS PEDNEQKQLF  1500
VEQHKHYLDE IIEQISEFSK RVILADANLD KVLSAYNKHR DKPIREQAEN IIHLFTLTNL  1560
GAPAAFKYFD TTIDRKRYTS TKEVLDATLI HQSITGLYET RIDLSQLGGD SGGSGGSGGS  1620
TNLSDIIEKE TGKQLVIQES ILMLPEEVEE VIGNKPESDI LVHTAYDEST DENVMLLTSD  1680
APEYKPWALV IQDSNGENKI KMLSGGSGGS GGSTNLSDII EKETGKQLVI QESILMLPEE  1740
VEEVIGNKPE SDILVHTAYD ESTDENVMLL TSDAPEYKPW ALVIQDSNGE NKIKMLSGGS  1800
KRTADGSEFE PKKKRKV                                                 1817

SEQ ID NO: 11           moltype = DNA  length = 1374
FEATURE                 Location/Qualifiers
source                  1..1374
                        mol_type = other DNA
                        organism = Synthetic construct
SEQUENCE: 11
cggcgcacga aaaacgcgaa agcgtttcac gataaatgcg aaaactctgg aggatctagc   60
ggccggatcc ctggaagcga gacaccaggc acaagcgagt ccgccacacc agagagctcc  120
ggcggctcct ccggaggatc tctgaggtg gagttttccc acgagtactg gatgagacat   180
gccctgaccc tggccaagag ggcatggat gaaagagaag tccccgtggg cgccgtgctg   240
gtgcacaaca atagagtgat cggagaggga tggaacaggc caatcggccg ccacgcccct   300
accgcacacg cagagatcat ggactgagg caggaggcc tggtcatgca gaattaccgc   360
ctgatcgatg ccaccctgta tgtgacactg agccatgcc tgatgtgcgc aggagcaatg   420
atccacagca ggatcggaag agtggtgttc ggagcacgga acgccaagac cggcgcagca   480
ggctccctga tggatgtgct gcaccacccc ggcatgaacc accgggtgga gatcacagag   540
ggaatcctgg cagacgagtg cgccgccctg ctgagcgatt ctttagaat gcggagacag   600
gagatcaagg cccagaagaa ggcacagagc tccaccgact ctggaggatc tagcggcgga   660
tcctctggaa gcagagacac aggcacaagc gagtccgcca caccagagag ctccggcgga   720
tcctccggag gatcctctga ggtggagttt tcccacgagt actggatgag acatgccctg   780
accctggcca gagggcacg cgatgagagg gaggtgcctg tgggagccgt gctggtgctg   840
aacaatagag tgatcggcga gggctggaac agagccatcg gcctgcacga cccaacagcc  900
catgccgaaa ttatgccct gagacagggc ggcctggtca tgcagaacta cagactgatt   960
gacgccaccc tgtacgtgac attcgagcct tgcgtgatgt gcgccggcgc catgatccac  1020
tctaggatcg gccgcgtggt gtttggcgtg aggaacgcaa aaaccggcgc cgcaggctcc  1080
ctgatggacg tgctgcacta ccccggcatg aataccgcg tcgaaattac cgagggaatc  1140
ctggcagatg aatgtgccgc cctgctgtgc tatttcttc ggatgcctag acaggtgttc  1200
aatgctcaga agaaggccca gagctccacc gactccggag gatctagcgg aggctcctga  1260
ggctctgaga cacctggcac aagcgagagc gcaacacctg aaagcagcgg gggcagcagc  1320
gggggggtcag ttttcgcatt tatcgtgaaa cgctttcgcg tttttcgtgc gccg        1374

SEQ ID NO: 12           moltype = DNA  length = 23
FEATURE                 Location/Qualifiers
source                  1..23
                        mol_type = other DNA
                        organism = Synthetic construct
SEQUENCE: 12
gaacacaaag catagactgc ggg                                           23

SEQ ID NO: 13           moltype = DNA  length = 23
FEATURE                 Location/Qualifiers
source                  1..23
                        mol_type = other DNA
                        organism = Synthetic construct
SEQUENCE: 13
tacagcttgt agtactcata ggg                                           23

SEQ ID NO: 14           moltype = DNA  length = 23
FEATURE                 Location/Qualifiers
source                  1..23
                        mol_type = other DNA
```

-continued

```
                           organism = Synthetic construct
SEQUENCE: 14
catatctcct aacttcaggt tgg                                              23

SEQ ID NO: 15              moltype = DNA   length = 23
FEATURE                    Location/Qualifiers
source                     1..23
                           mol_type = other DNA
                           organism = Synthetic construct
SEQUENCE: 15
ggagtagggg ctcagcaggg cgg                                              23

SEQ ID NO: 16              moltype = DNA   length = 23
FEATURE                    Location/Qualifiers
source                     1..23
                           mol_type = other DNA
                           organism = Synthetic construct
SEQUENCE: 16
gtatgaagac aataactata agg                                              23

SEQ ID NO: 17              moltype = DNA   length = 23
FEATURE                    Location/Qualifiers
source                     1..23
                           mol_type = other DNA
                           organism = Synthetic construct
SEQUENCE: 17
ggaacagtgt gtagaggtgg ggg                                              23

SEQ ID NO: 18              moltype = DNA   length = 23
FEATURE                    Location/Qualifiers
source                     1..23
                           mol_type = other DNA
                           organism = Synthetic construct
SEQUENCE: 18
ctgtatgggt cccggggcgc tgg                                              23

SEQ ID NO: 19              moltype = DNA   length = 23
FEATURE                    Location/Qualifiers
source                     1..23
                           mol_type = other DNA
                           organism = Synthetic construct
SEQUENCE: 19
tgtgcacacg ctgcagagca tgg                                              23

SEQ ID NO: 20              moltype = DNA   length = 23
FEATURE                    Location/Qualifiers
source                     1..23
                           mol_type = other DNA
                           organism = Synthetic construct
SEQUENCE: 20
gcgggacagc ccggaagtcc agg                                              23

SEQ ID NO: 21              moltype = DNA   length = 23
FEATURE                    Location/Qualifiers
source                     1..23
                           mol_type = other DNA
                           organism = Synthetic construct
SEQUENCE: 21
attgatgtaa tggatgcagt ggg                                              23

SEQ ID NO: 22              moltype = DNA   length = 23
FEATURE                    Location/Qualifiers
source                     1..23
                           mol_type = other DNA
                           organism = Synthetic construct
SEQUENCE: 22
gtttcagaat cgaagggtga agg                                              23

SEQ ID NO: 23              moltype = DNA   length = 23
FEATURE                    Location/Qualifiers
source                     1..23
                           mol_type = other DNA
                           organism = Synthetic construct
SEQUENCE: 23
agacatattc ctcactacaa agg                                              23

SEQ ID NO: 24              moltype = DNA   length = 23
FEATURE                    Location/Qualifiers
source                     1..23
```

```
                            mol_type = other DNA
                            organism = Synthetic construct
SEQUENCE: 24
ctttagcttg acatgcagcg cgg                                              23

SEQ ID NO: 25               moltype = DNA  length = 23
FEATURE                     Location/Qualifiers
source                      1..23
                            mol_type = other DNA
                            organism = Synthetic construct
SEQUENCE: 25
agccaggtgg gcggttctct tgg                                              23

SEQ ID NO: 26               moltype = DNA  length = 23
FEATURE                     Location/Qualifiers
source                      1..23
                            mol_type = other DNA
                            organism = Synthetic construct
SEQUENCE: 26
ccccacagga agtggccatg cgc                                              23

SEQ ID NO: 27               moltype = DNA  length = 23
FEATURE                     Location/Qualifiers
source                      1..23
                            mol_type = other DNA
                            organism = Synthetic construct
SEQUENCE: 27
aattcactgt aaagctggaa agg                                              23

SEQ ID NO: 28               moltype = DNA  length = 23
FEATURE                     Location/Qualifiers
source                      1..23
                            mol_type = other DNA
                            organism = Synthetic construct
SEQUENCE: 28
ctgtaaaaag gggctgctcc cgg                                              23

SEQ ID NO: 29               moltype = DNA  length = 23
FEATURE                     Location/Qualifiers
source                      1..23
                            mol_type = other DNA
                            organism = Synthetic construct
SEQUENCE: 29
gccaaaacgt gaagaaataa tgg                                              23

SEQ ID NO: 30               moltype = DNA  length = 23
FEATURE                     Location/Qualifiers
source                      1..23
                            mol_type = other DNA
                            organism = Synthetic construct
SEQUENCE: 30
agttaaaaga gaggggctcc cgg                                              23

SEQ ID NO: 31               moltype = DNA  length = 23
FEATURE                     Location/Qualifiers
source                      1..23
                            mol_type = other DNA
                            organism = Synthetic construct
SEQUENCE: 31
ataaaaatgg atcccaacac tgg                                              23

SEQ ID NO: 32               moltype = DNA  length = 23
FEATURE                     Location/Qualifiers
source                      1..23
                            mol_type = other DNA
                            organism = Synthetic construct
SEQUENCE: 32
acccaaggaa tcgaaaaccc agg                                              23

SEQ ID NO: 33               moltype = DNA  length = 7629
FEATURE                     Location/Qualifiers
source                      1..7629
                            mol_type = other DNA
                            organism = Synthetic construct
SEQUENCE: 33
atatgccaag tacgccccct attgacgtca atgacggtaa atggcccgcc tggcattatg      60
cccagtacat gaccttatgg gactttccta cttggcagta catctacgta ttagtcatcg     120
ctattaccat ggtgatgcgg ttttggcagt acatcaatgg gcgtggatag cggtttgact     180
cacggggatt tccaagtctc cacccccattg acgtcaatgg gagtttgttt tggcaccaaa    240
```

```
atcaacggga ctttccaaaa tgtcgtaaca actccgcccc attgacgcaa atgggcggta    300
ggcgtgtacg gtgggaggtc tatataagca gagctggttt agtgaaccgt cagatccgct    360
agagatccgc ggccgctaat acgactcact atagggagag ccgccaccat gaaacggaca    420
gccgacggaa gcgagttcga gtcaccaaag aagaagcgga agtcagcag tgacaagaag    480
tacagcatcg gcctggccat cggcaccaac tctgtgggct gggccgtgat caccgacgag    540
tacaaggtgc ccagcaagaa attcaaggtg ctgggcaaca ccgaccggca cagcatcaag    600
aagaacctga tcggagccct gctgttcgac agcggcgaaa cagccgaggc cacccggctg    660
aagagaaccg ccagaagaag atacaccaga cggaagaacc ggatctgcta tctgcaagag    720
atcttcagca acgagatggc caaggtggac gacagcttct tccacagact ggaagagtgt    780
ttcctggtgg aagaggataa gaagcacgag cggcacccca tcttcggcaa catcgtggac    840
gaggtggcct accacgagaa gtaccccacc atctaccacc tgagaaagaa actggtggac    900
agcaccgaca aggccgacct gcggctgatc tatctggccc tggccacat gatcaagttc    960
cggggccact tcctgatcga gggcgacctg aaccccgaca cagcgacgt ggacaagctg   1020
ttcatccagc tggtgcagac ctacaaccag ctgttcgagg aaaacccat caacgccagc   1080
ggcgtggacg ccaaggccat cctgtctgcc agactgagca gagcagacg gctgaaaat   1140
ctgatcgccc agctgccgg cgagaagaag aatggcctgt cggaaacct gattgccctg   1200
agcctgggcc tgaccccaa cttcaagagc aacttcgacc tggccgagga tgccaaactg   1260
cagctgagca aggacacta cgacgacgac ctggacaacc tgctggccca tcggcagc    1320
cagtacgccg acctgtttct ggccgccaag aacctgtccg acgccatcct gctgagcgac   1380
atcctgagag tgaacaccga gatcaccaag gcccccctga gcgcctctat gatcaagaga   1440
tacgacgagc accaccagga cctgaccctg ctgaaagctc tcgtgcgca gcagctgcct   1500
gagaagtaca aagagatttt cttcgaccag agcaagaacg gctacgccgg ctacattgac   1560
ggcggagcca gccaggaaga gttctacaag ttcatcaagc ccatcctgga aaagatggac   1620
ggcaccgagg aactgctcgt gaagctgaac agagaggacc tgctgcgaa gcagcggacc   1680
ttcgacaacg gcagcatccc ccaccagatc cacctgggag agctgcacgc cattctgcgg   1740
cggcaggaag atttttaccc attcctgaag gacaaccgga aaaagatcga gaagatcctg   1800
accttccgca tcccctacta cgtgggccct ctggccaggg gaaacagcag attcgcctg   1860
atgaccagaa agagcgagga aaccatcacc cctggaact cgaggaagt ggtgacaag   1920
ggcgcttccg cccagagctt catcgagcgg atgaccaact cgataagaa cctgcccaac   1980
gagaaggtgc tgcccaagca cagcctgctg tacgagtact tcaccgtgta taacgagctg   2040
accaaagtga aatacgtgac cgagggaatg agaaagcccg ccttcctgag cggcgagcag   2100
aaaaaggcca tcgtggacct gctgttcaag accaaccgga aagtgaccgt gaagcagctg   2160
aaagaggact acttcaagaa aatcgagtgc ttcgactccg tggaaatctc cggcgtggaa   2220
gatcggttca acgcctccct gggcacatac cacgatctgc tgaaaattat caaggacaag   2280
gacttcctgg acaatgagga aaacgaggac attctggaag atatcgtgct gaccctgaca   2340
ctgtttgagg acagagagat gatcgaggaa cggctgaaaa cctatgccca cctgttcgac   2400
gacaaagtga tgaagcagct gaagcggcgg agatacaccg gctggggcag gctgagccgg   2460
aagctgatca acggcatccg ggacaagcag tccggcaaga caatcctgga tttcctgaag   2520
tccgacggct tcgccaacag aaacttcatg cagctgatcc acgacgacag cctgaccttt   2580
aaagaggaca tccagaaagc ccaggtgtcc ggccagggcg atagcctgca cgagcacatt   2640
gccaatctgg ccggcagccc cgccattaag aagggcatcc tgcagacagt gaaggtggtg   2700
gacgagctcg tgaaagtgat gggccggcac aagcccgaga acatcgtgat cgaaatggcc   2760
agagagaacc agaccaccca gaagggacag aagaacagcc gcgagagaat gaagcggatc   2820
gaagagggca tcaaagagct gggcagccag atcctgaaag aacacccgt ggaaaacacc   2880
cagctgcaga acgagaagct gtacctgtac tacctgcaga atgggcggga tatgtacgtg   2940
gaccaggaac tggacatcaa ccggctgtcc gactacgatg tggaccatat cgtgcctcag   3000
agcttctga aggacgactc catcgacaac aaggtgctga cagaagcga caagaaccgg   3060
ggcaagagcg acaacgtgcc ctccgaagag gtcgtgaaga agatgaagaa ctactggcgg   3120
cagctgctga acgccaagct gattaccag agaaagttcg acaatctgac caaggccgag   3180
agaggcggcc tgagcgaact ggataaggcc ggcttcatca agacagctct ggtggaaacc   3240
cggcagatca caaagcacgt ggcacagatc ctggactccc tgaacgaact taagtacgac   3300
gagaatgaca gcctgatccg ggaagtgaaa gtgatcaccc tgaagtccaa gctggtgtcc   3360
gatttccgga aggatttcca gttttacaaa gtgcgcgaga tcaacaacta ccaccacgcc   3420
cacgacgcct acctgaacgc cgtcgtggga accgccctga tcaaaagta ccctaagctg   3480
gaaagcgagt tcgtgtacgg cgactacaag gtgtacgacg tgcggaagat gatcgccaag   3540
agcgagcagg aaatcggcaa ggctaccgcc aagtacttct tctacagcaa catcatgaac   3600
tttttcaaga ccgagattac cctgccaac ggcgagatcc ggaagcggcc tctgatcgag   3660
acaaacggca gaaaccggga gatcgtgtgg gataagggcc gggattttgc caccgtgcgg   3720
aaagtgctga gcatgcccca agtgaatatc gtgaaaaga cggggtca gacaggcggc   3780
ttcagcaaag agtctatcct gcccaagagg aacagcgata agctgatcgc cagaaagaag   3840
gactgggacc ctaagaagta cggcggcttc gacagcccca ccgtggccta ttctgtgctg   3900
gtggtggcca agtggaaaa gggcaagtcc aagaaactga agagtgtgaa agagctgctg   3960
gggatcacca tcatggaaag aagcagcttc gagaagaatc ccatcgactt tctggaagcc   4020
aagggctaca aagaagtgaa aaaggacctg atcatcaagc tgcctaagta ctccctgttc   4080
gagctggaaa acggcggaa gagaatgctg gcctctgccg gcgaactgca aaagggaaac   4140
gaactggccc tgcctccaa atatgtgaac ttcctgtacc tggccagcca ctatgagaag   4200
ctgaagggct cccccgagga taatgagcag aaacagctgt tgtgaaca gcacaagcac   4260
tacctggacg agatcatcga gcagatcagc gagttctcta agagagtgat cctggccgac   4320
gctaatctgg acaaagtgct gtccgcctac aacaagcacc gggataagcc catcagagaa   4380
caggccgaga atatcatcca cctgtttacc ctgaccaatc tgggagcccc tgccgccttc   4440
aagtactttg acaccaccat cgaccggaag aggtacacca gcaccaaga ggtgctggac   4500
gccaccctga tccaccagag catcaccggc ctgtacgaga cacggatcga cctgtctcag   4560
ctgggaggtg actctggcgg ctcaaaaaga accgccgacg gcagcgaatt cgagcccaag   4620
aagaagagga aagtctaacc ggtcatcatc accatcacca ttgagtttaa acccgctgat   4680
cagcctcgac tgtgccttct agttgccagc catctgttgt ttgcccctcc cccgtgcctt   4740
ccttgaccct ggaaggtgcc actcccactg tcctttccta taaaatgag gaaattgcat   4800
cgcattgtct gagtaggtgt cattctattc tggggggtgg ggtggggcag gacagcaagg   4860
gggaggattg ggaagacaat agcaggcatg ctggggatgc ggtgggctct atggcttctg   4920
aggcggaaag aaccagctgg ggctcgatac cgtcgacctc tagctagagc ttggcgtaat   4980
```

```
catggtcata gctgtttcct gtgtgaaatt gttatccgct cacaattcca cacaacatac   5040
gagccggaag cataaagtgt aaagcctagg gtgcctaatg agtgagctaa ctcacattaa   5100
ttgcgttgcg ctcactgccc gctttccagt cgggaaacct gtcgtgccag ctgcattaat   5160
gaatcggcca acgcgcgggg agaggcggtt tgcgtattgg gcgctcttcc gcttcctcgc   5220
tcactgactc gctgcgctcg tcgttcggc tgcggcgagc ggtatcagct cactcaaagg   5280
cggtaatacg gttatccaca gaatcagggg ataacgcagg aaagaacatg tgagcaaaag   5340
gccagcaaaa ggccaggaac cgtaaaaagg ccgcgttgct ggcgtttttc cataggctcc   5400
gcccccctga cgagcatcac aaaaatcgac gctcaagtca gaggtggcga acccgacag   5460
gactataaag ataccaggcg tttccccctg gaagctccct cgtgcgctct cctgttccga   5520
ccctgccgct taccggatac ctgtccgcct ttctccctc gggaagcgtg gcgctttctc   5580
atagctcacg ctgtaggtat ctcagttcgg tgtaggtcgt tcgctccaag ctgggctgtg   5640
tgcacgaacc ccccgttcag cccgaccgct gcgccttatc cggtaactat cgtcttgagt   5700
ccaacccggt aagacacgac ttatcgccac tggcagcagc cactggtaac aggattagca   5760
gagcgaggta tgtaggcggt gctacagagt tcttgaagtg gtggcctaac tacggctaca   5820
ctagaagaac agtatttggt atctgcgctc tgctgaagcc agttaccttc ggaaaaagag   5880
ttggtagctc ttgatccggc aaacaaacca ccgctggtag cggtggtttt tttgtttgca   5940
agcagcagat tacgcgcaga aaaaaggat ctcaagaaga tcctttgatc ttttctacgg   6000
ggtctgacac tcagtggaac gaaaactcac gttaaggat tttggtcatg agattatcaa   6060
aaaggatctt cacctagatc cttttaaatt aaaaatgaag ttttaaatca atctaaagta   6120
tatatgagta aacttggtct gacagttacc aatgcttaat cagtgaggca cctatctcag   6180
cgatctgtct atttcgttca tccatagttg cctgactccc cgtcgtgtag ataactacga   6240
tacggggggg cttaccatct ggccccagtg ctgcaatgat accgcgagac ccacgctcac   6300
cggctccaga tttatcagca ataaaccagc cagccggaag ggccgagcgc agaagtggtc   6360
ctgcaacttt atccgcctcc atccagtcta ttaattgttg ccgggaagct agagtaagta   6420
gttcgccagt taatagtttg cgcaacgttg ttgccattgc tacaggcatc gtggtgtcac   6480
gctcgtcgtt tggtatggct tcattcagct ccggttccca acgatcaagg cggttacat   6540
gatccccat gttgtgcaaa aaagcggtta gctccttcgg tcctccgatc gttgtcagaa   6600
gtaagttggc cgcagtgtta tcactcatgg ttatggcagc actgcataat tctcttactg   6660
tcatgccatc cgtaagatgc ttttctgtga ctggtgagta ctcaaccaag tcattctgag   6720
aatagtgtat gcggcgaccg agttgctctt gcccggcgtc aatacgggat aataccgcgc   6780
cacatagcag aactttaaaa gtgctcatca ttggaaaacg ttcttcgggg cgaaaactct   6840
caaggatctt accgctgttg agatccagtt cgatgtaacc cactcgtgca cccaactgat   6900
cttcagcatc ttttactttc accagcgttt ctgggtgagc aaaaacagga aggcaaaatg   6960
ccgcaaaaaa gggaataagg gcgacacgga aatgttgaat actcatactc ttcctttttc   7020
aatattattg aagcatttat cagggttatt gtctcatgag cggatacata tttgaatgta   7080
tttagaaaaa taaacaaata ggggttccgc gcacatttcc ccgaaaagtg ccacctgacg   7140
tcgacggatc gggagatcga tctcccgatc cctagggtc gactctcagt acaatctgct   7200
ctgatgccga tagttaagc cagtatctgc tccctgcttg tgtgttggag gtcgctgagt   7260
agtgcgcgag caaaatttaa gctacaacaa ggcaaggctt gaccgacaat tgcatgaaga   7320
atctgcttag ggttaggcgt tttgcgctgc ttcgcgatgt acgggccaga tatacgcgtt   7380
gacattgatt attgactagt tattaatagt aatcaattac gggtcatta gttcatagcc   7440
catatatgga gttccgcgtt acataactta cggtaaatgg cccgcctggc tgaccgccca   7500
acgacccccg cccattgacg tcaataatga cgtatgttcc catagtaacg ccaataggga   7560
ctttccattg acgtcaatgg gtggagtatt tacggtaaac tgcccacttg gcagtacatc   7620
aagtgtatc                                                          7629
```

SEQ ID NO: 34       moltype = DNA  length = 10864
FEATURE             Location/Qualifiers
source              1..10864
                     mol_type = other DNA
                     organism = Synthetic construct
SEQUENCE: 34

```
gacaagaagt acagcatcgg cctggccatc ggcaccaact ctgtgggctg ggccgtgatc     60
accgacgagt acaaggtgcc cagcaagaaa ttcaaggtgc tgggcaacac cgaccggcac    120
agcatcaaga agaacctgat cggagccctg ctgttcgaca gcggcgaaac agccgaggcc    180
acccggctga gagaaccgc cagaagaaga taccagac ggaagaaccg gatctgctat    240
ctgcaagaga tcttcagcaa cgagatggcc aaggtggacg acagcttctt ccacagactg    300
gaagagtcct tcctggtgga agaggataag agcacgagc ggcaccccat cttcggcaac    360
atcgtggacg aggtggccta ccacgagaag taccccacca tctaccacct gagaaagaaa    420
ctggtggaca gcaccgacaa ggccgacctg cggctgatct atctggccct ggcccacatg    480
atcaagttcc ggggccactt cctgatcgag ggcgacctga accccgacaa cagcgacgtg    540
gacaagctgt tcatccagct ggtgcagacc tacaaccagc tgttcgagga aaaccccatc    600
aacgccagcg cgtggacgc caaggccatc ctgtctgcca actgagcaa gagcagacgg    660
ctggaaaatc tgatcgccca gctgcccggc gagaagaaga atggcctgtt cggaaactg    720
attgccctga gcctgggcct gaccccaac ttcaagcagca acttcgacct ggccgaggat    780
gccaaactgc agctgagcaa ggacacctac gacgacgacc tggacaacct gctggcccag    840
atcggcgacc agtacgccga cctgtttctg gccgccaaga acctgtccga cgccatcctg    900
ctgagcgaca tcctgagagt gaacaccgag atcaccaagg ccccccctga gcgcctctatg    960
atcaagagat acgacgagca ccaccaggac ctgaccctgc tgaaagctct cgtgcggcag   1020
cagctgcctg agaagtacaa agagattttc ttcgaccaga gcaagaacgg ctacgccggc   1080
tacattgacg gcggagccag ccaggaagag ttctacaagt tcatcaagcc catcctggaa   1140
aagatggacg gcaccgagga actgctcgtg aagctgaaca gagaggacct gctgcggaag   1200
cagcggacct tcgacaacgg cagcatcccc caccagatcc acctgggaga gctgcacgcc   1260
attctgcgga ggcaggaaga tttttacccca ttcctgaagg acaaccggga aaagatcgag   1320
aagatcctga ccttccgcat ccctactac gtgggccctc tggccagggg aaacagcaga   1380
ttcgcctgga tgaccagaaa gagcgaggaa accatcaccc cctggaactt cgaggaagtg   1440
gtggacaagg gcgcttccgc ccagagcttc atcgagcgga tgaccaactt cgataagaac   1500
ctgcccaacg agaaggtgct gcccaagcac agcctgctgt acgagtactt caccgtgtat   1560
aacgagctga ccaaagtgaa atacgtgacc gagggaatga gaaagcccgc cttcctgagc   1620
```

```
ggcgagcaga aaaaggccat cgtggacctg ctgttcaaga ccaaccggaa agtgaccgtg  1680
aagcagctga agaggacta cttcaagaaa atcgagtgct tcgactccgt ggaaatctcc  1740
ggcgtggaag atcggttcaa cgcctccctg ggcacatacc acgatctgct gaaaattatc  1800
aaggacaagg acttcctgga caatgaggaa aacgaggaca ttctggaaga tatcgtgctg  1860
accctcgacac tgtttgagga cagagagatg atcgaggaac ggctgaaaac ctatgcccac  1920
ctgttcgacg acaaagtgat gaagcagctg aagcggcgga gatacaccgg ctggggcagg  1980
ctgagccgga agctgatcaa cggcatccgg gacaagcagt ccggcaagac aatcctggat  2040
ttcctgaagt ccgacggctt cgccaacaga aacttcatgc agctgatcca cgacgacagc  2100
ctgaccttta aagaggacat ccagaaagcc caggtgtccg gccagggcga tagcctgcac  2160
gagcacattg ccaatctggc cggcagcccc gccattaaga agggcatcct gcagacagtg  2220
aaggtggtgg acgagctcgt gaaagtgatg ggccggcaca agcccgagaa catcgtgatc  2280
gaaatggcca gagagaacca gaccacccag aagggacaga agaacagccg cgagagaatg  2340
aagcggatcg aagagggcat caaagagctg ggcagccaga tcctgaaaga cacccccgtg  2400
gaaaacaccc agctgcagaa cgagaagctg tacctgtact acctgcagaa tgggcgggat  2460
atgtacgtgg accaggaact ggacatcaac cggctgtccg actacgatgt ggaccatatc  2520
gtgcctcaga gctttctgaa ggacgactcc atcgacaaca aggtgctgac cagaagcgac  2580
aagaaccggg gcaagagcga caacgtgccc tccgaagagg tcgtgaagaa gatgaagaac  2640
tactggcgac agctgctgaa cgccaagctg attacccaga gaaagttcga caatctgacc  2700
aaggccgaga gaggcggcct gagcgaactg gataaggccg gcttcatcaa gagacagctg  2760
gtggaaaccc ggcagatcac aaagcacgtg gcacagatcc tggactcccg gatgaacact  2820
aagtacgacg agaatgacaa gctgatccgg gaagtgaaag tgatcaccct gaagtccaag  2880
ctggtgtccg atttccggaa ggatttccag ttttacaaag tcgcgagat caacaactac  2940
caccacgccc acgacgccta cctgaacgcc gtcgtgggaa ccgccctgat caaaaagtac  3000
cctaagctgg aaagcgagtt cgtgtacggc gactacaagg tgtacgacgt gcggaagatg  3060
atcgccaaga gcgagcagga aatcggcaag gctaccgcca agtacttctt ctacagcaac  3120
atcatgaact ttttcaagac cgagattacc ctggccaacg cgagatccg gaagcggcct  3180
ctgatcgaga caaacggcga aaccggggag atcgtgtggg ataagggccg ggattttgcc  3240
accgtgcgga aagtgctgag catgcccaa gtgaatatcg tgaaaaagac cgaggtgcag  3300
acaggcggct tcagcaaaga gtctatcctg cccaagagga cagcgataa gctgatcgcc  3360
agaaagaagg actgggaccc taagaagtac ggcggctcta cagccccac cgtggcctat  3420
tctgtgctgg tggtggccaa agtggaaaag ggcaagtcca agaaactgaa gagtgtgaaa  3480
gagctgctgg gatcaccat catggaaaga agcagcttcg agaagaatcc catcgacttt  3540
ctggaagcca agggctacaa agaagtgaaa aaggacctga tcatcaagct gcctaagtac  3600
tccctgttcg agctggaaaa cggccggaag agaatgctgg cctctgccgg cgaactgcag  3660
aagggaaacg aactggccct gccctccaaa tatgtgaact tcctgtacct ggccagccac  3720
tatgagaagc tgaagggctc ccccgaggat aatgagcaga aacagctgtt tgtgaacag  3780
cacaagcact acctggacga gatcatcgag cagatcagcg agttctccaa gagagtgatc  3840
ctggccgacg ctaatctgga caaagtgctg tccgcctaca acaagcaccg ggataagccc  3900
atcagagaac aggccgagaa tatcatccac ctgtttaccc tgaccaatct ggagccctc  3960
gccgccttca gtactttga caccaccatc gaccggaaga ggtacaccag caccaaagag  4020
gtgctggacg ccacccctgat ccaccagagc atcaccggcc tgtacgagac acggatcgac  4080
ctgtctcagc tgggaggtga ctctggcggc tcaaaaagaa ccgccgacgg cagcgaattc  4140
gagcccaaga agaaggagaa agtctaaccg gtcatcatca ccatcaccat tgagtttaaa  4200
cccgctgatc agcctcgact gtgccttcta gttgccagcc atctgttgtt tgcccctccc  4260
ccgtgccttc cttgaccctg gaaggtgcca ctcccactgt cctttcctaa taaaatgagg  4320
aaattgcatc gcattgtctg agtaggtgtc attctattct ggggggtggg gtggggcagg  4380
acagcaaggg ggaggattgg gaagacaata gcaggcatgc tggggatgcg gtgggctcta  4440
tggcttctga ggcggaaaga accagctggg gctcgttgac agctagctca gtcctaggta  4500
taatactagt gctcttgccc ggcgtcaata cgttttagag ctagaaatag caagttaaaa  4560
taaggctagt ccgttatcaa cttgaaaaag tggcaccgag tcggtgcttt ttttgatccg  4620
gctgctaaca agcccgaaa ggaagctgag ttggctgctg ccaccgctga gcaataacta  4680
gcataacccc ttgggccctc taaacgggtc ttgaggggtt ttttgctgaa aggaggaact  4740
atatccggat tggcgaatgg gacgcgccct gtagcggcgc attaagcgcg gcgggtgtgg  4800
tggttacgcg cagcgtgacc gctacacttg ccagcgccct agcgccgct cctttcgctt  4860
tcttcccttc ctttctcgcc acgttcgccg gctttccccg tcaagctcta aatcgggggc  4920
tccctttagg gttccgattt agtgctttac ggcacctcga ccccaaaaa cttgattagg  4980
gtgatggttc acgtagtggg ccatcgccct gatagacggt ttttcgccct ttgacgttgg  5040
agtccacgtt ctttaatagt ggactcttgt tccaaactgg aacaacactc aaccctatct  5100
cggtctattc ttttgattta taaggattt tgccgatttc ggcctattgg ttaaaaaatg  5160
agctgattta acaaaaattt aacgcgaatt ttaacaaaat attaacgttt acaatttcag  5220
gtggcacttt tcggggaat gtgggaaatg tgcgcggaac ccctatttgt ttatttttct  5280
aaatacattc aaatatgtat ccgctcatga gacaataacc ctgataaatg cttcaataat  5340
attgaaaaag gaagagtatg agtattcaac atttccgtgt cgcccttatt cccttttttg  5400
cggcattttg ccttcctgtt tttgctcacc cagaaacgct ggtgaaagta aaagatgctg  5460
aagatcagtt gggtgcacga gtgggttaca tcgaactgga tctcaacagc ggtaagatcc  5520
ttgagagttt tcgccccgaa gaacgttttt caatgatgag cacttttaaa gttctgctat  5580
gtggcgcggt attatcccgt attgacgccg ggtaagagca actcggtcgc cgcatacact  5640
attctcagaa tgacttggtt gagtactcac cagtcacaga aaagcatctt acggatggca  5700
tgacagtaag agaattatgc agtgctgcca taaccatgag tgataacact gcggccaact  5760
tacttctgac aacgatcgga ggaccgaagg agctaaccgc ttttttgcac aacatggggg  5820
atcatgtaac tcgccttgat cgttgggaac cggagctgaa tgaagccata ccaaacgacg  5880
agcgtgacac cacgatgcct gtagcaatgg caacaacgtt gcgcaaacta ttaactggcg  5940
aactacttac tctagcttcc cggcaacaat taatagactg gatggaggcg gataaagttg  6000
caggaccact tctgcgctcg gcccttccgg ctggctggtt tattgctgat aaatctggag  6060
ccggtgagcg tgggtctcgc ggtatcattg cagcactggg gccagatggt aagccctccc  6120
gtatcgtagt tatctacacg acggggagtc aggcaactat ggatgaacga aatagacaga  6180
tcgctgagat aggtgcctca ctgattaagc attggtaagc gcggaacccc tatttgttta  6240
tttttctaaa tacattcaaa tatgtatccg ctcatgaatt aatcttaga aaactcatc  6300
gagcatcaaa tgaaactgca atttattcat atcaggatta tcaataccat atttttgaaa  6360
```

```
aagccgtttc tgtaatgaag gagaaaactc accgaggcag ttccatagga tggcaagatc  6420
ctggtatcgg tctgcgattc cgactcgtcc aacatcaata caacctatta atttcccctc  6480
gtcaaaaata aggttatcaa gtgagaaatc accatgagtg acgactgaat ccggtgagaa  6540
tggcaaaagt ttatgcattt ctttccagac ttgttcaaca ggccagccat tacgctcgtc  6600
atcaaaatca ctcgcatcaa ccaaaccgtt attcattcgt gattgcgcct gagcgagacg  6660
aaatacgcga tcgctgttaa aaggacaatt acaaacagga atcgaatgca accggcgcag  6720
gaacactgcc agcgcatcaa caatattttc acctgaatca ggatattctt ctaatacctg  6780
gaatgctgtt ttcccgggga tcgcagtggt gagtaaccat gcatcatcag gagtacggat  6840
aaaatgcttg atggtcggaa gaggcataaa ttccgtcagc cagtttagtc tgaccatctc  6900
atctgtaaca tcattggcaa cgctaccttt gccatgtttc agaaacaact ctggcgcatc  6960
gggcttccca tacaatcgat agattgtcgc acctgattgc ccgacattat cgcgagccca  7020
tttatacccca tataaatcag catccatgtt ggaatttaat cgcggcctag agcaagacgt  7080
ttcccgttga atatggctca taacacccct tgtattactg tttatgtaag cagacagttt  7140
tattgttcat gaccaaaatc ccttaacgtg agttttcgtt ccactgagcg tcagaccccg  7200
tagaaaagat caaaggatct tcttgagatc ctttttttct gcgcgtaatc tgctgcttgc  7260
aaacaaaaaa accaccgcta ccagcggtgg tttgtttgcc ggatcaagag ctaccaactc  7320
tttttccgaa ggtaactggc ttcagcagag cgcagatacc aaatactgtc cttctagtgt  7380
agccgtagtt aggccaccac ttcaagaact ctgtagcacc gcctacatac ctcgctctgc  7440
taatcctgtt accagtggct gctgccagtg gcgataagtc gtgtcttacc gggttggact  7500
caagacgata gttaccggat aaggcgcagc ggtcgggctg aacggggggt tcgtgcacac  7560
agcccagctt ggagcgaacg acctacaccg aactgagata cctacagcgt gagctatgag  7620
aaagccgcac gcttcccgaa gggagaaagg cggacagqta tccggtaagc ggcagggtcg  7680
gaacaggaga gcgcacgagg gagcttccag ggggaaacgc ctggtatctt tatagtcctg  7740
tcgggtttcg ccacctctga cttgagcgtc gatttttgtg atgctcgtca gggggcgga  7800
gcctatggaa aaacgccagc aacgcggcct ttttacggtt cctggccttt tgctggcctt  7860
ttgctcacat gttctttcct gcgttatccc ctgattctgt ggataaccgt attaccgcct  7920
ttgagtgagc tgataccgct cgccgcagcc gaacgaccga gcgcagcgag tcagtgagcg  7980
aggaagcgga agagcgcctg atgcggtatt ttctccttac gcatctgtgc ggtatttcac  8040
accgcatata tggtgcactc tcagtacaat ctgctctgat gccgcatagt taagccagta  8100
tacactccgc tatcgctacg tgactgggtc atggctcgcg cccgacaccc gccaacacc  8160
gctgacgcgc cctgacgggg ttgtctgctc ccggcatccg cttacagaca agctgtgacc  8220
gtctccggga gctgcatgtg tcagaggttt tcaccgtcat caccgaaacg cgcgaggcag  8280
ctgcggtaaa gctcatcagc gtggtcgtga agcgattcac agatgtctgc ctgttcatcc  8340
gcgtccagct cgttgagttt ctccagaagc gttaatgtct ggcttctgat aaagcgggcc  8400
atgttaaggg cggttttttc ctgtttggtc actgatgcct ccgtgtaagg gggatttctg  8460
ttcatggggg taatgatacc gatgaaacga gagaggatgc tcacgatacg ggttactgat  8520
gatgaacatg cccggttact ggaacgttgt gagggtaaac aactggcggt atggatgcgg  8580
cgggaccaga gaaaaatcac tcagggtcaa tgccagcgct tcgttaatac agatgtaggt  8640
gttccacagg gtagccagca gcatcctgcg atgcagatcc gaacataat ggtgcagggc  8700
gctgacttcc gcgtttccag actttacgaa acacgaaac cgaagaccat tcatgttgtt  8760
gctcaggtcg cagacgtttt gcagcagcag tcgcttcacg ttcgctcgcg tatcggtgat  8820
tcattctgct aaccagtaag gcaaccccgc cagcctagcc gggtcctcaa cgacaggagc  8880
acgatcatgc gcacccgtgg ggccgccatg ccggcgataa tggcctgctt ctcgccgaaa  8940
cgtttggtgg cgggaccagt gacgaaggct tgagcgaggg cgtgcaagat tccgaatacc  9000
gcaagcgaca ggccgatcat cgtcgcgctc cagcgaaagc ggtcctcgcc gaaaatgacc  9060
cagagcgctg ccggcacctg tcctacgagt tgcatgataa agaagacagt cataagtgcg  9120
gcgacgatag tcatgccccg cgcccaccgg aaggagctga ctgggttgaa ggctctcaag  9180
ggcatcggtc gagatcccgg tgcctaatga gtgagctaac ttacattaat tgcgttgcgc  9240
tcactgcccg ctttccagtc gggaaacctg tcgtgccagc tgcattaatg aatcggccaa  9300
cgcgcgggga gaggcggttt gcgtattggg cgccagggtg ttttctttt tcaccagtga  9360
gacgggcaac agctgattgc ccttcaccgc ctggccctga gagagttgca gcaagcggtc  9420
cacgctggtt tgccccagca ggcgaaaatc ctgtttgatg gtggttaacg gcgggatata  9480
acatgagctg tcttcggtat cgtcgtatcc cactaccgag atgtccgcac caacgcgcag  9540
cccggactcg gtaatggcgc gcattgcgcc cagcgccatc tgatcgttgg caaccagcat  9600
cgcagtggga acgatgccct cattcagcat ttgcatggtt tgttgaaaac cggacatggc  9660
actccagtcg ccttcccgtt ccgctatcgg ctgaatttga ttgcgagtga gatatttatg  9720
ccagccagcc agacgcagac gcgccgagac agaacttaat gggcccgcta acagcgcgat  9780
ttgctggtga cccaatgcga ccagatgctc acgcccagt cgcgtaccgt cttcatggga  9840
gaaaataaata ctgttgatgg gtgtctggtc agagacatca agaaataacg ccggaacatt  9900
agtgcaggca gcttccacag caatggcatc ctggtcatcc agcggatagt taatgatcag  9960
cccactgacg cgttgcgcga agattgtg caccgccgct ttacaggctt cgacgccgct  10020
tcgttctacc atcgacacca ccacgctggc acccagttga tcggcgcgag atttaatcgc  10080
cgcgacaatt tgcgacggcg cgtgcagggc cagactggag gtggcaacgc caatcagcaa  10140
cgactgtttg cccgccagtt gttgtgccac gcggttgggga atgtaattca gctccgccat  10200
cgccgcttcc acttttccc gcgttttcgc agaaacgtgg ctggcctggt tcaccacgcg  10260
ggaaacggtc tgataagaga caccggcata tctgcgaca tcgtataacg ttactggttt  10320
cacattcacc accctgaatt gactctcttc cgggcgctat catgccatac cgcgaaaggt  10380
tttgcgccat tcgatggtgt ccgggatctc gacgctctcc cttatgcgac tcctgcatta  10440
ggaagcagcc cagtagtagg ttgaggccgt tgagcaccgc cgccgcaagg aatggtgcat  10500
gcaaggagat ggcgcccaac agtccccgg ccacggggcc tgccaccata cccacgccga  10560
aacaagcgct catgagcccg aagtggcgag cccgatcttc cccatcggtg atgtcggcga  10620
tataggcgcc agcaaccgca cctgtggcgc cggtgatgcc ggccacgatg cgtccggcgt  10680
agaggatcga gatcgatctc gatcccgcga aattaatacg actcactata ggggaattgt  10740
gagcggataa caattcccct ctagaaataa ttttgtttaa cttaagaag gagatataca  10800
tgccaccatg aaacggacag ccgacggaag cgagttcgag tcaccaaaga agaagcggaa  10860
agtc                                                              10864
SEQ ID NO: 35          moltype = DNA   length = 9243
FEATURE                Location/Qualifiers
```

```
source                  1..9243
                        mol_type = other DNA
                        organism = Synthetic construct
SEQUENCE: 35
gacaagaagt acagcatcgg cctggccatc ggcaccaact ctgtgggctg ggccgtgatc    60
accgacgagt acaaggtgcc cagcaagaaa ttcaaggtgc tgggcaacac cgaccggcac   120
agcatcaaga agaacctgat cggagccctg ctgttcgaca cgcggcgaaac agccgaggcc   180
acccggctga agagaaccgc cagaagaaga tacaccgacg gaagaaccg gatctgctat    240
ctgcaagaga tcttcagcaa cgagatggcc aaggtggacg acagcttctt ccacagactg   300
gaagagtcct tcctggtgga agaggataag aagcacgagc ggcaccccat cttcggcaac   360
atcgtggacg aggtggccta ccacgagaag taccccacca tctaccacct gagaaagaaa   420
ctggtggaca gcaccgacaa ggccgacctg cggctgatct atctggccct ggcccacatg   480
atcaagttcc ggggccactt cctgatcgag ggcgacctga accccgacaa cagcgacgtg   540
gacaagctgt tcatccagct ggtgcagacc tacaaccagc tgttcgagga aaaccccatc   600
aacgccagcg gcgtggacgc caaggccatc ctgtctgcca gactgagcaa gagcagacgt   660
ctggaaaatc tgatcgccca gctgccggc gagaagaaga atggcctgtt cggaaacctg    720
attgccctga gcctgggcct gaccccaac ttcaagagca cttcgacct ggccgaggat      780
gccaaactgc agctgagcaa ggacacctac gacgacgacc tggacaacct gctggccagc   840
atcggcgacc agtacgccga cctgtttctg gccgccaaga acctgtccga cgccatcctg   900
ctgagcgaca tcctgagagt gaacaccgag atcaccaagg cccccctgag cgcctctatg   960
atcaagagat acgacgagca ccaccaggac ctgaccctgc tgaaagctct cgtgcggcag  1020
cagctgcctg agaagtacaa agagattttc ttcgaccaga agaacgtg ctacgccggc    1080
tacattgacg gcggagccag ccaggaagag ttctacaagt tcatcaagcc catcctggaa  1140
aagatggacg gcaccgagga actgctcgtg aagctgaaca gagaggacct gctgcggaag  1200
cagcggacct tcgacaacgg cagcatcccc accagatcc acctgggaga gctgcacgcc   1260
attctgcggc ggcaggaaga ttttaccca ttcctgaagg acaaccggga aaagatcgag    1320
aagatcctga ccttccgcat cccctactac gtgggccctc tggccagggg aaacagcaga  1380
ttcgcctgga tgaccagaaa gagcgaggaa accatcaccc cctggaactt cgaggaagtg  1440
gtggacaagg gcgcttccgc ccagagcttc atcgagcgga tgaccaactt cgataagaac  1500
ctgcccaacg agaaggtgct gcccaagcac agcctgctgt acgagtactt caccgtgtat  1560
aacgagctga ccaaagtgaa atacgtgacc gagggaatga gaaagcccgc cttcctgagc  1620
ggcgagcaga aaaaggccat cgtggacctg ctgttcaaga ccaaccggaa agtgaccgtg  1680
aagcagctga aagaggacta cttcaagaaa atcgagtgct tcgactccgt ggaaatctcc  1740
ggcgtggaag atcggttcaa cgcctccctg ggcacatacc acgatctgct gaaaattatc  1800
aaggacaagg acttcctgga caatgaggaa aacgaggaca ttctggaaga tatcgtgctg  1860
accctgacac tgtttgagga cagagagatg atcgaggaac ggctgaaaac ctatgcccac  1920
ctgttcgacg acaaagtgat gaagcagctg aagcggcgga gatacaccgg ctggggcagg  1980
ctgagccgga agctgatcaa cggcatccgg gacaagcagt ccggcaagac aatcctggat  2040
ttcctgaagt ccgacggctt cgccaacaga aacttcatgc agctgatcca cgacgacagc  2100
ctgacctta aagaggacat ccagaaagcc caggtgtccg gccagggcga tagcctgcac  2160
gagcacattg ccaatctggc cggcagcccc gccattaaga agggcatcct gcagacagtg  2220
aaggtggtga cgagctcgt gaaagtgatg ggccggcaca gcccgagaa catcgtgatc    2280
gaaatggcca gagagaacca gaccacccag aagggacaga agaacagccg cgagagatg   2340
aagcggatcg aagagggcat caaagagctg ggcagccaga tcctgaaaga acaccccgtg  2400
gaaaacaccc agctgcagaa cgagaagctg tacctgtact acctgcagaa tgggcgggat  2460
atgtacgtgg accaggaact ggacatcaac cggctgtccg actacgatgt ggaccatatc  2520
gtgcctcaga gctttctgaa ggacgactcc atcgacaaca aggtgctgac cagaagcgac  2580
aagaaccggg gcaagagcga caacgtgccc tccgaagagg tcgtgaagaa gatgaagaac  2640
tactggcggc agctgctgaa cgccaagctg attacccaga gaaagttcga caatctgacc  2700
aaggccgaga aggcggcct gagcgaactg gataaggccg gcttcatcaa gagacagctg  2760
gtggaaaccc ggcagatcac aaagcacgtg gcacagatcc tggactccg atgaacact   2820
aagtacgacg agaatgacaa gctgatccgg gaagtgaaag tgatcaccct gaagtccaag  2880
ctggtgtccg atttccggaa ggatttccag ttttacaaag tgcgcgagat caacaactac  2940
caccacgccc acgacgccta cctgaacgcc gtcgtgggaa ccgccctgat caaaaagtac  3000
cctaagctgg aaagcgagtt cgtgtacggc gactacaagg tgtacgacgt gcggaagatg  3060
atcgccaaga gcgagcagga aatcggcaag gctaccgcca gtacttctt ctacagcaac   3120
atcatgaact ttttcaagac cgagattacc ctggccaacg gcgagatccg gaagcggcct  3180
ctgatcgaga caaacggcga aaccggggag atcgtgtggg ataagggccg ggattttgcc  3240
accgtgcgga aagtgctgag catgccccaa gtgaatatcg tgaaaaagac cgaggtgcag  3300
acaggcggct tcagcaaga gtctatcctg cccaaggagg acagcgataa gctgatcgcc  3360
agaaagaagg actgggaccc taagaagtac ggcggcttcg acagcccac cgtggcctat   3420
tctgtgctgg tggtggccaa agtggaaag ggcaagtcca gaaactgaa gagtgtgaaa   3480
gagctgctgg ggatcaccat catggaaaga agcagcttcg agaagaatcc catcgacttt  3540
ctggaagcca agggctacaa agaagtgaaa aaggaccttga tcatcaagct gcctaagtac  3600
tccctgttcg agctgaaaa cggccggaag agaatgctgg cctctgccgg cgaactgcag  3660
aagggaaacg aactggccct gccctccaaa tatgtgaact tcctgtacct ggccagccac  3720
tatgagaagc tgaagggctc ccccgaggat aatgagcaga acagctgtt tgtggaacag   3780
cacaagcact acctggacga gatcatcgag cagatcagcg agttctccaa gagagtgatc  3840
ctggccgacg ctaatctgga caaagtgctg tccgcctaca acaagcaccg ggataagccc  3900
atcagagagc aggccgagaa tatcatccac ctgtttaccc tgaccaatct gggagcccct  3960
gccgccttca gtactttga caccaccatc gaccggaaga gtacaccag caccaaagag   4020
gtgctggacg ccacccctga tccaccagagc atcaccggcc tgtacgagac acggatcgac  4080
ctgtctcagc tgggaggtga ctctggcggc tcaaaaagaa ccgccgacgg cagcgaattc  4140
gagcccaaga gaagaggaaa gtctaaccg gtcatcatca ccatccaccat tgagtttaaa   4200
cccgctgatc agcctcgact gtgccttcta gttgccagcc atctgttgtt tgcccctccc  4260
ccgtgccttc cttgacccctg aaggtgccac ctcccactgt cctttcctaa taaaatgagg  4320
aaattgcatc gcattgtctg agtaggtgtc attctattct ggggggtggg gtggggcagg  4380
acagcaaggg ggaggattgg gaagacaata gcaggcatgc tggggatgcg gtgggctcta  4440
tggcttctga ggcggaaaga accagctggg gctcgttgac agctagctca gtcctaggta  4500
```

```
taatactagt gctcttgccc ggcgtcaata cgttttagag ctagaaatag caagttaaaa   4560
taaggctagt ccgttatcaa cttgaaaaag tggcaccgag tcggtgcttt ttttgatccg   4620
gctgctaaca aagcccgaaa ggaagctgag ttggctgctg ccaccgctga gcaataacta   4680
gcataacccc ttggggcctc taaacgggtc ttgaggggtt ttttgctgaa aggaggaact   4740
atatccggat tggcgaatgg gacgcgccct gtagcggcgc attaagcgcg gggtgtgg    4800
tggttacgcg cagcgtgacc gctacacttg ccagcgccct agcgcccgct cctttcgctt   4860
tcttcccttc ctttctcgcc acgttcgccg gctttccccg tcaagctcta atcgggggc   4920
tccctttagg gttccgattt agtgctttac ggcacctcga ccccaaaaaa cttgattagg   4980
gtgatggttc acgtagtggg ccatcgccct gatagacggt ttttcgccct ttgacgttgg   5040
agtccacgtt ctttaatagt ggactcttgt tccaaactgg aacaacactc aaccctatct   5100
cggtctattc ttttgattta taagggattt tgccgatttc ggcctattgg ttaaaaaatg   5160
agctgattta acaaaaattt aacgcgaatt ttaacaaaat attaacgttt acaatttcag   5220
gtggcacttt tcggggaaat gtgggaaatg tgcgcggaac ccctatttgt ttatttttct   5280
aaatacattc aaatatgtat ccgctcatga gacaataacc ctgataaatg cttcaataat   5340
attgaaaaag gaagagtatg agtattcaac atttccgtgt cgcccttatt ccctttttg    5400
cggcattttg ccttcctgtt tttgctcacc cagaaacgct ggtgaaagta aaagatgctg   5460
aagatcagtt gggtgcacga gtgggttaca tcgaactgga tctcaacagc ggtaagatcc   5520
ttgagagttt tcgccccgaa gaacgttttc caatgatgag cacttttaaa gttctgctat   5580
gtggcgcggt attatcccgt attgacgccg ggtaagagca actcggtcgc cgcatacact   5640
attctcagaa tgacttggtt gagtactcac cagtcacaga aaagcatctt acggatggca   5700
tgacagtaag agaattatgc agtgctgcca taaccatgag tgataacact gcggccaact   5760
tacttctgac aacgatcgga ggaccgaagg agctaaccgc ttttttgcac aacatggggg   5820
cccaagaaga agaggaaagt ctaaccggtc atcatcacca tcaccattga gtttaaaccc   5880
gctgatcagc ctcgactgtg ccttctagtt gccagccatc tgttgtttgc cctccccccg   5940
tgccttcctt gaccctggaa ggtgccactc ccactgtcct ttcctaataa aatgaggaaa   6000
ttgcatcgca ttgtctgagt aggtgtcatt ctattctggg gggtggggtg gggcaggaca   6060
gcaaggggga ggattgggaa gacaatagca ggcatgctgg ggatgcggtg ggctctatgg   6120
cttctgaggc ggaaagaacc agctgggggct cgataccgtc gacctctagc tagagcttgg   6180
cgtaatcatg gtcatagctg tttcctgtgt gaaattgtta tccgctcaca attccacaca   6240
acatacggaa gcata aagtgtaaag cctagggtgc ctaatgagtg agctaactca         6300
cattaattgc gttgcgctca ctgcccgctt tccagtcggg aaacctgtcg tgccagctgc   6360
attaatgaat cggccaacgc gcggggagag cggtttgcg tattgggcgc tcttccgctt    6420
cctcgctcac tgactcgctg cgctcggtcg ttcggctgcg gcgagcggta tcagctcact   6480
caaaggcggt aatacggtta tccacagaat caggggataa acgcaggaaag aacatgtgag   6540
caaaaggcca gcaaaaggcc aggaaccgta aaaaggccgc gttgctggcg ttttttccata   6600
ggctccgccc cctgacgag catcacaaaa atcgacgctc aagtcagagg tggcgaaacc   6660
cgacaggact ataaagatac caggcgtttc ccctggaag ctccctcgtg cgctctcctg     6720
ttccgaccct gccgcttacc ggatacctgt ccgcctttct cccttcggga agcgtggcgc   6780
tttctcatag ctcacgctgt aggtatctca gttcggtgta ggtcgttcgc tccaagctgg   6840
gctgtgtgca cgaaccccc gttcagcccg accgctgcgc cttatccggt aactatcgtc    6900
ttgagtccaa cccggtaaga cacgacttat cgccactggc agcagccact ggtaacagga   6960
ttagcagagc gaggtatgta ggcggtgcta cagagttctt gaagtggtgg cctaactacg   7020
gctacactag aagaacagta tttggtatct gcgctctgct gaagccagtt accttcggaa   7080
aaagagttgg tagctcttga tccggcaaac aaaccaccgc tggtagcggt ggttttttg     7140
tttgcaagca gcagattacg cgcagaaaaa aaggatctca agaagatcct ttgatctttt   7200
ctacgggtc tgacactcag tggaacgaaa actcacgtta agggattttg gtcatgagat     7260
tatcaaaaag gatcttcacc tagatccttt taaattaaaa atgaagtttt aaatcaatct   7320
aaagtatata tgagtaaact tggtctgaca gttaccaatg cttaatcagt gaggcaccta   7380
tctcagcgat ctgtctattt cgttcatcca tagttgcctg actccccgtc gtgtagataa   7440
ctacgatacg ggagggctta ccatctggcc ccagtgctgc aatgataccg cgagacccac   7500
gctcacgctc tccagattta tcagcaataa accagccagc cggaagggcc gagcgcagaa   7560
gtggtcctgc aactttatcc gcctccatcc agtctattaa ttgttgccgg gaagctagag   7620
taagtagttc gccagttaat agtttgcgca acgttgttgc cattgctaca ggcatcgtgg   7680
tgtcacgctc gtcgtttggt atggcttcat tcagctccgg ttcccaacga tcaaggcgag   7740
ttacatgatc ccccatgttg tgcaaaaaag cggttagctc cttcggtcct ccgatcgttg   7800
tcagaagtaa gttggccgca gtgttatcac tcatggttat ggcagcactg cataattctc   7860
ttactgtcat gccatccgta agatgctttt ctgtgactgg tgagtactca accaagtcat   7920
tctgagaata gtgtatgcgg cgaccgagtt gctcttgccc ggcgtcaata cgggataata   7980
ccgcgccaca tagcagaact ttaaaagtgc tcatcattgg aaaacgttct cggggcgaa    8040
aactctcaag gatcttaccg ctgttgagat ccagttcgat gtaacccact cgtgcaccca   8100
actgatcttc agcatctttt actttcacca gcgtttctgg gtgagcaaaa acaggaaggc   8160
aaaatgccgc aaaaaaggga ataagggcga cacggaaatg ttgaatactc atactcttcc   8220
tttttcaata ttattgaagc atttatcagg gttattgtct catgagcgga tacatatttg   8280
aatgtattta gaaaaataaa caaatagggg ttccgcgcac atttccccga aaagtgccac   8340
ctgacgtcga cggatcggga gatcgatctc ccgatcccct agggtcgact ctcagtacaa   8400
tctgctctga tgccgcatag ttaagccagt atctgctccc tgcttgtgtg ttggaggtcg   8460
ctgagtagtg cgcgagcaaa atttaagcta caacaaggca aggcttgacc gacaattgca   8520
tgaagaatct gcttagggtt aggcgttttg cgctgcttcg cgatgtacgg gccagatata   8580
cgcgttgaca ttgattattg actagttatt aatagtaatc aattacgggg tcattagttc   8640
atagcccata tatggagttc cgcgttacat aacttacggt aaatggcccg cctggctgac   8700
cgcccaacga cccccgccca ttgacgtcaa taatgacgta tgttcccata gtaacgccaa   8760
tagggacttt ccattgacgt caatgggtgg agtatttacg gtaaactgcc cacttggcag   8820
tacatcaagt gtatcatatg ccaagtacgc cccctattga cgtcaatgac ggtaaatggc   8880
ccgcctggca ttatgcccag tacatgacct tatgggactt tcctacttgg cagtacatct   8940
acgtattagt catcgctatt accatggtga tgcggttttg gcagtacatc aatgggcgtg   9000
gatagcggtt tgactcacgg ggatttccaa gtctccaccc cattgacgtc aatgggagtt   9060
tgttttggca ccaaaatcaa cgggactttc caaaatgtcg taacaactcc gccccattga   9120
cgcaaatggg cggtaggcgt gtacggtggg aggtctatat aagcagagct ggtttagtga   9180
accgtcagat ccgctagaga tccgcggccg ctaatacgac tcactatagg gagagccgcc   9240
```

| | | | | |
|---|---|---|---|---|
| acc | | | | 9243 |

| SEQ ID NO: 36 | moltype = DNA   length = 8913 |
|---|---|
| FEATURE | Location/Qualifiers |
| source | 1..8913 |
| | mol_type = other DNA |
| | organism = Synthetic construct |

SEQUENCE: 36

```
atatgccaag tacgcccct attgacgtca atgacggtaa atggcccgcc tggcattatg    60
cccagtacat gaccttatgg gactttccta cttggcagta catctacgta ttagtcatcg   120
ctattaccat ggtgatgcgg ttttggcagt acatcaatgg gcgtggatag cggtttgact   180
cacgggatt tccaagtctc caccccattg acgtcaatgg gagtttgttt tggcaccaaa    240
atcaacggga ctttccaaaa tgtcgtaaca actccgcccc attgacgcaa atgggcggta   300
ggcgtgtacg gtgggaggtc tatataagca gagctggttt agtgaaccgt cagatccgct   360
agagatccgc ggccgctaat acgactcact atagggagag ccgccaccat gaaacgaca   420
gccgacggaa gcgagttcga gtcaccaaag aagaagcgga aagtcagcag tgacaagaag   480
tacagcatcg gcctggccat cggcaccaac tctgtgggct gggccgtgat caccgacgag   540
tacaaggtgc ccagcaagaa attcaaggtg ctgggcaaca ccgaccggca cagcatcaag   600
aagaacctga tcggagccct gctgttcgac agcggcgaaa cagccgaggc cacccggctg   660
aagagaaccg ccagaagaag atacaccaga cggaagaacc ggatctgcta tctgcaagag   720
atcttcagca acgagatggc caaggtggac acagcttct tccacagact ggaagagtcc    780
ttcctggtgg aagaggataa gaagcacgag cggcacccca tcttcggcaa catcgtggac   840
gaggtggcct accacgagaa gtaccccacc atctaccacc tgagaaagaa actggtggac   900
agcaccgaca aggccgacct gcggctgatc tatctggccc tggccacat gatcaagttc   960
cggggccact tcctgatcga gggcgacctg aaccccgaca cagcgacgt ggacaagctg  1020
ttcatccaga ctggtgcaga ctacaaccag ctgttcgagg aaaacccct caacgccagc  1080
ggcgtggacg ccaaggccat cctgtctgcc agactgagca gagcagacg gctgaaaat   1140
ctgatcgccc agctgccggg cgagaagaag aatggcctgt cggaaacct gattgccctg  1200
agcctggcc tgacccccaa cttcaagagc aacttcgacc tggccgagga tgccaaactg   1260
cagctgagca aggacaccta cgacgacgac ctggacaacc tgctggcca gatcggcgac  1320
cagtacgccg acctgttct ggccgccaag aacctgtccg acgccatcct gctgagcgac  1380
atcctgagag tgaacaccga gatcaccaag gccccctga gcgcctctat gatcaagaga  1440
tacgacgagc accaccagga cctgaccctg ctgaaagctc tcgtgcggca gcagctgcct  1500
gagaagtaca aagagattt cttcgaccag agcaagaacg gctacgccgg ctacatgac   1560
ggcggagcca gccaggaaga gttctacaag ttcatcaagc ccatcctgga aaagatggac  1620
ggcaccgagg aactgctcgt gaagctgaac agagaggacc tgctgcggaa gcagcggacc  1680
ttcgacaacg gcagcatccc caccagatc cacctgggag agctcacgc cattctgcgg  1740
cggcaggaag atttttaccc attcctgaag gacaacccggg aaagatcga gaagatcctg  1800
accttccgca tccctacta cgtgggcct ctggccaggg gaaacagcag attcgctgg   1860
atgaccagaa agagcgagga aaccatcacc ccctggaact tcgaggaagt ggtggacaag  1920
ggcgcttccg cccagagctt catcgagcgg atgaccaact tcgataagaa cctgcccaac  1980
gagaaggtgc tgcccaagca cagcctgctg tacgagtact tcaccgtgta taacgagctg  2040
accaaagtga aatacgtgac ctctggagga tctagcggtg gttcctctgg aagcgagaca  2100
ccaggcacaa gcgagtccgc cacaccagag agctccggcg gctcctccgg aggatcctct  2160
gaggtggagt tttcccacga gtactggatg agacatgccc tgaccctggc caagagggca  2220
tgggatgaaa gagaagtcc cgtgggcgcc gtgctggtgc acaacaatag agtgatcgga  2280
gagggatgga acaggccaat cggccgccac gaccctaccg cacacgcaga gatcatggca  2340
ctgaggcagg aggcctggt catgcagaat taccgcctga tcgatgccac cctgtatgtg  2400
acactggagc catgcgtgat gtgcgcagga gcaatgatcc acagcaggat cggaagagtg  2460
gtgttcgag cacgggacgc caagaccggc gcagcaggct ccctgatgga tgtgctgcac  2520
caccccggca tgaaccaccg ggtggagatc acagagggaa tcctggccga cgagtgctcc  2580
gccctgctga gcgatttctt tagaatgcgg agacaggaga tcaaggccca gaagaaggca  2640
cagagctcca ccgactctgg aggatctagc ggcggatcct ctggaagcga gacaccaggc  2700
acaagcgagt ccgccacacc agagagctcc ggcggctcct ccgaggatc tctgaggtg   2760
gagtttccc acgagtactg gatgagacat gccctgaccc tggccaagag ggcacgcgat  2820
gagagggagg tgcctgtggg agccgtgctg gtgctgaaca atagagtgat cggcgagggc  2880
tggaacagag ccatcggcct gcacgaccca acagcccatg ccgaaattat ggccctgaga  2940
cagggcggcc tggtcatgca gaactacaga ctgattgacg ccaccctgta cgtgacattc  3000
gagccttgcg tgatgtgcgc cggcgccatg atccactcta ggatcggccg cgtggtgttt  3060
ggcgtgagca acgcaaaaac cggccgccga gctccctga tggacgtgct gcactacccc  3120
ggcatgaatc accgcgtcga aattaccgag ggaatcctgg cagatgaatg tgccgccctg  3180
ctgtgctatt tctttcggat gcctagacag gtgttcaatg ctcagaagaa ggcccagagc  3240
tccaccgact ccggaggatc tagcggaggc tcctctggct ctgagacacc tggcacaagc  3300
gagagccaa cacctgaaag cagcggggc agcagcggga atgagaaag aataagaaa    3360
cccgccttcc tgagcggcga gcagaaaag gccatcgtgg acctgctgtt caagaccaac  3420
cggaaagtga ccgtgaagca gctgaaagag gactacttca gaaaatcga gtgcttcgac  3480
tccgtggaaa tctccggcgt ggaagatcgg ttcaacgcct cctgggcac ataccacgat  3540
ctgctgaaaa ttatcaagga caaggacttc ctggacaatg aggaaaacga ggacattctg  3600
gaagatatcg tgctgaccct gacactgttt gaggacagag agatgatcga ggaacgtctg  3660
aaaacctatg cccacctgtt cgacgacaaa gtgatgaagc agctgaagcg gcggagatac  3720
accggctggg gcaggctgag ccggaagctg atcaacggca tccggacaa cagtccggc   3780
aagacaatcc tggatttcct gaagtccgac ggcttcgcca cagaaactt catgcagctg  3840
atccacgacg acagcctgac ctttaaagag gacatccaga agccaggt gtccggcag    3900
ggcgactca tgcacgagca cattgccaat ctggccggca gccccgccat taaaaaggc   3960
atcctgcaga cagtgaaggt ggtggacgag ctcgtgaaag tgatgggccg gcacaagccc  4020
gagaacatct gatcgaaat ggccagagag aaccagacca cccagaaggg acagaagaac  4080
agccgcgaga gaatgaagcg gatcgaagag ggcatcaaag agctgggcag ccagatcctg  4140
aaagaacacc ccgtggaaaa cacccagctg cagaacgaga gctgtacct gtactacctg  4200
cagaatgggc gggatatgta cgtggaccag gaactggaca tcaaccggct gtccgactac  4260
```

```
gatgtggacc atatcgtgcc tcagagcttt ctgaaggacg actccatcga caacaaggtg  4320
ctgaccagaa gcgacaagaa ccggggcaag agcgacaacg tgccctccga agaggtcgtg  4380
aagaagatga agaactactg gcggcagctg ctgaacgcca agctgattac ccagagaaag  4440
ttcgacaatc tgaccaaggc cgagagaggc ggcctgagcg aactggataa ggccggcttc  4500
atcaagagac agctggtgga aacccagcag atcacaaagc acgtggcaca gatcctggac  4560
tcccggatga acactaagta cgacgagaat gacaagctga tccgggaagt gaaagtgatc  4620
accctgaagt ccaagctggt gtccgatttc cggaaggatt tccagtttta caaagtgcgc  4680
gagatcaaca actaccacca cgcccacgac gcctacctga acgccgtcgt gggaaccgcc  4740
ctgatcaaaa agctggaaag cgagttcgtg acggcgacta caaggtgtac  4800
gacgtgcgga agatgatcgc caagagcgag caggaaatcg gcaaggctac cgccaagtac  4860
ttcttctaca gcaacatcat gaactttttc aagaccgaga ttaccctggc caacggcgag  4920
atccggaagc ggcctctgat cgagacaaac ggcgaaaccg gggagatcgt gtgggataag  4980
ggccgggatt ttgccaccgt gcggaaagtg ctgagcatgc cccaagtgaa tatcgtgaaa  5040
aagaccgagg tgcagacagg cggcttcagc aaagagtcta tcctgcccaa gaggaacagc  5100
gataagctga tcgccagaaa gaaggactgg gaccctaaga agtacggcgg cttcgacagc  5160
cccaccgtga cctattctgt gctggtggtg gccaaagtgg aaaagggcaa gtccaagaaa  5220
ctgaagagtg tgaaagagct gctggggatc accatcatga aagaagcag cttcgagaag  5280
aatcccatcg actttctgga agccaagggc tacaaagaag tgaaaaagga cctgatcatc  5340
aagctgccta agtactccct gttcgagctg gaaaacggcc ggaagagaat gctggcctct  5400
gccggcgaac tgcagaaggg aaacgaactg gccctgcct ccaaatatgt gaacttcctg  5460
tacctggcca gccactatga aagctgaag ggctccccg aggataatga gcagaaacag  5520
ctgtttgtgg aacagcacaa gcactacctg gacgagatca tcgagcagat cagcgagttc  5580
tccaagagag tgatcctggc cgacgctaat ctggacaaaa tgctgtccgc ctacaacaag  5640
caccgggata agcccatcag agagcaggcc gagaatatca tccacctgtt taccctgacc  5700
aatctgggag ccctgccgc cttcaagtac tttgacacca ccatcgaccg gaagaggtac  5760
accagcacca aagaggtgct ggacgccacc ctgatccacc agagcatcac cggcctgtac  5820
gagacacgga tcgacctgtc tcagctggga ggtgactctg gcggctcaaa agaaccgcc  5880
gacggcagcg aattcgagcc caagaagaag aggaaagtct aaccggtcat catccaccatc  5940
accattgagt ttaaacccgc tgatcagcct cgactgtgcc ttctagttgc cagccatctg  6000
ttgttttgccc ctcccccgtg ccttccttga ccctggaaag tgccactccc actgtcctt  6060
cctaataaaa tgaggaaatt gcatcgcatt gtctgagtag tgtcattct attctggggg  6120
gtggggtggg gcaggacagc aagggggagg attgggaaga caatagcagg catgctgggg  6180
atgcggtggg ctctatggct tctgaggcgg aagaaccag ctgggctcg ataccgtcga  6240
cctctagcta gagcttggcg taatcatggt catagctgtt tcctgtgtga aattgttatc  6300
cgctcacaat tccacacaac atacggccg gaagcataaa gtgtaaagcc tagggtgcct  6360
aatgagtgag ctaactcaca ttaattgcgt tgcgctcact gcccgctttc cagtcgggaa  6420
acctgtcgtg ccagctgcat taatgaatcg gccaacgcgc ggggagaggc ggtttgcgta  6480
ttgggcgctc ttccgcttcc tcgctcactg actcgctgcg ctcggtcgtt cggctgcggc  6540
gagcggtatc agctcactca aaggcggtaa tacggttatc cacagaatca ggggataacg  6600
caggaaagaa catgtgagca aaaggccagc aaaaggccag gaaccgtaaa aaggccgcgt  6660
tgctggcgtt tttccatagg ctccgcccc ctgacgagca tcacaaaaat cgacgctcaa  6720
gtcagaggtg gcgaaaccg acaggactat aaagatacca ggcgtttccc cctggaagct  6780
ccctcgtgcg ctctcctgtt ccgaccctgc cgcttaccgg atacctgtcc gcctttctcc  6840
cttcgggaag cgtggcgctt tctcatagct cacgctgtag gtatctcagt tcggtgtagg  6900
tcgttcgctc caagctgggc tgtgtgcacg aaccccccgt tcagcccgac cgctgcgcct  6960
tatccggtaa ctatcgtctt gagtccaacc cggtaagaca cgacttatcg ccactggcag  7020
cagccactgg taacaggatt agcagagcga ggtatgtagg cggtgctaca gagttcttga  7080
agtggtggcc taactacggc tacactagaa gaacagtatt tggtatctgc gctctgctga  7140
agccagttac cttcggaaaa agagttggta gctcttgatc cggcaaacaa accaccgctg  7200
gtagcggtgg ttttttgtt tgcaagcagc agattacgcg cagaaaaaaa ggatctcaag  7260
aagatccttt gatcttttct acggggtctg acactcagtg gaacgaaaac tcacgttaag  7320
ggattttggt catgagatta tcaaaaagga tcttcaccta gatccttta aattaaaaat  7380
gaagttttaa atcaatctaa agtatatatg agtaaacttg gtctgacagt taccaatgct  7440
taatcagtga ggcacctatc tcagcgatct gtctatttcg ttcatccata gttgcctgac  7500
tccccgtcgt gtagataact acgatacggg agggcttacc atctggcccc agtgctgcaa  7560
tgataccgcg agacccacgc tcaccggctc cagatttatc agcaataaac cagccagccg  7620
gaagggccga gcgcagaagt ggtcctgcaa ctttatccgc ctccatccag tctattaatt  7680
gttgccggga agctagagta agtagttcgc cagttaatag tttgcgcaac gttgttgcca  7740
ttgctacagg catcgtggtg tcacgctcgt cgtttggtat ggcttcattc agctccggtt  7800
cccaacgatc aaggcgagtt acatgatccc ccatgttgtg caaaaaagcg gttagctcct  7860
tcggtcctcc gatcgttgtc agaagtaagt tggccgcagt gttatcactc atggttatgg  7920
cagcactgca taattctctt actgtcatgc catccgtaag atgcttttct gtgactggtg  7980
agtactcaac caagtcattc tgagaatagt gtatgcggcg accgagttgc tcttgcccgg  8040
cgtcaatacg ggataatacc gcgccacata gcagaacttt aaaagtgctc atcattggaa  8100
aacgttcttc ggggcgaaaa ctctcaagga tcttaccgct gttgagatcc agttcgatgt  8160
aacccactcg tgcacccaac tgatcttcag catctttta tttcaccagc gtttctgggt  8220
gagcaaaaac aggaaggcaa aatgccgcaa aaaagggaat aagggcgaca cggaaatgtt  8280
gaatactcat actcttcctt tttcaatatt attgaagcat ttatcagggt tattgtctca  8340
tgagcggata catatttgaa tgtatttaga aaaataaaca aataggggtt ccgcgcacat  8400
ttccccgaaa agtgccacct gacgtcgacg gatcgggaga tcgatctccc gatcccctag  8460
ggtcgactct cagtacaatc tgctctgatg ccgcatagtt aagccagtat ctgctccctg  8520
cttgtgtgtt ggaggtcgct gagtagtgcg cgagcaaaat ttaagctaca acaaggcaag  8580
gcttgaccga caattgcatg aagaatctgc ttagggttag gcgttttgcg ctgcttcgcg  8640
atgtagcgca cagatatacg cgttgacatt gattattgac tagttattaa tagtaatcaa  8700
ttacgggtc attagttcat agcccatata tggagttccg cgttacataa cttacggtaa  8760
atggcccgcc tggctgaccg cccaacgacc cccgcccatt gacgtcaata atgacgtatg  8820
ttcccatagt aacgccaata gggactttcc attgacgtca atgggtggag tatttacggt  8880
aaactgccca cttggcagta catcaagtgt atc                                8913
```

```
SEQ ID NO: 37            moltype = DNA   length = 8913
FEATURE                  Location/Qualifiers
source                   1..8913
                         mol_type = other DNA
                         organism = Synthetic construct
SEQUENCE: 37
atatgccaag tacgcccct attgacgtca atgacggtaa atggcccgcc tggcattatg   60
cccagtacat gaccttatgg gactttccta cttggcagta catctacgta ttagtcatcg  120
ctattaccat ggtgatgcgg ttttggcagt acatcaatgg gcgtggatag cggtttgact  180
cacggggatt tccaagtctc cacccattg acgtcaatgg gagtttgttt tggcaccaaa  240
atcaacggga ctttccaaaa tgtcgtaaca actccgcccc attgacgcaa atgggcggta  300
ggcgtgtacg gtgggaggtc tatataagca gagctggttt agtgaaccgt cagatccgct  360
agagatccgc ggccgctaat acgactcact atagggagag ccgccaccat gaaacggaca  420
gccgacggaa gcgagttcga gtcaccaaag aagaagcgga aagtcgactg tgacaagaag  480
tacagcatcg gcctggccat cggcaccaac tctgtgggct gggccgtgat caccgacgag  540
tacaaggtgc ccagcaagaa attcaaggtg ctgggcaaca ccgaccggca cagcatcaag  600
aagaacctga tcggagccct gctgttcgac agcggcgaaa cagccgaggc cacccggctg  660
aagagaaccg ccagaagaag ataccagaca cggaagaacc ggatctgcta tctgcaagag  720
atcttcagca acgagatggc caaggtggac gacagcttct tccacagact ggaagagtcc  780
ttcctggtgg aagaggataa gaagcacgag cggcaccca tcttcggcaa catcgtggac  840
gaggtggcct accacgagaa gtaccccacc atctaccacc tgagaaagaa actggtggac  900
agcaccgaca aggccgacct gcggctgatc tatctggccc tggcccacat gatcaagttc  960
cggggccact tcctgatcga gggcgacctg aaccccgaca cagcgacgt ggacaagctg 1020
ttcatccagc tggtgcagac ctacaaccag ctgttcgagg aaaaccccat caacgccagc 1080
ggcgtggacg ccaaggccat cctgtctgcc agactgagca gagcagacg gctggaaaat 1140
ctgatcgccc agctgcccgg cgagaagaag aatggcctgt tcggaaacct gattgccctg 1200
agcctgggcc tgaccccaa cttcaagagc aacttcgacc tggccgagga tgccaaactg 1260
cagctgagca aggacaccta cgacgacgac ctggacaacc tgctggccca gatcggcgac 1320
cagtacgccg acctgtttct ggccgccaag aacctgtccg acgccatcct gctgagcgac 1380
atcctgagag tgaacaccga gatcaccaag gccccctg gcgcctctat gatcaagaga 1440
tacgacgagc accaccagga cctgaccctg ctgaaagctc tcgtgcggca cagctgcct 1500
gagaagtaca agagatttt cttcgaccag agcaagaacg gctacgccgg ctacattgac 1560
ggcggagcca gccaggaaga gttctacaag ttcatcaagc catcctgga aaagatggac 1620
ggcaccgagg aactgctcgt gaagctgaac agagaggacc tgctgcggaa gcagcggacc 1680
ttcgacaacg gcagcatccc ccaccagatc cacctgggag agctgcacgc cattctgcgg 1740
cggcaggaag atttttaccc attcctgaag gacaacaggg aaaagatcga gaagatcctg 1800
accttccgca tccctacta cgtgggccct ctggccaggg aaacagcag attcgcctgg 1860
atgaccagaa agagcgagga aaccatcacc cctggaact tcgaggaagt ggtggacaag 1920
ggcgcttccg cccagagctt catcgagcgg atgaccaact tcgataagaa cctgcccaac 1980
gagaaggtgc tgcccaagca cagcctgctg tacgagtact tcaccgtgta taacgagctg 2040
accaaagtga aatacgtgac cgagggaatg agaaagcccg ccttcctgag cggcgagcag 2100
aaaaaggcca tcgtggacct gctgttcaag accaaccgga agtgaccgt gaagcagctg 2160
aaagagtgac acttcaagaa aatcgagtgc ttcgactccg tggaaatctc cggcgtggaa 2220
tctggaggat ctagcggtgg ttcctctgga agcgagacac caggcacaag cgagtccgcc 2280
acaccagaga gctccggcgg ctcctccgga ggatcctctg aggtggagtt ttcccacgag 2340
tactggatga gacatgccct gaccctggcc aagagggcat gggatgaaag agaagtcccc 2400
gtgggcgccg tgctggtgca caacaataga gtgatcggaa agggatgaa caggccaatc 2460
ggccgccacg acctaccgc acacgcagag atcatggcac tgaggcaggg aggcctggtc 2520
atgcagaatt accgctgat cgatgccacc tgtatgtga cactgaagcc atgcgtgatg 2580
tgcgcaggag caatgatcca cagcaggatc ggaagagtgg tgttcggagc acgggacgcc 2640
aagaccgaga cagcaggctc cctgatggat gtgctgcacc accccggcat gaaccaccgg 2700
gtggagatca cagagggaat cctggcagac gagtgcgccg ccctgctgag cgatttcttt 2760
agaatgcgga gacaggagat caaggcccag aagaaggcac agagctccac cgactctgga 2820
ggatctagcg gcgatcctc tggaagcgag acaccaggca agcgagtc gccacacca 2880
gagagctccg gcggctcctc cggaggatcc tctgaggtgg agttttccca cgagtactgg 2940
atgagacatg ccctgaccct ggccaagagg gcacgcgatg agaggaggt gcctgtggga 3000
gccgtgctgt gctgaacaa tagagtgatc ggcgagggct ggaacagagc catcggcctg 3060
cacgacccaa cagcccatgc cgaaattatg gccctgagac agggcggcct ggtcatgcag 3120
aactacagac tgattgacgc caccctgtac gtgacattcg agccttgcgt gatgtgcgcc 3180
ggcgccatga tccactctag gatcggccgc gtggtgtttg gcgtgaggaa cgcaaaaacc 3240
ggcgccgcag gctccctgat ggacgtgctg cactaccccg gcatgaatca ccgcgtcgaa 3300
attaccgagg aatcctggc agatgaatgt gccgccctgc tgtgctattt ctttcggatg 3360
cctagacagg tgttcaatgc tcagaagaag gcccagagct ccaccgactc cggaggatct 3420
agcggaggct cctctggctc tgagacacct ggcacaagcg agagcgccac acctgaaagc 3480
agcggggca gcagcggggg gtcagatcgg ttcaacgcct ccctgggcac ataccacgat 3540
ctgctgaaa ttatcaagga caaggacttc tggacaatg aggaaaacga ggacattctg 3600
gaagatatcg tgctgacct gacactgttt gaggacagag atgatcga ggaacggctg 3660
aaaacctatg cccacctgtt cgacgacaaa gtgatgaagc agctgaagcg gcggagatac 3720
accggctggg gcaggctgag ccggaagctg atcaacggca tcagggacaa gcagtccggc 3780
aagacaatcc tggatttcct gaagtccgac ggcttcgcca acagaaactt catgcagctg 3840
atccacgacg acagcctgac cttaaagag gacatccaga agcccagt gtccggccag 3900
ggcgatagcc tgcacgagca cattgccaat ctggccggca gccccgccat taagaagggc 3960
atcctgcaga cagtgaaggt ggtggacgag ctcgtgaaa tgatgggccg gcacaagccc 4020
gagaacatcg tgatcgaaat ggccagagag aaccagacca cacagaagaac 4080
agccgcgaga gaatgaagcg gatcgaagag ggcatcaaag agctgggcag ccagatcctg 4140
aaagaacacc ccgtggaaaa cacccagctg cagaacgaga gctgtacct gtactacctg 4200
cagaatgggc gggatatgta cgtggaccag gaactggaca tcaacggct gtccgactac 4260
gatgtggacc atatcgtgcc tcagagcttt ctgaaggacg actccatcga caacaaggtg 4320
ctgaccagaa gcgacaagaa ccggggcaag agcgacaacg tgcctccga agaggtcgtg 4380
```

```
aagaagatga agaactactg gcggcagctg ctgaacgcca agctgattac ccagagaaag  4440
ttcgacaatc tgaccaaggc cgagagaggc ggcctgagcg aactggataa ggccggcttc  4500
atcaagagac agctggtgga aacccggcag atcacaaagc acgtggcaca gatcctggac  4560
tcccggatga acactaagta cgacgagaat gacaagctga tccgggaagt gaaagtgatc  4620
accctgaagt ccaagctggt gtccgatttc cggaaggatt tccagttttt a caaagtgcgc  4680
gagatcaaca actaccacca cgcccacgac gcctacctga acgccgtcgt gggaaccgcc  4740
ctgatcaaaa agtaccctaa gctgaaagc gagttcgtgt acggcgacta caaggtgtac  4800
gacgtgcgga agatgatcgc caagagcgag caggaaatcg gcaaggctac cgccaagtac  4860
ttcttctaca gcaacatcat gaactttttc aagaccgaga ttaccctggc caacggcgag  4920
atccggaagc ggcctctgat cgagacaaac ggcgaaaccg gggagatcgt gtgggataag  4980
ggccgggatt tgccaccgt gcggaaagtg ctgagcatgc cccaagtgaa tatcgtgaaa  5040
aagaccgagg tgcagacagg cggcttcagc aaagagtcta tcctgcccaa gaggaacagc  5100
gataagctga tcgccagaaa gaaggactgg gaccctaaga agtacggcgg cttcgacagc  5160
cccaccgtgg cctattctgt gctggtggtg gccaaagtgg aaaagggcaa gtccaagaaa  5220
ctgaagagtg tgaaagagct gctggggatc accatcatgg aaagaagcag cttcgagaag  5280
aatcccatcg actttctgga agccaagggc tacaaagaag tgaaaaagga cctgatcatc  5340
aagctgccta agtactccct gttcgagctg gaaaacggcc ggaagagaat gctggcctct  5400
gccgcgaac tgcagaaggg aaacgaactg gccctgcct ccaaatatgt gaacttcctg  5460
tacctggcca gccactatga gaagctgaag ggctcccccg aggataatga gcagaaacag  5520
ctgtttgtgg aacagcacaa gcactacctg gacgagatca tcgagcagat cagcgagttc  5580
tccaagagag tgatcctggc cgacgctaat ctggacaaaa tgctgtccgc ctacaacaag  5640
caccgggata agcccatcag agagcaggcc gagaatatca tccacctgtt taccctgacc  5700
aatctgggga cccctgccgc cttcaagtac tttgacacca ccatcgaccg gaagaggtac  5760
accagcacca aagaggtgct ggacgccacc ctgatccacc agagcatcac cggcctgtac  5820
gagacacgga tcgacctgtc tcagctggga ggtgactctg cggctcaaa aagaaccgcc  5880
gacggcacgg aattcgagcc caagaagaag aggaaagtct aaccggtcat catcaccatc  5940
accattgagt ttaaacccgc tgatcagcct cgactgtgcc ttctagttgc cagccatctg  6000
ttgtttgccc ctccccgtg ccttccttga ccctggaagg tgccactccc actgtccttt  6060
cctaataaaa tgaggaaatt gcatcgcatt gtctgagtag tgtcattct attctggggg  6120
gtggggtggg gcaggacagc aagggggagg attgggaaga caatagcagc catgctgggg  6180
atgcggtggg ctctatggct tctgaggcgg aaagaaccag ctgggctcg ataccgtcga  6240
cctctagcta gagcttggcg taatcatggt catagctgtt tcctgtgtga aattgttatc  6300
cgctcacaat tccacacaac atacgagccg gaagcataaa gtgtaaagcc tagggtgcct  6360
aatgagtgag ctaactcaca ttaattgcgt tgcgctcact gcccgctttc cagtcgggaa  6420
acctgtcgtg ccagctgcat taatgaatcg gccaacgcgc ggggagaggc ggtttgcgta  6480
ttgggcgctc ttccgcttcc tcgctcactg actcgctgcg ctcggtcgtt cggctgcggc  6540
gagcggtatc agctcactca aaggcggtaa tacggttatc cacagaatca ggggataacg  6600
caggaaagaa catgtgagca aaaggccagc aaaaggccag gaaccgtaaa aaggccgcgt  6660
tgctggcgtt tttccatagg ctccgccccc ctgacgagca tcacaaaaat cgacgctcaa  6720
gtcagaggtg gcgaaacccg acaggactat aaagatacca ggcgtttccc cctggaagct  6780
ccctcgtgcg ctctcctgtt ccgaccctgc cgcttaccgg atacctgtcc gcctttctcc  6840
cttcgggaag cgtggcgctt tctcatagct cacgctgtag gtatctcagt tcggtgtagg  6900
tcgttcgctc caagctgggc tgtgtgcacg aacccccgtt tcagcccgac cgctgcgcct  6960
tatccggtaa ctatcgtctt gagtccaacc cggtaagaca cgacttatcg ccactggcag  7020
cagccactgg taacaggatt agcagagcga ggtatgtagg cggtgctaca gagttcttga  7080
agtggtggcc taactacggc tacactagaa gaacagtatt tggtatctgc gctctgctga  7140
agccagttac cttcggaaaa agagttggta gctcttgatc cggcaaacaa accaccgctg  7200
gtagcggtgg tttttttgtt tgcaagcagc agattacgcg cagaaaaaaa ggatctcaag  7260
aagatccttt gatcttttct acggggtctg acactcagtg gaacgaaaac tcacgttaag  7320
ggatttttggt catgagatta tcaaaaagga tcttcaccta gatccttta aattaaaaat  7380
gaagttttaa atcaatctaa agtatatatg agtaaacttg gtctgacagt taccaatgct  7440
taatcagtga ggcacctatc tcagcgatct gtctatttcg ttcatccata gttgcctgac  7500
tccccgtcgt gtagataact acgatacggg agggcttacc atctggcccc agtgctgcaa  7560
tgataccgcg agacccacgc tcaccggctc cagatttatc agcaataaac cagccagccg  7620
gaagggccga gcgcagaagt ggtcctgcaa cttatccgc ctccatccag tctattaatt  7680
gttgccggga agctagagta gtagttcgc cagttaatag tttgcgcaac gttgttgcca  7740
ttgctacagg catcgtggtg tcacgctcgt cgtttggtat ggcttcattc agctccggtt  7800
cccaacgatc aaggcgagtt acatgatccc ccatgttgtg caaaaaagcg gttagctcct  7860
tcggtcctcc gatcgttgtc agaagtaagt tggccgcagt gttatcactc atggttatgg  7920
cagcactgca taattctctt actgtcatgc catccgtaag atgcttttct gtgactggtg  7980
agtactcaac caagtcattc tgagaatagt gtatgcggcg accgagttgc tcttgcccgg  8040
cgtcaatacg gataatacc cgccacata gcagaacttt aaaagtgctc atcattggaa  8100
aacgttcttc ggggcgaaaa ctctcaagga tcttaccgct gttgagatcc agttcgatgt  8160
aacccactcg tgcacccaac tgatcttcag catctttttac tttcaccagc gtttctgggt  8220
gagcaaaaac aggaaggcaa aatgccgcaa aaaagggaat aagggcgaca cggaaatgtt  8280
gaatactcat actcttcctt tttcaatatt attgaagcat ttatcagggt tattgtctca  8340
tgagcggata catatttgaa tgtatttaga aaaataaaca aataggggtt ccgcgcacat  8400
ttccccgaaa agtgccacct gacgtcgacg gatcgggaga tcgatcccc gatccctag  8460
ggtcgactct cagtacaatc tgctctgatg ccgcatagtt aagccagtat ctgctccctg  8520
cttgtgtgtt ggaggtcgct gagtagtgcg cgagcaaaat ttaagctaca caaggcaag  8580
gcttgaccga caattgcatg aagaatctgc ttagggttag gcgttttgcg ctgcttcgcg  8640
atgtacgggc cagatatacg cgttgacatt gattattgac tagttattaa tagtaatcaa  8700
ttacgggtc attagttcat agcccatata tggagttccg cgttacataa cttacgtaa  8760
atggcccgcc tggctgaccg cccaacgacc cccgcccatt gacgtcaata atgacgtatg  8820
ttcccatagt aacgccaata gggactttcc attgacgtca atgggtggag tatttacggt  8880
aaactgccca cttggcagta catcaagtgt atc                                8913

SEQ ID NO: 38         moltype = DNA  length = 8913
FEATURE               Location/Qualifiers
```

| source | 1..8913 |
| | mol_type = other DNA |
| | organism = Synthetic construct |

SEQUENCE: 38

```
atatgccaag tacgcccct attgacgtca atgacggtaa atggcccgcc tggcattatg    60
cccagtacat gaccttatgg gactttccta cttggcagta catctacgta ttagtcatcg   120
ctattaccat ggtgatgcgg ttttggcagt acatcaatgg gcgtggatag cggtttgact   180
cacgggatt tccaagtctc caccccattg acgtcaatgg gagtttgttt tggcaccaaa    240
atcaacggga ctttccaaaa tgtcgtaaca actccgcccc attgacgcaa atgggcggta   300
ggcgtgtacg gtgggaggtc tatataagca gagctggttt agtgaaccgt cagatccgct   360
agagatccgc ggccgctaat acgactcact atagggagag ccgccaccat gaaacggaca   420
gccgacggaa gcgagttcga gtcaccaaag aagaagcgga aagtcagcag tgacaagaag   480
tacagcatcg gcctggccat cggcaccaac tctgtgggct gggccgtgat caccgacgag   540
tacaaggtgc ccagcaagaa attcaaggtg ctgggcaaca ccgaccggca cagcatcaag   600
aagaacctga tcggagccct gctgttcgac agcggcgaaa cagccgaggc cacccggctg   660
aagagaaccg ccagaagaag atacaccaga cggaagaacc ggatctgcta tctgcaagag   720
atcttcagca acgagatggc caaggtggac gacagcttct ccacagact ggaagagtcc    780
ttcctggtgg aagaggataa gaagcacgag cggcacccca tcttcggcaa catcgtggac   840
gaggtggcct accacgagaa gtaccccacc atctaccacc tgagaaagaa actggtggac   900
agcaccgaca aggccgacct gcggctgatc tatctggccc tggcccacat gatcaagttc   960
cggggccact tcctgatcga gggcgacctg aaccccgaca cagcgacgt ggacaagctg   1020
ttcatccagc tggtgcagac ctacaaccag ctgttccagg aaaacccat caacgccagc   1080
ggcgtggacg ccaaggccat cctgtctgcc agactgagca gagcagacg gctgaaaaat   1140
ctgatcgccc agctgccgg cgagaagaag aatggcctgt cggaaacct gattgccctg   1200
agcctgggcc tgacccccaa cttcaagagc aacttcgacc tggccgagga tgccaaactg   1260
cagctgagca aggacaccta cgacgacgac ctggacaacc tgctggccca gatcggcgac   1320
cagtacgccg acctgtttct ggccgccaag aacctgtccg acgccatcct gctgagcgac   1380
atcctgagag tgaacaccga gatcaccaag gccccctga gcgcctctat gatcaagaga   1440
tacgacgagc accaccagga cctgaccctg ctgaaagctc tcgtgcggca gcagctgcct   1500
gagaagtaca aagagatttt cttcgaccag agcaagaacg gctacgccgg ctacattgac   1560
ggcggagcca gccaggaaga gttctacaag ttcatcaagc catcctgga aaagatggac   1620
ggcaccgagg aactgctcgt gaagctgaac agagaggacc tgctgcggaa gcagcggacc   1680
ttcgacaacg gcagcatccc caccagatc cacctgggag agctgcacgc cattctgcgg   1740
cggcaggaag attttaccc attcctgaag gacaaccggg aaaagatcga aaagatcctg   1800
accttccgca tccctacta cgtgggccct ctggccagga gaaacagcag attcgcctgg   1860
atgaccagaa agagcgagga aaccatcacc ccctggaact tcgaggaagt ggtggacaag   1920
ggcgcttccg cccagagctt catcgagcgg atgaccaact cgataagaa cctgcccaac   1980
gagaaggtgc tgcccaagca cagcctgctg tacgagtact tcaccgtgta taacgagctg   2040
accaaagtga aatacgtgac cgagggaatg agaaagcccg ccttcctgag cggcgagcag   2100
aaaaaggcca tcgtggacct gctgttcaag accaaccgga aagtgaccgt gaagcagctg   2160
aaagaggact acttcaagaa aatcgagtgc ttcgactccg tggaaatctc cggcgtggaa   2220
gatcggttca acgcctccct gggcacatac acgatctgc tgaaaattat caaggacaag   2280
gacttcctgg acaatgagga aaacgaggac attctgaag atatcgtgct gaccctgaca   2340
ctgtttgagg acagagagat gatcgaggaa cggctgaaaa cctatgccca cctgttcgac   2400
gacaaagtga tgaagcagct gaagcggcgg agatacaccg gctggggcag gctgagccgg   2460
aagctgatca acggcatccg ggacaagcag tccggcaaga caatcctgga tttcctgaag   2520
tccgacggct tcgccaacag aaacttcatg cagctgatcc acgacgacag cctgacctt    2580
aaagaggaca tccagaaagc ccaggtgtcc ggccaggcg atagcctgca cgagcacatt   2640
gccaatctgg ccggcagccc cgccattaag aagggcatcc tgcagacagt gaaggtggtg   2700
gacgagctcg tgaaagtgat gggccggcac aagcccgaga catcgtgat cgaaatggcc   2760
agagaaaacc agtctggagg atctagcgg ggttcctctg gaagcgagac accaggcaca   2820
agcgagtccg ccacaccaga gagctccggc ggctcctccg gaggatctc tgaggtggag   2880
ttttcccacg agtactggat gagacatgcc ctgaccctgg ccaagagggc atgggatgaa   2940
agagaagtcc ccgtgggcgc cgtgctggtg cacaacaata gagtgatcgg agagggatgg   3000
aacaggccaa tcggccgcca cgaccctacc gcacacgcag agatcatggc actgaggcag   3060
ggaggcctgg tcatgcagaa ttaccgcctg atcgatgcca ccctgtatgt gacactggag   3120
ccatgcgtga tgtgcgcagg agcaatgatc cacagcagga tcggaagagt ggtgttcgga   3180
gcacgggacg ccaagaccgg cgcagcaggc tccctgatgg atgtgctgca ccaccccggc   3240
atgaaccacc gggtggagat cacagaggga atcctggcac acgatgcgc cgccctgctg   3300
agcgatttct ttagaatgcg gagacaggag atcaaggccc agaagaaggc acagagctcc   3360
accgactctg gaggatctag cggcggatcc tctggaagcg agacaccagg cacaagcgag   3420
tccgccacac cagagagctc cggcggctcc tccggaggat cctctgaggt ggagttttcc   3480
cacgagtact ggatgagaca tgccctgacc ctggccaaga gggcacgcga tgagagggag   3540
gtgcctgtgg gagccgtgct ggtgctgaac aatagagtga tcggagaggg ctggaacaga   3600
gccatcggcc tgcacgaccc aacagcccat gccgaaatta tggccctgag acagggcggc   3660
ctggtcatga gaaactacag actgattgac gccaccctgt acgtgacatt cgagccttgc   3720
gtgatgtgcg ccggcgccat gatccactct aggatcggcc gcgtggtgtt tggcgtgagg   3780
aacgcaaaa ccggcgccgc aggctccctg atggacgtgc tgcactaccc cggcatgaat   3840
caccgcgtcg aaattaccga gggaatcctg gcagatgaat gtgccgccct gctgtgtat    3900
ttcttcgga tgcctagaca ggtgttcaat gctcagaaga aggcccagag ctccaccgac   3960
tccgaggat ctagcggagg ctcctctggc tctgagacac tggcacaag cgagagcgca    4020
acacctgaaa gcagcggggg cagcagcggg ggtcaacca cccagaaggg acagaagaac   4080
agccgcgaga gaatgaagcg gatcgaagag ggcatcaaag agctgggcag ccagatcctg   4140
aaagaacacc ccgtggaaaa cacccagctg cagaacgaga agctgtacct gtactacctg   4200
cagaatgggc gggatatgta cgtggaccag gaactggaca tcaaccgct gtccgactac   4260
gatgtgacc atatcgtgcc tcagagcttt ctgaaggacg actccatcga caacaaggtg   4320
ctgaccagaa gcgacaagaa ccgggggcaag agcgacaacg tgcctccga agaggtcgtg   4380
aagaagatga aaactactg gcggcagctg ctgaacgcca agctgattac ccagagaaag   4440
ttcgacaatc tgaccaaggc cgagagaggc ggcctgagcg aactggataa ggccggcttc   4500
```

```
atcaagagac agctggtgga aacccggcag atcacaaagc acgtggcaca gatcctggac  4560
tcccggatga acactaagta cgacgagaat gacaagctga tccggaagt gaaagtgatc   4620
accctgaagt ccaagctggt gtccgatttc cggaaggatt tccagtttta caaagtgcgc  4680
gagatcaaca actaccacca cgcccacgac gcctacctga acgccgtcgt gggaaccgcc  4740
ctgatcaaaa agtaccctaa gctggaaagc gagttcgtgt acggcgacta caaggtgtac  4800
gacgtgcgga agatgatcgc caagagcgag caggaaatcg gcaaggctac cgccaagtac  4860
ttcttctaca gcaacatcat gaacttttc aagaccgaga ttaccctggc caacggcgag  4920
atccggaagc ggcctctgat cgagacaaac ggcgaaaccg gggagatcgt gtgggataag  4980
ggcgggatt ttgccaccgt gcggaaagtg ctgagcatgc cccaagtgaa tatcgtgaaa   5040
aagaccgagg tgcagacagg cggcttcagc aaagagtcta tcctgcccaa gaggaacagc  5100
gataagctga tcgccagaaa gaaggactgg gaccctaaga agtacggcgg cttcgacagc  5160
cccaccgtgg cctattctgt gctggtggtg gccaaagtgg aaaagggcaa gtccaagaaa  5220
ctgaagagtg tgaaagagct gctggggatc accatcatgg aaagaagcag cttcgagaag  5280
aatcccatcg actttctgga agccaagggc tacaaagagg tgaaaaagga cctgatcatc  5340
aagctgccta agtactccct gttcgagctg gaaaacggcc ggaagagaat gctggcctct  5400
gccggcgaac tgcagaaggg aaacgaactg gccctgccct ccaaatatgt gaacttcctg  5460
tacctggcca gccactatga gaagctgaag ggctcccccg aggataatga gcagaaacag  5520
ctgtttgtgg aacagcacaa gcactacctg gacgagatca tcgagcagat cagcgagttc  5580
tccaagagag tgatcctggc cgacgctaat ctggacaaag tgctgtccgc ctacaacaag  5640
caccgggata agcccatcag agagcaggcc gagaatatca tccacctgtt taccctgacc  5700
aatctgggag cccctgccgc cttcaagtac tttgacacca ccatcgaccg gaagaggtac  5760
accagcacca aagaggtgct ggacgccaac ctgatccacc agagcatcac cggcctgtac  5820
gagacacgga tcgacctgtc tcagctggga ggtgactctg gcggctcaaa agaaccgcc   5880
gacggcagcg aattcgagcc caagaagaag aggaaagtct aaccggtcat catcaccatc  5940
accattgagt ttaaacccgc tgatcagcct cgactgtgcc ttctagttgc cagccatctg  6000
ttgtttgccc ctcccccgtg ccttccttga ccctggaagg tgccactccc actgtcctt   6060
cctaataaaa tgaggaaatt gcatcgcatt gtctgagtag tgtcattct attctggggg   6120
gtggggtggg gcaggacagc aaggggagg attgggaaga caatagcagg catgctgggg   6180
atgcggtggg ctctatggct tctgaggcgg aaagaaccag ctggggctcg ataccgtcga  6240
cctctagcta gagcttggcg taatcatggt catagctgtt tcctgtgtga aattgttatc  6300
cgctcacaat tccacacaac atacgagccg aagcataaa gtgtaaagcc tagggtgcct   6360
aatgagtgag ctaactcaca ttaattgcgt tgcgctcact gcccgctttc cagtcgggaa  6420
acctgtcgtg ccagctgcat taatgaatcg gccaacgcgc ggggagaggc ggtttgcgta  6480
ttgggcgctc ttccgcttcc tcgctcactg actcgctgcg ctcggtcgtt cggctgcggc  6540
gagcggtatc agctcactca aaggcggtaa tacggttatc cacagaatca ggggataacg  6600
caggaaagaa catgtgagca aaaggccagc aaaaggccag gaaccgtaaa aaggccgcgt  6660
tgctggcgtt tttccatagg ctccgccccc ctgacgagca tcacaaaaat cgacgctcaa  6720
gtcagaggtg gcgaaacccg acaggactat aaagatacca ggcgtttccc cctggaagct  6780
ccctcgtgcg ctctcctgtt ccgaccctgc cgcttaccgg atacctgtcc gcctttctcc  6840
cttcggaag cgtggcgctt tctcatagct cacgctgtag gtatctcagt tcggtgtagg   6900
tcgttcgctc caagctgggc tgtgtgcacg aaccccccgt tcagcccgac cgctgcgcct  6960
tatccggtaa ctatcgtctt gagtccaacc cggtaagaca cgacttatcg ccactggcag  7020
cagccactgg taacaggatt agcagagcga ggtatgtagg cggtgctaca gagttcttga  7080
agtggtggcc taactacggc tacactagaa gaacagtatt tggtatctgc gctctgctga  7140
agccagttac cttcggaaaa agagttggta gctcttgatc cggcaaacaa accaccgctg  7200
gtagcggtgg ttttttgtt tgcaagcagc agattacgcg cagaaaaaaa ggatctcaag   7260
aagatccttt gatcttttct acggggtctg acactcaggt gaacgaaaac tcacgttaag  7320
ggattttggt catgagatta tcaaaaagga tcttcaccta tccttttta aattaaaaat   7380
gaagttttaa atcaatctaa agtatatatg agtaaacttg gtctgacagt taccaatgct  7440
taatcagtga ggcacctatc tcagcgatct gtctatttcg ttcatccata gttgcctgac  7500
tccccgtcgt gtagataact acgatacggg agggcttacc atctggcccc agtgctgcaa  7560
tgataccgcg agaccacgc tcaccggctc cagatttatc agcaataaac cagccagccg   7620
gaagggccga gcgcagaagt ggtcctgcaa ctttatccgc ctccatccag tctattaatt  7680
gttgccggga agctagagta agtagttcgc cagttaatag tttgcgcaac gttgttgcca  7740
ttgctacagg catcgtggtg tcacgctcgt cgtttggtat ggcttcattc agctccggtt  7800
cccaacgatc aaggcgagtt acatgatccc ccatgttgtg caaaaaagcg gttagctcct  7860
tcggtcctcc gatcgttgtc agaagtaagt tggccgcagt gttatcactc atggttatgg  7920
cagcactgca taattctctt actgtcatgc catccgtaag atgcttttct gtgactggtg  7980
agtactcaac caagtcattc tgagaatagt gtatgcggcg accgagttgc tcttgcccgg  8040
cgtcaatacg ggataatacc gcgccacata gcagaacttt aaaagtgctc atcattggaa  8100
aacgttcttc ggggcgaaaa ctctcaagga tcttaccgct gttgagatcc agttcgatgt  8160
aacccactcg tgcacccaac tgatcttcag catctttac tttcaccagc gtttctgggt   8220
gagcaaaaac aggaaggcaa aatgccgcaa aaagggaat aagggcgaca cggaaatgtt   8280
gaatactcat actcttcctt tttcaatatt attgaagcat ttatcagggt tattgtctca  8340
tgagcggata catatttgaa tgtatttaga aaaataaaca aataggggtt ccgcgcacat  8400
ttccccgaaa agtgccacct gacgtcgacg gatcgggaga tcgatctccc gatccctag   8460
ggtcgactct cagtacaatc tgctctgatg ccgcatagtt aagccagtat ctgctccctg  8520
cttgtgtgtt ggaggtcgct gagtagtgcg cgagcaaaat ttaagctaca acaaggcagg  8580
gcttgaccga caattgcatg aagaatctgc ttagggtag gcgttttgcg ctgcttcgcg  8640
atgtacgggc cagatatacg cgttgacatt gattattgac tagttattaa tagtaatcaa  8700
ttacggggtc attagttcat agcccatata tggagttccg cgttacataa cttacggtaa  8760
atggcccgcc tggctgaccg cccaacgacc cccgcccatt gacgtcaata atgacgtatg  8820
ttcccatagt aacgccaata gggactttcc attgacgtca atgggtggag tatttacggt  8880
aaactgccca cttggcagta catcaagtgt atc                                8913

SEQ ID NO: 39      moltype = DNA   length = 8913
FEATURE            Location/Qualifiers
source             1..8913
                   mol_type = other DNA
``` organism = Synthetic construct
SEQUENCE: 39

```
atatgccaag tacgcccct attgacgtca atgacggtaa atggcccgcc tggcattatg    60
cccagtacat gaccttatgg gactttccta cttggcagta catctacgta ttagtcatcg   120
ctattaccat ggtgatgcgg ttttggcagt acatcaatgg gcgtggatag cggtttgact   180
cacgggatt tccaagtctc caccccattg acgtcaatgg gagtttgttt tggcaccaaa    240
atcaacggga ctttccaaaa tgtcgtaaca actccgcccc attgacgcaa atgggcggta   300
ggcgtgtacg gtgggaggtc tatataagca gagctggttt agtgaaccgt cagatccgct   360
agagatccgc ggccgctaat acgactcact atagggagag ccgccaccat gaaacggaca   420
gccgacggaa gcgagttcga gtcaccaaag aagaagcgga aagtcagcag tgacaagaag   480
tacagcatcg gcctggccat cggcaccaac tctgtgggct gggccgtgat caccgacgag   540
tacaaggtgc ccagcaagaa attcaaggtg ctgggcaaca ccgaccggca cagcatcaag   600
aagaacctga tcggagccct gctgttcgac agcggcgaaa cagccgaggc cacccggctg   660
aagagaaccg ccagaagaag ataccaccaga cggaagaacc ggatcgtgcta tctgcaagag   720
atcttcagca acgagatggc caaggtggac gacagcttct tccacagact ggaagagtcc   780
ttcctggtgg aagaggataa gaagcacgag cggcacccca tcttcggcaa catcgtggac   840
gaggtggcct accacgagaa gtaccccacc atctaccacc tgagaaagaa actggtggac   900
agcaccgaca aggccgacct gcggctgatc tatctggccc tggcccacat gatcaagttc   960
cggggccact tcctgatcga gggcgacctg aaccccgaca cagcgacgt ggacaagctg   1020
ttcatccagc tggtgcagac ctacaaccag ctgttcgagg aaaacccat caacgccagc   1080
ggcgtggacg ccaaggccat cctgtctgcc agactgagca gagcagacg gctggaaaat   1140
ctgatcgccc agctgcccgg cgagaagaag aatggctgt tcggaaacct gattgccctg   1200
agcctgggcc tgacccccaa cttcaagagc aacttcgacc tggccgagga tgccaaactg   1260
cagctgagca aggacaccta cgacgacgac ctggacaacc tgctggccca gatcggcgac   1320
cagtacgccg acctgttct ggccgccaag aacctgtccg acgccatcct gctgagcgac   1380
atcctgagag tgaacaccga gatcaccaag gccccctga gcgcctctat gatcaagaga   1440
tacgacgagc accaccagga cctgaccctg ctgaaagctc tcgtgcggca gcagctgcct   1500
gagaagtaca agagattttt cttcgaccag agcaagaacg gctacgccgg ctacattgac   1560
ggcggagcca gccaggaaga gttctacaag ttcatcaagc ccatcctgga aaagatggac   1620
ggcaccgagg aactgctcgt gaagctgaac agagaggacc tgctgcggaa gcagcggacc   1680
ttcgacaacg gcagcatccc ccaccagatc cacctgggag agctgcacgc cattctgcgg   1740
cggcaggaag atttttaccc attcctgaag gacaaccggg aaaagatcga gaagatcctg   1800
accttccgca tccctacta cgtgggccct ctggccaggg aaacagcag attcgcctgg   1860
atgaccagaa agagcgagga aaccatcacc cctggaact tcgaggaagt ggtgacaag   1920
ggcgcttccg cccagagctt catcgagcgg atgaccaact tcgataagaa cctgcccaac   1980
gagaaggtgc tgcccaagca cagcctgctg tacgagtact tcaccgtgta taacgagctg   2040
accaaagtga aatacgtgac cgagggaatg agaaagcccg ccttcctgag cggcgagcag   2100
aaaaggcca tcgtggacct gctgttcaag accaaccgga agtgaccgt gaagcagctg   2160
aaagaggact acttcaagaa aatcgagtgc ttcgactccg tggaaatctc cggcgtggaa   2220
gatcggttca acgcctccct gggcacatac cacgatctgc tgaaaattat caaggacaag   2280
gacttcctgg acaatgagga aaacgaggac attctggaag atatcgtgct gaccctgaca   2340
ctgtttgagg acagagagat gatcgaggaa cggctgaaaa cctatgccca cctgttcgac   2400
gacaaagtga tgaagcagct gaagcggcga agatacaccg gctggggcag gctgagccgg   2460
aagctgatca acggcatccg ggacaagcag tccggcaaga caatcctgga tttcctgaag   2520
tccgacggct cgccaacag aaacttcatg cagctgatcc acgacgacag cctgaccttt   2580
aaagaggaca tccagaaagc ccaggtgtcc ggccagggcg atagcctgca cgagcacatt   2640
gccaatctgg ccggcagccc cgccattaag aagggcactc tgcagacagt gaaggtggtg   2700
gacgagctcg tgaaagtgat gggccggcac aagcccgaga acatcgtgat cgaaatggcc   2760
agagagaacc agaccacccca gaagggacag aagaactctg gaggatctag cggtggttcc   2820
tctgaagcg agacaccagg cacaagcgag tccgccacac cagagagctc cggcggctcc   2880
tccggaggat cctctgaggt ggagttttcc cacgagtact gatgagaca tgccctgacc   2940
ctggccaaga gggcatggga tgaaagaaga gtcccgtgg gcgccgtgct ggtgcacaac   3000
aatagagtga tcggagaggg atggaacagg ccaatcggcc gccacgaccc taccgcacac   3060
gcagagatca tggcactgag gcaggaggc ctggtcatgc agaattaccg cctgatcgat   3120
gccaccctgt atgtgacact ggagccatgc gtgatgtgcg caggagcaat gatccacagc   3180
aggatcggaa gagtggtgtt cggagcacgg gacgccaaga ccggcgcagc aggctccctg   3240
atggatgtgc tgcaccaccc cggcatgaac caccgggtgg agatcacaga gggaatcctg   3300
gcagacgagt gcgccgccct gctgagcgat ttctttagaa tgcggagaca ggagatcaag   3360
gcccagaaga aggcacagag ctccaccgaa tctggaggat ctagcggcgg atcctctgga   3420
agcagagaca caggcacaag cgagtccgcc acaccaggaa gctccggcgg ctcctccgga   3480
ggatcctctg aggtggagtt tccccacgag tactggatga gacatgccct gaccctggcc   3540
aagagggcac gcgatgagag ggaggtgcct gtgggagccg tgctggtgct gaacaataga   3600
gtgatcggcg agggctggaa cagagccatc ggcctgcacg acccaacagc catgccgaa   3660
attatggccc tgagacaggg cggcctggtc atgcagaat acagactgat tgacgccacc   3720
ctgtacgtga cattcgagcc ttgcgtgatg tgcgccggcg ccatgatcca ctctaggatc   3780
ggccgcgtgg tgtttggcgt gaggaacgca aaaccggcg ccgcaggctc cctgatggac   3840
gtgctgcact cccgggcat gaatcaccgc gtcgaatta ccgagggaat cctggcagat   3900
gaatgtgccg ccctgctgtg ctatttcttt cggatgccta gacaggtgtt caatgctcag   3960
aagaaggccc agagctccac cgactccgga ggatctctgag gaggctcctc tggctctgag   4020
acacctggca caagcgagag cgcaacacct gaaagcagcg ggggcagcag cgggggtca   4080
agccgcgaga aatgaagcg gatcgaagag gcatcaaag agctgggcag ccagatcctg   4140
aaagaacacc ccgtggaaaa cacccagctg cagaacgaga gctgtacct gtactacctg   4200
cagaatgggc gggatatgta cgtggaccag gaactggaca tcaaccggct gtccgactac   4260
gatgtggacg ccatcgtgcc tcagagcttt ctgaaggacg actccatcga caacaaggtg   4320
ctgaccagaa gcgacaagaa ccggggcaag agcgacaacg tgcccctccga agaggtcgtg   4380
aagaagatga gaactactg gcggcagctg ctgaacgcca agctgattac ccagagaaag   4440
ttcgacaatc tgaccaaggc cgagagaggc ggcctgagcg aactggataa ggccggcttc   4500
atcaagagac agctggtgga aacccggcag atcacaaagc acgtggcaca gatcctggac   4560
tcccggatga acactaagta cgacgagaat gacaagctga tccgggaagt gaaagtgatc   4620
```

```
accctgaagt ccaagctggt gtccgatttc cggaaggatt tccagttttta caaagtgcgc   4680
gagatcaaca actaccacca cgcccacgac gcctacctga acgccgtcgt gggaaccgcc   4740
ctgatcaaaa agtaccctaa gctggaaagc gagttcgtgt acggcgacta caaggtgtac   4800
gacgtgcgga agatgatcgc caagagcgag caggaaatcg gcaaggctac cgccaagtac   4860
ttcttctaca gcaacatcat gaactttttc aagaccgaaa ttaccctggc caacggcgag   4920
atccggaagc ggcctctgat cgagacaaac ggcgaaaccg gggagatcgt gtgggataag   4980
ggccgggatt tgccaccgt gcggaaagtg ctgagcatgc cccaagtgaa tatcgtgaaa   5040
aagaccgagg tgcagacagg cggcttcagc aaagagtcta tcctgcccaa gaggaacagc   5100
gataagctga tcgccagaaa gaaggactgg gaccctaaga agtacggcgg cttcgacagc   5160
cccaccgtgg cctattctgt gctggtggtg gccaaagtgg aaaagggcaa gtccaagaaa   5220
ctgaagagtg tgaaagagct gctggggatc accatcatgg aaagaagcag cttcgagaag   5280
aatcccatcg actttctgga agccaagggc tacaagaag tgaaaaagga cctgatcatc   5340
aagctgccta agtactccct gttcgagctg aaaacggcc ggaagagaat gctggcctct   5400
gccggcgaac tgcagaaggg aaacgaactg gccctgccct ccaaatatgt gaacttcctg   5460
tacctggcca gccactatga gaagctgaag ggctcccccg aggataatga gcagaaacag   5520
ctgtttgtgg aacagcacaa gcactacctg gacgagatca tcgagcagat cagcgagttc   5580
tccaagagag tgatcctggc cgacgctaat ctggacaaag tgctgtccgc ctacaacaag   5640
caccgggata agcccatcag agagcaggcc gagaatatca tccacctgtt taccctgacc   5700
aatctgggag cccctgccgc cttcaagtac tttgacacca ccatcgaccg gaagaggtac   5760
accagcacca aagaggtgct ggacgccacc ctgatccacc agagcatcac cggcctgtac   5820
gagacacgga tcgacctgtc tcagctggga ggtgactctg gcggtcaaa aagaaccgcc   5880
gacggcagcg aattcgagcc caagaagaag aggaaagtct aaccggtcat catcaccatc   5940
accattgagt ttaaacccgc tgatcagcct cgactgtgcc ttctagttgc cagccatctg   6000
ttgtttgccc ctccccgtg ccttccttga ccctggaagg tgccactccc actgtccttt   6060
cctaataaaa tgaggaaatt gcatcgcatt gtctgagtag tgtcattct attctggggg   6120
gtggggtggg gcaggacagc aaggggggag attgggaaga caatagcagg catgctgggg   6180
atgcggtggg ctctatggct tctgaggcgg aaagaaccag ctgggctcg ataccgtcga   6240
cctctagcta gagcttggcg taatcatggt catagctgtt tcctgtgtga aattgttatc   6300
cgctcacaat tccacacaac atacgagccg gaagcataaa gtgtaaagcc tagggtgcct   6360
aatgagtgag ctaactcaca ttaattgcgt tgcgctcact gcccgctttc cagtcgggaa   6420
acctgtcgtg ccagctgcat taatgaatcg gccaacgcgc ggggagaggc ggtttgcgta   6480
ttgggcgctc ttccgcttcc tcgctcactg actcgctgcg ctcggtcgtt cggctgcggc   6540
gagcggtatc agctcactca aaggcggtaa tacggttatc cacagaatca ggggataacg   6600
caggaaagaa catgtgagca aaaggccagc aaaaggccag gaaccgtaaa aaggccgcgt   6660
tgctggcgtt tttccatagg ctccgccccc ctgacgagca tcacaaaaat cgacgctcaa   6720
gtcagaggtg gcgaaacccg acaggactat aaagatacca ggcgtttccc cctggaagct   6780
ccctcgtgcg ctctcctgtt ccgaccctgc cgcttaccgg atacctgtcc gcctttctcc   6840
cttcgggaag cgtggcgctt tctcatagct cacgctgtag gtatctcagt tcggtgtagg   6900
tcgttcgctc caagctgggc tgtgtgcacg aaccccccgt tcagcccgac cgctgcgcct   6960
tatccggtaa ctatcgtctt gagtccaacc cggtaagaca cgacttatcg ccactggcag   7020
cagccactgg taacaggatt agcagagcga ggtatgtagg cggtgctaca gagttcttga   7080
agtggtggcc taactacggc tacactagaa gaacagtatt tggtatctgc gctctgctga   7140
agccagttac cttcggaaaa agagttggta gctcttgatc cggcaaacaa accaccgctg   7200
gtagcggtgg tttttttgtt tgcaagcagc agattacgcg cagaaaaaaa ggatctcaag   7260
aagatccttt gatcttttct acggggtctg acactcagtg gaacgaaaac tcacgttaag   7320
ggattttggt catgagatta tcaaaaagga tcttcaccta gatccttta aattaaaaat   7380
gaagttttaa atcaatctaa agtatatatg agtaaacttg gtctgacagt taccaatgct   7440
taatcagtga ggcaccctatc tcagcgatct gtctatttcg ttcatccata gttgcctgac   7500
tccccgtcgt gtagataact acgatacggg agggcttacc atctggcccc agtgctgcaa   7560
tgataccgcg agacccacgc tcaccggctc cagatttatc agcaataaac cagccagccg   7620
gaagggccga gcgcagaagt ggtcctgcaa ctttatccgc ctccatccag tctattaatt   7680
gttgccggga agctagagta agtagttcgc cagttaatag tttgcgcaac gttgttgcca   7740
ttgctacagg catcgtggtg tcacgctcgt cgtttggtat ggcttcattc agctccggtt   7800
cccaacgatc aaggcgagtt acatgatccc ccatgttgtg caaaaaagcg gttagctcct   7860
tcggtcctcc gatcgttgtc agaagtaagt tggccgcagt gttatcactc atggttatgg   7920
cagcactgca taattctctt actgtcatgc catccgtaag atgcttttct gtgactggtg   7980
agtactcaac caagtcattc tgagaatagt gtatgcggcg accgagttgc tcttgcccgg   8040
cgtcaatacg ggataatacc gcgccacata gcagaacttt aaaagtgctc atcattggaa   8100
aacgttcttc ggggcgaaaa ctctcaagga tcttaccgct gttgagatcc agttcgatgt   8160
aacccactcg tgcacccaac tgatcttcag catcttttac tttcaccagc gtttctgggt   8220
gagcaaaaac aggaaggcaa aatgccgcaa aaaagggaat aagggcgaca cggaaatgtt   8280
gaatactcat actcttcctt tttcaatatt attgaagcat ttatcagggt tattgtctca   8340
tgagcggata catatttgaa tgtatttaga aaaataaaca aataggggtt ccgcgcacat   8400
ttccccgaaa agtgccacct gacgtcgacg gatcgggaga tcgatctccc gatccctag   8460
ggtcgactct cagtacaatc tgctctgatg ccgcatagtt aagccagtat ctgctccctg   8520
cttgtgtgtt ggaggtcgct gagtagtgcg cgagcaaaat ttaagctaca caaggcaag   8580
gcttgaccga caattgcatg aagaatctgc ttagggttag gcgttttgcg ctgcttcgcg   8640
atgtacgggc cagatatacg cgttgacatt gattattgac tagttattaa tagtaatcaa   8700
ttacggggtc attagttcat agcccatata tggagttccg cgttacataa cttacggtaa   8760
atggcccgcc tggctgaccg cccaacgacc cccgcccatt gacgtcaata atgacgtatg   8820
ttcccatagt aacgccaata gggactttcc attgacgtca atgggtggag tatttacggt   8880
aaactgccca cttggcagta catcaagtgt atc                                 8913

SEQ ID NO: 40         moltype = DNA   length = 8913
FEATURE               Location/Qualifiers
source                1..8913
                      mol_type = other DNA
                      organism = Synthetic construct
SEQUENCE: 40
```

```
atatgccaag tacgccccct attgacgtca atgacggtaa atggcccgcc tggcattatg   60
cccagtacat gaccttatgg gactttccta cttggcagta catctacgta ttagtcatcg  120
ctattaccat ggtgatgcgg ttttggcagt acatcaatgg gcgtggatag cggttttgact 180
cacgggatt tccaagtctc cacccccattg acgtcaatgg gagtttgttt tggcaccaaa  240
atcaacggga ctttccaaaa tgtcgtaaca actccgcccc attgacgcaa atgggcggta  300
ggcgtgtacg gtgggaggtc tatataagca gagctggttt agtgaaccgt cagatccgct  360
agagatccgc ggccgctaat acgactcact atagggagag ccgccaccat gaaacggaca  420
gccgacggaa gcgagttcga gtcaccaaag aagaagcgga aagtcagcag tgacaagaag  480
tacagcatcg gcctggccat cggcaccaac tctgtgggct gggccgtgat caccgacgag  540
tacaaggtgc ccagcaagaa attcaaggtg ctgggcaaca ccgaccggca cagcatcaag  600
aagaacctga tcgagccct gctgttcgac agcggcgaaa cagccgaggc cacccggctg  660
aagagaaccg ccagaagaag ataccaccaga cggaagaacc ggatctgcta tctgcaagag  720
atcttcagca acgagatggc caaggtggac gacagcttct ccacagact ggaagagtgg  780
ttcctggtgg aagaggataa gaagcacgag cggcacccca tcttcggcaa catcgtggac  840
gaggtggcct accacgagaa gtaccccacc atctaccacc tgagaaagaa actggtggac  900
agcaccgaca aggccgacct gcggctgatc tatctggccc tggcccacat gatcaagttc  960
cggggccact tcctgatcga gggcgacctg aaccccgaca cagcgacgt ggacaagctg 1020
ttcatccagc tggtgcagac ctacaaccag ctgttcgagg aaaacccat caacgccagc 1080
ggcgtgacg ccaaggccat cctgtctgcc agactgagca gagcagacg gctgaaaaat 1140
ctgatcgccc agctgcccgg cgagaagaag aatggcctgt cggaaacct gattgccctg 1200
agcctgggcc tgacccccaa cttcaagagc aacttcgacc tggccgagga tgccaaactg 1260
cagctgacga aggacaccta cgacgacgac ctggacaacc tgctggccca gatcggcgac 1320
cagtacgccg acctgtttct ggccgccaag aacctgtccg acgccatcct gctgagcgac 1380
atcctgagag tgaacaccga gatcaccaag gcccccctga cgcctctat gatcaagaga 1440
tacgacgagc accaccagga cctgaccctg ctgaaagctc tcgtgcggca gcagctgcct 1500
gagaagtaca aagagatttt cttcgaccag agcaagaacg gctacgccgg ctacattgac 1560
ggcggagcca gccaggaaga gttctacaag ttcatcaagc ccatcctgga aaagatggac 1620
ggcaccgagg aactgctcgt gaagctgaac agagaggacc tgctgcggaa gcagcggacc 1680
ttcgacaacg gcagcatccc ccaccagatc cacctgggag agctgcacgc cattctgcgg 1740
cggcaggaag attttaccc attcctgaag gacaaccggg aaaagatcga agatcctgg 1800
accttccgca tccctactga cgtgggccct ctggccaggg gaaacagcag attcgcctgg 1860
atgaccagaa agagcgagga aaccatcacc cctggaactc gaggaagt ggtggacaag 1920
ggcgcttccg cccagagctt catcgagcgg atgaccaact cgataagaa cctgcccaac 1980
gagaaggtgc tgcccaagca cagcctgctg tacgagtact tcaccgtgta taacgagctg 2040
accaaagtga aatacgtgac cgagggaatg agaaagcccg ccttcctgag cggcgagcag 2100
aaaaaggcca tcgtggacct gctgttcaag accaaccgga aagtgaccgt gaagcagctg 2160
aaagaggact acttcaagaa aatcgagtgc ttcgactccg tggaaatctc cggcgtggaa 2220
gatcggttca acgcctccct gggcacatac cacgatctgc tgaaaattat caaggacaag 2280
gacttcctgg acaatgagga aaacgaggac atttctgaag atatcgtgct gaccctgaca 2340
ctgtttgagg acagagagat gatcgaggaa cggctgaaaa cctatgccca cctgttcgac 2400
gacaaagtga tgaagcagct gaagcggcgg agatacaccg gctggggcag gctgagccgg 2460
aagctgatca acggcatccg ggacaagcag tccggcaaga caatcctgga tttcctgaag 2520
tccgacggct tcgccaacag aaacttcatg cagctgatcc acgacgacag cctgaccttt 2580
aaagaggaca tccagaaagc ccaggtgtcc ggccagggcg atagcctgca cgagcacatt 2640
gccaatctgg ccggcagccc cgccattaag aagggcatcc tgcagacagt gaaggtggtg 2700
gacgagctcg tgaaagtgat gggccggcac aagcccgaga catcgtgat cgaaatggcc 2760
agagagaacc agaccaccca gaagggacaa gaaacgcc gcagagaat gaagcggatc 2820
gaagagggca tcaaagagct gggcagccag atcctgaaag aacacccgt ggaaaacacc 2880
cagctgcaga acgagaagct gtacctgtac tacctgcaga atgggtctgg aggatctagc 2940
ggtggttcct ctgaagcga gacaccaggc acaagcgagt ccgccacacc agagagctcc 3000
ggcggctcct ccggaggatc ctctgaggtg gagtttccc acgagtactg gatgagacat 3060
gccctgaccc tggccaagag ggcatgggat gaaagagaag tccccgtggg cgccgtgctg 3120
gtgcacaaca atagagtgat cggagaggga tggaacaggc aatcggccg ccacgaccct 3180
accgcacacg cagagatcat ggcactgagg cagggaggcc tggtcatgca gaattaccgc 3240
ctgatcgatg ccaccctgta tgtgacactg gagccatgc tgatgtgcgc aggagcaatg 3300
atccacagca ggatcggaag agtggtgttc ggagcacggg acgccaagac cggcgcagca 3360
ggctccctga tggatgtgct gcaccacccc ggcatgaacc accgggtgga gatcacagag 3420
ggaatcctgg cagacgagtg cgccgccctg ctgagcgatt tctttagaat gcggagacag 3480
gagatcaagg cccagaagaa ggcacagagc tccaccgact tcagcttcta tcggccgga 3540
tcctctggaa gcgagacacc aggcacaagc gagtccgcca caccagagag ctccggcgga 3600
tcctccggag gatcctctga ggtggagttt ccccacgagt actggatgag acatgccctg 3660
accctggcca gagggcacg cgatgagagg gaggtgcctg tgggagccgt gctggtgctg 3720
aacaatagag tgatcggcga gggctggaac agagccatcg gcctgcacga cccaacagcc 3780
catgccgaaa ttatgcccct gagacagggc cctgctgca cagaacta cagactgatt 3840
gacgccaccc tgtacgtgac attcgagcct tgcgtgatgt gcgccggcgc catgatccac 3900
tctaggatcg gccgcgtggt gttggcgtg aggaacgcaa aaccggcgc cgcaggctcc 3960
ctgatgacg tgctgcacta cccggcatg aataccgcg tcgaaattac cgagggaatc 4020
ctggcagatg aatgtgccgc cctgctgtgc tatttctttc ggatgcctag acaggtgttc 4080
aatgctcaga agaaggccca gagctccacc gactccggaa gtctagcgg aggctcctct 4140
ggctctgaga cacctggcac aagcgagagc gcaacacctg aaagcagcgg gggcagcagc 4200
gggggtcac gggatatgta cgtggaccag gaactggaca tcaaccggct gtccgactac 4260
gatgtggacc atatcgtgcc tcagagcttt ctgaaggacg actccatcga caacaaggtg 4320
ctgaccagaa gcgacaagaa ccgggcaag agcgacaacg tgccctccga gaggtcgtg 4380
aagaagatga aaaactactg gcggcagctg ctgaacgcca agctgattac cagagaaag 4440
ttcgacaatc tgaccaaggc cgagagaggc ggcctgagcg aactggataa ggccggcttc 4500
atcaagagac agctggtgga aacccggcag atcacaaagc acgtggcaca gatcctggac 4560
tcccggatga acactaagta cgacgagaat gacaagctga tccggaagt gaaagtgatc 4620
accctgaagt ccaagctggt gtccgatttc cggaaggatt ccagttttta caagtgcgc 4680
gagatcaaca actaccacca cgcccacgac gcctacctga acgccgtcgt gggaaccgcc 4740
```

```
ctgatcaaaa agtaccctaa gctggaaagc gagttcgtgt acggcgacta caaggtgtac   4800
gacgtgcgga agatgatcgc caagagcgag caggaaatcg gcaaggctac cgccaagtac   4860
ttcttctaca gcaacatcat gaacttttc aagaccgaga ttaccctggc caacggcgag    4920
atccggaagc ggcctctgat cgagacaaac ggcgaaaccg gggagatcgt gtgggataag   4980
ggccgggatt ttgccaccgt gcggaaagtg ctgagcgatg cccaagtgaa tatcgtgaaa   5040
aagaccgagg tgcagacagg cggcttcagc aaagagtcta tcctgcccaa gaggaacagc   5100
gataagctga tcgccagaaa gaaggactgg gaccctaaga agtacggcgg cttcgacagc   5160
cccaccgtgg cctattctgt gctggtggtg gccaaagtgg aaaagggcaa gtccaagaaa   5220
ctgaagatgt gtgaaagagct gctggggatc accatcgat aaagaagcag cttcgagaag   5280
aatcccatcg actttctgga agccaagggc tacaaagagg tgaaaaagga cctgatcatc   5340
aagctgccta agtactccct gttcgagctg gaaaacggcc ggaagagaat gctggcctct   5400
gccggcgaac tgcagaaggg aaacgaactg ccctgccct ccaaatatgt gaacttcctg    5460
tacctggcca gccactatga aagctgaag ggctcccccg aggataatga gcagaaacag    5520
ctgtttgtgg aacagcacaa gcactacctg gacgagatca tcgagcagat cagcgagttc   5580
tccaagagag tgatcctggc cgacgctaat ctggacaaag tgctgtccgc ctacaacaag   5640
caccgggata agcccatcag agagcaggcc gagaatatca tccacctgtt taccctgacc   5700
aatctgggag cccctgccgc cttcaagtac tttgacacca ccatcgaccg gaagaggtac   5760
accagcacca aagaggtgct ggacgcacc ctgatccacc agagcatcac cggcctgtac    5820
gagacacgga tcgacctgtc tcagctggga ggtgactctg gcggctcaaa agaaccgcc    5880
gacggcagcg aattcgagcc caagaagaag aggaaagtct aaccggtcat catcaccatc   5940
accattgagt ttaaacccgc tgatcagcct cgactgtgcc ttctagttgc cagccatctg   6000
ttgtttgccc ctcccccgtg ccttccttga ccctggaagg tgccactccc actgtccttt   6060
cctaataaaa tgaggaaatt gcatcgcatt gtctgagtag tgtcattct attctggggg     6120
gtggggtggg gcaggacagc aagggggagg attgggaaga caatagcagg catgctgggg   6180
atgcggtggg ctctatggct tctgaggcgg aaagaaccag ctggggctcg ataccgtcga   6240
cctctagcta gagcttggcg taatcatggt catagctgtt tcctgtgtga aattgttatc   6300
cgctcacaat tccacacaac atacgagccg gaagcataaa gtgtaaagcc tagggtgcct   6360
aatgagtgag ctaactcaca ttaattgcgt tgcgctcact gcccgctttc cagtcgggaa   6420
acctgtcgtg ccagctgcat taatgaatcg gccaacgcgc ggggagaggc ggtttgcgta   6480
ttgggcgctc ttccgcttcc tcgctcactg actcgctgcg ctcggtcgtt cggctgcggc   6540
gagcggtatc agctcactca aaggcggtaa tacggttatc cacagaatca ggggataacg   6600
caggaaagaa catgtgagca aaaggccagc aaaaggccag gaaccgtaaa aaggccgcgt   6660
tgctggcgtt tttccatagg ctccgccccc ctgacgagca tcacaaaaat cgacgctcaa   6720
gtcagaggtg gcgaaacccg acaggactat aaagatacca ggcgtttccc cctggaagct   6780
ccctcgtgcg ctctcctgtt ccgaccctgc cgcttaccgg atacctgtcc gcctttctcc   6840
cttcgggaag cgtggcgctt tctcatagct cacgctgtag gtatctcagt tcggtgtagg   6900
tcgttcgctc caagctgggc tgtgtgcacg aaccccccgt tcagcccgac cgctgcgcct   6960
tatccggtaa ctatcgtctt gagtccaacc cggtaagaca cgacttatcg ccactggcag   7020
cagccactgg taacaggatt agcagagcga ggtatgtagg cggtgctaca gagttcttga   7080
agtggtggcc taactacggc tacactagaa gaacagtatt tggtatctgc gctctgctga   7140
agccagttac cttcggaaaa agagttggta gctcttgatc cggcaaacaa accaccgctg   7200
gtagcggtgg ttttttttgtt tgcaagcagc agattacgcg cagaaaaaaa ggatctcaag   7260
aagatccttt gatcttttct acggggtctg acactcaggta gaacgaaaac tcacgttaag   7320
ggattttggt catgagatta tcaaaaagga tcttcaccta gatcctttta aattaaaaat   7380
gaagttttaa atcaatctaa agtatatatg agtaaacttg gtctgacagt taccaatgct   7440
taatcagtga ggcacctatc tcagcgatct gtctatttcg ttcatccata gttgcctgac   7500
tccccgtcgt gtagataact acgatacggg agggcttacc atctggcccc agtgctgcaa   7560
tgataccgcg agaccacgc tcaccggctc cagatttatc agcaataaac cagccagccg    7620
gaagggccga gcgcagaagt ggtcctgcaa ctttatccgc ctccatccag tctattaatt   7680
gttgccggga agctagagta agtagttcgc cagttaatag tttgcgcaac gttgttgcca   7740
ttgctacagg catcgtggtg tcacgctcgt cgtttggtat ggcttcattc agctccggtt   7800
cccaacgatc aaggcgagtt acatgatccc ccatgttgtg caaaaaagcg gttagctcct   7860
tcggtcctcc gatcgttgtc agaagtaagt tggccgcagt gttatcactc atggttatgg   7920
cagcactgca taattctctt actgtcatgc catccgtaag atgcttttct gtgactggtg   7980
agtactcaac caagtcattc tgagaatagt gtatgcggcg accgagttgc tcttgcccgg   8040
cgtcaatacg ggataatacc gcgccacata gcagaacttt aaaagtgctc atcattggaa   8100
aacgttcttc ggggcgaaaa ctctcaagga tcttaccgct gttgagatcc agttcgatgt   8160
aacccactcg tgcacccaac tgatcttcag catcttttac tttcaccagc gtttctgggt   8220
gagcaaaaac aggaaggcaa aatgccgcaa aaaagggaat aagggcgaca cggaaatgtt   8280
gaatactcat actcttcctt tttcaatatt attgaagcat ttatcagggt tattgtctca   8340
tgagcggata catatttgaa tgtatttaga aaaataaaca aataggggtt ccgcgcacat   8400
ttccccgaaa agtgccacct gacgtcgacg gatcgggaga tcgatctccc gatccctag   8460
ggtcgactct cagtacaatc tgctctgatg ccgcatagtt aagccagtat ctgctccctg   8520
cttgtgtgtt ggaggtcgct gagtagtgcg cgagcaaaat ttaagctaca acaaggcaag   8580
gcttgaccga caattgcatg aagaatctgc ttagggttag gcgttttgcg ctgcttcgcg   8640
atgtacgggc cagatatacg cgttgacatt gattattgac tagttattaa tagtaatcaa   8700
ttacggggtc attagttcat agcccatata tggagttccg cgttacataa cttacggtaa   8760
atggcccgcc tggctgaccg cccaacgacc cccgcccatt gacgtcaata atgacgtatg   8820
ttcccatagt aacgccaata gggactttcc attgacgtca tgggtggag tatttacggt     8880
aaaactgccca cttggcagta catcaagtgt atc                                8913

SEQ ID NO: 41       moltype = DNA  length = 8913
FEATURE             Location/Qualifiers
source              1..8913
                    mol_type = other DNA
                    organism = Synthetic construct
SEQUENCE: 41
atatgccaag tacgcccct attgacgtca atgacggtaa atggcccgcc tggcattatg     60
cccagtacat gaccttatgg gactttccta cttggcagta catctacgta ttagtcatcg    120
```

-continued

```
ctattaccat ggtgatgcgg ttttggcagt acatcaatgg gcgtggatag cggtttgact    180
cacgggggatt tccaagtctc caccccattg acgtcaatgg gagtttgttt tggcaccaaa    240
atcaacggga ctttccaaaa tgtcgtaaca actccgcccc attgacgcaa atgggcggta    300
ggcgtgtacg gtgggaggtc tatataagca gagctggttt agtgaaccgt cagatccgct    360
agagatccgc ggccgctaat acgactcact atagggagac ccgccaccct gaaacggaca    420
gccgacggaa gcgagttcga gtcaccaaag aagaagcgga aagtcagcag tgacaagaag    480
tacagcatcg gcctggccat cggcaccaac tctgtgggct gggccgtgat caccgacgag    540
tacaaggtgc ccagcaagaa attcaaggtg ctgggcaaca ccgaccggca cagcatcaag    600
aagaacctga tcggagccct gctgttcgac agcggcgaaa cagccgaggc caccccggctg   660
aagagaaccg ccagaagaag ataccaccaga cggaagaacc ggatctgcta tctgcaagag    720
atcttcagca acgagatggc caaggtggac gacagcttct tccacagact ggaagagtcc    780
ttcctggtgg aagaggataa aagcacgag cggcacccca tcttcggcaa catcgtggac    840
gaggtggcct accacgagaa gtaccccacc atctaccacc tgagaaagaa actggtggac    900
agcaccgaca aggccgacct gcggctgatc tatctgggcct tggcccacat gatcaagttc    960
cggggccact tcctgatcga gggcgacctg aaccccgaca acagcgacgt ggacaagctg   1020
ttcatccagc tggtgcagac ctacaaccag ctgttcgagg aaaacccat caacgccagc   1080
ggcgtggacg ccaaggccat cctgtctgcc agactgagca gagcagacg gctggaaaat   1140
ctgatcgccc agctgcccgg cgagaagaag aatggcctgt tcggaaacct gattgccctg   1200
agcctgggcc tgaccccaa cttcaagagc aacttcgacc tggccgagga tgccaaactg   1260
cagctgagca aggacaccta cgacgacgac ctggacaacc tgctggccca gatcggcgac   1320
cagtacgccg acctgtttct ggccgccaag aacctgtccg acgccatcct gctgagcgac   1380
atcctgagag tgaacaccga gatcaccaag gccccccctg gcctctat gatcaagaga     1440
tacgacgagc accaccagga cctgaccctg ctgaaagctc tcgtgcggca gcagctgcct   1500
gagaagtaca aagagatttt cttcgaccag agcaagaacg gctacgccgg ctacattgac   1560
ggcggagcca gccaggaaga gttctacaag ttcatcaagc ccatcctgga aaagatggac   1620
ggcaccgagg aactgctcgt gaagctgaac agagaggacc tgctgcggaa aaccgtggcc   1680
ttcgacaacg gcagcatccc ccaccagatc cacctgggga agctgcacgc cattctgcgg   1740
cggcaggaag attttttacccc attcctgaag gacaaccggg aaaagatcga gaagatcctg   1800
accttccgca tccctacta cgtgggccct ctggccaggg gaaacagcag attcgcctgg   1860
atgaccagaa agagcgagga aaccatcacc cctgaggaagt ggtggacaag               1920
ggcgcttccg cccagagctt catcgagcgg atgaccaact tcgataagaa cctgcccaac   1980
gagaaggtgc tgcccaagca cagcctgctg tacgagtact tcaccgtgta taacgagctg   2040
accaaagtga aatacgtgac cgaggggaatg agaaagcccg ccttcctgag cggcgagcag   2100
aaaaaggcca tcgtggacct gctgttcaag accaaccgga aagtgaccgt gaagcagctg   2160
aaagaggact acttcaagaa aatcgagtgc ttcgactccg tggaaatctc cggcgtggaa   2220
gatcggttca acgcctccct gggcacatac cacgatctgc tgaaaattat caaggacaag   2280
gacttcctgg acaatgagga aaacgaggac attctggaag atatcgtgct gaccctgaca   2340
ctgtttgagg acagagagat gatcgaggaa cggctgaaaa cctatgccca cctgttcgac   2400
gacaaagtga tgaagcagct gaagcggcgg agatacacgg gctgggcag gctgagccgg   2460
aagctgatca acggcatccg ggacaagcag tccggcaaga caatcctgga tttcctgaag   2520
tccgacggct cgccaacag aaacttcatg cagctgatcc acgacgacag cctgaccttt   2580
aaagaggaca tccagaaagc ccaggtgtcc ggccagggcg atagcctgca cgagcacatt   2640
gccaatctgg ccggcagccc cgccattaag aagggactc tgcagacagt gaaggtggtg   2700
gacgagctcg tgaaagtgat gggccggcac aagcccgaga acatcgtgat cgaaatggcc   2760
agagagaacc agaccacca gaagggacag aagaacagcc gcgagagaat gaagcggatc   2820
gaagagggca tcaaagagct gggcagccag atcctgaaag aacacccgt ggaaaacacc   2880
cagctgcaga acgagaaagct gtacctgtac tacctgcaga atggggcgga tatgtacgtg   2940
gaccaggaac tggacatcaa ctctggagga tctagcggtg ttcctctgg aagcgagaca   3000
ccaggcacaa gcgagtccgc cacaccagag agctccggcg gctcctccgg aggatcctct   3060
gaggtggagt tttcccacga gtactggatg agacatgccc tgaccctggc caagagggca   3120
tgggatgaaa gagaagtccc cgtgggcgcc gtgctggtgc acaacaatag agtgatcgga   3180
gagggatgga acaggccaat cggccggcca gaccctaccg cacacgcaga gatcatggca   3240
ctgaggcagg gaggcctggt catgcagaat accgcctga tcgatgccac cctgtatgtg   3300
acactggagc catgcgtgat gtgcgcagga gcaatgatcc acagcaggat cggaagagtg   3360
gtgttcggag cacgggacgc caagaccggc gcagcaggct ccctgatgga tgtgctgcac   3420
caccccggca tgaaccaccg ggtgagatc acagagggaa tcctggcaga cgagtgcgcc   3480
gccctgctga gcgatttctt tagaatgcgg agacaggaga tcaaggccca gaagaaggca   3540
cagagctcca ccgactctgg aggatctagc ggcggatcct ctggaagcga gacaccaggc   3600
acaagcgagt ccgccacacc agagagctcc ggcggctcct ctggaggtg                3660
gagttttccc acgagtactg gatgagacat gccctgaccc tggccaagag ggcacgcat   3720
gagagggagg tgcctgtggg agccgtgctg gtgctgaaca atagagtgat cggcgagggc   3780
tggaacagag ccatcggcct gcacgaccca acagccatg ccgaaattat ggccctgaga   3840
cagggcgcc tggtcatgca gaactacaga ctgattacg ccacccctgta cgtgacattc   3900
agccttgcg tgatgtgcgc cggcgccatg atccactcta ggatcggccg cgtggtgttt   3960
ggcgtgagga acgcaaaaac cggcgccgca ggctccctga tggacgtgct gcactacccc   4020
ggcatgaatc accgcgtcga aattaccgag ggaatcctgg cagatgaatg tgccgccctg   4080
ctgtgctatt tctttcggat gcctagacag gtgttcaatg ctcagaagaa ggcccagagc   4140
tccaccgact ccggaggatc tagcggaggc tcctctggct ctgagacacc tggcacaagc   4200
gagagcgcaa cacctgaaag cagcggggc agcagcggga gtcacggctc gtccgactac   4260
gatgtggacc atatcgtgcc tcagagcttt ctgaaggacg actccatcga caacaaggtg   4320
ctgaccagaa gcgacaagaa ccggggcaag agcgacaacg tgccctccga agaggtcgtg   4380
aagaagatga agaactactg gcggcagctg ctgaacgcca agctgattac ccagagaaag   4440
ttcgacaatc tgaccaaggc cgagagaggc ggcctgagcg aactggataa ggccggcttc   4500
atcaagagac agctggtgga aacccggcag atcacaaagc acgtggccaa gatcctggac   4560
tcccggatga acactaagta cgacgagaat gacaagctga tccggaagt gaaagtgatc   4620
accctgaagt ccaagctggt gtccgatttc cggaaggatt tccagtttta caaagtgcgc   4680
gagatcaaca actaccacca cgcccacgac gcctacctga acgccgtcgt gggaaccgcc   4740
ctgatcaaaa agtaccctaa gctggaaagc gagttcgtgt acggcgacta caaggtgtac   4800
gacgtgcgga agatgatcgc caagagcgag caggaaatcg gcaaggctac cgccaagtac   4860
```

```
ttcttctaca gcaacatcat gaacttttc aagaccgaga ttaccctggc caacggcgag    4920
atccggaagc ggcctctgat cgagacaaac ggcgaaaccg gggagatcgt gtgggataag    4980
ggccgggatt tgccaccgt gcggaaagtg ctgagcatgc cccaagtgaa tatcgtgaaa    5040
aagaccgagg tgcagacagg cggcttcagc aaagagtcta tcctgcccaa gaggaacagc    5100
gataagtcga tcgccagaaa gaaggactgg gaccctaaga agtacggcgg cttcgacagc    5160
cccaccgtgg cctattctgt gctggtggtg gccaaagtgg aaaagggcaa gtccaagaaa    5220
ctgaagagtg tgaaagagct gctggggatc accatcatgg aaagaagcag cttcgagaag    5280
aatcccatcg actttctgga agccaagggc tacaaagaag tgaaaaagga cctgatcatc    5340
aagctgccta gtactccct gttcgagctg gaaaaccggc ggaagagaat gctggcctct    5400
gccggcgaac tgcagaaggg aaacgaactg gccctgccct ccaaatatgt gaacttcctg    5460
tacctggcca gccactatga gaagctgaag ggctcccccg aggataatga gcagaaacag    5520
ctgtttgtgg aacagcacaa gcactacctg gacgagatca tcgagcagat cagcgagttc    5580
tccaagagag tgatcctggc cgacgctaat ctggacaaaa tgctgtccgc ctacaacaag    5640
caccgggata agcccatcag agagcaggcc gagaatatca tccacctgtt taccctgacc    5700
aatctgggga cccctgccgc cttcaagtac tttgacacca ccatcgaccg gaagaggtac    5760
accagcacca aagaggtgct ggacgccacc ctgatccacc agagcatcac cggcctgtac    5820
gagacacgga tcgacctgtc tcagctggga ggtgactctg cgggctcaaa agaaccgcgc    5880
gacggcagcg aattcgagcc caagaagaag aggaaagtct aaccggtcat catcaccatc    5940
accattgagt ttaaacccgc tgatcagcct cgactgtgcc ttctagttgc cagccatctg    6000
ttgtttgccc ctcccccgtg ccttccttga ccctggaagg tgccactccc actgtccttt    6060
cctaataaaa tgaggaaatt gcatcgcatt gtctgagtag tgtcattct attctgggggg    6120
gtggggtggg gcaggacagc aagggggagg attgggaaga caatagcaag catgctgggg    6180
atgcggtggg ctctatggct tctgaggcgg aaagaaccag ctgggctcg ataccgtcga    6240
cctctagcta gagcttggcg taatcatggt catagctgtt tcctgtgtga aattgttatc    6300
cgctcacaat tccacacaac atacgagccg gaagcataaa gtgtaaagcc tagggtgcct    6360
aatgagtgag ctaactcaca ttaattgcgt tgcgctcact gcccgctttc cagtcgggaa    6420
acctgtcgtg ccagctgcat taatgaatcg gccaacgcgc ggggagaggc ggtttgcgta    6480
ttgggcgctc ttccgcttcc tcgctcactg actcgctgcg ctcggtcgtt cggctgcggc    6540
gagcggtatc agctcactca aaggcggtaa tacggttatc cacagaatca ggggataacg    6600
caggaaagaa catgtgagca aaaggccagc aaaaggccag gaaccgtaaa aaggccgcgt    6660
tgctggcgtt tttccatagg ctccgccccc ctgacgagca tcacaaaaat cgacgctcaa    6720
gtcagaggtg gcgaaacccg acaggactat aaagatacca ggcgtttccc cctggaagct    6780
ccctcgtgcg ctctcctgtt ccgaccctgc cgcttaccgg atacctgtcc gcctttctcc    6840
cttcgggaag cgtggcgctt tctcatagct cacgctgtag gtatctcagt tcggtgtagg    6900
tcgttcgctc caagctgggc tgtgtgcacg aaccccccgt tcagcccgac cgctgcgcct    6960
tatccggtaa ctatcgtctt gagtccaacc cggtaagaca cgacttatcg ccactggcag    7020
cagccactgg taacaggatt agcagagcga ggtatgtagg cggtgctaca gagttcttga    7080
agtggtggcc taactacggc tacactagaa gaacagtatt tggtatctgc gctctgctga    7140
agccagttac cttcggaaaa agagttggta gctcttgatc cggcaaacaa accaccgctg    7200
gtagcggtgg tttttttgtt tgcaagcagc agattacgcg cagaaaaaaa ggatctcaag    7260
aagatccttt gatcttttct acggggtctg acactcagtg gaacgaaaac tcacgttaag    7320
ggattttggt catgagatta tcaaaaagga tcttcaccta gatcctttta aattaaaaat    7380
gaagttttaa atcaatctaa agtatatatg agtaaacttg gtctgacagt taccaatgct    7440
taatcagtga ggcacctatc tcagcgatct gtctatttcg ttcatccata gttgcctgac    7500
tccccgtcgt gtagataact acgatacggg agggcttacc atctggcccc agtgctgcaa    7560
tgataccgcg agacccacgc tcaccggctc cagatttatc agcaataaac cagccagccg    7620
gaagggccga gcgcagaagt ggtcctgcaa ctttatccgc ctccatccag tctattaatt    7680
gttgccggga agctagagta agtagttcgc cagttaatag tttgcgcaac gttgttgcca    7740
ttgctacagg catcgtggtg tcacgctcgt cgtttggtat ggcttcattc agctccggtt    7800
cccaacgatc aaggcgagtt acatgatccc ccatgttgtg caaaaaagcg gttagctcct    7860
tcggtcctcc gatcgttgtc agaagtaagt tggccgcagt gttatcactc atggttatgg    7920
cagcactgca taattctctt actgtcatgc catccgtaag atgcttttct gtgactggtg    7980
agtactcaac caagtcattc tgagaatagt gtatgcggcg accgagttgc tcttgcccgg    8040
cgtcaatacg gataataccg cgccacata gcagaacttt aaaagtgctc atcattggaa    8100
aacgttcttc ggggcgaaaa ctctcaagga tcttaccgct gttgagatcc agttcgatgt    8160
aacccactcg tgcacccaac tgatcttcag catctttac tttcaccagc gtttctgggt    8220
gagcaaaaac aggaaggcaa aatgccgcaa aaaagggaat aagggcgaca cggaaatgtt    8280
gaatactcat actcttcctt tttcaatatt attgaagcat ttatcagggt tattgtctca    8340
tgagcggata catatttgaa tgtatttaga aaaataaaca aataggggtt ccgcgcacat    8400
ttccccgaaa agtgccacct gacgtcgacg gatcgggaga tcgatctccc gatccctag    8460
ggtcgactct cagtacaatc tgctctgatg ccgcatagtt aagccagtat ctgctccctg    8520
cttgtgtgtt ggaggtcgct gagtagtgcg cgagcaaaat ttaagctaca acaaggcaag    8580
gcttgaccga caattgcatg aagaatctgc ttagggttag gcgttttgcg ctgcttcgcg    8640
atgtacgggc cagatatacg cgttgacatt gattattgac tagttattaa tagtaatcaa    8700
ttacggggtc attagttcat agcccatata tggagttccg cgttacataa cttacggtaa    8760
atggcccgcc tggctgaccg cccaacgacc cccgcccatt gacgtcaata atgacgtatg    8820
ttcccatagt aacgccaata gggactttcc attgacgtca atgggtggag tatttacggt    8880
aaactgccca cttggcagta catcaagtgt atc                                 8913

SEQ ID NO: 42        moltype = DNA   length = 8913
FEATURE              Location/Qualifiers
source               1..8913
                     mol_type = other DNA
                     organism = Synthetic construct
SEQUENCE: 42
atatgccaag tacgccccct attgacgtca atgacggtaa atggcccgcc tggcattatg     60
cccagtacat gaccttatgg gactttccta cttggcagta catctacgta ttagtcatcg    120
ctattaccat ggtgatgcgg ttttggcagt acatcaatgg gcgtggatag cggtttgact    180
cacggggatt tccaagtctc caccccattg acgtcaatgg gagtttgttt tggcaccaaa    240
```

```
atcaacggga ctttccaaaa tgtcgtaaca actccgcccc attgacgcaa atgggcggta    300
ggcgtgtacg gtgggaggtc tatataagca gagctggttt agtgaaccgt cagatccgct    360
agagatccgc ggccgctaat acgactcact atagggagag ccgccaccat gaaacgaca    420
gccgacggaa gcgagttcga gtcaccaaag aagaagcgga agtcagcag tgacaagaag    480
tacagcatcg gcctggccat cggcaccaac tctgtgggct gggccgtgat caccgacgag    540
tacaaggtgc ccagcaagaa attcaaggtg ctgggcaaca ccgaccggca cagcatcaag    600
aagaacctga tcggagccct gctgttcgac agcggcgaaa cagccgaggc cacccggctg    660
aagagaaccg ccagaagaag atacaccaga cggaagaacc ggatctgcta tctgcaagag    720
atcttcagca acgagatggc caaggtggac gacagcttct tccacagact ggaagagtcc    780
ttcctggtgg aagaggataa gaagcacgag cggcacccca tcttcggcaa catcgtggac    840
gaggtggcct accacgagaa gtaccccacc atctaccacc tgagaaagaa actggtggac    900
agcaccgaca aggccgacct gcggctgatc tatctggccc tggccacat gatcaagttc    960
cggggccact tcctgatcga gggcgacctg aaccccgaca cagcgacgt ggacaagctg   1020
ttcatccagc tggtgcagac ctacaaccag ctgttccaga aaaaccccat caacgccagc   1080
ggcgtggacg ccaaggccat cctgtctgcc agactgagca gagcagacg gctgaaaat   1140
ctgatcgccc agctgccgg cgagaagaag aatggcctgt tcggaaacct gattgccctg   1200
agcctgggcc tgaccccaa cttcaagagc aacttcgacc tggccgagga tgccaaactg   1260
cagctgagca aggacaccta cgacgacgac ctggacaacc tgctggccca gatcggcgac   1320
cagtacgccg acctgtttct ggccgccaag aacctgtccg acgccatcct gctgagcgac   1380
atcctgagag tgaacaccga gatcaccaag gcccccctga gcgcctctat gatcaagaga   1440
tacgacgagc accaccagga cctgacctg ctgaaagctc tcgtgcgca gcagctgcct   1500
gagaagtaca aagagatttt cttcgaccag agcaagaacg gctacgccgg ctacattgac   1560
ggcggagcca gccaggaaga gttctacaag ttcatcaagc catcctgga aagatggac   1620
ggcaccgagg aactgctcgt gaagctgaac agagaggacc tgctgcgaa gcagcggacc   1680
ttcgacaacg gcagcatccc ccaccagatc cacctgggag agctgcacg cattctgcgg   1740
cggcaggaag attttaccc attcctgaag gacaaccgg aaagatcga gaagatcctg   1800
accttccgca tcccctacta cgtgggccct ctggccaggg gaaacagcag attcgcctgg   1860
atgaccagaa agagcgagga aaccatcacc cctggaact tcgaggaagt ggtgacaag   1920
ggcgcttccg cccagagctt catcgagcgg atgaccaact tcgataagaa cctgcccaac   1980
gagaaggtgc tgcccaagca cagcctgctg tacgagtact tcaccgtgta taacgagctg   2040
accaaagtga atacgtgac cgagggaatg agaaagcccg cttcctgag cggcgagcag   2100
aaaaaggcca tcgtgacct gctgttcaag accaaccgga aagtgaccgt gaagcagctg   2160
aaagaggact acttcaagaa atcgagtgc ttcgactccg tggaaatctc cggcgtggaa   2220
gatcggttca acgcctccct gggcacatac cacgatctgc tgaaaattat caaggacaag   2280
gacttcctgg acaatgagga aaacgaggac attctggaag atatcgtgct gaccctgaca   2340
ctgtttgagg acagagagat gatcgaggaa cggctgaaaa cctatgccca cctgttcgac   2400
gacaaagtga tgaagcagct gaagcggcgg agatacaccg ctggggcag gctgagccgg   2460
aagctgatca acggcatccg ggacaagcag tccggcaaga caatcctgga tttcctgaag   2520
tccgacggct tcgccaacag aaacttcatg cagctgatcc acgacgacag cctgaccttt   2580
aaagaggaca tccagaaagc ccaggtgtcc ggccagggcg atagcctgca cgagcacatt   2640
gccaatctgg ccggcagccc cgccattaag aagggcatcc tgcagacagt gaaggtggtg   2700
gacgagctcg tgaaagtgat gggccggcac aagcccgaga catcgtgat cgaaatggcc   2760
agagagaaacc agaccaccca gaagggacag aagaacagcc gcgagagaat gaagcggat   2820
gaagagggca tcaaagagct gggcagccag atcctgaaag aacacccggt ggaaaacacc   2880
cagctgcaga acgagaagct gtacctgtac tacctgcaga atgggcggga tatgtacgtg   2940
gaccaggaac tggacatcaa ccggctgtcc gactacgatg tggaccatat cgtgcctcag   3000
agcttcctga aggacgactc catcgacaac aagtgctga ccagaagcga caagaaccgg   3060
ggcaagagcg acaacgtgcc ctccgaagag gtcgtgaaga agatgaagaa ctactggcg   3120
cagctgctga acgccaagct gattaccag agaaagttcg acaatctgac caaggccgag   3180
agaggcggcc tgagcgaact ggataaggcc ggcttcatca gagacagct ggtggaaacc   3240
tctgcaggat ctagcggtgg ttcctctgga agcgagacac caggcacaag cgagtccgga   3300
acaccagaga gctccggcgg ctcctccgga ggatcctcg aggtggagtt ttcccacgag   3360
tactggatga gacatgccct gacccctggcc aagagggcat gggatgaaag agaagtcccc   3420
gtgggcgccg tgctggtgca acaatagag gatcggag agggatgaa caggccaatc   3480
ggccgccacg acccacgc acacgcagag atcatgcgac tgaggcaggg aggcctggtc   3540
atgcagaatt accgcctgat cgatgccacc ctgtatgtga cactggagcc atgcgtgatg   3600
tgcgcaggag caatgatcca cagcaggatc ggaagagtgg tgttcggagc acggacgcc   3660
aagaccggcg cagcaggctc cctgatggat gtgctgcacc accccggcat gaaccaccgg   3720
gtggagatca cagagggaat cctggcagag gagtgcgccg ccctgctgag cgatttcttt   3780
agaatgcgga gacaggagat caaggcccag aagaaggcac agagctccac cgactctgga   3840
ggatctagcg gcggatcctc tggaagcgag acaccaggca aagcgagtc cgccacacca   3900
gagagctccg gcggctcctc cggaggatcc tctgaggtgg agtttcccca cgagtactgg   3960
atgagacatg ccctgaccct ggccaagagg gcacgcgatg agagggaggt gcctgtggga   4020
gccgtgctgg tgctgaacaa tagtgatc gcgagggct ggaacagag catcggcctg   4080
cacgacccaa cagcccatgc cgaaattatg gccctgagac agggcggcct ggtcatgcag   4140
aactacagac tgattgacgc cacctgtac gtgacattcg agcctgcgt gatgtgcgcc   4200
ggcgccatga tccactctag gatcggccgc gtggtgtttg gcgtgaggaa cgcaaaaacc   4260
ggcgccgcag gctccctgat ggacgtgctg cactacccg gcatgaatca ccgcgtcgaa   4320
attaccggga gaatcctggc agatgaatgt gccgccctgc tgtgctatt ctttcggatg   4380
cctagacagg tgttcaatgc tcagaagaag gcccagagct ccaccgactc cggaggatct   4440
agcggaggct cctctggctc tgagacacct ggcacaagcg agagcgcaac acctgaaagc   4500
agcggggca gcagcggggg gtcacggcag atcacaaagc acgtggcaca gatcctggac   4560
tcccggatga acactaagta cgacgagaat gacaagctga tccgggaagt gaaagtgatc   4620
accctgaagt ccaagctggt gtccgatttc cggaaggatt tccagtttta caaagtgcga   4680
gagatcaaca actaccacca cgcccacgac gcctacctga acgccgtcgt gggaaccgcc   4740
ctgatcaaaa agtaccctaa gctggaaagc gagttcgtgt acggcgacta caaggtgtac   4800
gacgtgcgga agatgatcgc caagagcgag caggaaatcg gcaaggctac cgccaagtac   4860
ttcttctaca gcaacatcat gaactttttc aagaccgaga ttaccctggc caacggcgag   4920
atccggaagc ggcctctgat cgagacaaac ggcgaaaccg gggagatcgt gtgggataag   4980
```

```
ggccgggatt tgccaccgt gcggaaagtg ctgagcatgc cccaagtgaa tatcgtgaaa    5040
aagaccgagg tgcagacagg cggcttcagc aaagagtcta tcctgcccaa gaggaacagc    5100
gataagctga tcgccagaaa gaaggactgg gaccctaaga agtacggcgg cttcgacagc    5160
cccaccgtgg cctattctgt gctggtggtg gccaagtggg aaaagggcaa gtccaagaaa    5220
ctgaaggtg tgaaagagct gctggggatc accatcatga aaagaagcag cttcgagaag    5280
aatcccatcg actttctgga agccaagggc tacaaagaag tgaaaaagga cctgatcatc    5340
aagctgccta agtactccct gttcgagctg aaaacggcc ggaagagaat gctggcctct    5400
gccggcgaac tgcagaaggg aaacgaactg ccctgccct ccaaatatgt gaacttcctg    5460
tacctggcca gccactatga gaagctgaag ggctcccccg aggataatga gcagaaacag    5520
ctgtttgtgg aacagcacaa gcactacctg gacgagatca tcgagcagat cagcgagttc    5580
tccaagagag tgatcctggc cgacgctaat ctggacaaag tgctgtccgc ctacaacaag    5640
caccgggata agcccatcag agagcaggcc gagaatatca tccacctgtt taccctgacc    5700
aatctgggag cccctgccgc cttcaagtac tttgacacca ccatcgaccg gaagaggtac    5760
accagcacca aagaggtgct ggacgccacc ctgatccacc agagcatcac cggcctgtac    5820
gagacacgga tcgacctgtc tcagctggga ggtgactctg gcggctcaaa aagaaccgcc    5880
gacggcagcg aattcgagcc caagaagaag aggaaagtct aaccggtcat catcaccatc    5940
accattgagt ttaaacccgc tgatcagcct cgactgtgcc ttctagttgc cagccatctg    6000
ttgtttgccc ctcccccgtg ccttccttga ccctggaagg tgccactccc actgtccttt    6060
cctaataaaa tgaggaaatt gcatcgcatt gtctgagtag tgtcattct attctggggg    6120
gtggggtggg gcaggacagc aagggggagg attgggaaga caatagcagg catgctgggg    6180
atgcggtggg ctctatggct tctgaggcgg aaagaaccag ctgggctcg ataccgtcga    6240
cctctagcta gagcttggcg taatcatggt catagctgtt tcctgtgtga aattgttatc    6300
cgctcacaat tccacacaac atacgagccg gaagcataaa gtgtaaagcc tagggtgcct    6360
aatgagtgag ctaactcaca ttaattgcgt tgcgctcact gcccgctttc cagtcgggaa    6420
acctgtcgtg ccagctgcat taatgaatcg gccaacgcgc ggggagaggc ggtttgcgta    6480
ttgggcgctc ttccgcttcc tcgctcactg actcgctgcg ctcggtcgtt cggctgcggc    6540
gagcggtatc agctcactca aaggcggtaa tacggttatc cacagaatca ggggataacg    6600
caggaaagaa catgtgagca aaaggccagc aaaaggccag gaaccgtaaa aaggccgcgt    6660
tgctggcgtt tttccatagg ctccgccccc ctgacgagca tcacaaaaat cgacgctcaa    6720
gtcagaggtg gcgaaacccg acaggactat aaagataccag gcgtttccc cctggaagct    6780
ccctcgtgcg ctctcctgtt ccgaccctgc cgcttaccgg atacctgtcc gcctttctcc    6840
cttcgggaag cgtggcgctt tctcatagct cacgctgtag gtatctcagt tcggtgtagg    6900
tcgttcgctc caagctgggc tgtgtgcacg aaccccccgt tcagcccgac cgctgcgcct    6960
tatccggtaa ctatcgtctt gagtccaacc cggtaagaca cgacttatcg ccactggcag    7020
cagccactgg taacaggatt agcagagcga ggtatgtagg cggtgctaca gagttcttga    7080
agtggtggcc taactacggc tacactagaa gaacagtatt tggtatctgc gctctgctga    7140
agccagttac cttcggaaaa agagttggta gctcttgatc cggcaaacaa accaccgctg    7200
gtagcggtgg tttttttgtt tgcaagcagc agattacgcg cagaaaaaaa ggatctcaag    7260
aagatccttt gatcttttct acggggtctg acactcagtg gaacgaaaac tcacgttaag    7320
ggattttggt catgagatta tcaaaaagga tcttcaccta gatcctttta aattaaaaat    7380
gaagttttaa atcaatctaa agtatatatg agtaaacttg gtctgacagt taccaatgct    7440
taatcagtga ggcacctatc tcagcgatct gtctatttcg ttcatccata gttgcctgac    7500
tccccgtcgt gtagataact acgatacggg agggcttac cagtcgtgca    7560
tgataccgcg agacccacgc tcaccggctc cagatttatc agcaataaac cagccagccg    7620
gaagggccga gcgcagaagt ggtcctgcaa ctttatccgc ctccatccag tctattaatt    7680
gttgccggga agctagagta agtagttcgc cagttaatag tttgcgcaac gttgttgcca    7740
ttgctacagg catcgtggtg tcacgctcgt cgtttggtat ggcttcattc agctccggtt    7800
cccaacgatc aaggcgagtt acatgatccc ccatgttgtg caaaaaagcg gttagctcct    7860
tcggtcctcc gatcgttgtc agaagtaagt tggccgcagt gttatcactc atggttatgg    7920
cagcactgca taattctctt actgtcatgc catccgtaag atgcttttct gtgactggtg    7980
agtactcaac caagtcattc tgagaatagt gtatgcggcg accgagttgc tcttgcccgg    8040
cgtcaatacg ggataatacc gcgccacata gcagaacttt aaaagtgctc atcattggaa    8100
aacgttcttc gggggcgaaaa ctctcaagga tcttaccgct gttgagatcc agttcgatgt    8160
aacccactcg tgcacccaac tgatcttcag catctttac tttcaccagc gtttctgggt    8220
gagcaaaaac aggaaggcaa aatgccgcaa aaaagggaat aagggcgaca cggaaatgtt    8280
gaatactcat actcttcctt tttcaatatt attgaagcat ttatcagggt tattgtctca    8340
tgagcggata catatttgaa tgtatttaga aaaataaaca aataggggtt ccgcgcacat    8400
ttccccgaaa agtgccacct gacgtcgacg gatcgggaga tcgatctccc gatccctag    8460
ggtcgactct cagtacaatc tgctctgatg ccgcatagtt aagccagtat ctgctccctg    8520
cttgtgtgtt ggaggtcgct gagtagtgcg cgagcaaaat ttaagctaca acaaggcaag    8580
gcttgaccga caattgcatg aagaatctgc ttagggttag gcgttttgcg ctgcttcgcg    8640
atgtacgggc cagatatacg cgttgacatt gattattgac tagttattaa tagtaatcaa    8700
ttacggggtc attagttcat agcccatata tggagttccg cgttacataa cttacggtaa    8760
atggcccgcc tggctgaccg cccaacgacc cccgcccatt gacgtcaata atgacgtatg    8820
ttcccatagt aacgccaata gggactttcc attgacgtca atgggtggag tatttacggt    8880
aaactgccca cttggcagta catcaagtgt atc                                  8913

SEQ ID NO: 43         moltype = DNA  length = 8913
FEATURE               Location/Qualifiers
source                1..8913
                      mol_type = other DNA
                      organism = Synthetic construct
SEQUENCE: 43
atatgccaag tacgcccct attgacgtca atgacggtaa atggcccgcc tggcattatg    60
cccagtacat gaccttatgg gactttccta cttggcagta catctacgta ttagtcatcg    120
ctattaccat ggtgatgcgg ttttggcagt acatcaatgg gcgtggatag cggtttgact    180
cacggggatt tccaagtctc caccccattg acgtcaatgg gagtttgttt tggcaccaaa    240
atcaacggga ctttccaaaa tgtcgtaaca actccgcccc attgacgcaa atgggcggta    300
ggcgtgtacg gtgggaggtc tatataagca gagctggttt agtgaaccgt cagatccgct    360
```

```
agagatccgc ggccgctaat acgactcact atagggagag ccgccaccat gaaacggaca   420
gccgacggaa gcgagttcga gtcaccaaag aagaagcgga aagtcagcag tgacaagaag   480
tacagcatcg gcctggccat cggcaccaac tctgtgggct gggccgtgat caccgacgag   540
tacaaggtgc ccagcaagaa attcaaggtg ctgggcaaca ccgaccggca cagcatcaag   600
aagaacctga tcggagccct gctgttcgac agcggcgaaa cagccgaggc caccaggctg   660
aagagaaccg ccagaagaag ataccaccaga cggaagaacc ggatctgcta tctgcaagag   720
atcttcagca acgagatggc caaggtggac gacagcttct tccacagact ggaagagtcc   780
ttcctggtgg aagaggataa gaagcacgag cggcacccca tcttcggcaa catcgtggac   840
gaggtggcct accacgagaa gtaccccacc atctaccacc tgagaaagaa actggtggac   900
agcaccgaca aggccgacct gcggctgatc tatctggccc tggcccacat gatcaagttc   960
cggggccact tcctgatcga gggcgacctg aaccccgaca cagcgacgt ggacaagctg  1020
ttcatccagc tggtgcagac ctacaaccag ctgttcgagg aaaacccat caacgccagc  1080
ggcgtggacg ccaaggccat cctgtctgcc agactgagca gagcagacg gctgaaaat  1140
ctgatcgcg agctgccgt cgagaagaag aatggcctgt tcggaaacct gattgccctg  1200
agcctgggcc tgaccccaa cttcaagagc aacttcgacc tggccgagga tgccaaactg  1260
cagctgagca aggacaccta cgacgacgac ctggacaacc tgctggccca gatcggcgac  1320
cagtacgccg acctgtttct ggccgccaag aacctgtccg acgccatcct gctgagcgac  1380
atcctgagag tgaacaccga gatcaccaag gcccccctga tcagaagaga  1440
tacgacgagc accaccagga cctgaccctg ctgaaagctc tcgtgcggca gcagctgcct  1500
gagaagtaca agagattttt cttcgaccag agcaagaacg gctacgccgg ctacattgac  1560
ggcggagcca gccaggaaga gttctacaag ttcatcaagc ccatcctgga aaagatggac  1620
ggcaccgagg aactgctcgt gaagctgaac agagaggacc tgctgcggaa gcagcggacc  1680
ttcgacaacg gcagcatccc ccaccagatc cacctgggag agctgcacgc cattctgcgg  1740
cggcaggaag atttttaccc attcctgaag gacaaccggg aaaagatcga gaagatcctg  1800
accttccgca tcccctacta cgtgggccct ctggccaggg aaacagcag attcgcctgg  1860
atgaccagaa agagcgagga aaccatcacc cctgaggaagt tcgaggaagg ggtgacaag  1920
ggcgcttccg cccagagctt catcgagcgg atgaccaact tcgataagaa cctgcccaac  1980
gagaaggtgc tgcccaagca cagcctgctg tacgagtact tcaccgtgta taacgagctg  2040
accaaagtga aatacgtgac cgagggaatg agaaagcccg ccttcctgag cggcgagcag  2100
aaaaaggcca tcgtggacct gctgttcaag accaaccgga aagtgaccgt gaagcagctg  2160
aaagaggact acttcaagaa aatcgagtgc ttcgactccg tggaaatctc cggcgtggaa  2220
gatcggttca acgcctccct gggcacatac cacgatctgc tgaaaattat caggacaag  2280
gacttcctgg acaatgagga aaacgaggac attctggaag atatcgtgct gaccctgaca  2340
ctgtttgagg acagagagat gatcgaggaa cggctgaaaa cctatgccca cctgttcgac  2400
gacaaagtga tgaagcagct gaagcggcgg agatacaccg gctgggcag gctgagccgg  2460
aagctgatca acggcatccg ggacaagcag tccggcaaga caatcctgga tttcctgaag  2520
tccgacggct cgccaacag aaacttcatg cagctgatcc acgacgacag cctgaccttt  2580
aaagaggaca tccagaaagc ccaggtgtcc ggccagggcg atagcctgca cgagcacatt  2640
gccaatctgg ccggcagccc cgccattaag aagggcatct gcagacagt gaaggtgctg  2700
gacgagctcg tgaaagtgat gggccggcac aagcccgaga acatcgtgat cgaaatggcc  2760
agagagaacc agaccaccca gaagggacag aagaacagcc gcgagagaat gaagcggatc  2820
gaagagggca tcaaagagct gggcagccag atcctgaaag aacaccccgt ggaaaacacc  2880
cagctgcaga acgagaagct gtacctgtac tacctgcaga atgggcggga tatgtacgtg  2940
gaccaggaac tggacatcaa ccggctgtcc gactacgatg tggaccatat cgtgcctcag  3000
agctttctga aggacgactc catcgacaac aaggtgctga ccagaagcga caagaaccgg  3060
ggcaagagcg acaacgtgcc ctccgaagag gtcgtgaaga gatgaagaa ctactggcgg  3120
cagctgctga acgccaagct gattaccag agaaagttcg acaatctgac aaaggccgac  3180
agaggcggcc tgagcgaact ggataaggcc ggcttcatca agagacagct ggtgaaaacc  3240
cggcagatca caaagcacgt ggcacagatc ctggactccc ggatgaacac taagtacgac  3300
gagaatgaca agctgatccg ggaagtgaaa gtgatcaccc tgaagtccaa gctggtgtcc  3360
gatttccgga aggatttcca gttttacaaa gtgcgcgaga tcaacaacta ccaccacgcc  3420
cacgacgcct acctgaacgc cgtcgtggga accgccctga tcaaaaagta ccctaagctg  3480
gaaagcgagt tcgtgtctgg aggatctagc ggtggttcct ctggaagcga gacaccaggc  3540
acaagcgagt ccgccacacc agagagctcc ggcggctcct ccggaggatc ctctgaggtg  3600
gagttttccc acgagtactg gatgagacat gccctgacct tggccaagag ggcatgggat  3660
gaaagagaag tccccgtggg cgccgtgctg gtgcacaaca atagagtgat cggagaggga  3720
tggaacaggc caatcggccg ccacgaccct accgcacacg cagagatcat ggcactgagg  3780
cagggaggcc tggtcatgca gaattaccgc ctgatcgatg ccaccctgta tgtgacactg  3840
gagccatgcg tgatgtgcgc aggagcaatg atccacagca ggatcggaag agtggtgttc  3900
ggagcacggg acgccaagac cggcgcagca ggctccctga tggatgtgct gcaccaccc  3960
ggcatgaacc accgggtgga gatcacagag ggaatcctgg cagacgagtg cgccgccctg  4020
ctgagcgatt tctttagaat gcggagacag gagatcaagg cccagaagaa ggcacagagc  4080
tccaccgact ctggaggatc tagcggcgga tcctctggaa gcgagacacc aggcacaagc  4140
gagtccgcca caccagagag ctccggcggc tcctccggaa gatcctctga ggtggagttt  4200
tcccacgagt actggatgag acatgccctg accctggcca gagggcacg cgatgagagg  4260
gaggtgcctg tgggagccgt gctggtgctg aacaatagag tgatcggcga gggctggaac  4320
agagccatcg gcctgcacga cccaacagcc atgccgaaa ttatgccct gagacagggc  4380
ggcctggtca tgcagaacta cagactgatt gacgccaccc tgtacgtgac attcgagcct  4440
tgcgtgatgt gcgccggcgc catgatccac tctaggatcg gccgcgtgt gtttggcgtg  4500
aggaacgcaa aaaccggcgc cgcaggctcc ctgatgacg tgctgcacta ccccggcatg  4560
aatcaccgcg tcgaaattac cgagggaatc ctggcagatg aatgtgccgc cctgctgtgc  4620
tatttctttc ggatgcctag acaggtgttc aatgctcaga agaaggccca gagctccacc  4680
gactccggag gatctagcgg aggctcctct ggctctgaga cacctggcac aagcgagagc  4740
gcaacacctg aaagcagcgg ggggctcat ccggggacta caaggtcgtac  4800
gacgtgcgga gatgatcgc caagagcgag caggaaatcg gcaaggctac cgccaagtac  4860
ttcttctaca gcaacatcat gaactttttt aagaccgaga ttaccctggc caacggcgag  4920
atccggaagc ggcctctgat cgagacaaac ggcgaaaccg gggagatcgt gtgggataag  4980
ggccgggatt ttgccaccgt gcggaaagtg ctgagcatgc ccaagtgaa tatcgtgaaa  5040
aagaccgagg tgcagacagg cggcttcagc aaagagtcta tcctgcccaa gaggaacagc  5100
```

```
gataagctga tcgccagaaa gaaggactgg gaccctaaga agtacggcgcg cttcgacagc  5160
cccaccgtgg cctattctgt gctggtggtg gccaaagtgg aaaagggcaa gtccaagaaa  5220
ctgaagagtg tgaaagagct gctggggatc accatcatgg aaaagaagcag cttcgagaag  5280
aatcccatcg actttctgga agccaagggc tacaaagaag tgaaaaagga cctgatcatc  5340
aagctgccta agtactccct gttcgagctg gaaaacgcc ggaagagaat gctggcctct  5400
gccggcgaac tgcagaaggg aaacgaactg gccctgccct ccaaatatgt gaacttcctg  5460
tacctggcca gccactatga gaagctgaag ggctcccccg aggataatga gcagaaacag  5520
ctgtttgtgg aacagcacaa gcactacctg gacgagatca tcgagcagat cagcgagttc  5580
tccaagagag tgatcctggc cgacgctaat ctggacaaag tgctgtccgc ctacaacaag  5640
caccgggata agcccatcag agagcaggcc gagaatatca tccacctgtt taccctgacc  5700
aatctgggag cccctgccgc cttcaagtac tttgacacca ccatcgaccg gaagaggtac  5760
accagcacca aagaggtgct ggacgccacc ctgatccacc agagcatcac cggcctgtac  5820
gagacacgga tcgacctgtc tcagctggga ggtgactctg cggctcaaa aagaaccgcc  5880
gacggcagcg aattcgagcc caagaagaag aggaaagtct aaccggtcat catcaccatc  5940
accattgagt ttaaacccgc tgatcagcct cgactgtgcc ttctagttgc cagccatctg  6000
ttgtttgccc ctcccccgtg ccttccttga ccctggaagg tgccactccc actgtccttt  6060
cctaataaaa tgaggaaatt gcatcgcatt gtctgagtag gtgtcattct attctggggg  6120
gtggggtggg gcaggacagc aagggggagg attgggaaga caatagcagg catgctgggg  6180
atgcggtggg ctctatggct tctgaggcgg aaagaaccag ctgggctgcg ataccgtcga  6240
cctctagcta gagcttggcg taatcatggt catagctgtt tcctgtgtga aattgttatc  6300
cgctcacaat tccacacaac atacgagccg aagcataaa gtgtaaagcc tagggtgcct  6360
aatgagtgag ctaactcaca ttaattgcgt tgcgctcaat gcccgctttc cagtcgggaa  6420
acctgtcgtg ccagctgcat taatgaatcg gccaacgcgc ggggagaggc ggtttgcgta  6480
ttgggcgctc ttccgcttcc tcgctcactg actcgctgcg ctcggtcgtt cggctgcggc  6540
gagcggtatc agctcactca aaggcggtaa tacgttatc cacagaatca ggggataacg  6600
caggaaagaa catgtgagca aaaggccagc aaaaggccag gaaccgtaaa aaggccgcgt  6660
tgctggcgtt tttccatagg ctccgccccc ctgacgagca tcacaaaaat cgacgctcaa  6720
gtcagaggtg gcgaaacccg acaggactat aaagatacca ggcgtttccc cctggaagct  6780
ccctcgtgcg ctctcctgtt ccgaccctgc cgcttaccgg atacctgtcc gcctttctcc  6840
cttcggaaag cgtggcgctt tctcatagct cacgctgtag gtatctcagt tcggtgtagg  6900
tcgttcgctc caagctgggc tgtgtgcacg aaccccccgt tcagcccgac cgctgcgcct  6960
tatccggtaa ctatcgtctt gagtccaacc cggtaagaca cgacttatcg ccactggcag  7020
cagccactgg taacaggatt agcagagcga ggtatgtagg cggtgctaca gagttcttga  7080
agtggtggcc taactacggc tacactagaa gaacagtatt tggtatctgc gctctgctga  7140
agccagttac cttcggaaaa agagttggta gctcttgatc cggcaaacaa accaccgctg  7200
gtagcggtgg tttttttgtt tgcaagcagc agattacgcg cagaaaaaaa ggatctcaag  7260
aagatccttt gatcttttct acggggtctg acactcagtg gaacgaaaac tcacgttaag  7320
ggattttggt catgagatta tcaaaaagga tcttcaccta gatccttta aattaaaaat  7380
gaagttttaa atcaatctaa agtatatatg agtaaacttg gtctgacagt taccaatgct  7440
taatcagtga ggcacctatc tcagcgatct gtctatttcg ttcatccata gttgcctgac  7500
tccccgtcgt gtagataact acgatacggg agggcttacc atctggcccc agtgctgcaa  7560
tgataccgcg agacccacgc tcaccggctc cagatttatc agcaataaac cagccagccg  7620
gaagggccga gcgcagaagt ggtcctgcaa cttatccgc ctccatccag tctattaatt  7680
gttgccggga agctagagta agtagttcgc cagttaatag tttgcgcaac gttgttgcca  7740
ttgctacagg catcgtggtg tcacgctcgt cgtttggtat ggcttcattc agctccggtt  7800
cccaacgatc aaggcgagtt acatgatccc ccatgttgtg caaaaaagcg gttagctcct  7860
tcggtcctcc gatcgttgtc agaagtaagt tggccgcagt gttatcactc atggttatgg  7920
cagcactgca taattctctt actgtcatgc catccgtaag atgctttct gtgactggtg  7980
agtactcaac caagtcattc tgagaatagt gtatgcggcg accgagttgc tcttgcccgg  8040
cgtcaatacg ggataatacc gcgccacata gcagaacttt aaaagtgctc atcattggaa  8100
aacgttcttc ggggcgaaaa ctctcaagga tcttaccgct gttgagatcc agttcgatgt  8160
aacccactcg tgcacccaac tgatcttcag catcttttac tttcaccagc gtttctgggt  8220
gagcaaaaac aggaaggcaa aatgccgcaa aaaagggaat aagggcgaca cggaaatgtt  8280
gaatactcat actcttcctt tttcaatatt attgaagcat ttatcagggt tattgtctca  8340
tgagcggata catatttgaa tgtatttaga aaaataaaca ataggggttc cgcgcacat  8400
ttccccgaaa agtgccacct gacgtcgacg gatcgggaga tcgatctccc gatccctag  8460
ggtcgactct cagtacaatc tgctctgatg ccgcatagtt aagccagtat ctgctccctg  8520
cttgtgtgtt ggaggtcgct gagtagtgcg cgagcaaaat ttaagctaca acaaggcaag  8580
gcttgaccga caattgcatg aagaatctgc ttagggttag gcgttttgcg ctgcttcgcg  8640
atgtacgggc cagatatacg cgttgacatt gattattgac tagttattaa tagtaatcaa  8700
ttacggggtc attagttcat agcccatata tggagttccg cgttacataa cttacggtaa  8760
atggcccgcc tggctgaccg cccaacgacc cccgcccatt gacgtcaata atgacgtatg  8820
ttcccatagt aacgccaata gggactttcc attgacgtca atgggtggag tatttacggt  8880
aaactgccca cttggcagta catcaagtgt atc                                8913

SEQ ID NO: 44          moltype = DNA    length = 8913
FEATURE                Location/Qualifiers
source                 1..8913
                       mol_type = other DNA
                       organism = Synthetic construct SEQUENCE: 44
atatgccaag tacgccccct attgacgtca atgacggtaa atggcccgcc tggcattatg   60
cccagtacat gaccttatgg gactttccta cttggcagta catctacgta ttagtcatcg  120
ctattaccat ggtgatgcgg ttttggcagt acatcaatgg gcgtggatag cggtttgact  180
cacggggatt tccaagtctc caccccattg acgtcaatgg gagtttgttt tggcaccaaa  240
atcaacggga ctttccaaaa tgtcgtaaca actccgcccc attgacgcaa atgggcggta  300
ggcgtgtacg gtgggaggtc tatataagca gagctggttt agtgaaccgt cagatccgct  360
agagatccgg ccgctaat acgactcact ataggggagac cgccaccat gaaacgcgaca  420
gccgacggaa gcgagttcga gtcaccaaag aagaagcgga aagtcagcag tgacaagaag  480
```

```
tacagcatcg gcctggccat cggcaccaac tctgtgggct gggccgtgat caccgacgag   540
tacaaggtgc ccagcaagaa attcaaggtg ctgggcaaca ccgaccggca cagcatcaag   600
aagaacctga tcggagccct gctgttcgac agcggcgaaa cagccgaggc cacccggctg   660
aagagaaccg ccagaagaag atacaccaga cggaagaacc ggatctgcta tctgcaagag   720
atcttcagca acgagatggc caaggtggac gacagttct tccacagact ggaagagtcc   780
ttcctggtgg aagaggataa gaagcacgag cggcacccca tcttcggcaa catcgtggac   840
gaggtggcct accacgagaa gtaccccacc atctaccacc tgagaaagaa actggtggac   900
agcaccgaca aggccgacct gcggctgatc tatctggccc tggcccacat gatcaagttc   960
cggggccact tcctgatcga gggcgacctg aaccccgaca acagcgacgt ggacaagctg  1020
ttcatccagc tggtgcagac ctacaaccag ctgttcgagg aaaaccccat caacgccagc  1080
ggcgtggacg ccaaggccat cctgtctgcc agactgagca gagcagacg gctgaaaat   1140
ctgatcgccc agctgcccgg cgagaagaag aatggcctgt tcggaaacct gattgccctg  1200
agcctgggcc tgaccccaa cttcaagagc aacttcgacc tggccgagga tgccaaactg  1260
cagctgagca aggacaccta cgacgacgac ctggacaacc tgctggccca gatcggcgac  1320
cagtacgccg acctgtttct ggccgccaag aacctgtccg acgccatcct gctgagcgac  1380
atcctgagag tgaacaccga gatcaccaag gccccctga gcgcctctat gatcaagaga  1440
tacgacgagc accaccagga cctgaccctg ctgaaagctc tcgtgcggca gcagctgcct  1500
gagaagtaca aagagatttt cttcgaccag agcaagaacg gctacgccgg ctacattgac  1560
ggcggagcca gccaggaaga gttctacaag ttcatcaagc ccatcctgga aaagatggac  1620
ggcaccgagg aactgctcgt gaagctgaac agagaggacc tgctgcgaa gcagcggacc  1680
ttcgacaacg cagcatccc ccaccagatc cacctgggag agctgcacgc cattctgcgg  1740
cggcaggaag atttttaccc attcctgaag gacaaccgga aaaagatcga agatctgg   1800
accttccgca tccctacta cgtgggccct ctggccaggg aaacagcag attcgcctg   1860
atgaccagaa agagcgagga aaccatcacc cctggaact tcgaggaagt ggtggacaag   1920
ggcgcttccg cccagagctt catcgagcgg atgaccaact tcgataagaa cctgcccaac   1980
gagaaggtgc tgcccaagca cagcctgctg tacgagtact tcaccgtgta taacgagctg   2040
accaaagtga aatacgtgac cgagggaatg agaaagcccg ccttcctgag cggcgagcag   2100
aaaaaggcca tcgtggacct gctgttcaag accaaccgga aagtgaccgt gaagcagctg   2160
aaagaggact acttcaagaa aatcgagtgc ttcgactccg tggaaatctc cggcgtggaa   2220
gatcggttca acgcctccct gggcacatac cacgatctgc tgaaaattat caaggacaag   2280
gacttcctgg acaatgagga aaacgaggac attctggaag atatcgtgct gaccctgaca   2340
ctgtttgagg acagagagat gatcgaggaa cggctgaaaa cctatgccca cctgttcgac   2400
gacaaagtga tgaagcagct gaagcggcgg agatacaccg ctggggcag gctgagccgg   2460
aagctgatca acggcatccg ggacaagcag tccggcaaga caatcctgga tttcctgaag   2520
tccgacggct tcgccaacag aaacttcatg cagctgatcc acgacgacag cctgaccttt   2580
aaagaggaca tccagaaagc ccaggtgtcc ggccagggcg atagcctgca cgagcacatt   2640
gccaatctgg ccggcagccc cgccattaag aagggcatcc tgcagacagt gaaggtggtg   2700
gacgagctcg tgaaagtgat gggccggcac aagcccgaga acatcgtgat cgaaatggcc   2760
agagagaaa gaccaccca gaagggacag agaacagcc gcgagagaat gaagcggatc   2820
gaagagggca tcaaagagct gggcagccag atcctgaaag aacacccgt ggaaaacacc   2880
cagctgcaga acgagaagct gtacctgtac tacctgcaga atgggcggga tatgtacgtg   2940
gaccaggaac tggacatcaa ccggctgtcc gactacgatg tggaccatat cgtgcctcag   3000
agcttttctga aggacgactc catcgacaac aaggtcgtg ccagaagcga caagaaccgg   3060
ggcaagagcg acaacgtgcc ctccgaagag gtcgtgaaga agatgaagaa ctactgcgg   3120
cagctgctga acgccaagct gattacccag agaaagttcg acaatctgac caaggccgag   3180
agaggcggcc tgagcgaact ggataaggcc ggcttcatca gagacagct ggtggaaacc   3240
cggcagatca caaagcacgt ggcacagatc ctggactccc tgaacaca taagtacgac   3300
gagaatgaca agctgatccg ggaagtgaa gtgatcaccc tgaagtccaa gctggtgtcc   3360
gatttccgga aggatttcca gttttacaaa gtgcgcgaga tcaacaacta ccaccacgcc   3420
cacgacgcct acctgaacgc cgtcgtggga accgccctga tcaaaagta ccctaagctg   3480
gaaagcgagt tcgtgtacgg cgactacaag gtgtacgacg tgtctggagg atctagcggt   3540
ggttcctctg gaagcgagac accaggcaca agcgagtccg ccacaccaga gagctccggc   3600
ggctcctccg gaggatcctc tgaggtggag ttttcccacg agtactggat gagacatgcc   3660
ctgaccctgg ccaagagggc atgggatgaa agagaagtcc ccgtgggcgc cgtgctggtg   3720
cacaacaata gagtgatcgg agagggatgg aacaggccaa tcggccgcca cgaccctacc   3780
gcacacgcag agatcatggc actgaggcag ggaggcctgg tcatgcagaa ttaccgcctg   3840
atcgatgcca ccctgtatgt gacactggag ccatgcgtga tgtgcgcagg agcaatgatc   3900
cacagcagga tcggaagagt ggtgttcgga gcacgggacg ccaagaccgg cgcagcaggc   3960
tccctgatgg atgtgctgca ccaccccggc atgaaccacc gggtggagat cacagaggga   4020
atcctggcag acgagtgcgc cgccctgctg agcgatttct ttagaatgcg gagacaggag   4080
atcaaggccc agaagaaggc acagagctcc accgactctg gaggatctag cggcggatcc   4140
tctgaagcg agacaccagg cacaagcgag tccgccacac cagagagctc cggcggctcc   4200
tccggaggat cctctgaggt ggagtttccc cacgagtact ggatgagaca tgccctgacc   4260
ctggccaaga gggcacgcga tgagagggag gtgcctgtg gagccgtgct ggtgctgaac   4320
aatagagtga tcggcgaggg ctggaacaga gccatcggcc tgcacgaccc aacagcccat   4380
gccgaaatta tggccctgag acagggcggc tggtcatgc agaactacag actgattgac   4440
gccacccctgt acgtgacatt cgagccttgc gtgatgtgcg ccggcgccat gatccactct   4500
aggatcggcc gcgtggtgtt tggcgtgagg aacgcaaaaa ccggcgccgc aggctccctg   4560
atggacgtgc tgcactaccc cggcatgaat caccgcgtcg aaattaccga ggaatcctg   4620
gcagatgaat gtgccgccct gctgtgctat ttctttcgga tgcctagaca ggtgttcaat   4680
gctcagaaga aggcccagag ctccaccgac tccgaggat ctagcggagg ctcctctggc   4740
tctgagacac tggcacaag cgagagcca cacctgaaa gcagcggggg cagcagcggg   4800
gggtcacgga agatgatcgc caagagcgag caggaaatcg gcaaggctac cgccaagtac   4860
ttcttctaca gcaacatcat gaactttttc aagaccgaaa tcctggcc caacggcgag   4920
atccggaagc ggcctctgat cgagacaaac ggcgaaaccg gggagatcgt gtgggataag   4980
ggccgggatt tgccaccgt gcggaaagtg ctgagcatgc ccaagtgaa atcgtgaaa   5040
aagaccgagt gcagacagg cggcttcagc aaagagtcta tcctgcccaa gaggaacagc   5100
gataagctga tcgccagaaa gaaggactgg gacccctaaga agtacggcgg cttcgacagc   5160
cccaccgtgg cctattctgt gctggtggtg gccaaagtgg aaaagggcaa gtccaagaaa   5220
```

```
ctgaagagtg tgaaagagct gctggggatc accatcatgg aaagaagcag cttcgagaag 5280
aatcccatcg actttctgga agccaagggc tacaaagaag tgaaaaagga cctgatcatc 5340
aagctgccta agtactccct gttcgagctg aaaacggcc ggaagagaat gctggcctct 5400
gccggcgaac tgcagaaggg aaacgaactg ccctgccct ccaaatatgt gaacttcctg 5460
tacctggcca gccactatga gaagctgaag ggctcccccg aggataatga gcagaaacag 5520
ctgtttgtgg aacagcacaa gcactacctg gacgagatca tcgagcagat cagcgagttc 5580
tccaagagag tgatcctggc cgacgctaat ctggacaaag tgctgtccgc ctacaacaag 5640
caccgggata agcccatcag agagcaggcc gagaatatca tccacctgtt taccctgacc 5700
aatctgggag cccctgccgc cttcaagtac tttgacacca ccatcgaccg gaagaggtac 5760
accagcacca aagaggtgct ggacgccacc ctgatccacc agagcatcac cggcctgtac 5820
gagacacgga tcgacctgtc tcagctggga ggtgactctg gcggctcaaa aagaaccgcc 5880
gacggcagcg aattcgagcc caagaagaag aggaaagtct aaccggtcat catcaccatc 5940
accattgagt ttaaacccgc tgatcagcct cgactgtgcc ttctagttgc cagccatctg 6000
ttgtttgccc ctcccccgtg ccttccttga ccctggaagg tgccactccc actgtccttt 6060
cctaataaaa tgaggaaatt gcatcgcatt gtctgagtag gtgtcattct attctggggg 6120
gtggggtggg gcaggacagc aagggggagg attgggaaga caatagcagg catgctgggg 6180
atgcggtggg ctctatggct tctgaggcgg aaagaaccag ctggggctcg ataccgtcga 6240
cctctagcta gagcttggcg taatcatggt catagctgtt tcctgtgtga aattgttatc 6300
cgctcacaat tccacacaac atacgagccg gaagcataaa gtgtaaagcc tagggtgcct 6360
aatgagtgag ctaactcaca ttaattgcgt tgcgctcact gcccgctttc cagtcgggaa 6420
acctgtcgtg ccagctgcat taatgaatcg gccaacgcgc ggggagaggc ggtttgcgta 6480
ttgggcgctc ttccgcttcc tcgctcactg actcgctgcg ctcggtcgtt cggctgcggc 6540
gagcggtatc agctcactca aaggcggtaa tacggttatc cacagaatca ggggataacg 6600
caggaaagaa catgtgagca aaaggccagc aaaaggccag gaaccgtaaa aaggccgcgt 6660
tgctggcgtt tttccatagg ctccgccccc ctgacgagca tcacaaaaat cgacgctcaa 6720
gtcagaggtg gcgaaacccg acaggactat aaagatacca ggcgtttccc cctggaagct 6780
ccctcgtgcg ctctcctgtt ccgaccctgc cgcttaccgg atacctgtcc gcctttctcc 6840
cttcgggaag cgtggcgctt tctcatagct cacgctgtag gtatctcagt tcggtgtagg 6900
tcgttcgctc caagctgggc tgtgtgcacg aaccccccgt tcagcccgac cgctgcgcct 6960
tatccggtaa ctatcgtctt gagtccaacc cggtaagaca cgacttatcg ccactggcag 7020
cagccactgg taacaggatt agcagagcga ggtatgtagg cggtgctaca gagttcttga 7080
agtggtggcc taactacggc tacactagaa gaacagtatt tggtatctgc gctctgctga 7140
agccagttac cttcggaaaa agagttggta gctcttgatc cggcaaacaa accaccgctg 7200
gtagcggtgg ttttttttgtt tgcaagcagc agattacgcg cagaaaaaaa ggatctcaag 7260
aagatccttt gatcttttct acggggtctg acactcagtg gaacgaaaac tcacgttaag 7320
ggattttggt catgagatta tcaaaaagga tcttcaccta gatccttta aattaaaaat 7380
gaagttttaa atcaatctaa agtatatatg agtaaacttg gtctgacagt taccaatgct 7440
taatcagtga ggcacctatc tcagcgatct gtctatttcg ttcatccata gttgcctgac 7500
tccccgtcgt gtagataact acgatacggg agggcttacc atctggcccc agtgctgcaa 7560
tgataccgcg agacccacgc tcaccggctc cagatttatc agcaataaac cagccagccg 7620
gaagggccga gcgcagaagt ggtcctgcaa ctttatccgc ctccatccag tctattaatt 7680
gttgccggga agctagagta agtagttcgc cagttaatag tttgcgcaac gttgttgcca 7740
ttgctacagg catcgtggtg tcacgctcgt cgtttggtat ggcttcattc agctccggtt 7800
cccaacgatc aaggcgagtt acatgatccc ccatgttgtg caaaaaagcg gttagctcct 7860
tcggtcctcc gatcgttgtc agaagtaagt tggccgcagt gttatcactc atggttatgg 7920
cagcactgca taattctctt actgtcatgc catccgtaag atgcttttct gtgactggtg 7980
agtactcaac caagtcattc tgagaatagt gtatgcggcg accgagttgc tcttgcccgg 8040
cgtcaatacg ggataatacc gcgccacata gcagaacttt aaaagtgctc atcattggaa 8100
aacgttcttc gggggcgaaaa ctctcaagga tcttaccgct gttgagatcc agttcgatgt 8160
aacccactcg tgcacccaac tgatcttcag catctttac tttcaccagc gtttctgggt 8220
gagcaaaaac aggaaggcaa aatgccgcaa aaaagggaat aagggcgaca cggaaatgtt 8280
gaatactcat actcttcctt tttcaatatt attgaagcat ttatcagggt tattgtctca 8340
tgagcggata catatttgaa tgtatttaga aaaataaaca aataggggtt ccgcgcacat 8400
ttccccgaaa agtgccacct gacgtcgacg gatcgggaga tcgatctccc gatccctag 8460
ggtcgactct cagtacaatc tgctctgatg ccgcatagtt aagccagtat ctgctccctg 8520
cttgtgtgtt ggaggtcgct gagtagtgcg cgagcaaaat ttaagctaca acaaggcaag 8580
gcttaccgga caattgcatg aagaatctgc ttagggttag gcgttttgcg ctgcttcgcg 8640
atgtacgggc cagatatacg cgttgacatt gattattgac tagttattaa tagtaatcaa 8700
ttacggggtc attagttcat agcccatata tggagttccg cgttacataa cttacggtaa 8760
atggcccgcc tggctgaccg cccaacgacc cccgcccatt gacgtcaata atgacgtatg 8820
ttcccatagt aacgccaata gggactttcc attgacgtca atgggtggag tatttacggt 8880
aaactgccca cttggcagta catcaagtgt atc                               8913

SEQ ID NO: 45           moltype = DNA   length = 8868
FEATURE                 Location/Qualifiers
source                  1..8868
                        mol_type = other DNA
                        organism = Synthetic construct
SEQUENCE: 45
atatgccaag tacgccccct attgacgtca atgacggtaa atggcccgcc tggcattatg 60
cccagtacat gaccttatgg gactttccta cttggcagta catctacgta ttagtcatcg 120
ctattaccat ggtgatgcgg ttttggcagt acatcaatgg gcgtggatag cggtttgact 180
cacggggatt tccaagtctc cacccccattg acgtcaatgg gagtttgttt tggcaccaaa 240
atcaacggga ctttccaaaa tgtcgtaaca actccgcccc attgacgcaa atgggcggta 300
ggcgtgtacg gtgggaggtc tatataagca gagctggttt agtgaaccgt cagatccgct 360
agagatccgc ggccgctaat acgactcact atagggagag ccgccaccat gaaacggaca 420
gccgacggaa gcgagttcga gtcaccaaag aagaagcgga agtcagcag tgacaagaag 480
tacagcatcg gcctggccat cggcaccaac tctgtgggct gggccgtgat caccgacgag 540
tacaaggtgc cagcaagaa attcaaggtg ctgggcaaca ccgaccggca cagcatcaag 600
```

```
aagaacctga tcggagccct gctgttcgac agcggcgaaa cagccgaggc caccaggctg   660
aagagaaccg ccagaagaag atacaccaga cggaagaacc ggatctgcta tctgcaagag   720
atcttcagca acgagatggc caaggtggac gacagcttct tccacagact ggaagagtcc   780
ttcctggtgg aagaggataa gaagcacgag cggcacccca tcttcggcaa catcgtggac   840
gaggtggcct accacgagaa gtaccccacc atctaccacc tgagaaagaa actggtggac   900
agcaccgaca aggccgacct gcggctgatc tatctggccc tggcccacat gatcaagttc   960
cggggccact tcctgatcga gggcgacctg aaccccgaca cagcgacgt ggacaagctg   1020
ttcatccagc tggtgcagac ctacaaccag ctgttcgagg aaaacccccat caacgccagc   1080
ggcgtggacg ccaaggccat cctgtctgcc agactgagca agagcagacg gctggaaaat   1140
ctgatcgccc agctgccccgg cgagaagaag aatggcctgt tcggaaacct gattgccctg   1200
agcctgggcc tgaccccaa cttcaagagc aacttcgacc tggccgagga tgccaaactg   1260
cagctgagca aggacaccta cgacgacgac ctggacaacc tgctggccca gatcggcgac   1320
cagtacgccg acctgtttct ggccgccaag aacctgtccg acgccatcct gctgagcgac   1380
atcctgagag tgaacaccga gatcaccaag gcccccctga gcgcctctat gatcaagaga   1440
tacgacgagc accaccagga cctgaccctg ctgaaagctc tcgtgcggca gcagctgcct   1500
gagaagtaca agagattttt cttcgaccag agcaagaacg gctacgccgg ctacattgac   1560
ggcggagcca gccaggaaga gttctacaag ttcatcaagc ccatcctgga aaagatggac   1620
ggcaccgaga aactgctcgt gaagctgaac agagaggacc tgctgcggaa gcagagcgacc   1680
ttcgacaacg gcagcatccc caccagatc cacctgggag agctgcacgc cattctgcgg   1740
cggcaggaag attttttaccc attcctgaag gacaaccggg aaaagatcga gaagatcctg   1800
accttccgca tcccctacta cgtgggccct ctggccaggg gaaacagcag attcgcctgg   1860
atgaccagaa agagccgagga aaccatcacc cctggaaaatc tcgaggaagt ggtggacaag   1920
ggcgcttccg cccagagctt catcgagcgg atgaccaact tcgataagaa cctgcccaac   1980
gagaaggtgc tgcccaagca cagcctgctg tacgagtact tcaccgtgta taagagctg   2040
accaaagtga aatacgtgac cgaggaaatg agaaagcccg ccttcctgag cggcgagcag   2100
aaaaaggcca tcgtgacct gctgttcaag accaaccgga aagtgaccgt gaagcagctg   2160
aaagaggact acttcaagaa aatcgagtgc ttcgactccg tggaaatctc cggcgtggaa   2220
gatcggttca acgcctccct gggcacatac cacgatctgc tgaaaattat caaggacaag   2280
gacttcctgg acaatgagga aaacgaggac attctggaag atatcgtgct gacccctgaca   2340
ctgttttgagg acagagagat gatcgaggaa cggctgaaaa cctatgccca cctgttcgac   2400
gacaaagtga tgaagcagct gaagcggcgg agatacaccg gctggggcag gctgagccgga   2460
aagctgatca acggcatccg ggacaagcag tccggcaaga caatcctgga tttcctgaag   2520
tccgacggct tcgccaacag aaacttcatg cagctgatcc acgacgacag cctgaccttt   2580
aaagaggaca tccagaaagc ccaggtgtcc ggccagggcg atagcctgca cgagcacatt   2640
gccaatctgg ccggcagccc cgccattaag aagggcatcc tgcagacagt gaaggtggtg   2700
gacgagctcg tgaaagtgat gggccggcac aagcccgaga acatcgtgat cgaaatggcc   2760
agagagaacc agaccaccca aagggacag aagaacagcc gcgagagaat gaagcggatc   2820
gaagagggca tcaaagagct gggcagccag atcctgaaag aacaccccgt ggaaaacacc   2880
cagctgcaga acgagaagct gtacctgtac tacctgcaga atggccggga tatgtacgtg   2940
gaccaggaac tggacatcaa ccggctgtcc gactacgatg tggaccatat cgtgcctcag   3000
agctttctga aggacgactc catcgacaac aaggtgctga ccagaagcga caagaaccgg   3060
ggcaagagcg acaacgtgcc ctccgaagag gtcgtgaaga gatgaagaa ctactggcgg   3120
cagctgctga acgccaagct gattacccag agaaagttcg acaatctgac caaggccgag   3180
agaggcggcc tgagcgaact ggataaggcc ggcttcatca gagacagct ggtgaaaacc   3240
cggcagatca caaagcacgt ggcacagatc ctggactccc ggatgaacac taagtacgac   3300
gagaatgaca agctgatccg ggaagtgaaa gtgatcaccc tgaagtccaa gctggtgtcc   3360
gatttccgga aggattttcca gttttacaaa gtgcgcgaaa tcaacaacta ccaccacgcc   3420
cacgacgcct acctgaacgc cgtcgtggga accgccctga tcaaaaagta ccctaagctg   3480
gaaagcgagt tcgtgtacgg cgactacaag gtgtacgacg tgcggaagat gatcgccaag   3540
agcgagcagg aaatcggcaa ggctaccgcc aagtacttct tctacagcaa catcatgaac   3600
ttttcaaga cctctggagg atctagcggt ggttcctcga gaagcgagac accaggcaca   3660
agcgagtccg ccacaccaga gagctccggc ggctcctccg gaggatcctc tgaggtggaa   3720
ttttcccacg agtactggat gagacatgcc ctgaccctgg ccaagagggc atgggatgaa   3780
agagaagtcc ccgtgggcgc cgtgctggtg cacaacaata gagtgatcgg agagggatgg   3840
aacaggccaa tcggccgcca cgaccctacc gcacacgcag agatcatgcc actgaggcag   3900
ggaggcctgg tcatgcagaa ttacgcctgc atcgatgcca cctgtatgt gacactggag   3960
ccatgcgtga tgtgcgcagg agcaatgatc cacagcagga tcggaagagt ggtgttcgga   4020
gcacgggacg ccaagaccgg cgcagcaggc tccctgatgg atgtgctgca ccaccccggc   4080
atgaaccacc gggtggagat cacagaggga atcctggcag acgatgcgc cgccctgctg   4140
agcgatttct ttagaatgcg gagacaggag atcaaggccc agaagaaggc cacagagctcc   4200
accgactctg gaggatctag cggcggatcc tctggaagcg agacaccagg cacaagcgag   4260
tccgccacac cagagagctc cggcggctcc tccggaggat cctctgaggt ggagtttttcc   4320
cacgagtact ggatgagaca tgccctgacc ctggccaaga gggcacgcga tgagggag    4380
gtgcctgtgg gagccgtgct ggtgctgaac aatagagtga gggggatgga ctggaacaga   4440
gccatcggcc tgcacgaccc aacagcccat gccgaaatta tggccctgag acagggcggc   4500
ctggtcatgc agaactacag actgattgac gccaccctgt acgtgacatt cgagccttgc   4560
gtgatgtgcg ccggcgccat gatccactct aggatcggcc gcgtggtgtt tggcgtgagg   4620
aacgcaaaaa ccggcgccgc aggctccctg atggacgtgc tgcactaccc cggcatgaat   4680
caccgcgtcg aaattaccga gggaatcctg cagatgaat gtgccgccct gctgtgctat   4740
ttctttcgga tgcctagaca ggtgttcaat gctcagaaga aggcccagag ctccaccgac   4800
tccggaggat ctagcggagg ctccctctgc tctgagacac ctggcacaag cgagagcgca   4860
acacctgaaa gcagcggggg cagcagcggg ggtcagaga caaacggcga aaccggggag   4920
atcgtgtggg ataagggccg ggatttttgcc accgtgcgga aagtgctgag catgccccaa   4980
gtgaatatcg tgaaaaagac cgaggtcgac accggtcagt gtcagaaaga gtctatcctg   5040
cccaaggaga acagcgataa gctgatcgcc agaagaaggg actgggaccc taagaagtac   5100
ggcggcttcg acagccccac cgtggcctat tctgtgctgg tggtggccaa agtgggaaag   5160
ggcaagtcca gaaactgaa gagtgtgaaa gagctgctgg gatcaccat catggaaaga   5220
agcagcttcg agaagaatcc catcgacttt ctggaagcca agggctacaa agaagtgaaa   5280
aaggacctga tcatcaagct gcctaagtac tccctgttcg agctggaaaa cggccggaag   5340
```

```
agaatgctgg cctctgccgg cgaactgcag aagggaaacg aactggccct gccctccaaa 5400
tatgtgaact tcctgtacct ggccagccac tatgagaagc tgaagggctc ccccgaggat 5460
aatgagcaga acagctgtt tgtggaacag cacaagcact acctggacga gatcatcgag 5520
cagatcagcg agttctccaa gagagtgatc ctggccgacg ctaatctgga caaagtgctg 5580
tccgcctaca acaagcaccg ggataagccc atcagagagc aggccgagaa tatcatccac 5640
ctgtttaccc tgaccaatct gggagcccct gccgccttca agtactttga caccaccatc 5700
gaccggaaga ggtacaccag caccaaagag gtgctggacg ccaccctgat ccaccagagc 5760
atcaccggcc tgtacgagac acggatcgac ctgtctcagc tggggaggtga ctctggcggc 5820
tcaaaaagaa ccgccgacgg cagcgaattc gagcccaaga agaagaggaa agtctaaccg 5880
gtcatcatca ccatcaccat tgagtttaaa cccgctgatc agcctcgact gtgccttcta 5940
gttgccagcc atctgttgtt tgcccctccc ccgtgccttc cttgaccctg gaaggtgcca 6000
ctcccactgt cctttcctaa taaaatgagg aaattgcatc gcattgtctg agtaggtgtc 6060
attctattct ggggggtggg gtggggcagg acagcaaggg ggaggattgg gaagacaata 6120
gcaggcatgc tggggatgcg gtgggctcta tggcttctga ggcggaaaga accagctggg 6180
gctcgatacc gtcgacctct agctagagct tggcgtaatc atggtcatag ctgtttcctg 6240
tgtgaaattg ttatccgctc acaattccac acaacatacg agccgaaagc ataaagtgta 6300
aagcctaggg tgcctaatga gtgagctaac tcacattaat tgcgttgcgc tcactgcccg 6360
ctttccagtc gggaaacctg tcgtgccagc tgcattaatg aatcggccaa cgcgcgggga 6420
gaggcggttt gcgtattggg cgctcttccg cttcctcgct cactgactcg ctgcgctcgg 6480
tcgttcggct gcggcgagcg gtatcagctc actcaaaggc ggtaatacgg ttatccacag 6540
aatcagggga taacgcagga agaacatgt gagcaaaagg ccagcaaaag gccaggaacc 6600
gtaaaaaggc cgcgttgctg gcgtttttcc ataggctccg cccccctgac gagcatcaca 6660
aaaatcgacg ctcaagtcag aggtggcgaa acccgacagg actataaaga taccaggcgt 6720
ttccccctgg aagctccctc gtgcgctctc ctgttccgac cctgccgctt accggatacc 6780
tgtccgcctt tctcccttcg ggaagcgtgg cgctttctca tagctcacgc tgtaggtatc 6840
tcagttcggt gtaggtcgtt cgctccaagc tgggctgtgt gcacgaaccc cccgttcagc 6900
ccgaccgctg cgccttatcc ggtaactatc gtcttgagtc caacccggta agacacgact 6960
tatcgccact ggcagcagcc actggtaaca ggattagcag agcgaggtat gtaggcggtg 7020
ctacagagtt cttgaagtgg tggcctaact acggctacac tagaagaaca gtatttggta 7080
tctgcgctct gctgaagcca gttaccttcg gaaaaagagt tggtagctct tgatccggca 7140
aacaaaccac cgctggtagc ggtggttttt tgtttgcaa gcagcagatt acgcgcagaa 7200
aaaaaggatc tcaagaagat cctttgatct tttctacggg gtctgacact cagtggaacg 7260
aaaactcacg ttaagggatt ttggtcatga gattatcaaa aaggatcttc acctagatcc 7320
ttttaaatta aaaatgaagt tttaaatcaa tctaaagtat atatgagtaa acttggtctg 7380
acagttacca atgcttaatc agtgaggcac ctatctcagc gatctgtcta tttcgttcat 7440
ccatagttgc ctgactcccc gtcgtgtaga taactacgat acgggagggc ttaccatctg 7500
gccccagtgc tgcaatgata ccgcgagacc cacgctcacc ggctccagat ttatcagcaa 7560
taaaccagcc agccggaagg gccgagcgca gaagtggtcc tgcaactttta tccgcctcca 7620
tccagtctat taattgttgc cgggaagcta gagtaagtag ttcgccagtt aatagtttgc 7680
gcaacgttgt tgccattgct acaggcatcg tggtgtcacg ctcgtcgttt ggtatggctt 7740
cattcagctc cggttcccaa cgatcaaggc gagttacatg atccccatg ttgtgcaaaa 7800
aagcggttag ctccttcggt cctccgatcg ttgtcagaag taagttggcc gcagtgttat 7860
cactcatggt tatggcagca ctgcataatt ctcttactgt catgccatcc gtaagatgct 7920
tttctgtgac tggtgagtac tcaaccaagt cattctgaga atagtgtatg cggcgaccga 7980
gttgctcttg cccggcgtca atacgggata taccgcgcc acatagcaga actttaaaag 8040
tgctcatcat tggaaaacgt tcttcgggc gaaaactctc aaggatctta ccgctgttga 8100
gatccagttc gatgtaaccc actcgtgcac ccaactgatc ttcagcatct tttactttca 8160
ccagcgtttc tgggtgagca aaaacaggaa ggcaaaatgc cgcaaaaaag ggaataaggg 8220
cgacacggaa atgttgaata ctcatactct tcctttttca atattattga agcatttatc 8280
agggttattg tctcatgagc ggatacatat ttgaatgtat ttagaaaaat aaacaaatag 8340
gggttccgcg cacatttccc cgaaaagtgc cacctgacgt cgacgatcg ggagatcgat 8400
ctcccgatcc cctagggtcg actctcagta caatctgctc tgatgccgca tagttaagcc 8460
agtatctgct ccctgcttgt gtgttggagg tcgctgagta gtgcgcgagc aaaatttaag 8520
ctacaacaag gcaaggcttg accgacaatt gcatgaagaa tctgcttagg gttaggcgtt 8580
ttgcgctgct tcgcgatgta cgggccagat atacgcgttg acattgatta ttgactagtt 8640
attaatagta atcaattacg gggtcattag ttcatagccc atatatgag ttccgcgtta 8700
cataacttac ggtaaatggc ccgcctggct gaccgcccaa cgacccccgc ccattgacgt 8760
caataatgac gtatgttccc atagtaacgc caatagggac tttccattga cgtcaatggg 8820
tggagtattt acgtaaact gcccacttgg cagtacatca agtgtatc       8868
```

SEQ ID NO: 46        moltype = DNA  length = 8913
FEATURE          Location/Qualifiers
source            1..8913
                  mol_type = other DNA
                  organism = Synthetic construct
SEQUENCE: 46

```
atatgccaag tacgccccct attgacgtca atgacggtaa atggcccgcc tggcattatg  60
cccagtacat gaccttatgg gactttccta cttggcagta catctacgta ttagtcatcg 120
ctattaccat ggtgatgcgg ttttggcagt acatcaatgg gcgtggatag cggtttgact 180
cacggggatt tccaagtctc caccccattg acgtcaatgg gagtttgttt tggcaccaaa 240
atcaacggga ctttccaaaa tgtcgtaaca actccgcccc attgacgcaa atgggcggta 300
ggcgtgtacg gtgggaggtc tatataagca gagctggttt agtgaaccgt cagatccgct 360
agagatccgc ggccgctaat acgactcact atagggagag ccgccaccat gaaacgcaca 420
gccgacggaa gcgagttcga gtcaccaaag aagaagcgga aagtcagcag tgacaagaag 480
tacagcatcg gcctggccat cggcaccaac tctgtgggct gggccgtgat caccgacgag 540
tacaaggtgc ccagcaagaa attcaaggtg ctggccaaca ccgaccggca cagcatcaag 600
aagaacctga tcgagcccct gctgttcgac agcggcgaaa cagccgaggc cacccggctg 660
aagagaaccg ccagaagaag atacaccaga cggaagaacc ggatctgcta tctgcaagag 720
atcttcagca acgagatggc caaggtggac gacagcttct tccacagact ggaagagtcc 780
```

```
ttcctggtgg aagaggataa gaagcacgag cggcacccca tcttcggcaa catcgtggac  840
gaggtggcct accacgagaa gtaccccacc atctaccacc tgagaaagaa actggtggac  900
agcaccgaca aggccgacct gcggctgatc tatctggccc tggcccacat gatcaagttc  960
cggggccact tcctgatcga gggcgacctg aaccccgaca cagcgacgt ggacaagctg 1020
ttcatccagc tggtgcagac ctacaaccag ctgttcgagg aaaacccat caacgccagc 1080
ggcgtggacg ccaaggccat cctgtctgcc agactgagcg agagcagacg gctggaaaat 1140
ctgatcgccc agctgcccgg cgagaagaag aatggcctgt tcggaaacct gattgccctg 1200
agcctgggcc tgacccccaa cttcaagagc aacttcgacc tggccgagga tgccaaactg 1260
cagctgagca aggacaccta cgacgacgac ctggacaact tgctggccca gatcggcgac 1320
cagtacgccg acctgtttct ggccgccaag aacctgtccg acgccatcct gctgagcgac 1380
atcctgagag tgaacaccga gatcaccaag gcccccctga gcgcctctat gatcaagaga 1440
tacgacgagc accaccagga cctgaccctg ctgaaagctc tcgtgcggca gcagctgcct 1500
gagaagtaca aagagatttt cttcgaccag agcaagaacg gctacgccgg ctacattgac 1560
ggcggagcca gccaggaaga gttctacaag ttcatcaagc ccatcctgga aaagatggac 1620
ggcaccgagg aactgctcgt gaagctgaac agagaggacc tgctgcggaa gcagcggacc 1680
ttcgacaacg gcagcatccc ccaccagatc cacctgggag agctgcacgc cattctgcgg 1740
cggcaggaag atttttaccc attcctgaag gacaaccggg aaaagatcga gaagatcctg 1800
accttccgca tccccactaa cgtgggccct ctggccaggg gaaacagcag attcgcctgg 1860
atgaccagaa agagcgagga aaccatcacc ccctggaact tcgaggaagt ggtggacaag 1920
ggcgcttccg cccagagctt catcgagcgg atgaccaact tcgataagaa cctgcccaac 1980
gagaaggtgc tgcccaagca cagcctgctg tacgagtact tcaccgtgta taacgagctg 2040
accaaagtga aatacgtgac cgagggaatg agaaagcccg ccttcctgag cggcgagcag 2100
aaaaaggcca tcgtggacct gctgttcaag accaaccgga aagtgaccgt gaagcagctg 2160
aaagaggact acttcaagaa aatcgagtgc ttcgactccg tggaaatctc cggcgtggaa 2220
gatcggttca acgcctccct gggcacatac cacgatctgc tgaaaattat caaggacaag 2280
gacttcctgg acaatgagga aaacgaggac atttctggaaa atatcgtgct gaccctgaca 2340
ctgtttgagg acagagagat gatcgaggaa cggctgaaaa cctatgccca cctgttcgac 2400
gacaaagtga tgaagcagct gaagcggcgg agatacaccg gctggggcag gctgagccgg 2460
aagctgatca acggcatccg ggacaagcag tccggcaaga caatcctgga tttcctgaag 2520
tccgacggct tcgccaacag aaacttcatg cagctgatcc acgacgacag cctgaccttt 2580
aaagaggaca tccagaaagc ccaggtgtcc ggccaggcg atagcctgca cgagcacatt 2640
gccaatctgg ccggcagccc cgccattaag aagggcatcc tgcagacagt gaaggtggtg 2700
gacgagctcg tgaaagtgat gggccggcac aagcccgaga catcgtgat cgaaatggcc 2760
agagagaacc agaccaccca gaagggacag aagaacagcc gcgagagaat gaagcggatc 2820
gaagagggca tcaaagagct gggcagccag atcctgaaag aacacccgt ggaaaaacacc 2880
cagctgcaga acgagaagct gtacctgtac tacctgcaga atgggcggga tatgtacgtg 2940
gaccaggaac tggacatcaa ccggctgtcc gactacgatg tggaccatat cgtgcctcag 3000
agctttctga aggacgactc catcgacaac aaggtgctga ccagaagcga caagaaccgg 3060
ggcaagagcg acaacgtgcc ctccgaagag gtcgtgaaga agatgaagaa ctactggcgg 3120
cagctgctga acgccaagct gattacccag agaaagttcg acaatctgac caaggccgag 3180
agaggcggcc tgagcgaact ggataaggcc ggcttcatca agagacagct ggtggaaacc 3240
cggcagatca caaagcacgt ggcacagatc ctggactccc ggatgaacac taagtacgac 3300
gagaatgaca agctgatccg ggaagtgaaa gtgatcaccc tgaagtccaa gctggtgtcc 3360
gatttccgga aggatttcca gttttacaaa gtgcgcgaga tcaacaacta ccaccacgcc 3420
cacgacgcct acctgaacgc cgtcgtggga accgccctga tcaaaaagta ccctaagctg 3480
gaaagcgagt tcgtgtacgg cgactacaag gtgtacgacg tgcggaagat gatcgccaag 3540
agcgaacagg aaatcggcaa ggctaccgcc aagtacttct tctacagcaa catcatgaac 3600
tttttcaaga ccgagattac cctggccaac ggcgagatcc ggaagcgcc tctgatcgag 3660
acaaacggcg aaaccgggga gatctctgga ggatctagcg gtggttcctc tggaagcgag 3720
acaccaggca aagcgagtc cgccacacca gagagctccg cgggctcctc cggaggatcc 3780
tctgaggtgg agttttccca cgagtactgg atgagacatg ccctgaccct ggccaagagg 3840
gcatgggatg aaagagaagt ccccgtgggc gccgtgctgg tgcacaacaa tagagtgatc 3900
ggagagggat ggaacaggcc aatcggccgc cacgaccta ccgcacacgc agagatcatg 3960
gcactgaggc agggaggcct ggtcatgcag aattaccgcc tgatcgatgc caccctgtat 4020
gtgacactgg agccatcgt gatgtgcgca ggagcaatga tccacagcag gatcggaaga 4080
gtggtgttcg agcacggga cgccaagacc ggcgcagcag gctccctgat ggatgtgctg 4140
caccacccg gcatgaacca ccgggtggag atcacagagg gaatcctggc agacgagtgc 4200
gccgccctgc tgagcgatt ctttagaatg cggagacagg agatcaaggc ccagaagaag 4260
gcacagagct ccaccgactc tggaggatct agcggcggat cctctggaag cgacaccacca 4320
ggcacaagcg agtccgccac accaggagagc tccggcggct cctccgagg atcctctgag 4380
gtggagtttt cccacgagta ctggatgaga catgcccctga ccctggccaa gagggcacgc 4440
gatgagaggg aggtgcctgt gggagccgtg ctggtgctga acaatagagt gatcggcgag 4500
ggctggaaca gagccatcgg cctgcacgac ccaacagccc atgccgaaat tatggccctg 4560
agacagggcg gcctggtcat gcagaactac agactgattg acgccacctg gtacgtgaca 4620
ttcgagcctt gcgtgatgtg cgccggcgcc atgatccact ctaggatcgg ccgcgtggtg 4680
tttggcgtga ggaacgcaaa aaccggcgcc caggctccc tgatgacgt gctgcactac 4740
cccggcatga atcaccgcgt cgaaattacc gagggaatcc tggcagatga atgtgccgcc 4800
ctgctgtgct atttctttcg gatgcctaga caggtgttca atgctcagaa gaaggcccag 4860
agctccaccg actccgagg atctagcgga ggctcctctg gctctgagac acctggcaca 4920
agcgagagcg caacacctga agcagcgggg ggcagcagcg ggggtcagt gtgggataag 4980
ggccgggatt tgccaccgt gcggaaagtg ctgagcatgc ccaagtgaa tatcgtgaaa 5040
aagaccgagt gcagacaggg cggcttcagc aaagagtcta tcctgcccaa gaggaacagc 5100
gataagctga tcgccagaaa gaaggactgg gacccctaaga agtacggcgg cttcgacagc 5160
cccaccgtgc cctattctgt cctggtggtg gccaaagtgg aaaagggcaa gtccaagaaa 5220
ctgaagagtg tgaaagctct gctgggcatc accatcatgg aaagaagcag cttcgagaag 5280
aatcccatcg actttctgga agccaaaggc tacaaagaag tgaaaagga cctgatcatc 5340
aagctgccta gtactcccct gttcgagctg gaaaacggcc ggaagagaat gctggcctct 5400
gccgcgaac tgcagaaggg aaacgaactg gccctgccct ccaaatatgt gaacttcctg 5460
tacctggcca gccactatga aagctgaag ggctccccg aggataatga gcagaaacag 5520
```

```
ctgtttgtgg aacagcacaa gcactacctg gacgagatca tcgagcagat cagcgagttc    5580
tccaagagag tgatcctggc cgacgctaat ctggacaaag tgctgtccgc ctacaacaag    5640
caccgggata agcccatcag agagcaggcc gagaatatca tccacctgtt taccctgacc    5700
aatctggag ccccctgccgc cttcaagtac tttgacacca ccatcgaccg gaagaggtac    5760
accagcacca aagaggtgct ggacgccacc ctgatccacc agagcatcac cggcctgtac    5820
gagacacgga tcgacctgtc tcagctggga ggtgactctg gcggctcaaa aagaaccgcc    5880
gacggcagcg aattcgagcc caagaagaag aggaaagtct aaccggtcat catcaccatc    5940
accattgagt ttaaacccgc tgatcagcct cgactgtgcc ttctagttgc cagccatctg    6000
ttgtttgccc ctcccccgtg ccttccttga ccctggaagg tgccactccc actgtccttt    6060
cctaataaaa tgaggaaatt gcatcgcatt gtctgagtag tgtgcattct attctggggg    6120
gtggggtggg gcaggacagc aagggggagg attgggaaga caatagcagg catgctgggg    6180
atgcggtggg ctctatggct tctgaggcgg aaagaaccag ctggggctcg ataccgtcga    6240
cctctagcta gagcttggcg taatcatggt catagctgtt tcctgtgtga aattgttatc    6300
cgctcacaat tccacacaac atacgagccg gaagcataaa gtgtaaagcc tagggtgcct    6360
aatgagtgag ctaactcaca ttaattgcgt tgcgctcact gcccgctttc cagtcgggaa    6420
acctgtcgtg ccagctgcat taatgaatcg gccaacgcgc ggggagaggc ggtttgcgta    6480
ttgggcgctc ttccgcttcc tcgctcactg actcgctgcg ctcggtcgtt cggctgcggc    6540
gagcggtatc agctcactca aaggcggtaa tacggttatc cacagaatca ggggataacg    6600
caggaaagaa catgtgagca aaaggccagc aaaaggccag gaaccgtaaa aaggccgcgt    6660
tgctggcgtt tttccatagg ctccgccccc ctgacgagca tcacaaaaat cgacgctcaa    6720
gtcagaggtg gcgaaacccg acaggactat aaagatacca ggcgtttccc cctggaagct    6780
ccctcgtgcg ctctcctgtt ccgaccctgc cgcttaccgg atacctgtcc gcctttctcc    6840
cttcgggaag cgtggcgctt tctcatagct cacgctgtag gtatctcagt tcggtgtagg    6900
tcgttcgctc caagctgggc tgtgtgcacg aaccccccgt tcagcccgac cgctgcgcct    6960
tatccggtaa ctatcgtctt gagtccaacc cggtaagaca cgacttatcg ccactggcag    7020
cagccactgg taacaggatt agcagagcga ggtatgtagg cggtgctaca gagttcttga    7080
agtggtggcc taactacggc tacactagaa gaacagtatt tggtatctgc gctctgctga    7140
agccagttac cttcggaaaa agagttggta gctcttgatc cggcaaacaa accaccgctg    7200
gtagcggtgg tttttttgtt tgcaagcagc agattacgcg cagaaaaaaa ggatctcaag    7260
aagatccttt gatcttttct acggggtctg acactcagtg gaacgaaaac tcacgttaag    7320
ggattttggt catgagatta tcaaaaagga tcttcaccta gatccttta aattaaaaat    7380
gaagttttaa atcaatctaa agtatatatg agtaaacttg gtctgacagt taccaatgct    7440
taatcagtga ggcacctatc tcagcgatct gtctatttcg ttcatccata gttgcctgac    7500
tccccgtcgt gtagataact acgatacggg agggcttacc atctggcccc agtgctgcaa    7560
tgataccgcg agacccacgc tcaccggctc cagatttatc agcaataaac cagccagccg    7620
gaagggccga gcgcagaagt ggtcctgcaa ctttatccgc ctccatccag tctattaatt    7680
gttgccggga agctagagta agtagttcgc cagttaatag tttgcgcaac gttgttgcca    7740
ttgctacagg catcgtggtg tcacgctcgt cgtttggtat ggcttcattc agctccggtt    7800
cccaacgatc aaggcgagtt acatgatccc ccatgttgtg caaaaaagcg gttagctcct    7860
tcggtcctcc gatcgttgtc agaagtaagt tggccgcagt gttatcactc atggttatgg    7920
cagcactgca taattctctt actgtcatgc catccgtaag atgcttttct gtgactggtg    7980
agtactcaac caagtcattc tgagaatagt gtatgcggcg accgagttgc tcttgcccgg    8040
cgtcaatacg ggataatacc gcgccacata gcagaacttt aaaagtgctc atcattggaa    8100
aacgttcttc ggggcgaaaa ctctcaagga tcttaccgct gttgagatcc agttcgatgt    8160
aacccactcg tgcacccaac tgatcttcag catcttttac tttcaccagc gtttctgggt    8220
gagcaaaaac aggaaggcaa aatgccgcaa aaaagggaat aagggcgaca cggaaatgtt    8280
gaatactcat actcttcctt tttcaatatt attgaagcat ttatcagggt tattgtctca    8340
tgagcggata catatttgaa tgtatttaga aaaataaaca aataggggtt ccgcgcacat    8400
ttccccgaaa agtgccacct gacgtcgacg gatcgggaga tcgatctccc gatccctag    8460
ggtcgactct cagtacaatc tgctctgatg ccgcatagtt aagccagtat ctgctccctg    8520
cttgtgtgtt ggaggtcgct gagtagtgcg cgagcaaaat ttaagctaca acaaggcagg    8580
gcttgaccga caattgcatg aagaatctgc ttagggttag gcgttttgcg ctgcttcgcg    8640
atgtacgggc cagatatacg cgttgacatt gattattgac tagttattaa tagtaatcaa    8700
ttacggggtc attagttcat agcccatata tggagttccg cgttacataa cttacggtaa    8760
atggcccgcc tggctgaccg cccaacgacc cccgcccatt gacgtcaata atgacgtatg    8820
ttcccatagt aacgccaata gggactttcc attgacgtca atgggtggag tatttacggt    8880
aaactgccca cttggcagta catcaagtgt atc                                8913

SEQ ID NO: 47           moltype = DNA   length = 8913
FEATURE                 Location/Qualifiers
source                  1..8913
                        mol_type = other DNA
                        organism = Synthetic construct
SEQUENCE: 47
atatgccaag tacgccccct attgacgtca atgacggtaa atggcccgcc tggcattatg     60
cccagtacat gaccttatgg gactttccta cttggcagta catctacgta ttagtcatcg    120
ctattaccat ggtgatgcgg ttttggcagt acatcaatgg gcgtggatag cggtttgact    180
cacgggggatt tccaagtctc caccccattg acgtcaatgg gagtttgttt tggcaccaaa    240
atcaacgtga ctttccaaaa tgtcgtaaca actccgcccc attgacgcaa atgggcggta    300
ggcgtgtacg gtgggaggtc tatataagca gagctggttt agtgaaccgt cagatccgct    360
agagatccgc ggccgctaat acgactcact atagggagag ccgccaccat gaaacggaca    420
gccgacggaa gcgagttcga gtcaccaaag aagaagcgga agtcagcag tgacaagaag    480
tacagcatcg gcctggccat cggcaccaac tctgtgggct gggccgtgat caccgacgag    540
tacaaggtgc ccagcaagaa attcaaggtg ctgggcaaca ccgaccggca gagcatcaag    600
aagaacctga tcgagccct gctgttcgac agcggcgaaa cagccgaggc cacccggctg    660
aagagaaccg ccagaagaag ataccaccaga cggaagaacc ggatctgcta tctgcaagag    720
atcttcagca acgagatggc caaggtggac gacagcttct tccacagact ggaagagtcc    780
ttcctggtgg aagaggataa gaagcacgag cggcacccca tcttcggcaa catcgtggac    840
gaggtggcct accacgagaa gtaccccacc atctaccacc tgagaaagaa actggtggac    900
```

```
agcaccgaca aggccgacct gcggctgatc tatctggccc tggcccacat gatcaagttc   960
cggggccact tcctgatcga gggcgacctg aaccccgaca acagcgacgt ggacaagctg  1020
ttcatccagc tggtgcagac ctacaaccag ctgttcgagg aaaacccat caacgccagc  1080
ggcgtggacg ccaaggccat cctgtctgcc agactgagca gagcagacg gctggaaaat  1140
ctgatcgccc agctgcccgg cgagaagaag aatggcctgt tcggaaacct gattgccctg  1200
agcctgggcc tgaccccca cttcaagagc aacttcgacc tggccgagga tgccaaactg  1260
cagctgagca aggacaccta cgacgacgac ctggacaacc tgctggccca gatcggcgac  1320
cagtacgccg acctgtttct ggccgccaag aacctgtccg acgccatcct gctgagcgac  1380
atcctgagag tgaacaccga gatcaccaag gcccccctga gcgcctctat gatcaagaga  1440
tacgacgagc accaccagga cctgaccctg ctgaaagctc tcgtgcggca gcagctgcct  1500
gagaagtaca agagattttt cttcgaccag agcaagaacg gctacgccgg ctacattgac  1560
ggcggagcca gccaggaaga gttctacaag ttcatcaagc ccatcctgga aaagatggac  1620
ggcaccgagg aactgctcgt gaagctgaac agagaggacc tgctgcggaa gcagcggacc  1680
ttcgacaacg gcagcatccc ccaccagatc cacctgggag agctgcacgc cattctgcgg  1740
cggcaggaag attttaccc attcctgaag gacaacgggg aaaagatcga gaagatcctg  1800
accttccgca tccctacta cgtgggcccct ctggccaggg aaacagcag attcgcctgg  1860
atgaccagaa agagcgagga aaccatcacc ccctggaact tcgaggaagt ggtggacaag  1920
ggcgcttccg cccagagctt catcgagcgg atgaccaact tcgataagaa cctgcccaac  1980
gagaaggtgc tgcccaagca cagcctgctg tacgagtact tcaccgtgta taacgagctg  2040
accaaagtga aatacgtgac cgagggaatg agaaagcccg ccttcctgag cggcgagcag  2100
aaaaaggcca tcgtggacct gctgttcaag accaaccgga aagtgaccgt gaagcagctg  2160
aaagaggact acttcaagaa aatcgagtgc ttcgactccg tggaaatctc cggcgtggaa  2220
gatcggttca acgcctccct gggcacatac cacgatctgc tgaaaattat caaggacaag  2280
gacttcctgg acaatgagga aaacgaggac attctggaag atatcgtgct gaccctgaca  2340
ctgtttgagg acagagagat gatcgaggaa cggctgaaaa cctatgccca cctgttcgac  2400
gacaaagtga tgaagcagct gaagcgcgg agatacgcga gctggggcag gctgagccgg  2460
aagctgatca acggcatccg ggacaagcag tccggcaaga caatcctgga tttcctgaag  2520
tccgacggct cgccaacag aaacttcatg cagctgatcc acgacgacag cctgacccttt  2580
aaagaggaca tccagaaagc ccaggtgtcc ggccagggcg atagcctgca cgagcacatt  2640
gccaatctgg ccggcagccc cgccattaag aagggcactc tgcagacagt gaaggtggtg  2700
gacgagctcg tgaaagtgat gggccggcac aagcccgaga acatcgtgat cgaaatggcc  2760
agagagaacc agaccaccca aagggacaag aagaacagcc gcgagagaat gaagcggatc  2820
gaagagggca tcaaagagct gggcagccag atcctgaaag aacaccccgt ggaaaacacc  2880
cagctgcaga acgagaagct gtacctgtac tacctgcaga atgggcggga tatgtacgtg  2940
gaccaggaac tggacatcaa ccggctgtcc gactacgatg tggaccatat cgtgcctcag  3000
agctttctga aggacgactc catcgacaac aaggtgctga ccagaagcga caagaaccgg  3060
ggcaagagcg acaacgtgcc ctccgaagag gtcgtgaaga agatgaagaa ctactggcgg  3120
cagctgctga acgccaagct gattacccag agaaagttcg acaatctgac caaggccgag  3180
agaggcggcc tgagcgaact ggataaggcc ggcttcatca agagacagct ggtggaaacc  3240
cggcagatca caaagcacgt ggcacagatc ctggactccc ggatgaacac taagtacgac  3300
gagaatgaca agctgatccg ggaagtgaaa gtgatcaccc tgaagtccaa gctggtgtcc  3360
gatttccgga aggatttcca gttttacaaa gtgcgcgaga tcaacaacta ccaccacgcc  3420
cacgacgcct acctgaacgc cgtcgtggga accgccctga tcaaaaagta ccctaagctg  3480
gaaagcgagt tcgtgtacgg cgactacaag gtgtacgacg tgcggaagat gatcgccaag  3540
agcgagcagg aaatcggcaa ggctaccgcc aagtactctc tctacagcaa catcatgaac  3600
ttttcaaga ccgagattac cctggccaac ggcgagatcc ggaagcggcc tctgatcgag  3660
acaaacggcg aaaccgggga gatcgtgtct ggaggatcta gcggtggttc ctctggaagc  3720
gagacaccag gcacaagcga gtccgccaca ccagagagct ccggcggctc ctccggagga  3780
tcctctgagg tggagttttc ccacgagtac tggatgagac atgccctgac cctgccaag  3840
agggcatggg atgaaagaga agtccccgtg gcgccgtgc tggtgcacaa caatagagtg  3900
atcggaggg gatggaacag gccaatcggc cgccacgacc ctaccgcaca cgcagagatc  3960
atggcactga gcagggagg cctggtcatg cagaattacc gcctgatcga tgccaccctg  4020
tatgtgacac tggagccatg cgtgatgtgc gcaggagcaa tgatccacag caggatcgga  4080
agagtggtgt tcgagcacg ggacgccaag accggcgcag caggctccct gatggatgtg  4140
ctgcaccacc ccggcatgaa ccacccgggtg gagatcaacg agggaatcct ggcagacgag  4200
tgcgccgccc tgctgagcga tttctttaga atgcggagac aggagatcaa ggccagaag  4260
aaggcacaga gctccaccga ctctggagga tctagcggcg atcctctgg aagcgagaca  4320
ccaggcacaa gcgagtccgc cacaccagag agctccggcg ctcctccgg aggatcctct  4380
gaggtggagt tttcccacga gtactggatg agacatgcc tgaccctggc caagagggca  4440
cgcgatgaa gggaggtgcc tgtgggagcc gtgctggtgc tgaacaatag agtgatcgg  4500
gagggctgga acagagccat cggcctgcac gacccaacag cccatgccga aattatggcc  4560
ctgagacagg gcggcctggt catgcagaac tacagactga ttgacgccac cctgtacgtg  4620
acattcgagc cttgcgtgat gtgcgccggc gccatgatcc actctaggat cggccgcgtg  4680
gtgtttggcg tgaggaacgc aaaaaccggc gccgcaggct ccctgatgga cgtgctgcac  4740
taccccggca tgaatcaccg cgtcgaaatt accgaggtga tcctggcaga tgaatgtgcc  4800
gccctgctgt gctattcttt tcggatgcct agacaggtgt tcaatgctca gaagaaggcc  4860
cagagctcca ccgactccgg aggatctagc ggaggtcctt ctggctcga cacctggc  4920
acaagcgaga gcgcaaacac tgaaagcagc gggggcagca gcgggggtc atgggataag  4980
ggccgggatt ttgccaccgt gcgaaagtg ctgagcatgc cccaagtgaa tatcgtgaaa  5040
aagaccgagg tgcagacagg cggcttcagc aaagagtcta tcctgcccaa gaggaacagc  5100
gataagctga tcgccagaaa gaaggactgg gaccctaaga agtacggcgg cttcgacagc  5160
cccaccgtgg cctattctgt gctggtggtg gccaaagtgg aaaagggcaa gtccaagaaa  5220
ctgaagagtg tgaaagagct gctggggatc accatcatgg aaaagcag cttcgagaag  5280
aatcccatcg actttctgga agccaagggc tacaaagagt gaaaaagga cctgatcatc  5340
aagctgccta agtactccct gttcgagctg gaaaacggcc ggaagagaat gctggcctct  5400
gccggcgaac tgcagaaggg aaacgaactg gccctgcct ccaaatatgt gaacttcctg  5460
tacctggcca gccactatga gaagctgaag ggctcccccg aggataatga gcagaaacag  5520
ctgtttgtgt aacagcacaa gcactacctg gacgagatca tcgagcagat cagcgagttc  5580
tccaagagag tgatcctggc cgacgctaat ctggacaaag tgctgtccgc ctacaacaag  5640
```

```
caccgggata agcccatcag agagcaggcc gagaatatca tccacctgtt taccctgacc 5700
aatctgggag cccctgccgc cttcaagtac tttgacacca ccatcgaccg gaagaggtac 5760
accagcacca aagaggtgct ggacgccacc ctgatccacc agagcatcac cggcctgtac 5820
gagacacgga tcgacctgtc tcagctggga ggtgactctg gcggctcaaa aagaaccgcc 5880
gacggcagcg aattcgagcc caagaagaag aggaaagtct aaccggtcat catcaccatc 5940
accattgagt ttaaacccgc tgatcagcct cgactgtgcc ttctagttgc cagccatctg 6000
ttgtttgccc ctcccccgtg ccttccttga ccctggaagg tgccactccc actgtccttt 6060
cctaataaaa tgaggaaatt gcatcgcatt gtctgagtag tgtcattct attctggggg 6120
gtggggtggg gcaggacagc aaggggagg attgggaaga caatagcagg catgctgggg 6180
atgcggtggg ctctatggct tctgaggcgg aaagaaccag ctggggctcg ataccgtcga 6240
cctctagcta gagcttggcg taatcatggt catagctgtt tcctgtgtga aattgttatc 6300
cgctcacaat tccacacaac atacgagccg aagcataaa gtgtaaagcc tagggtgcct 6360
aatgagtgag ctaactcaca ttaattgcgt tgcgctcact gcccgctttc cagtcgggaa 6420
acctgtcgtg ccagctgcat taatgaatcg gccaacgcgc ggggagaggc ggtttgcgta 6480
ttgggcgctc ttccgcttcc tcgctcactg actcgctgcg ctcggtcgtt cggctgcggc 6540
gagcggtatc agctcactca aaggcggtaa tacggttatc cacagaatca ggggataacg 6600
caggaaagaa catgtgagca aaaggccagc aaaaggccag gaaccgtaaa aaggccgcgt 6660
tgctggcgtt tttccatagg ctccgccccc ctgacgagca tcacaaaaat cgacgctcaa 6720
gtcagaggtg gcgaaacccg acaggactat aaagatacca ggcgtttccc cctggaagct 6780
ccctcgtgcg ctctcctgtt ccgaccctgc cgcttaccgg atacctgtcc gcctttctcc 6840
cttcgggaag cgtggcgctt tctcatagct cacgctgtag gtatctcagt tcggtgtagg 6900
tcgttcgctc caagctgggc tgtgtgcacg aaccccccgt tcagcccgac cgctgcgcct 6960
tatccggtaa ctatcgtctt gagtccaacc cggtaagaca cgacttatcg ccactggcag 7020
cagccactgg taacaggatt agcagagcga ggtatgtagg cggtgctaca gagttcttga 7080
agtggtggcc taactacggc tacactagaa gaacagtatt tggtatctgc gctctgctga 7140
agccagttac cttcggaaaa agagttggta gctcttgatc cggcaaacaa accaccgctg 7200
gtagcggtgg tttttttgtt tgcaagcagc agattacgcg cagaaaaaaa ggatctcaag 7260
aagatccttt gatcttttct acggggtctg acactcagtg gaacgaaaac tcacgttaag 7320
ggattttggt catgagatta tcaaaaagga tcttcaccta gatccttta aattaaaaat 7380
gaagttttaa atcaatctaa agtatatatg agtaaacttg gtctgacagt taccaatgct 7440
taatcagtga ggcacctatc tcagcgatct gtctatttcg ttcatccata gttgcctgac 7500
tccccgtcgt gtagataact acgatacggg agggcttacc atctggcccc agtgctgcaa 7560
tgataccgcg agacccacgc tcaccggctc cagatttatc agcaataaac cagccagccg 7620
gaagggccga gcgcagaagt ggtcctgcaa ctttatccgc ctccatccag tctattaatt 7680
gttgccggga agctagagta agtagttcgc cagttaatag tttgcgcaac gttgttgcca 7740
ttgctacagg catcgtggtg tcacgctcgt cgtttggtat ggcttcattc agctccggtt 7800
cccaacgatc aaggcgagtt acatgatccc ccatgttgtg caaaaaagcg gttagctcct 7860
tcggtcctcc gatcgttgtc agaagtaagt tggccgcagt gttatcactc atggttatgg 7920
cagcactgca taattctctt actgtcatgc catccgtaag atgcttttct gtgactggtg 7980
agtactcaac caagtcattc tgagaatagt gtatgcggcg accgagttgc tcttgcccgg 8040
cgtcaatacg ggataatacc gcgccacata gcagaacttt aaaagtgctc atcattggaa 8100
aacgttcttc ggggcgaaaa ctctcaagga tcttaccgct gttgagatcc agttcgatgt 8160
aacccactcg tgcacccaac tgatcttcag catcttttac tttcaccagc gtttctgggt 8220
gagcaaaaac aggaaggcaa aatgccgcaa aaaagggaat aagggcgaca cggaaatgtt 8280
gaatactcat actcttcctt tttcaatatt attgaagcat ttatcagggt tattgtctca 8340
tgagcggata catatttgaa tgtatttaga aaaataaaca aataggggtt ccgcgcacat 8400
ttccccgaaa agtgccacct gacgtcgacg gatcgggaga tcgatctccc gatccctag 8460
ggtcgactct cagtacaatc tgctctgatg ccgcatagtt aagccagtat ctgctccctg 8520
cttgtgtgtt ggaggtcgct gagtagtgcg cgagcaaaat ttaagctaca caaggcaag 8580
gcttgaccga caattgcatg aagaatctgc ttagggttag gcgttttgcg ctgcttcgcg 8640
atgtacgggc cagatatacg cgttgacatt gattattgac tagttattaa tagtaatcaa 8700
ttacggggtc attagttcat agcccatata tggagttccg cgttacataa cttacggtaa 8760
atggcccgcc tggctgaccg cccaacgacc cccgcccatt gacgtcaata atgacgtatg 8820
ttcccatagt aacgccaata gggactttcc attgacgtca atgggtggag tatttacggt 8880
aaactgccca cttggcagta catcaagtgt atc                                8913

SEQ ID NO: 48            moltype = DNA   length = 8913
FEATURE                  Location/Qualifiers
source                   1..8913
                         mol_type = other DNA
                         organism = Synthetic construct
SEQUENCE: 48
atatgccaag tacgccccct attgacgtca atgacggtaa atggcccgcc tggcattatg 60
cccagtacat gaccttatgg gactttccta cttggcagta catctacgta ttagtcatcg 120
ctattaccat ggtgatgcgg ttttggcagt acatcaatgg gcgtggatag cggtttgact 180
cacgggatt tccaagtctc caccccattg acgtcaatgg gagtttgttt tggcaccaaa 240
atcaacggga ctttccaaaa tgtcgtaaca actccgcccc attgacgcaa atgggcggta 300
ggcgtgtacg gtgggaggtc tatataagca gagctggttt agtgaaccgt cagatccgct 360
agagatccgc ggccgctaat acgactcact atagggagag ccgccaccat gaaacggaca 420
gccgacggaa gcgagttcga gtcaccaaag aagaagcgga aagtcagcag tgacaagaag 480
tacagcatcg gcctggccat cggcaccaac tctgtgggct gggccgtgat caccgacgag 540
tacaaggtgc ccagcaagaa attcaaggtg ctgggcaaca ccgaccggca cagcatcaag 600
aagaacctga tcggagccct gctgttcgac agcggcgaaa cagccgaggc cacccggctg 660
aagagaaccg ccagaagaag ataccagga tctctgcta tctgcaagag 720
atcttcagca acgagatggc caaggtggac gacagcttct ccacagact ggaagagtcc 780
ttcctggtgg aagaggataa gaagcacgag cggcaccca tcttcggcaa catcgtggac 840
gaggtggcct accacgagaa gtaccccacc atctaccacc tgagaagaa actggtggac 900
agcaccgaca aggccgacct gcggctgatc tatctgccc tggcccacat gatcaagttc 960
cggggccact tcctgatcga gggcgacctg aaccccgaca cagcgacgt ggacaagctg 1020
```

-continued

```
ttcatccagc tggtgcagac ctacaaccag ctgttcgagg aaaacccat caacgccagc   1080
ggcgtggacg ccaaggccat cctgtctgcc agactgagca agagcagacg gctgaaaaat   1140
ctgatcgccc agctgccgg cgagaagaag aatggcctgt tcggaaacct gattgccctg   1200
agcctgggcc tgaccccaa cttcaagagc aacttcgacc tggccgagga tgccaaactg   1260
cagctgagca aggacaccta cgacgacgac ctggacaacc tgctggccca gatcggcgac   1320
cagtacgccg acctgtttct ggccgccaag aacctgtccg acgccatcct gctgagcgac   1380
atcctgagag tgaacaccga gatcaccaag gccccctga gcgcctctat gatcaagaga   1440
tacgacgagc accaccagga cctgaccctg ctgaaagctc tcgtgcggca gcagctgcct   1500
gagaagtaca aagagatttt cttcgaccag agcaagaacg gctacgccgg ctacattgca   1560
ggcggagcca gccaggaaga gttctacaag ttcatcaagc ccatcctgga aaagatggac   1620
ggcaccgagg aactgctcgt gaagctgaac agagaggacc tgctgcggaa gcagcggacc   1680
ttcgacaacg gcagcatccc ccaccagatc cacctgggag agctgcacgc cattctgcgg   1740
cggcaggaag attttttacc attcctgaag gacaacgggg aaaagatcga gaagatcctg   1800
accttccgca tcccctacta cgtgggccct ctggccaggg gaaacagcag attcgcctgg   1860
atgaccagaa agagcgagga aaccatcacc ccctggaact tcgaggaagt ggtggacaag   1920
ggcgcttccg cccagagctt catcgagcgg atgaccaact tcgataagaa cctgcccaac   1980
gagaaggtgc tgcccaagca cagcctgctg tacgagtact tcaccgtgta taacgagctg   2040
accaaagtga aatacgtgac cgagggaatg agaaagcccg ccttcctgag cggcgagcag   2100
aaaaaggcca tcgtggacct gctgttcaag accaaccgga aagtgaccgt gaagcagctg   2160
aaagaggact acttcaagaa aatcgagtgc ttcgactccg tggaaatctc cggcgtggaa   2220
gatcggttca acgcctccct gggcacatac cacgatctgc tgaaaattat caaggacaag   2280
gacttcctgg acaatgagga aaacgaggac attctggaag atatcgtgct gaccctgaca   2340
ctgtttgagg acagagagat gatcgaggaa cggctgaaaa cctatgccca cctgttcgac   2400
gacaaagtga tgaagcagct gaagcggcgg agatacaccg ctggggcag gctgagccgg   2460
aagctgatca acggcatccg ggacaagcag tccggcaaga caatcctgga tttcctgaag   2520
tccgacggct tcgccaacag aaacttcatg cagctgatcc acgacgacg cctgaccttt   2580
aaagaggaca tccagaaagc ccaggtgtcc ggccagggcg atagcctgca cgagcacatt   2640
gccaatctgg ccggcagccc cgccattaag aagggcatcc tgcagacagt gaaggtggtg   2700
gacgagctcg tgaaagtgat gggccggcac aagcccgaga acatcgtgat cgaaatggcc   2760
agagagaaac agaccaccca gaagggacag aagaacagcc gcgagagaat gaagcggata   2820
gaagagggca tcaaagagct gggcagccaa atcctgaaag aacacccgt ggaaaacacc   2880
cagctgcaga acgagaagct gtacctgtac tacctgcaga atgggcggga tatgtacgtg   2940
gaccaggaac tggacatcaa ccggctgtcc gactacgatg tggaccatat cgtgcctcag   3000
agctttctga aggacgactc catcgacaac aaggtgctga ccagaagcga caagaaccgg   3060
ggcaagagcg acaacgtgcc ctccgaagag gtcgtgaaga agatgaagaa ctactggcgg   3120
cagctgctga acgccaagct gattacccag agaaagttcg acaatctgac caaggccgag   3180
agaggcggcc tgagcgaact ggataaggcc ggcttcatca gagacagct ggtggaaacc   3240
cggcagatca caaagcacgt ggcacagatc ctggactccc ggatgaacac taagtacgac   3300
gagaatgaca agtcgatccg ggaagtgaaa gtgatcaccc tgaagtccaa gctggtgtcc   3360
gatttccgga aggatttcca gttttacaaa gtgcgcgaga tcaacaacta ccaccacgcc   3420
cacgacgcct acctgaacgc cgtcgtggga accgccctga tcaaaagta ccctaagctg   3480
gaaagcgagt tcgtgtacgg cgactacaag gtgtacgacg tgcggaagat gatcgccaag   3540
agcgagcagg aaatcggcaa ggctaccgcc aagtacttct tctacagcaa catcatgaac   3600
ttttttcaaga ccgagattac cctgccaaac ggcgagatcc ggaagcggcc tctgatcgag   3660
acaaacggcg aaaccgggga gatcgtgtgg gataaggcc gggattttgc cacccgtgcgg   3720
aaagtgctga gcatgccca gtgaatatc gtgaaaaaga ccgaggtgca gacaggcggc   3780
ttcagcaaag agtctatcct gcccaagagg aacagcgata agctgatcgc cagaaagaag   3840
gactgggacc ctaagaagta cggcggcttc gacagcccca ccgtggccta ttctgtgctg   3900
gtggtggcca aagtggaaaa gggcaagtcc aagaaactga agagtgtgaa agagctgctg   3960
gggatcacca tcatggaaag aagcagcttc gagaagaatc ccatcgactt tctggaagcc   4020
aagggctaca aagaagtgaa aaaggacctg atcatcaagc tgcctaagta ctccctgttc   4080
gagctgaaaa acggccggaa gagaatgctg gcctctgccg cgaactgca aagggaaac   4140
gaactggcct ctgaggatc tagcggtggt tcctctggaa gcgagacacc aggcacaagc   4200
gagtccgcca caccagagag ctccggcggc tcctccggag atcctctga ggtggagttt   4260
tcccacgagt actggatgag acatgccctg acccttgcgca agagggcatg ggatgaaaga   4320
gaagtcccog tgggcgccgt gctggtgcac aacaatagag tgatcggaga gggatgaaac   4380
aggccaatcg gcgccacga ccctaccgca cacgcagaga tcatggcact gaggcaggga   4440
ggcctggtca tgcagaatta ccgctgatc gatgccaccc tgtatgtgac actggagcca   4500
tgcgtgatgt gcgcaggagc aatgatccac agcaggatcg gaagagtggt gttcggagca   4560
cggacgcca agaccggcgc agcaggctcc ctgatggatg tgctgcacca ccccggcatg   4620
aaccaccggg tggagatcac agaggaatc ctggcagacg agtgcgccgc cctgctgagc   4680
gatttcttta gaatgcggag acaggagatc aaggcccaga gaaggcaca gagctccacc   4740
gactctggag gatctagcgg cggatcctct ggaagcgaga caccaggcac aagcgagtcc   4800
gccacaccag agagctccgg cggtcctcc ggaggatcgg cagtgggtga gtttttccac   4860
gagtactgga tgagacatgc cctgaccctg gccaagaggg cacgcgatga gaggaggtg   4920
cctgtgggag ccgtgctggt gctgaacaat agagtgatcg gcgaggggctg aacagagcc   4980
atcggcctgc acgacccaac agcccatgcc gaaattatgg ccctgagaca gggcggcctg   5040
gtcatgcaga actacagact gattgacgac accctgtacg tgacattcga gccttgcgtg   5100
atgtgccgg cgcgcatgat ccactctagg atccgccgc tggtgttttgg cgtgaggaac   5160
gcaaaaaccg gcgccgcagg ctccctgatg gacgtgctgc actacccggg catgaatcac   5220
cgcgtcgaaa ttaccgaggg aatcctggca gatgaatgtg ccgccctgct gtgctatttc   5280
tttcggatgc ctagacaggt gttcaatgct cagaagaagg cccagagctc caccgactcc   5340
ggaggatcta gcggaggctc ctctggctct gagacacctg gcacaagcga gagcgcaaca   5400
cctgaaagca gcggggggcag cagcgggga tcactgcct ccaaatatgt gaacttcctg   5460
tacctggcca gccactatga aagctgaag gctccccg aggataatga gcagaaacag   5520
ctgtttgtgg aacagcacaa gcactacctg gacgagatca tcgagcagat cagcgagttc   5580
tccaagagag tgatcctggc cgacgctaat ctggacaaag tgctgtccgc ctacaacaag   5640
caccgggata agcccatcag agagcaggcc gagaatatca tccacctgtt taccctgacc   5700
aatctgggag cccctgccgc cttcaagtac tttgacacca ccatcgaccg gaagaggtac   5760
```

```
accagcacca aagaggtgct ggacgccacc ctgatccacc agagcatcac cggcctgtac 5820
gagacacgga tcgacctgtc tcagctggga ggtgactctg gcggctcaaa agaaccgcc  5880
gacggcagcg aattcgagcc caagaagaag aggaaagtct aaccggtcat catcaccatc 5940
accattgagt ttaaacccgc tgatcagcct cgactgtgcc ttctagttgc cagccatctg 6000
ttgtttgccc ctccccgtg ccttccttga ccctggaagg tgccactccc actgtccttt  6060
cctaataaaa tgaggaaatt gcatcgcatt gtctgagtag gtgtcattct attctggggg 6120
gtggggtggg gcaggacagc aaggggagg attgggaaga caatagcagg catgctgggg  6180
atgcggtggg ctctatggct tctgaggcgg aagaaccag ctggggctcg ataccgtcga   6240
cctctagcta gagcttggcg taatcatggt catagctgtt tcctgtgtga aattgttatc  6300
cgctcacaat tccacacaac atacgagccg gaagcataaa gtgtaaagcc tagggtgcct  6360
aatgagtgag ctaactcaca ttaattgcgt tgcgctcact gcccgctttc cagtcgggaa  6420
acctgtcgtg ccagctgcat taatgaatcg gccaacgcgc ggggagaggc ggtttgcgta  6480
ttgggcgctc ttccgcttcc tcgctcactg actcgctgcg ctcggtcgtt cggctgcggc  6540
gagcggtatc agctcactca aaggcggtaa tacggttatc cacagaatca ggggataacg  6600
caggaaagaa catgtgagca aaaggccagc aaaaggccag gaaccgtaaa aaggccgcgt  6660
tgctggcgtt tttccatagg ctccgccccc ctgacgagca tcacaaaaat cgacgctcaa  6720
gtcagaggtg gcgaaacccg acaggactat aaagatacca ggcgtttccc cctggaagct  6780
ccctcgtgcg ctctcctgtt ccgaccctgc cgcttaccgg atacctgtcc gcctttctcc  6840
cttcgggaag cgtggcgctt tctcatagct cacgctgtag gtatctcagt tcggtgtagg  6900
tcgttcgctc caagctgggc tgtgtgcacg aaccccccgt tcagcccgac cgctgcgcct  6960
tatccggtaa ctatcgtctt gagtccaacc cggtaagaca cgacttatcg ccactggcag  7020
cagccactgg taacaggatt agcagagcga ggtatgtagg cggtgctaca gagttcttga  7080
agtggtggcc taactacggc tacactagaa gaacagtatt tggtatctgc gctctgctga  7140
agccagttac cttcggaaaa agagttggta gctcttgatc cggcaaacaa accaccgctg  7200
gtagcggtgg ttttttttgtt tgcaagcagc agattacgcg cagaaaaaaa ggatctcaag  7260
aagatccttt gatcttttct acggggtctg acactcagtg gaacgaaaac tcacgttaag  7320
ggattttggt catgagatta tcaaaaagga tcttcaccta gatccttttta aattaaaaat  7380
gaagttttaa atcaatctaa agtatatatg agtaaacttg gtctgacagt taccaatgct  7440
taatcagtga ggcacctatc tcagcgatct gtctatttcg ttcatccata gttgcctgac  7500
tccccgtcgt gtagataact acgatacggg agggcttacc atctggcccc agtgctgcaa  7560
tgataccgcg agaccacgc tcaccggctc cagatttatc agcaataaac cagccagccg    7620
gaagggccga gcgcagaagt ggtcctgcaa ctttatccgc ctccatccag tctattaatt  7680
gttgccggga agctagagta agtagttcgc cagttaatag tttgcgcaac gttgttgcca  7740
ttgctacagg catcgtggtg tcacgctcgt cgtttggtat ggcttcattc agctccggtt  7800
cccaacgatc aaggcgagtt acatgatccc ccatgttgtg caaaaaagcg gttagctcct  7860
tcggtcctcc gatcgttgtc agaagtaagt tggccgcagt gttatcactc atggttatgg  7920
cagcactgca taattctctt actgtcatgc catccgtaag atgcttttct gtgactggtg  7980
agtactcaac caagtcattc tgagaatagt gtatgcggcg accgagttgc tcttgcccgg  8040
cgtcaatacg ggataatacc gcgccacata gcagaacttt aaaagtgctc atcattggaa  8100
aacgttcttc ggggcgaaaa ctctcaagga tcttaccgct gttgagatcc agttcgatgt  8160
aacccactcg tgcacccaac tgatcttcag catcttttac tttcaccagc gtttctgggt  8220
gagcaaaaac aggaaggcaa aatgccgcaa aaaagggaat aagggcgaca cggaaatgtt  8280
gaatactcat actcttcctt tttcaatatt attgaagcat ttatcagggt tattgtctca  8340
tgagcggata catatttgaa tgtatttaga aaaataaaca aataggggtt ccgcgcacat  8400
ttccccgaaa agtgccacct gacgtcgacg gatcgggaga tcgatctccc gatccctag    8460
ggtcgactct cagtacaatc tgctctgatg ccgcatagtt aagccagtat ctgctccctg  8520
cttgtgtgtt ggaggtcgct gagtagtgcg cgagcaaaat ttaagctaca acaaggcaag  8580
gcttgaccga caattgcatg aagaatctgc ttagggttag gcgttttgcg ctgcttcgcg  8640
atgtacgggc cagatatacg cgttgacatt gattattgac tagttattaa tagtaatcaa  8700
ttacggggtc attagttcat agcccatata tggagttccg cgttacataa cttacggtaa  8760
atggcccgcc tggctgaccg cccaacgacc cccgcccatt gacgtcaata atgacgtatg  8820
ttcccatagt aacgccaata gggactttcc attgacgtca atgggtggag tatttacggt  8880
aaactgccca cttggcagta catcaagtgt atc                              8913
```

```
SEQ ID NO: 49          moltype = DNA   length = 8913
FEATURE                Location/Qualifiers
source                 1..8913
                       mol_type = other DNA
                       organism = Synthetic construct
SEQUENCE: 49
atatgccaag tacgccccct attgacgtca atgacggtaa atggcccgcc tggcattatg  60
cccagtacat gaccttatgg gactttccta cttggcagta catctacgta ttagtcatcg  120
ctattaccat ggtgatgcgg ttttggcagt acatcaatgg gcgtggatag cggtttgact  180
cacggggatt tccaagtctc cacccattg acgtcaaatg gagtttgttt tggcaccaaa    240
atcaacggga ctttccaaaa tgtcgtaaca actccgcccc attgacgcaa atgggcggta  300
ggcgtgtacg gtgggaggtc tatataagca gagctggttt agtgaaccgt cagatccgct  360
agagatccgc ggccgctaat acgactcact atagggagag ccgccaccat gaacggaca    420
gccgacggaa gcgagttcga gtcaccaaag aagaagcgga aagtcagcag tgacaagaag  480
tacagcatcg gcctggccat cggcaccaac tctgtgggct gggccgtgat caccgacgag  540
tacaaggtgc ccagcaagaa attcaaggtg ctgggcaaca ccgaccggca cagcatcaag  600
aagaacctga tcgagcccct gctgttcgac agcggcgaaa cagccgaggc cacccggctg  660
aagagaaccg ccagaagaag atacaccaga cggaagaacc ggatctgcta tctgcaagag  720
atcttcagca acgagatggc caaggtggac gacagcttcc tccacagact ggaagagtcc  780
ttcctggtgg aagaggataa gaagcacgag cggcaccccc tcttcggcaa catcgtggac  840
gaggtggcct accacgagaa gtaccccacc atctaccacc tgagaaagaa actggtggac  900
agcaccgaca aggccgacct gcggctgatc tatctggccc tggcccacat gatcaagttc  960
cggggccact tcctgatcga gggcgacctg aaccccgaca cagcgacgt ggacaagctg    1020
ttcatccagc tggtgcagac ctacaaccag ctgttcgagg aaaaccccat caacgccagc  1080
ggcgtggacg ccaaggccat cctgtctgcc agactgagca agagcagacg gctggaaaat  1140
```

```
ctgatcgccc agctgcccgg cgagaagaag aatggcctgt tcggaaacct gattgccctg   1200
agcctgggcc tgaccccccaa cttcaagagc aacttcgacc tggccgagga tgccaaactg   1260
cagctgagca aggacaccta cgacgacgac ctggacaacc tgctggccca gatcggcgac   1320
cagtacgccg acctgtttct ggccgccaag aacctgtccg acgccatcct gctgagcgac   1380
atcctgagag tgaacaccga gatcaccaag gcccccctga gcgcctctat gatcaagaga   1440
tacgacgagc accaccagga cctgaccctg ctgaaagctc tcgtgcggca gcagctgcct   1500
gagaagtaca agagattttt cttcgaccag agcaagaacg gctacgccgg ctacattgac   1560
ggcggagcca gccaggaaga gttctacaag ttcatcaagc ccatcctgga aaagatggac   1620
ggcaccgagg aactgctcgt gaagctgaac agagaggacc tgctgcggaa gcagcggacc   1680
ttcgacaacg gcagcatccc ccaccagatc cacctgggag agctgcacgc cattctgcgg   1740
cggcaggaag attttttaccc attcctgaag gacaacgggg aaaagatcga gaagatcctg   1800
accttccgca tccctactaa cgtgggccct ctggccaggg gaaacagcag attcgcctgg   1860
atgaccagaa agagcgagga aaccatcacc ccctggaact tcgaggaagt ggtggacaag   1920
ggcgcttccg cccagagctt catcgagcgg atgaccaact tcgataagaa cctgcccaac   1980
gagaaggtgc tgcccaagca cagcctgctg tacgagtact tcaccgtgta taacgagctg   2040
accaaagtga aatacgtgac cgagggaatg agaaagcccg ccttcctgag cggcgagcag   2100
aaaaaggcca tcgtggacct gctgttcaag accaaccgga agtgaccgt gaagcagctg   2160
aaagaggact acttcaagaa aatcgagtgc ttcgactccg tggaaatctc cggcgtggaa   2220
gatcggttca acgcctccct gggcacatac cacgatctgc tgaaaattat caaggacaag   2280
gacttcctgg acaatgagga aaacgaggac attctggaag atatcgtgct gaccctgaca   2340
ctgtttgagg acagagagat gatcgaggaa cggctgaaaa cctatgccca cctgttcgac   2400
gacaaagtga tgaagcagct gaagcggcgg agatacaccg gctgggcag gctgagccgg   2460
aagctgatca acggcatccg ggacaagcag tccggcaaga caatcctgga tttcctgaag   2520
tccgacggct tcgccaacag aaacttcatg cagctgatcc acgacgacag cctgaccttt   2580
aaagaggaca tccagaaagc ccaggtgtcc ggccagggcg atagcctgca cgagcacatt   2640
gccaatctgg ccggcagccc cgccattaag aagggcatcc tgcagacagt gaaggtggtg   2700
gacgagctcg tgaaagtgat gggccggcac aagcccgaga acatcgtgat cgaaatggcc   2760
agagagaacc agaccaccca aagggacag aagaacagcc gcgagagaat gaagcggatc   2820
gaagagggca tcaaagagct gggcagccag atcctgaaag aacacccgt ggaaaacacc   2880
cagctgcaga acgagaagct gtacctgtac tacctgcaga atggccggga tatgtacgtg   2940
gaccaggaac tggacatcaa ccggctgtcc gactacgatg tggaccatat cgtgcctcag   3000
agctttctga aggacgactc catcgacaac aaggtgctga ccagaagcga caagaaccgg   3060
ggcaagagcc acaacgtgcc ctccgaagag gtcgtgaaga agatgaagaa ctactggcgg   3120
cagctgctga acgccaagct gattacccag agaaagttcg acaatctgac caaggccgag   3180
agaggcggcc tgagcgaact ggataaggcc ggcttcatca agagacagct ggtggaaacc   3240
cggcagatca caaagcacgt ggcacagatc ctggactccc ggatgaacac taagtacgac   3300
gagaatgaca agctgatccg ggaagtgaaa gtgatcaccc tgaagtccaa gctggtgtcc   3360
gatttccgga aggattttcca gttttacaaa gtgcgcgaga tcaacaacta ccaccacgcc   3420
cacgacgcct acctgaacgc cgtcgtggga accgccctga tcaaaaagta ccctaagctg   3480
gaaagcgagt tcgtgtacgg cgactacaag gtgtacgacg tgcggaagat gatcgccaag   3540
agcgagcagg aaatcggcaa ggctaccgcc aagtactttt tctacagcaa catcatgaac   3600
tttttcaaga ccgagattac cctggccaac ggcgagatcc ggaagcggcc tctgatcgag   3660
acaaacggcg aaaccgggga gatcgtgtgg gataagggcc gggattttgc caccgtgcgg   3720
aaagtgctga gcatgccca agtgaatatc gtgaaaaaga ccgaggtgca gacaggcggc   3780
ttcagcaaag agtctatcct gcccaagagg aacagcgata agctgatcgc cagaaagaag   3840
gactgggacc ctaagaagta cggcggcttc gacagccca ccgtggccta ttctgtgctg   3900
gtggtggcca aagtggaaaa gggcaagtcc aagaaactga aagtgtgaa agagctgctg   3960
gggatcacca tcatgaaaag aagcagcttc gagaagaatc ccatcgactt tctggaagcc   4020
aagggctaca aagaagtgaa aaaggacctg atcatcaagc tgcctaagta ctccctgttc   4080
gagctggaaa acggccggaa gagaatgctg gcctctgccg cgaactgca aagggaaac   4140
gaactggccc tgcccctccaa atatgtgaac ttcctgtacc tggccagcca ctatgaagaag   4200
ctgaagtctg gaggatctag cggtggttcc tctggaagcg agacaccagg cacaagcgag   4260
tccgccacac cagagagctc cggcggctcc tccggaggat cctctgaggt ggagttttcc   4320
cacgagtact ggatgagaca tgccctgacc ctggccaaga gggcatggga tgaaagagaa   4380
gtcccgtgg gcgccgtgct ggtgcacaac aatagagtga tcggagaggg atggaacagg   4440
ccaatcggcc gccacgaccc taccgcacac gcagagatca tggcactgag gcagggaggc   4500
ctggtcatgc agaattaccg cctgatcgat gccaccctgt atgtgacact ggagccatgc   4560
gtgatgtgcg caggagcaat gatccacagc aggatcggaa gagtggtgtt cggagcacgg   4620
gacgccaaga ccggcgcagc aggctcctg atggatgtgc tgcaccaccc cggcatgaac   4680
caccgggtgg agatcacaga gggaatcctg gcagacgagt gcgccgccct gctgagcgat   4740
ttctttagaa tgcggagaca ggagatcaag gcccagaaga aggcacagag ctccaccgac   4800
tctgaggat ctagcggcgg atcctctgga agcgagacac caggcacaag cgagtccgcc   4860
acaccagaga gctccggcgg ctcctccgga ggatcctctg aggtggagtt tccccacgag   4920
tactggatga gacatgccct gaccctggcc aagagggcct ggcatgagga ggggtgcct   4980
gtgggagccg tgctggtgct gaacaataga gtgatcggcg agggctgaa cagagccatc   5040
ggcctgcacg acccaacagc ccatgccgaa attatggccc tgagacaggg cggcctggtc   5100
atgcagaact acagactgat tgacgccacc ctgtacgtga cattcgagcc ttgcgtgatg   5160
tgcgccggcg ccatgatcca ctctaggatc ggccgcgtgg tgtttggcgt gaggaacgca   5220
aaaaccgggc ccgcaggctc ctgatggac gtgctgcact acccccggcact gaatcaccgc   5280
gtcgaaatta ccgagggaat cctggcagat gaatgtgccg ccctgctgtg ctatttcttt   5340
cggatgccta acaggtgtt caatgctcag aagaaggccc agagctccac cgactccgga   5400
ggatctagcg gaggctcctc tggctctgag acacctggca aagcgagag cgcaacacct   5460
gaaagcagcg ggggcagcag cggggggtca ggctcccccg aggataatga gcagaaacag   5520
ctgtttgtgg aacagcacaa gcactacctg gacgagatca tcgagcaaat cagcgagttc   5580
tccaagagag tgatcctggc cgacgctaat ctggacaaag tgctgtccgc ctacaacaag   5640
caccgggata agcccatcag agagcaggcc gagaatatca tccacctgtt taccctgacc   5700
aatctggag cccctgccgc cttcaagtac tttgacacca ccatcgaccg gaagaggtac   5760
accagcacca agaggtgct ggacgccacc ctgatccacc agagcatcac cggcctgtac   5820
gagacacgga tcgacctgtc tcagctggga ggtgactctg gcggctcaaa aagaaccgcc   5880
```

```
gacggcagcg aattcgagcc caagaagaag aggaaagtct aaccggtcat catcaccatc  5940
accattgagt ttaaacccgc tgatcagcct cgactgtgcc ttctagttgc cagccatctg  6000
ttgtttgccc ctccccgtg ccttccttga ccctggaagg tgccactccc actgtccttt  6060
cctaataaaa tgaggaaatt gcatcgcatt gtctgagtag gtgtcattct attctggggg  6120
gtggggtggg gcaggacagc aagggggagg attgggaaga caatagcagc catgctgggg  6180
atgcggtggg ctctatggct tctgaggcgg aaagaaccag ctggggctcg ataccgtcga  6240
cctctagcta gagcttggcg taatcatggt catagctgtt tcctgtgtga aattgttatc  6300
cgctcacaat tccacacaac atcgagccg gaagcataaa gtgtaaagcc tagggtgcct  6360
aatgagtgag ctaactcaca ttaattgcgt tgcgctcact gcccgctttc cagtcgggaa  6420
acctgtcgtg ccagctgcat taatgaatcg gccaacgcgc ggggagaggc ggtttgcgta  6480
ttgggcgctc ttccgcttcc tcgctcactg actcgctgcg ctcggtcgtt cggctgcggc  6540
gagcggtatc agctcactca aaggcggtaa tacggttatc cacagaatca ggggataacg  6600
caggaaagaa catgtgagca aaaggccagc aaaaggccag gaaccgtaaa aaggccgcgt  6660
tgctggcgtt tttccatagg ctccgccccc ctgacgagca tcacaaaaat cgacgctcaa  6720
gtcagaggtg gcgaaacccg acaggactat aaagatacca ggcgtttccc cctggaagct  6780
ccctcgtgcg ctctcctgtt ccgaccctgc cgcttaccgg atacctgtcc gcctttctcc  6840
cttcgggaag cgtggcgctt tctcatagct cacgctgtag gtatctcagt tcggtgtagg  6900
tcgttcgctc caagctgggc tgtgtgcacg aacccccgt tcagcccgac cgctgcgcct  6960
tatccggtaa ctatcgtctt gagtccaacc cggtaagaca cgacttatcg ccactggcag  7020
cagccactgg taacaggatt agcagagcga ggtatgtagg cggtgctaca gagttcttga  7080
agtggtggcc taactacggc tacactagaa gaacagtatt tggtatctgc gctctgctga  7140
agccagttac cttcggaaaa agagttggta gctcttgatc cggcaaacaa accaccgctg  7200
gtagcggtgg tttttttgtt tgcaagcagc agattacgcg cagaaaaaaa ggatctcaag  7260
aagatccttt gatcttttct acggggtctg acactcagtg gaacgaaaac tcacgttaag  7320
ggattttggt catgagatta tcaaaaagga tcttcaccta gatcctttta aattaaaaat  7380
gaagttttaa atcaatctaa agtatatatg agtaaacttg gtctgacagt taccaatgct  7440
taatcagtga ggcacctatc tcagcgatct gtctatttcg ttcatccata gttgcctgac  7500
tccccgtcgt gtagataact acgatacggg agggcttacc atctggcccc agtgctgcaa  7560
tgataccgcg agacccacgc tcaccggctc agatttatc agcaataaac cagccagccg  7620
gaagggccga gcgcagaagt ggtcctgcaa ctttatccgc ctccatccag tctattaatt  7680
gttgccggga agctagagta gtagttcgc cagttaatag tttgcgcaac gttgttgcca  7740
ttgctacagg catcgtggtg tcacgctcgt cgtttggtat ggcttcattc agctccggtt  7800
cccaacgatc aaggcgagtt acatgatccc ccatgttgtg caaaaaagcg gttagctcct  7860
tcggtcctcc gatcgttgtc agaagtaagt tggccgcagt gttatcactc atggttatgg  7920
cagcactgca taattctctt actgtcatgc catccgtaag atgcttttct gtgactggtg  7980
agtactcaac caagtcattc tgagaatagt gtatgcggcg accgagttgc tcttgcccgg  8040
cgtcaatacg ggataatacc gcgccacata gcagaacttt aaaagtgctc atcattggaa  8100
aacgttcttc ggggcgaaaa ctctcaagga tcttaccgct gttgagatcc agttcgatgt  8160
aacccactcg tgcacccaac tgatcttcag catctttttac ttcaccagc gtttctgggt  8220
gagcaaaaac aggaaggcaa aatgccgcaa aaaagggaat aagggcgaca cggaaatgtt  8280
gaatactcat actcttcctt tttcaatatt attgaagcat ttatcagggt tattgtctca  8340
tgagcggata catatttgaa tgtatttaga aaaataaaca aataggggtt ccgcgcacat  8400
ttccccgaaa agtgccacct gacgtcgacg gatcgggaga tcgatctccc gatccctag  8460
ggtcgactct cagtacaatc tgctctgatg ccgcatagtt aagccagtat ctgctccctg  8520
cttgtgtgtt ggaggtcgct gagtagtgcg cgagcaaaat ttaagctaca caaggcaag  8580
gcttgaccga caattgcatg aagaatctgc ttagggttag gcgttttgcg ctgcttcgcg  8640
atgtacgggc cagatatacg cgttgacatt gattattgac tagttattaa tagtaatcaa  8700
ttacggggtc attagttcat agcccatata tggagttccg cgttacataa cttacggtaa  8760
atggcccgcc tggctgaccg cccaacgacc cccgcccatt gacgtcaata atgacgtatg  8820
ttcccatagt aacgccaata gggactttcc attgacgtca atgggtggag tatttacggt  8880
aaactgccca cttggcagta catcaagtgt atc                               8913

SEQ ID NO: 50          moltype = DNA   length = 8913
FEATURE                Location/Qualifiers
source                 1..8913
                       mol_type = other DNA
                       organism = Synthetic construct
SEQUENCE: 50
atatgccaag tacgccccct attgacgtca atgacggtaa atggcccgcc tggcattatg   60
cccagtacat gaccttatgg gactttccta cttggcagta catctacgta ttagtcatcg  120
ctattaccat ggtgatgcgg ttttggcagt acatcaatgg gcgtggatag cggtttgact  180
cacgggggatt tccaagtctc caccccattg acgtcaatgg gagtttgttt tggcaccaaa  240
atcaacggga ctttccaaaa tgtcgtaaca actccgcccc attgacgcaa atgggcggta  300
ggcgtgtacg gtgggaggtc tatataagca gagctggttt agtgaaccgt cagatccgct  360
agagatccgc ggccgctaat acgactcact ataggggagag ccgccaccat gaaacggaca  420
gccgacggaa gcgagttcga gtcaccaaag aagaagcgga aagtcagcag tgacaagaag  480
tacagcatcg gcctggccat cggcaccaac tctgtgggct gggccgtgat caccgacgag  540
tacaaggtgc cagctgcaga aatcaaggtg ctgggcaaca ccgaccggca cagcatcaag  600
aagaacctga tcggagccct gctgttcgac agcggcgaaa cagccgaggc caccggcctg  660
aagagaaccg ccagaagaag atacaccaga cggaagaacc ggatctgcta tctgcaagag  720
atcttcagca acgagatggc caaggtggac gacagcttct tccacagact ggaagagtcc  780
ttcctggtgg aagaggataa gaagcacgag cggcacccca tcttcggcaa catcgtggac  840
gaggtggcct accacgagaa gtaccccacc atctaccacc tgagaaagaa actggtggac  900
agcaccgaca aggccgacct gcggctgatc tatctggccc tggcccacat gatcaagttc  960
cgggggccact tcctgatcga gggcgacctg aaccccgaca acagcgacgt ggacaagctg 1020
ttcatccagc tggtgcagac ctacaaccag ctgttcgagg aaaaccccat caacgccagc 1080
ggcgtggacg ccaaggccat cctgtctgcc agactgagca gagcagacg gctggaaaat 1140
ctgatcgccc agctgcccgg cgagaagaag aatggcctgt tcggaaacct gattgccctg 1200
agcctggccc tgacccccaa cttcaagagc aacttcgacc tggccgagga tgccaaactg 1260
```

```
cagctgagca aggacaccta cgacgacgac ctggacaacc tgctggccca gatcggcgac   1320
cagtacgccg acctgtttct ggccgccaag aacctgtccg acgccatcct gctgagcgac   1380
atcctgagag tgaacaccga gatcaccaag gccccctga gcgcctctat gatcaagaga    1440
tacgacgagc accaccagga cctgaccctg ctgaaagctc tcgtgcggca gcagctgcct   1500
gagaagtaca aagagatttt cttcgaccag agcaagaacg gctacgccgg ctacattgac   1560
ggcggagcca gccaggaaga gttctacaag ttcatcaagc ccatcctgga aaagatggac   1620
ggcaccgagg aactgctcgt gaagctgaac agagaggacc tgctgcggaa gcagcggacc   1680
ttcgacaacg gcagcatccc ccaccagatc cacctgggag agctgcacgc cattctgcgg   1740
cggcaggaag attttaccc attcctgaag gacaaccgga aaaagatcga gaagatcctg   1800
accttccgca tccctacta cgtgggccct ctggccgatg gaaacagcag attcgcctgg   1860
atgaccagaa agagcgagga aaccatcacc cctggaact tcgaggaagt ggtgacaag    1920
ggcgcttccg cccagagctt catcgagcgg atgaccaact tcgataagaa cctgcccaac   1980
gagaaggtgc tgcccaagca cagcctgctg tacgagtact tcaccgtgta taacgagctg   2040
accaaagtga aatacgtgac cgagggaatg aaaagcccg ccttcctgag cggcgagcag   2100
aaaaaggcca tcgtggacct gctgttcaag accaaccgga aagtgaccgt gaagcagctg   2160
aaagaggact acttcaagaa aatcgagtgc ttcgactccg tggaaatctc cggcgtggaa   2220
gatcggttca acgcctccct gggcacatac cacgatctgc tgaaaattat caaggacaag   2280
gacttcctgg acaatgagga aaacgaggac atttctgaag atatcgtgct gaccctgaca   2340
ctgtttgagg acagagagat gatcgaggaa cggctgaaaa cctatgccca cctgttcgac   2400
gacaaagtga tgaagcagct gaagcggcgg agatacaccg gctggggcag gctgagccgg   2460
aagctgatca acggcatccg ggacaagcag tccggcaaga caatcctgga tttcctgaag   2520
tccgacggct tcgccaacag aaacttcatg cagctgatcc acgacgacag cctgaccttt   2580
aaagaggaca tccagaaagc ccaggtgtcc ggccaggcg atagcctgca cgagcacatt   2640
gccaatctgg ccggcagccc cgccattaag aagggcatcc tgcagacagt gaaggtggtg   2700
gacgagctcg tgaaagtgat gggccggcac aagcccgaga acatcgtgat cgaaatggcc   2760
agagagaacc agaccaccca gaagggacag aagaacaccg gcgagagaat gaagcggatc   2820
gaagagggca tcaaagagct gggcagccag atcctgaaag aacacccgt ggaaaacacc   2880
cagctgcaga acgagaagct gtacctgtac tacctgcaga atgggcggga tatgtacgtg   2940
gaccaggaac tggacatcaa ccggctgtcc gactacgatg tggaccatat cgtgcctcag   3000
agctttctga aggacgactc catcgacaac aaggtgctga ccagaagcga caagaaccgg   3060
ggcaagagcg acaacgtgcc ctccgaaagg gtcgtgaaga agatgaagaa ctactggcgg   3120
cagctgctga acgccaagct gattacccag agaaagttcg acaatctgac caaggccgag   3180
agaggcggcc tgagcgaact ggataaggcc ggcttcatca gagacagct ggtggaaacc   3240
cggcagatca caaagcacgt ggcacagatc ctggactccc ggatgaacac taagtacgac   3300
gagaatgaca agctgatccg ggaagtgaaa gtgatcaccc tgaagtccaa gctggtgtcc   3360
gatttccgga aggatttcca gttttacaaa gtgcgcgaga tcaacaacta ccaccacgcc   3420
cacgacgcct acctgaacgc cgtcgtggga accgccctga tcaaaagta ccctaagctg   3480
gaaagcgagt tcgtgtacgg cgactacaag gtgtacgacg tgcggaagat gatcgccaag   3540
agcgagcagg aaatcggcaa ggctaccgcc aagtacttct tctacagcaa catcatgaac   3600
ttttccaaga ccgagattac cctgccaac ggcgagatcc ggaagcggcc tctgatcgag   3660
acaaacggcg aaaccgggga gatcgtgtgg gataagggcc gggattttgc caccgtgcgg   3720
aaagtgctga gcatgcccca agtgaatatc gtgaaaaaga ccgaggtgca gacaggcggc   3780
ttcagcaaag agtctatcct gcccaagagg aacagcgata gctgatcgc cagaaagaag   3840
gactgggacc ctaagaagta cggcggcttc gacagcccca ccgtggccta ttctgtgctg   3900
gtggtggcca aagtggaaaa gggcaagtcc aagaaactga agagtgtgaa agagctgctg   3960
gggatcacca tcatggaaag aagcagcttc gagaagaatc ccatcgactt tctggaagcc   4020
aagggctaca aagaagtgaa aaaggacctg atcatcaagc tgcctaagta ctcccctgttc   4080
gagctgaaaa acggccggaa gagaatgctg gcctctgccg gcgaactgca aagggaaac   4140
gaactggccc tgccctccaa atatgtgaac ttcctgtacc tggccagcca ctatgagaag   4200
ctgaagggct cctctggagg atctagcggt ggttcctctg gaagcgagac accaggcaca   4260
agcgagtccg ccacaccaga gagctccggc ggctcctccg gaggatcctc tgaggtgaag   4320
ttttcccacg agtactggat gagacatgcc ctgaccctgg ccaagagggc atggatgaa   4380
agagaagtcc ccgtgggcgc cgtgctggtg cacaacaata gagtgatcgg agagggatgg   4440
aacaggccaa tcgccgcca cgaccctacc gcacacgcag agatcatggc actgaggcag   4500
ggaggcctgg tcatgcagaa ttaccgcctg atcgatgcca ccctgtatgt gacactggag   4560
ccatgcgtga tgtgcgcagg agcaatgatc cacagcagga tcggaagagt ggtgttcgga   4620
gcacgggacg ccaagaccgg cgcagcaggc tccctgatgg atgtgctgca ccaccccggc   4680
atgaaccacc gggtggagat cacagaggga atcctggcag acgagtgcgc cgccctgctg   4740
agcgatttct ttagaatgcg gagacaggag atcaaggccc agaagaaggc acagagctcg   4800
accgactctg gaggatctag cggcggatcc tctggaagcg agacaccagg cacaagcgag   4860
tccgccacac cagagagctc cggcggctcc tccggaggat cctctgaggt ggagttttcc   4920
cacgagtact ggatgagaca tgccctgacc ctggccaaga gggcacgcga tgagagggag   4980
gtgcctgtgg gagccgtgct ggtgctgaac aatagagtga tcgcgaggg ctggaacaga   5040
gccatcggcc tgcacgaccc aacagcccat gccgaaatta caacgggcgg tgcctgatgcg   5100
ctggtcatgc agaactacag actgattgac gccaccctgt acgtgacatt cgagccttgc   5160
gtgatgtgcg ccggcgccat gatccactct aggatcggcc gcgtggtgtt tggcgtgagg   5220
aacgcaaaaa ccggcgccgc aggctccctg atggacgtgc tgcactaccc cggcatgaat   5280
caccgcgtcg aaattaccga gggaatcctg gcagatgaat gtgccgccct gctgtgctat   5340
ttcttttcgga tgcctagaca ggtgttcaat gctcagaaga aggccagag ctccaccgac   5400
tccggaggat ctagcggagg ctcctctggc tctgagacac tggcacaag cgagagcgca   5460
acacctgaaa gcagcgggg cagcagcggg ggtcacccg aggataatga gcagaaacag   5520
ctgtttgtg aacagcacaa gcactacctg gacgagatca tcgagcagat cagcgagttc   5580
tccaagagag tgatcctggc cgacgctaat ctggacaaag tgctgtccgc ctacaacaag   5640
caccgggata gcccatcag agagcaggcc gagaatatca tccacctgtt taccctgacc   5700
aatctgggag ccctgccgc cttcaagtac tttgacacca ccatcgaccg gaagaggtac   5760
accagcacca aagaggtgct ggacgccacc ctgatccacc agagcatcac cggcctgtac   5820
gagacacgga tcgacctgtc tcagctggga ggtgactctg cggctcaaaa agaaccgcc   5880
gacggcagcg aattcgagcc caagaagaag aggaaagtct aaccggtcat catcaccatc   5940
accattgagt ttaaacccgc tgatcagcct cgactgtgcc ttctagttgc cagccatctg   6000
```

```
ttgtttgccc ctcccccgtg ccttccttga ccctggaagg tgccactccc actgtccttt   6060
cctaataaaa tgaggaaatt gcatcgcatt gtctgagtag gtgtcattct attctggggg   6120
gtggggtggg gcaggacagc aaggggagg attgggaaga caatagcagg catgctgggg    6180
atgcggtggg ctctatggct tctgaggcgg aaagaaccag ctggggctcg ataccgtcga   6240
cctctagcta gagcttggcg taatcatggt catagctgtt tcctgtgtga aattgttatc   6300
cgctcacaat tccacacaac atacgagccg gaagcataaa gtgtaaagcc tagggtgcct   6360
aatgagtgag ctaactcaca ttaattgcgt tgcgctcact gcccgctttc cagtcgggaa   6420
acctgtcgtg ccagctgcat taatgaatcg gccaacgcgc ggggagaggc ggtttgcgta   6480
ttgggcgctc ttccgcttcc tcgctcactg actcgctgcg ctcggtcgtt cggctgcggc   6540
gagcggtatc agctcactca aaggcggtaa tacggttatc cacagaatca ggggataacg   6600
caggaaagaa catgtgagca aaaggccagc aaaaggccag gaaccgtaaa aaggccgcgt   6660
tgctggcgtt tttccatagg ctccgccccc ctgacgagca tcacaaaaat cgacgctcaa   6720
gtcagaggtg gcgaaacccg acaggactat aaagatacca ggcgtttccc cctggaagct   6780
ccctcgtgcg ctctcctgtt ccgaccctgc cgcttaccgg atacctgtcc gcctttctcc   6840
cttcggaag cgtggcgctt tctcatagct cacgctgtag gtatctcagt tcggtgtagg    6900
tcgttcgctc caagctgggc tgtgtgcacg aaccccccgt tcagcccgac cgctgcgcct   6960
tatccggtaa ctatcgtctt gagtccaacc cggtaagaca cgacttatcg ccactggcag   7020
cagccactgg taacaggatt agcagagcga ggtatgtagg cggtgctaca gagttcttga   7080
agtggtggcc taactacggc tacactagaa gaacagtatt tggtatctgc gctctgctga   7140
agccagttac cttcggaaaa agagttggta gctcttgatc cggcaaacaa accaccgctg   7200
gtagcggtgg ttttttttgtt tgcaagcagc agattacgcg cagaaaaaaa ggatctcaag   7260
aagatccttt gatcttttct acggggtctg acactcaggta gaacgaaaac tcacgttaag   7320
ggattttggt catgagatta tcaaaaagga tcttcaccta gatccttttta aattaaaaat   7380
gaagttttaa atcaatctaa agtatatatg agtaaacttg gtctgacagt taccaatgct   7440
taatcagtga ggcacctatc tcagcgatct gtctatttcg ttcatccata gttgcctgac   7500
tccccgtcgt gtagataact acgatacggg agggcttacc atctggcccc agtgctgcaa   7560
tgataccgcg agacccacgc tcaccggctc cagatttatc agcaataaac cagccagccg   7620
gaagggccga gcgcagaagt ggtcctgcaa ctttatccgc ctccatccag tctattaatt   7680
gttgccggga agctagagta agtagttcgc cagttaatag tttgcgcaac gttgttgcca   7740
ttgctacagg catcgtggtg tcacgctcgt cgtttggtat ggcttcattc agctccggtt   7800
cccaacgatc aaggcgagtt acatgatccc ccatgttgtg caaaaaagcg gttagctcct   7860
tcggtcctcc gatcgttgtc agaagtaagt tggccgcagt gttatcactc atggttatgg   7920
cagcactgca taattctctt actgtcatgc catccgtaag atgcttttct gtgactggtg   7980
agtactcaac caagtcattc tgagaatagt gtatgcggcg accgagttgc tcttgcccgg   8040
cgtcaatacg ggataatacc gcgccacata gcagaacttt aaaagtgctc atcattggaa   8100
aacgttcttc gggggcgaaaa ctctcaagga tcttaccgct gttgagatcc agttcgatgt   8160
aacccactcg tgcacccaac tgatcttcag catctttttac tttcaccagc gtttctgggt   8220
gagcaaaaac aggaaggcaa aatgccgcaa aaaagggaat aagggcgaca cggaaatgtt   8280
gaatactcat actcttcctt tttcaatatt attgaagcat ttatcagggt tattgtctca   8340
tgagcggata catatttgaa tgtatttaga aaaataaaca aataggggtt ccgcgcacat   8400
ttccccgaaa agtgccacct gacgtcgacg gatcgggaga tcgatctccc gatcccctag   8460
ggtcgactct cagtacaatc tgctctgatg ccgcatagtt aagccagtat ctgctccctg   8520
cttgtgtgtt ggaggtcgct gagtagtgcg cgagcaaaat ttaagctaca acaaggcagg   8580
gcttgaccga caattgcatg aagaatctgc ttagggttag gcgttttgcg ctgcttcgcg   8640
atgtacgggc cagatatacg cgttgacatt gattattgac tagttattaa tagtaatcaa   8700
ttacgggtc attagttcat agcccatata tggagttccg cgttacataa cttacggtaa    8760
atggcccgcc tggctgaccg cccaacgacc cccgcccatt gacgtcaata atgacgtatg   8820
ttcccatagt aacgccaata gggactttcc attgacgtca atgggtggag tatttacggt   8880
aaactgccca cttggcagta catcaagtgt atc                                 8913
```

SEQ ID NO: 51          moltype = DNA   length = 8913
FEATURE                Location/Qualifiers
source                 1..8913
                       mol_type = other DNA
                       organism = Synthetic construct
SEQUENCE: 51
```
atatgccaag tacgcccccc attgacgtca atgacggtaa atggcccgcc tggcattatg    60
cccagtacat gaccttatgg gactttccta cttggcagta catctacgta ttagtcatcg   120
ctattaccat ggtgatgcgg ttttggcagt acatcaatgg gcgtggatag cggtttgact   180
cacgggggatt tccaagtctc caccccattg acgtcaatgg gagtttgttt tggcaccaaa   240
atcaacggga ctttccaaaa tgtcgtaaca actccgcccc attgacgcaa atgggcggta   300
ggcgtgtacg gtgggaggtc tatataagca gagctggttt agtgaaccgt cagatccgct   360
agagatccgc ggccgctaat acgactcact atagggagag ccgccaccat gaaacggaca   420
gccgacggaa gcgagttcga gtcaccaaag aagaagcgga aagtcagcag tgacaaggag   480
tacagcatcg gcctggccat cggcaccaac tctgtgggct gggccgtgat caccgacgag   540
tacaaggtgc ccagcaagaa attcaaggtg ctgggcaaca ccgaccggca cagcatcaag   600
aagaacctga tcgagcccct gctgttcgac agcggcgaaa cagccgaggc cacccggctg   660
aagagaaccg ccagaagaag ataccagag cggaacagct ggatctgcta tctgcaagag   720
atcttcagca acgagatggc caaggtggac gacagcttct tccacagact tccagagtcc   780
ttcctggtgg aagaggataa gaagcacgag cggcacccca tcttcggcaa catcgtggac   840
gaggtggcct accacgagaa gtaccccacc atctaccacc tgagaaagaa actggtggac   900
agcaccgaca aggccgacct gcggctgatc tatctggccc tggcccacat gatcaagttc   960
cggggccact tcctgatcga gggcgacctg aaccccgaca cagcgacgt ggacaagctg   1020
ttcatcgtgc tggtcgac ctacaaccag ctgttcgagg aaaacccatc caacagcgac   1080
ggcgtggacg ccaaggccat cctgtctgcc agactgagca gagcagacg gctgaaaat   1140
ctgatcgccc agctgcccgg cgagaagaag aatggcctgt cggaaacct gattgccctg   1200
agcctgggcc tgacccccaa cttcaagagc aacttcgacc tggccgagga tgccaaactg   1260
cagctgagca aggacaccta cgacgacgac ctggacaacc tgctggccca gatcggcgac   1320
cagtacgccg acctgtttct ggccgccaag aacctgtccg acgccatcct gctgagcgac   1380
```

```
atcctgagag tgaacaccga gatcaccaag gcccccctga gcgcctctat gatcaagaga   1440
tacgacgagc accaccagga cctgaccctg ctgaaagctc tcgtgcggca gcagctgcct   1500
gagaagtaca aagagatttt cttcgaccag agcaagaacg gctacgccgg ctacattgac   1560
ggcggagcca gccaggaaga gttctacaag ttcatcaagc ccatcctgga aaagatggac   1620
ggcaccgagg aactgctcgt gaagctgaac agagaggacc tgctgcggaa gacgcggacc   1680
ttcgacaacg gcagcatccc ccaccagatc cacctgggag agctgcacgc cattctgcgg   1740
cggcaggaag attttttaccc attcctgaag gacaaccggg aaaagatcga gaagatcctg   1800
accttccgca tcccctacta cgtgggccct ctggccaggg gaaacagcag attcgcctgg   1860
atgaccagaa agagcgagga aaccatcacc ccctggaagt tcgaggaagt ggtggacaag   1920
ggcgcttccg cccagagctt catcgagcgg atgaccaact tcgataagaa cctgcccaac   1980
gagaaggtgc tgcccaagca cagcctgctg tacgagtact tcaccgtgta taacgagctg   2040
accaaagtga aatacgtgac cgagggaatg agaaagcccg ccttcctgag cggcgagcag   2100
aaaaaaggcca tcgtggacct gctgttcaag accaaccgga aagtgaccgt gaagcagctg   2160
aaagaggact acttcaagaa aatcgagtgc ttcgatctcg tggaaatctc cggcgtggaa   2220
gatcggttca acgcctccct gggcacatac cacgatctgc tgaaaattat caaggacaag   2280
gacttcctgg acaatgagga aaacgaggac attctggaag atatcgtgct gaccctgaca   2340
ctgtttgagg acagagagat gatcgaggaa cggctgaaaa cctatgccca cctgttcgac   2400
gacaaagtga tgaagcagct gaagcggcgg agatacaccg gctggggcag gctgagccgg   2460
aagctgatca acggcatccg ggacaagcag tccggcaaga caatcctgga tttcctgaag   2520
tccgacggct tcgccaacag aaacttcatg cagctgatcc acgacgacag cctgaccttt   2580
aaagaggaca tccagaaagc ccaggtgtcc ggccagggcg atagcctgca cgagcacatt   2640
gccaatctgg ccggcagccc cgccattaag aagggcatcc tgcagacagt gaaggtggtg   2700
gacgagctcg tgaaagtgat gggccggcac aagcccgaga acatcgtgat cgaaatggcc   2760
agagagaacc agaccaccca aagggacaag aagacagcc gcgagagaat gaagcggatc   2820
gaagagggca tcaaagagct gggcagccag atcctgaaag aacacccgt ggaaaacacc   2880
cagctgcaga acgagaagct gtacctgtac tacctgcaga atggcgggga tatgtacgtg   2940
gaccaggaac tggacatcaa ccggctgtcc gactacgatg tggaccatat cgtgcctcag   3000
agctttctga aggacgactc catcgacaac aaggtgctga ccagaagcga caagaaccgg   3060
ggcaagagcg acaacgtgcc ctccgaagag gtcgtgaaga gatgaagaa ctactggcgg   3120
cagctgctga acgccaagct gattacccag agaaagttcg acaatctgac caaggccgaa   3180
agaggcggcc tgagcgaact ggataaggcc ggcttcatca agagacagct ggtggaaacc   3240
cggcagatca caaagcacgt ggcacagatc ctggactccc ggatgaacac taagtacgac   3300
gagaatgaca agctgatccg ggaagtgaaa gtgatcaccc tgaagtccaa gctggtgtcc   3360
gatttccgga aggatttcca gttttacaaa gtgcgcgaga tcaacaacta ccaccacgcc   3420
cacgacgcct acctgaacgc cgtcgtggga accgccctga tcaaaaagta ccctaagctg   3480
gaaagcgagt tcgtgtacgg cgactacaag gtgtacgacg tgcggaagat gatcgccaag   3540
agcgagcagg aaatcggcaa ggctaccgcc aagtacttct ctacagcaa catcatgaac   3600
tttttcaaga ccgagattac cctggccaac ggcgagatcc ggaagcggcc tctgatcgag   3660
acaaacggcg aaaccggga gatcgtgtgg gataaggcc gggattttgc caccgtgcgg   3720
aaagtgctga gcatgcccca agtgaatatc gtgaaaaaga ccgaggtgca gacaggcggc   3780
ttcagcaaaa agtctatcct gcccaagagg aacagcgata agctgatcgc cagaaagaag   3840
gactgggacc ctaagaagta cggcggcttc gacagcccca ccgtgcccta ttctgtgctg   3900
gtggtggcca aagtggaaaa gggcaagtcc aagaaactga agagtgtgaa agagctgctg   3960
gggatcacca tcatgaaag aagcagcttc gagaagaatc ccatcgactt tctggaagcc   4020
aagggctaca aagaagtgaa aaaggacctg atcatcaagc tgcctaagta ctcccctgttc   4080
gagctggaaa acggccggaa gagaatgctg gcctctgccg cgaactgca aagggaaac   4140
gaactggccc tgcccctcca atatgtgaac ttcctgtacc tggccagcca ctatgagaag   4200
ctgaagggct cccccgagga taatgagtct ggaggatcta gcggtggttc ctctggaagc   4260
gagacaccag gcacaagcga gtccgccaca ccagagagct ccgcggctc ctccggagga   4320
tcctctgagg tggagttttc ccacgagtac tggatgagac atgccctgac cctggccaag   4380
agggcatggg atgaaagaga agtccccgtg ggcgccgtgc tggtgcacaa caatagagtg   4440
atcggagagg gatggaacag gccaatcggc cgccacgacc ctaccgcaca cgcagagatc   4500
atggcactga gcaggagg cctggtcatg cagaattacc gctgatcga tgccaccctg   4560
tatgtgcaca tggagccatg cgtgatgtgc gcaggagcaa tgatccacag caggatcgga   4620
agagtggtgt tcggagcacg ggacgccaag accggccagg ctccct gatggatgtg   4680
ctgcaccacc ccggcatgaa ccaccggtg gagatcacag agggaatcct ggcagacgag   4740
tgcgccgccc tgctgagcga tttctttaga atgcggagac aggagatcaa ggcccagaag   4800
aaggcacaga gctccaccga ctctggagga tctagcggcg atcctctgg aagcgagaca   4860
ccaggcacaa gcgagtccgc cacaccagag agctccggcg gctcctccgg aggatcctct   4920
gaggtggagt tttcccacga gtactggatg agacatgccc tgaccctggc caagagggca   4980
gcgatgaga gggaggtgcc tgtgggagcc gtgctggtgc tgaacaatag agtgatcggc   5040
gagggctgga caagagccat cggcctgcac gacccaacag cccatgccga aattatggcc   5100
ctgagacagg cggcctggt catgcagaac tacagactga ttgacgccac cctgtacgtg   5160
acattcgagc cttgcgtgat gtgcgccggc actctaggat cggccgcgtg   5220
gtgtttggcg tgaggaacgc aaaaaccggc gccgcaggct ccctgatgga cgtgctgcac   5280
taccccggca tgaatcaccg cgtcgaaatt accgagggaa tcctggcaga tgaatgtgcc   5340
gccctgctgt gctatttctt tcggatgcct agacaggtgt tcaatgctca agaagggcc   5400
cagagctcca ccgactccgg aggatctagc ggaggctcct ctggctctga cacacctggc   5460
acaagcgaga gcgcaacacc tgaaagcagc gggggtgc agaaaacag   5520
ctgtttgtgg aacagcacaa gcactacctg gacgagatca tcgagcagat cagcgagttc   5580
tccaagagag tgatcctggc cgacgctaat ctggacaaag tgctgccgc ctacaacaag   5640
caccgggata agcccatcag agagcaggcc gagaatatca tccacctgtt taccctgacc   5700
aatctgggag cccctgccgc cttcaagtac tttgacacca ccatcgaccg gaagaggtac   5760
accagcacca aagggtgct ggacgccacc ctgatccacc agagcatcac cggcctgtac   5820
gagacacgag tcgacctgtc tcagctggga gtgactctg gcggctcaaa aagaaccgcc   5880
gacggcagcg aattcgagcc caagaagaag aggaaagtct aaccggtcat catcaccatc   5940
accattgagt ttaaacccgc tgatcagcct cgactgtgcc ttctagttgc cagccatctg   6000
ttgtttgccc ctcccccgtg ccttccttga ccctggaagg tgccactccc actgtccttt   6060
cctaataaaa tgaggaaatt gcatcgcatt gtctgagtag gtgtcattct attctgggggg   6120
```

```
gtgggggtggg gcaggacagc aaggggggagg attgggaaga caatagcagg catgctgggg   6180
atgcggtggg ctctatggct tctgaggcgg aaagaaccag ctggggctcg ataccgtcga   6240
cctctagcta gagcttggcg taatcatggt catagctgtt tcctgtgtga aattgttatc   6300
cgctcacaat tccacacaac atacgagccg gaagcataaa gtgtaaagcc tagggtgcct   6360
aatgagtgag ctaactcaca ttaattgcgt tgcgctcact gcccgctttc cagtcgggaa   6420
acctgtcgtg ccagctgcat taatgaatcg gccaacgcgc ggggagaggc ggtttgcgta   6480
ttgggcgctc ttccgcttcc tcgctcactg actcgctgcg ctcggtcgtt cggctgcggc   6540
gagcggtatc agctcactca aaggcggtaa tacggttatc cacagaatca ggggataacg   6600
caggaaagaa catgtgagca aaaggccagc aaaaggccag gaaccgtaaa aaggccgcgt   6660
tgctggcgtt tttccatagg ctccgccccc ctgacgagca tcacaaaaat cgacgctcaa   6720
gtcagaggtg gcgaaacccg acaggactat aaagatacca ggcgtttccc cctggaagct   6780
ccctcgtgcg ctctcctgtt ccgaccctgc cgcttaccgg atacctgtcc gcctttctcc   6840
cttcgggaag cgtggcgctt tctcatagct cacgctgtag gtatctcagt tcggtgtagg   6900
tcgttcgctc caagctgggc tgtgtgcacg aaccccccgt tcagcccgac cgctgcgcct   6960
tatccggtaa ctatcgtctt gagtccaacc cggtaagaca cgacttatcg ccactggcag   7020
cagccactgg taacaggatt agcagagcga ggtatgtagg cggtgctaca gagttcttga   7080
agtggtggcc taactacggc tacactagaa gaacagtatt tggtatctgc gctctgctga   7140
agccagttac cttcggaaaa agagttggta gctcttgatc cggcaaacaa accaccgctg   7200
gtagcggtgg tttttttgtt tgcaagcagc agattacgcg cagaaaaaaa ggatctcaag   7260
aagatccttt gatcttttct acggggtctg acactcagtg gaacgaaaac tcacgttaag   7320
ggattttggt catgagatta tcaaaaagga tcttcaccta gatcctttta aattaaaaat   7380
gaagttttaa atcaatctaa agtatatatg agtaaacttg gtctgacagt taccaatgct   7440
taatcagtga ggcacctatc tcagcgatct gtctatttcg ttcatccata gttgcctgac   7500
tccccgtcgt gtagataact acgatacggg agggcttacc atctggcccc agtgctgcaa   7560
tgataccgcg agacccacgc tcaccggctc cagatttatc agcaataaac cagccagccg   7620
gaagggccga gcgcagaagt ggtcctgcaa ctttatccgc ctccatccag tctattaatt   7680
gttgccggga agctagagta agtagttcgc cagttaatag tttgcgcaac gttgttgcca   7740
ttgctacagg catcgtggtg tcacgctcgt cgtttggtat ggcttcattc agctccggtt   7800
cccaacgatc aaggcgagtt acatgatccc ccatgttgtg caaaaaagcg gttagctcct   7860
tcggtcctcc gatcgttgtc agaagtaagt tggccgcagt gttatcactc atggttatgg   7920
cagcactgca taattctctt actgtcatgc catccgtaag atgcttttct gtgactggtg   7980
agtactcaac caagtcattc tgagaatagt gtatgcggcg accgagttgc tcttgcccgg   8040
cgtcaatacg ggataatacc gcgccacata gcagaacttt aaaagtgctc atcattggaa   8100
aacgttcttc ggggcgaaaa ctctcaagga tcttaccgct gttgagatcc agttcgatgt   8160
aacccactcg tgcacccaac tgatcttcag catcttttac tttcaccagc gtttctgggt   8220
gagcaaaaac aggaaggcaa aatgccgcaa aaaagggaat aagggcgaca cggaaatgtt   8280
gaatactcat actcttcctt tttcaatatt attgaagcat ttatcagggt tattgtctca   8340
tgagcggata catatttgaa tgtatttaga aaaataaaca aataggggtt ccgcgcacat   8400
ttccccgaaa agtgccacct gacgtcgacg gatcgggaga tcgatctccc gatccctag   8460
ggtcgactct cagtacaatc tgctctgatg ccgcatagtt aagccagtat ctgctccctg   8520
cttgtgtgtt ggaggtcgct gagtagtgcg cgagcaaaat ttaagctaca acaaggcaag   8580
gcttgaccga caattgcatg aagaatctgc ttagggttag cgttttgcg ctgcttcgcg   8640
atgtacgggc cagatatacg cgttgacatt gattattgac tagttattaa tagtaatcaa   8700
ttacgggtc attagttcat agcccatata tggagttccg cgttacataa cttacgtaa   8760
atggcccgcc tggctgaccg cccaacgacc cccgcccatt gacgtcaata atgacgtatg   8820
ttcccatagt aacgccaata gggactttcc attgacgtca atgggtggag tatttacggt   8880
aaactgccca cttggcagta catcaagtgt atc                                8913

SEQ ID NO: 52         moltype = DNA   length = 8913
FEATURE               Location/Qualifiers
source                1..8913
                      mol_type = other DNA
                      organism = Synthetic construct
SEQUENCE: 52
atatgccaag tacgcccct attgacgtca atgacggtaa atggcccgcc tggcattatg     60
cccagtacat gaccttatgg gactttccta cttggcagta catctacgta ttagtcatcg    120
ctattaccat ggtgatgcgg ttttggcagt acatcaatgg gcgtggatag cggtttgact    180
cacggggatt tccaagtctc caccccattg acgtcaatgg gagtttgttt tggcaccaaa    240
atcaacggga cttttccaaa tgtcgtaaca actccgcccc attgacgcaa atgggcggta    300
ggcgtgtacg gtgggaggtc tatataagca gagctggttt agtgaaccgt cagatccgct    360
agagatccgc ggccgctaat acgactcact atagggagag ccgccaccat gaaacgggaca    420
gccgacggaa gcgagttcga gtcaccaaag aagaagcgga aagtcagcag tgacaagaag    480
tacagcatcg gcctggccat cggcaccaac tctgtgggct gggccgtgat caccgacgag    540
tacaaggtgc ccagcaagaa attcaaggtg ctgggcaaca ccgaccggca cagcatcaag    600
aagaacctga tcggagccct gctgttcgac agcggcgaaa cagccgaggc cacccggctg    660
aagagaaccg ccagaagaag atacaccaga cggaagaacc ggatctgcta tctgcaagag    720
atcttcagca acgagatggc caaggtggac gacagcttct tccacagact ggaagagtcc    780
ttcctggtgg aagaggataa gaagcacgag cggcacccca tcttcggcaa catcgtggac    840
gaggtggcct accacgagaa gtaccccacc atctaccacc tgagaaagaa actggtggac    900
agcaccgaca aggccgacct gcggctgatc tatctggccc tggcccacat gatcaagttc    960
cggggccact tcctgatcga gggcgacctg aaccccgaca cagcgacgt ggacaagctg   1020
ttcatccagc tggtgcagac ctacaaccag ctgttcgagg aaaaccccat caacgccagc   1080
ggcgtggacg ccaaggccat cctgtctgcc agactgagca gagcagacg gctggaaaat   1140
ctgatcgccc agctgcccgg cgagaagaag aatggcctgt tcggcaacct gattgccctg   1200
agcctgggcc tgacccccaa cttcaagagc aacttcgacc tggccgagga tgccaaactg   1260
cagctgagca aggacaccta cgacgacgac ctggacaacc tgctggccca gatcggcgac   1320
cagtacgccg acctgtttct ggccgccaag aacctgtccg acgccatcct gctgagcgac   1380
atcctgagag tgaacaccga gatcaccaag gccccctga gcgcctctat gatcaagaga   1440
tacgacgagc accaccagga cctgaccctg ctgaaagctc tcgtgcggca gcagctgcct   1500
```

```
gagaagtaca aagagatttt cttcgaccag agcaagaacg gctacgccgg ctacattgac 1560
ggcggagcca gccaggaaga gttctacaag ttcatcaagc ccatcctgga aaagatggac 1620
ggcaccgagg aactgctcgt gaagctgaac agagaggacc tgctgcggaa gcagcggacc 1680
ttcgacaacg gcagcatccc ccaccagatc cacctgggag agctgcacgc cattctgcgg 1740
cggcaggaag attttttacc attcctgaag gacaaccggg aaaagatcga gaagatcctg 1800
accttccgca tcccctacta cgtgggccct ctggccaggg gaaacagcag attcgcctgg 1860
atgaccagaa agagcgagga aaccatcacc ccctggaact tcgaggaagt ggtggacaag 1920
ggcgcttccg cccagagctt catcgagcgg atgaccaact tcgataagaa cctgcccaac 1980
gagaaggtgc tgcccaagca cagcctgctg tacgagtact tcaccgtgta taacgagctg 2040
accaaagtga aatacgtgac cgagggaatg agaaagcccg ccttcctgag cggcgagcag 2100
aaaaaaggca tcgtggacct gctgttcaag accaaccgga aagtgaccgt gaagcagctg 2160
aaagaggact acttcaagaa aatcgagtgc ttcgactccg tggaaatctc cggcgtggaa 2220
gatcggttca acgcctccct gggcacatac cacgatctgc tgaaaattat caaggacaag 2280
gacttcctgg acaatgagga aaacgaggac atttctggaa atatcgtgct gacccctgaca 2340
ctgtttgagg acagagagat gatcgaggaa cggctgaaaa cctatgccca cctgttcgac 2400
gacaaagtga tgaagcagct gaagcggcgg agatacaccg gctggggcag gctgagccgg 2460
aagctgatca acggcatccg ggacaagcag tccggcaaga caatcctgga tttcctgaag 2520
tccgacggct tcgccaacag aaacttcatg cagctgatcc acgacgacag cctgaccttt 2580
aaagaggaca tccagaaagc ccaggtgtcc ggccagggcg atagcctgca cgagcacatt 2640
gccaatctgg ccggcagccc cgccattaag aagggcatcc tgcagacagt gaaggtggtg 2700
gacgagctcg tgaaagtgat gggccggcac aagcccgaga acatcgtgat cgaaatggcc 2760
agagagaacc agaccaccca gaaggacaga aagaacagcc gcgagagaat gaagcggatc 2820
gaagagggca tcaaagagct gggcagccag atcctgaaag aacacccggt ggaaaacacc 2880
cagctgcaga acgagaagct gtacctgtac tacctgcaga atgggcggga tatgtacgtg 2940
gaccaggaac tggacatcaa ccggctgtcc gactacgatg tggaccatat cgtgcctcag 3000
agctttctga aggacgactc catcgacaac aaggtgctga ccagaagcga caaaaccgg 3060
ggcaagagcg acaacgtgcc ctccgaagag gtcgtgaaga agatgaagaa ctactggcgg 3120
cagctgctga acgccaagct gattacccag agaaagttcg acaatctgac caaggccgag 3180
agaggcggcc tgagcgaact ggataaggcc ggcttcatca agacagctgg tggaaacc 3240
cggcagatca caaagcacgt ggcacagatc ctggactccc ggatgaacac taagtacgac 3300
gagaatgaca agctgatccg ggaagtgaaa gtgatcaccc tgaagtccaa gctggtgtcc 3360
gatttccgga aggatttcca gttttacaaa gtgcgcgaga tcaacaacta ccaccacgcc 3420
cacgacgcct acctgaacgc cgtcgtggga accgccctga tcaaaagta ccctaagctg 3480
gaaagcgagt tcgtgtacgg cgactacaag gtgtacgacg tgcggaagat gatcgccaag 3540
agcgagcagg aaatcggcaa ggctaccgcc aagtacttct tctacagcaa catcatgaac 3600
ttttttcaaga ccgagattac cctgccaac ggcgagatcc ggaagcggcc tctgatcgag 3660
acaaacggcg aaaccgggga gatcgtgtgg gataagggcc gggattttgc caccgtgcgg 3720
aaagtgctga gcatgcccca agtgaatatc gtgaaaaaga ccgaggtgca gacaggcggc 3780
ttcagcaaag agtctatcct gcccaagagg aacagcgata agctgatcgc cagaaagaag 3840
gactgggacc ctaagaagta cggcggcttc gacagcccca ccgtggccta ttctgtgctg 3900
gtggtggcca aagtggaaaa gggcaagtcc aagaaactga agagtgtgaa agagctgctg 3960
gggatcacca tcatggaaag aagcagcttc gagaagaatc ccatcgactt tctggaagcc 4020
aagggctaca aagaagtgaa aaaggacctg atcatcaagc tgcctaagta ctccctgttc 4080
gagctggaaa acggccggaa gagaatgctg gcctctgccg gcgaactgca aaagggaaac 4140
gaactggccc tgccctccaa atatgtgaac ttcctgtacc tggccagcca ctatgagaag 4200
ctgaagggct ccccgagga taatgagcag aaacagctgt tgtgaatc tggaggatct 4260
agcggtggtt cctctggaag cgagacacca ggcacaagcg agtccgccac accagagagc 4320
tccggcggct cctccggagg atcctctgag gtggagtttt cccacgagta ctggatgaga 4380
catgccctga ccctggccaa gagggcatgg gatgaaagag aagtccccgt gggcgccgtg 4440
ctggtgcaca acaatagagt gatcggagag ggatggaaca ggccaatcgg ccgccacgac 4500
cctaccgcac acgcagagat catgcactg aggcagggac gcctggtcat cagaattac 4560
cgcctgatcg atgccaccct gtatgtgaca ctgagccat gcgtgatgtg cgcaggagca 4620
atgatccaca gcaggatcgg aagagtggtg ttcggagcac gggacgccaa gaccggcgca 4680
gcaggctccc tgatggatgt gctgcaccac cccggcatga ccaccgggt ggagatcaca 4740
gagggaatcc tggcagacga gtgcgccgcc ctgctgacga atttcttag aatgcggaga 4800
caggagatca aggcccagaa gaaggcacag agctccaccg actctggagg atctagcggc 4860
ggatcctctg gaagcgagac accaggcaca agcgagtccg ccacaccaga gagctccggc 4920
ggctcctccg gaggatcctc tgaggtggag ttttcccacg agtactggat gagacatgcc 4980
ctgaccctgg ccaagagggc acgcgatgag agggaggtgc ctgtgggagc cgtgctggtg 5040
ctgaacaata gagtgatcgg cgagggctgg aacagagcca tcggcctgca cgacccaaca 5100
gcccatgccg aaattatggc cctgagacag gcggcctgg tcatgcagaa ctacagactg 5160
attgacgcca ccctgtacgt gacattcgag ccttgcgtga tgtgcgccgg cgccatgatc 5220
cactctagga tcggccgcgt ggtgtttggc gtgaggaacg caaaaccgg cgccgcaggc 5280
tccctgatgg acgtgctgca ctaccccggc atgaatcacc gcgtcgaaat taccgaggga 5340
atcctggcag atgaatgtgc cgccctgctg tgctatttct ttcggatgcc tagacaggtg 5400
ttcaatgctc agaagaaggc ccagagctcc accgactccg gaggatctag cggaggctcc 5460
tctggctctg agacacctgg cacaagcgag agcgcaacac tgaaagcag cggggcagc 5520
agcggggggt cacagcacaa gcactacctg gacgagatca tcgagcagat cagcgagttc 5580
tccaagagag tgatcctggc ggacgcaaag ctgtctccgc ctacaacaag 5640
caccgggata gcccatcag agagcaggcc gagaatatca tccacctgtt taccctgacc 5700
aatctggag cccctgccgc cttcaagtac tttgacacca ccatcgaccg gaagaggtac 5760
accagcacca aagaggtgct ggacgccacc ctgatccacc agagcatcac cggcctgtac 5820
gagacacgga tcgacctgtc tcagctggga ggtgactctg cgcggctcaaa aagaaccgcc 5880
gacggcagca aattcgatcc caagaagaag aggaaagtct aaccgtgcat catcaccatc 5940
accattgagt ttaaacccgc tgatcagcct cgactgtgcc ttctagttgc cagccatctg 6000
ttgtttgccc ctccccgtg ccttccttga ccctggaagg tgccactccc actgtccttt 6060
cctaataaaa tgaggaaatt gcatcgcatt gtctgagtag gtgtcattct attctggggg 6120
gtggggtggg gcaggacagc aagggggagg attgggaaga caatagcagg catgctgggg 6180
atgcggtggg ctctatggct tctgaggcgg aaagaaccag ctggggctcg ataccgtcga 6240
```

```
cctctagcta gagcttggcg taatcatggt catagctgtt tcctgtgtga aattgttatc  6300
cgctcacaat tccacacaac atacgagccg gaagcataaa gtgtaaagcc tagggtgcct  6360
aatgagtgag ctaactcaca ttaattgcgt tgcgctcact gcccgctttc cagtcgggaa  6420
acctgtcgtg ccagctgcat taatgaatcg gccaacgcgc ggggagaggc ggtttgcgta  6480
ttgggcgctc ttccgcttcc tcgctcactg actcgctgcg ctcggtcgtt cggctgcggc  6540
gagcggtatc agctcactca aaggcggtaa tacggttatc cacagaatca ggggataacg  6600
caggaaagaa catgtgagca aaaggccagc aaaaggccag gaaccgtaaa aaggccgcgt  6660
tgctggcgtt tttccatagg ctccgccccc ctgacgagca tcacaaaaat cgacgctcaa  6720
gtcagaggtg gcgaaacccg acaggactat aaagatacca ggcgtttccc cctggaagct  6780
ccctcgtgcg ctctcctgtt ccgaccctgc cgcttaccgg atacctgtcc gcctttctcc  6840
cttcggggaag cgtggcgctt tctcatagct cacgctgtag gtatctcagt tcggtgtagg  6900
tcgttcgctc caagctgggc tgtgtgcacg aaccccccgt tcagcccgac cgctgcgcct  6960
tatccggtaa ctatcgtctt gagtccaacc cggtaagaca cgacttatcg ccactggcag  7020
cagccactgg taacaggatt agcagagcga ggtatgtagg cggtgctaca gagttcttga  7080
agtggtggcc taactacggc tacactagaa gaacagtatt tggtatctgc gctctgctga  7140
agccagttac cttcggaaaa agagttggta gctcttgatc cggcaaacaa accaccgctg  7200
gtagcggtgg ttttttgtt tgcaagcagc agattacgcg cagaaaaaaa ggatctcaag  7260
aagatccttt gatcttttct acggggtctg acactcagtg gaacgaaaac tcacgttaag  7320
ggattttggt catgagatta tcaaaaagga tcttcaccta gatccttttta aattaaaaat  7380
gaagttttaa atcaatctaa agtatatatg agtaaacttg gtctgacagt taccaatgct  7440
taatcagtga ggcacctatc tcagcgatct gtctatttcg ttcatccata gttgcctgac  7500
tccccgtcgt gtagataact acgatacggg agggcttacc atctggcccc agtgctgcaa  7560
tgataccgcg agacccacgc tcaccggctc cagatttatc agcaataaac cagccagccg  7620
gaagggccga gcgcagaagt ggtcctgcaa ctttatccgc ctccatccag tctattaatt  7680
gttgccggga agctagagta agtagttcgc cagttaatag tttgcgcaac gttgttgcca  7740
ttgctacagg catcgtggtg tcacgctcgt cgttggtat ggcttcattc agctccggtt  7800
cccaacgatc aaggcgagtt acatgatccc ccatgttgtg caaaaaagcg gttagctcct  7860
tcggtcctcc gatcgttgtc agaagtaagt tggccgcagt gttatcactc atggttatgg  7920
cagcactgca taattctctt actgtcatgc catccgtaag atgcttttct gtgactggtg  7980
agtactcaac caagtcattc tgagaatagt gtatgcggcg accgagttgc tcttgcccgg  8040
cgtcaatacg ggataatacc gcgccacata gcagaacttt aaaagtgctc atcattggaa  8100
aacgttcttc ggggcgaaaa ctctcaagga tcttaccgct gttgagatcc agttcgatgt  8160
aacccactcg tgcacccaac tgatcttcag catcttttac tttcaccagc gtttctgggt  8220
gagcaaaaac aggaaggcaa aatgccgcaa aaaagggaat aagggcgaca cggaaatgtt  8280
gaatactcat actcttcctt tttcaatatt attgaagcat ttatcagggt tattgtctca  8340
tgagcggata catatttgaa tgtatttaga aaaataaaca aataggggtt ccgcgcacat  8400
ttccccgaaa agtgccacct gacgtcgacg gatcgggaga tcgatctccc gatccctag  8460
ggtcgactct cagtacaatc tgctctgatg ccgcatagtt aagccagtat ctgctccctg  8520
cttgtgtgtt ggaggtcgct gagtagtgcg cgagcaaaat ttaagctaca acaaggcagg  8580
gcttgaccga caattgcatg aagaatctgc ttagggttag gcgttttgcg ctgcttcgcg  8640
atgtacgggc cagatatacg cgttgacatt gattattgac tagttattaa tagtaatcaa  8700
ttacgggtc attagttcat agcccatata tggagttccg cgttacataa cttacggtaa  8760
atggcccgcc tggctgaccg cccaacgacc cccgcccatt gacgtcaata atgacgtatg  8820
ttcccatagt aacgccaata gggactttcc attggctca atggggtgga tatttacggt  8880
aaactgccca cttggcagta catcaagtgt atc                                8913
```

SEQ ID NO: 53            moltype = DNA   length = 8913
FEATURE                  Location/Qualifiers
source                   1..8913
                         mol_type = other DNA
                         organism = Synthetic construct
SEQUENCE: 53

```
atatgccaag tacgcccct attgacgtca atgacggtaa atggcccgcc tggcattatg  60
cccagtacat gaccttatgg gactttccta cttggcagta catctacgta ttagtcatcg  120
ctattaccat ggtgatgcgg ttttggcagt acatcaatgg gcgtggatag cggtttgact  180
cacggggatt tccaagtctc caccccattg acgtcaatgg gagtttgttt tggcaccaaa  240
atcaacggga ctttccaaaa tgtcgtaaca actccgcccc attgacgcaa atgggcggta  300
ggcgtgtacg gtgggaggtc tatataagca gagctggttt agtgaaccgt cagatccgct  360
agagatccgc ggccgctaat acgactcact atagggagag ccgccaccat gaaacggaca  420
gccgacgaa gcgagttcga gtcaccaaag aagaagcgga aagtcagcag tgacaagaag  480
tacagcatcg gcctggccat cggcaccaac tctgtgggct gggccgtgat caccgacgag  540
tacaaggtgc ccagcaagaa attcaaggtg ctgggcaaca ccgaccggca cagcatcaag  600
aagaacctga tcggagccct gctgttcgac agcggcgaaa cagccgaggc cacccggctg  660
aagagaaccg ccagaagaag atacaccaga cggaagaacc ggatctgcta tctgcaagag  720
atcttcagca acgagatggc caaggtggac gacagcttct tccacagact ggaagagtcc  780
ttcctggtgg aagaggataa gaagcacgag cggcaccccca tcttcggcaa catcgtggac  840
gaggtggcct accacgagaa gtaccccacc atctaccacc tgaaaagaa actggtggac  900
agcaccgaca aggccgacct gcggctgatc tatctggccc tggcccatat gatcaagttc  960
cggggccact tcctgatcga gggcgacctg aaccccgaca acagcgacgt ggacaagttc  1020
ttcatccagc tggtgcagac ctacaaccag ctgttcgagg aaaaccccat caacgccagc  1080
ggcgtggacg ccaaggccat cctgtctgcc agactgagca agagcagacg gctggaaaat  1140
ctgatcgccc agctgcccgg cgagaagaag aatggcctgt tcggaaacct gattgccctg  1200
agcctgggcc tgacccccaa cttcaagagc aacttcgacc tggccgagga tgccaaactg  1260
cagctgagca aggacaccta cgacgacgac ctggacaacc tgctggccca gatcggcgac  1320
cagtacgccg acctgtttct ggccgccaag aacctgtccg acgccatcct gctgagcgac  1380
atcctgagag tgaacaccga gatcaccaag gccccctga gcgcctctat gatcaagaga  1440
tacgacgagc accaccagga cctgaccctg ctgaaagctc tcgtgcggca gcagctgcct  1500
gagaagtaca aagagatttt cttcgaccag agcaagaacg gctacgccgg ctacattgac  1560
ggcggagcca gccaggaaga gttctacaag ttcatcaagc catctctgga aaagatggac  1620
```

```
ggcaccgagg aactgctcgt gaagctgaac agagaggacc tgctgcggaa gcagcggacc   1680
ttcgacaacg gcagcatccc ccaccagatc cacctgggag agctgcacgc cattctgcgg   1740
cggcaggaag attttttaccc attcctgaag gacaaccggg aaaagatcga gaagatcctg   1800
accttccgca tccctacta cgtgggccct ctggccaggg gaaacagcag attcgcctgg   1860
atgaccagaa agagcgagga aaccatcacc ccctggaact tcgaggaagt ggtggacaag   1920
ggcgcttccg cccagagctt catcgagcgg atgaccaact tcgataagaa cctgcccaac   1980
gagaaggtgc tgcccaagca cagcctgctg tacgagtact tcaccgtgta taacgagctg   2040
accaaagtga aatacgtgac cgagggaatg agaaagcccg ccttcctgag cggcgagcag   2100
aaaaaggcca tcgtggacct gctgttcaag accaaccgga aagtgaccgt gaagcagctg   2160
aaagaggact acttcaagaa aatcgagtgc ttcgactccg tggaaatctc cggcgtggaa   2220
gatcggttca acgcctccct gggcacatac cacgatctgc tgaaaattat caaggacaag   2280
gacttcctgg acaatgagga aaacgaggac attctggaag atatcgtgct gaccctgaca   2340
ctgtttgagg acagagagat gatcgaggaa cggctgaaaa cctatgccca cctgttcgac   2400
gacaaagtga tgaagcagct gaagcggcgg agataccacg gctggggcag gctgagccgg   2460
aagctgatca acggcatccg ggacaagcag tccggcaaga caatcctgga tttcctgaag   2520
tccgacggct cgccaacag aaacttcatg cagctgatcc acgacgacag cctgaccttt   2580
aaagaggaca tccagaaagc ccaggtgtcc ggccagggcg atagcctgca cgagcacatt   2640
gccaatctgg ccggcagccc cgccattaag aagggcatcc tgcagacgat gaaggtggtg   2700
gacgagctcg tgaaagtgat gggccggcac aagcccgaga acatcgtgat cgaaatggcc   2760
agagagaacc agaccaccca gaagggacag aagaacagcc gcgagagaat gaagcggatc   2820
gaagagggca tcaaagagct gggcagccag atcctgaaag aacacccccgt ggaaaacacc   2880
cagctgcaga acgagaagct gtacctgtac tacctgcaga atgggcggga tatgtacgtg   2940
gaccaggaac tggacatcaa ccggctgtcc gactacgatg tggaccatat cgtgcctcag   3000
agctttctga aggacgactc catcgacaac aaggtgctga ccagaagcga caagaaccgg   3060
ggcaagagcg acaacgtgcc ctccgaagag gtcgtgaaga agatgaagaa ctactggcgg   3120
cagctgctga acgccaagct gattacccag agaaagttcg acaatctgac caaggccgac   3180
agaggcgggcc tgagcgaact ggataaggcc ggcttcatca agagacagct ggtggaaacc   3240
cggcagatca caaagcacgt ggcacagatc ctggactccc ggatgaacac taagtacgac   3300
gagaatgaca agctgatccg ggaagtgaaa gtgatcaccc tgaagtccaa gctggtgtcc   3360
gatttccgga aggatttcca gttttacaaa gtgcgcgaga tcaacaacta ccaccacgcc   3420
cacgacgcct acctgaacgc cgtcgtggga accgccctga tcaaaaagta ccctaagctg   3480
gaaagcgagt tcgtgtacgg cgactacaag gtgtacgacg tgcggaagat gatcgccaag   3540
agcgagcagg aaatcggcaa ggctaccgcc agtacttct tctacagcaa catcatgaac   3600
ttttttcaaga ccgagattac cctggccaac ggcgagatcc ggaagcggcc tctgatcgag   3660
acaaacggcg aaaccgggga gatcgtgtgg gataagggcc gggattttgc caccgtgcgg   3720
aaagtgctga gcatgcccca agtgaatatc gtgaaaaaga ccgaggtgca gacaggcggc   3780
ttcagcaaag agtctatcct gcccaagagg aacagcgata agctgatcgc cagaaagaag   3840
gactgggacc ctaagaagta cggcggcttc gacagcccca ccgtggccta ttctgtgctg   3900
gtggtggcca aagtggaaaa gggcaagtcc aagaaactga agagtgtgaa agagctgctg   3960
gggatcacca tcatggaaag aagcagcttc gagaagaatc ccatcgactt tctggaagcc   4020
aagggctaca aagaagtgaa aaaggacctg atcatcaagc tgcctaagta ctccctgttc   4080
gagctggaaa acggccggaa gagaatgctg gcctctgccg gcgaactgca gaagggaaac   4140
gaactggccc tgcccctccaa atatgtgaac ttcctgtacc tggccgccta ctatgaagag   4200
ctgaagggct cccccgagga taatgagcag aaacagctgt ttgtggaaca gcacaagtct   4260
ggaggatcta gcgtggttc ctctggaagc gagacaccag gcacaagcga gtccgccaca   4320
ccagagagct ccggcggctc ctccggagga tcctctgagg tggagttttc ccacgagtac   4380
tggatgagac atgccctgac cctggcacaa agggcatgg atgaaagaga agtccccgtg   4440
ggcgccgtgc tggtcacaa aatagagtg atcggagagg gatggaacag gccaatcggc   4500
cgccacgacc ctaccgcaca cgcagagatc atggcactga gcaggagg cctggtcatg   4560
cagaattacc gcctgatcga tgccaccctg tatgtgacac tggagccatg cgtgatgtgc   4620
gcaggagcaa tgatccacag caggatcgga agagtggtgt tcggagcagg agcgccaag   4680
accggcgcag caggctccct gatgatgtg ctgcaccacc ccggcatgaa ccaccgggtg   4740
gagatcacag agggaatcct ggcagacgag tgcgccgccc tgctgagcga tttctttaga   4800
atgcggagac aggagatcaa ggcccagaag aaggcacaga gctccaccga ctctggagga   4860
tctagcggcg gatcctctgg aagcgagaca ccaggcacca gcgagtccgc cacaccagag   4920
agctccggcg gctcctccgg aggatcctct gaggtggagt tttccacga gtactggatg   4980
agacatgccc tgaccctggc caagagggca cgcgatgaga gggaggtgcc tgtgggagcc   5040
gtgctggtgc tgaacaatag agtgatcggc gagggctgga acagagccat cggcctgcac   5100
gacccaacag cccatgccga aattatggcc ctgacacagg gcggcctggt catgcagaac   5160
tacagactga ttgacgccac cctgtacgtg acattcgag cttgcgtgat gtgcgccggc   5220
gccatgatcc actctaggat cggccgcgtg gtgtttggcg tgaggaacgc aaaaaccggc   5280
gccgcaggct ccctgatgga cgtgctgcac taccccggca tgaatcaccg cgtcgaaatt   5340
accgaggaaa tcctggcaga tgaatgtgcc gccctgctgt gctatttctt tcggatgcct   5400
agacaggtgt tcaatgctca gaagaaggcc cagagctccc cgactccgg aggatctagc   5460
ggaggctcct ctggctctga cacctggcc acaagcgaga gcgcaacacc tgaaagcagc   5520
gggggcagca gcgggggtc acactacctg gacgagatca tcgagcagat cagcgagttc   5580
tccaagagag tgatcctggc cgacgctaat ctggacaaaa tgctgtccgc ctacaacaag   5640
caccgggata agcccatcag agagcaggcc gagaatatca tccacctgtt taccctgacc   5700
aatctgggag ccctgcccgc cttcaagtac ttgacacca ccatcgaccg gaaaggtac   5760
accagcacca aagaggtgct ggacgccacc ctgatccacc agagcatcac cggcctgtac   5820
gagacacgga tcgacctgtc tcagctggga ggtgactctg cggctcaaaa agaaccgcc   5880
gacggcagcg aattcgagcc caagaagaag aggaaagtct aaccggtcat catcaccatc   5940
accattgagt ttaaacccgc tgatcagcct cgactgtgcc ttctagttgc cagccatctg   6000
ttgttttgccc ctcccccgtg ccttccttga ccctggaagg tgccactccc actgtcctt   6060
cctaataaaa tgaggaaatt gcatcgcatt gtctgagtag tgtcattct attctggggg   6120
gtgggtgggg gcaggacagc aaggggggagg attgggaaga caatagcagg catgctgggg   6180
atgcggtggg ctctatggct tctgaggcgg aaagaaccag ctggggctcg ataccgtcga   6240
cctctagcta gagcttggcg taatcatggt catagctgtt tcctgtgtga aattgttatc   6300
cgctcacaat tccacacaac atacgagccg gaagcataaa gtgtaaagcc tagggtgcct   6360
```

-continued

```
aatgagtgag ctaactcaca ttaattgcgt tgcgctcact gcccgctttc cagtcgggaa   6420
acctgtcgtg ccagctgcat taatgaatcg gccaacgcgc ggggagaggc ggtttgcgta   6480
ttgggcgctc ttccgcttcc tcgctcactg actcgctgcg ctcggtcgtt cggctgcggc   6540
gagcggtatc agctcactca aaggcggtaa tacggttatc cacagaatca ggggataacg   6600
caggaaagaa catgtgagca aaaggccagc aaaaggccag gaaccgtaaa aaggccgcgt   6660
tgctggcgtt tttccatagg ctccgccccc ctgacgagca tcacaaaaat cgacgctcaa   6720
gtcagaggtg gcgaaacccg acaggactat aaagatacca ggcgtttccc cctggaagct   6780
ccctcgtgcg ctctcctgtt ccgaccctgc cgcttaccgg atacctgtcc gcctttctcc   6840
cttcgggaag cgtggcgctt tctcatagct cacgctgtag gtatctcagt tcggtgtagg   6900
tcgttcgctc caagctgggc tgtgtgcacg aaccccccgt tcagcccgac cgctgcgcct   6960
tatccggtaa ctatcgtctt gagtccaacc cggtaagaca cgacttatcg ccactggcag   7020
cagccactgg taacaggatt agcagagcga ggtatgtagg cggtgctaca gagttcttga   7080
agtggtggcc taactacggc tacactagaa gaacagtatt tggtatctgc gctctgctga   7140
agccagttac cttcggaaaa agagttggta gctcttgatc cggcaaacaa accaccgctg   7200
gtagcggtgg tttttttgtt tgcaagcagc agattacgcg cagaaaaaaa ggatctcaag   7260
aagatccttt gatcttttct acggggtctg acactcagtg gaacgaaaac tcacgttaag   7320
ggattttggt catgagatta tcaaaaagga tcttcaccta gatcctttta aattaaaaat   7380
gaagttttaa atcaatctaa agtatatatg agtaaacttg gtctgacagt taccaatgct   7440
taatcagtga ggcacctatc tcagcgatct gtctatttcg ttcatccata gttgcctgac   7500
tccccgtcgt gtagataact acgatacggg agggcttacc atctggcccc agtgctgcaa   7560
tgataccgcg agacccacgc tcaccggctc cagatttatc agcaataaac cagccagccg   7620
gaagggccga gcgcagaagt ggtcctgcaa ctttatccgc ctccatccag tctattaatt   7680
gttgccggga agctagagta agtagttcgc cagttaatag tttgcgcaac gttgttgcca   7740
ttgctacagg catcgtggtg tcacgctcgt cgtttggtat ggcttcattc agctccggtt   7800
cccaacgatc aaggcgagtt acatgatccc ccatgttgtg caaaaaagcg gttagctcct   7860
tcggtcctcc gatcgttgtc agaagtaagt tggccgcagt gttatcactc atggttatgg   7920
cagcactgca taattctctt actgtcatgc catccgtaag atgcttttct gtgactggtg   7980
agtactcaac caagtcattc tgagaatagt gtatgcggcg accgagttgc tcttgcccgg   8040
cgtcaatacg ggataatacc gcgccacata gcagaacttt aaaagtgctc atcattggaa   8100
aacgttcttc ggggcgaaaa ctctcaagga tcttaccgct gttgagatcc agttcgatgt   8160
aacccactcg tgcacccaac tgatcttcag catctttta tttcaccagc gtttctgggt   8220
gagcaaaaac aggaaggcaa aatgccgcaa aaaagggaat aagggcgaca cggaaatgtt   8280
gaatactcat actcttcctt tttcaatatt attgaagcat ttatcagggt tattgtctca   8340
tgagcggata catatttgaa tgtatttaga aaaataaaca aataggggtt ccgcgcacat   8400
ttccccgaaa agtgccacct gacgtcgacg gatcgggaga tcgatctccc gatccctag    8460
ggtcgactct cagtacaatc tgctctgatg ccgcatagtt aagccagtat ctgctccctg   8520
cttgtgtgtt ggaggtcgct gagtagtgcg cgagcaaaat ttaagctaca caaggcaag    8580
gcttgaccga caattgcatg aagaatctgc ttagggttag gcgttttgcg ctgcttcgcg   8640
atgtacgggc cagatatacg cgttgacatt gattattgac tagttattaa tagtaatcaa   8700
ttacggggtc attagttcat agcccatata tggagttccg cgttacataa cttacggtaa   8760
atggcccgcc tggctgaccg cccaacgacc cccgcccatt gacgtcaata atgacgtatg   8820
ttcccatagt aacgccaata gggactttcc attgacgtca atgggtggag tatttacggt   8880
aaactgccca cttggcagta catcaagtgt atc                                8913

SEQ ID NO: 54         moltype = DNA   length = 8913
FEATURE               Location/Qualifiers
source                1..8913
                      mol_type = other DNA
                      organism = Synthetic construct
SEQUENCE: 54
atatgccaag tacgcccct attgacgtca atgacggtaa atggcccgcc tggcattatg    60
cccagtacat gaccttatgg gactttccta cttggcagta catctacgta ttagtcatcg   120
ctattaccat ggtgatgcgg ttttggcagt acatcaatgg gcgtggatag cggtttgact   180
cacgggggatt tccaagtctc cacccccattg acgtcaatgg gagtttgttt ggcaccaaa   240
atcaacggga cttttccaaaa tgtcgtaaca actccgcccc attgacgcaa atgggcggta   300
ggcgtgtacg gtgggaggtc tatataagca gagctggttt agtgaaccgt cagatccgct   360
agagatccgc ggccgctaat acgactcact atagggagag ccgccaccat gaaacggaca   420
gccgacggaa gcgagttcga gtcaccaaag aagaagcgga agtcagcag tgacaagaag    480
tacagcatcg gcctggccat cggcaccaac tctgtgggct gggccgtgat caccgacgag   540
tacaaggtgc cagcaagaa attcaaggtg ctgggcaaca ccgaccggca cagcatcaag   600
aagaacctga tcggagccct gctgttcgac agcggcgaaa cagccgaggc cacccggctg   660
aagagaaccg ccagaagaag atacaccaga cggaagaacc ggatctgcta tctgcaagag   720
atcttcagca acgagatggc caaggtggac gacagcttct tccacagact ggaagagtcc   780
ttcctggtgg aagaggataa gaagcacgag cggcacccca tcttcggcaa catcgtggac   840
gaggtggcct accacgagaa gtaccccacc atctaccacc tgagaaagaa actggtggac   900
agcaccgaca aggccgacct gcggctgatc tatctggccc tggcccacat gatcaagttc   960
cggggccact tcctgatcga gggcgacctg aaccccgaca cagcgacgt ggacaagctg   1020
ttcatccagc tggtgcagac ctacaaccag ctgttcgagg aaaacccat caacgccagc   1080
ggcgtggacg ccaaggccat cctgtctgcc agactggca gagcagacg gctggaaat    1140
ctgatcgccc agctgcccgg cgagaagaag aatggcctgt tcggaaacct gattgccctg   1200
agcctgggcc tgacccccaa cttcaagagc aacttcgacc tggccgagga tgccaaactg   1260
cagctgagca aggacaccta cgacgacgac ctggacaacc tgctggccca gatcggcgac   1320
cagtacgccg acctgtttct ggccgccaag aacctgtccg acgccatcct gctgagcgac   1380
atcctgagag tgaacacga gatcaccag gccccctag gcgcctctat gatcaagaga   1440
tacgacgagc accaccagga cctgaccctg ctgaaagctc tcgtgcgca gcagctgcct   1500
gagaagtaca agagattt cttcgaccag agcaagaacg gctacgccgg ctacattgac   1560
ggcggagcca gcaggaaga gttctacaag ttcatcaagc catcctgga aaagatggac   1620
ggcaccgagg aactgctcgt gaagctgaac agagaggacc tgctgcggaa gcagcggacc   1680
ttcgacaacg gcagcatccc ccaccagatc cacctggag agctgcacgc cattctgcgg   1740
```

```
cggcaggaag attttaccc attcctgaag gacaaccggg aaaagatcga gaagatcctg   1800
accttccgca tccctacta cgtgggccct ctggccaggg gaaacagcag attcgcctgg   1860
atgaccagaa agagcgagga aaccatcacc ccctggaact tcgaggaagt ggtggacaag   1920
ggcgcttccg cccagagctt catcgagcgg atgaccaact tcgataagaa cctgcccaac   1980
gagaaggtgc tgcccaagca cagcctgctg tacgagtact tcaccgtgta taacgagctg   2040
accaaagtga aatacgtgac cgagggaatg agaaagcccg ccttcctgag cggcgagcag   2100
aaaaaggcca tcgtggacct gctgttcaag accaaccgga aagtgaccgt gaagcagctg   2160
aaagaggact acttcaagaa aatcgagtgc ttcgactccg tggaaatctc cggcgtggaa   2220
gatcggttca acgcctccct gggcacatac cacgatctgc tgaaaattat caaggacaag   2280
gacttcctgg acaatgagga aaacgaggac attctggaag atatcgtgct gaccctgaca   2340
ctgtttgagg acagagagat gatcgaggaa cggctgaaaa cctatgccca cctgttcgac   2400
gacaaagtga tgaagcagct gaagcggcgg agatacaccg ctggggcag gctgagccgg   2460
aagctgatca acggcatccg ggacaagcag tccggcaaga caatcctgga tttcctgaag   2520
tccgacggct tcgccaacag aaacttcatg cagctgatcc acgacgacag cctgaccttt   2580
aaagaggaca tccagaaagc ccaggtgtcc ggccagggcg atagcctgca cgagcacatt   2640
gccaatctgg ccggcagccc cgccattaag aagggcatcc tgcagacagt gaaggtggtg   2700
gacgagctcg tgaaagtgat gggccggcac aagcccgaga acatcgtgat cgaaatggcc   2760
agagagaacc agaccaccca gaagggacag aagaacagcc gcgagagaat gaagcggatc   2820
gaagagggca tcaaagagct gggcagccag atcctgaaag aacacccgt ggaaaacacc   2880
cagctgcaga acgagaagct gtacctgtac tacctgcaga atgggcggga tatgtacgtg   2940
gaccaggaac tggacatcaa ccggctgtcc gactacgatg tggaccatat cgtgcctcag   3000
agctttctga aggacgactc catcgacaac aaggtgctga cccagaagcg caagaaccgg   3060
ggcaagagcg acaacgtgcc ctccgaagag gtcgtgaaga agatgaagaa ctactggcgg   3120
cagctgctga acgccaagct gattaccag agaaagttcg acaatctgac caaggccgag   3180
agaggcggcc tgagcgaact ggataaggcc ggcttcatca gagacagct ggtggaaacc   3240
cggcagatca caaagcacgt ggcacagatc ctggactccc ggatgaacac taagtacgac   3300
gagaatgaca agctgatccg ggaagtgaaa gtgatcaccc tgaagtccaa gctggtgtcc   3360
gatttccgga aggatttcca gttttacaaa gtgcgcgaga tcaacaacta ccaccacgcc   3420
cacgacgcct acctgaacgc cgtcgtggga accgccctga tcaaaagta ccctaagctg   3480
gaaagcgagt tcgtgtacgg cgactacaag gtgtacgacg tgcggaagat gatcgccaag   3540
agcgagcagg aaatcggcaa ggctaccgcc aagtacttct tctacagcaa catcatgaac   3600
ttttttcaaga ccgagattac cctgccaac ggcgagatcc ggaagcggcc tctgatcgag   3660
acaaacggcg aaaccgggga gatcgtgtgg gataagggcc gggattttgc caccgtgcgg   3720
aaagtgctga gcatgcccca agtgaatatc gtgaaaaaga ccgaggtgca gacaggcggc   3780
ttcagcaaag agtctatcct gcccaagagg aacagcgata agctgatcgc cagaaagaag   3840
gactgggacc ctaagaagta cggcggcttc gacagcccca ccgtggccta ttctgtgctg   3900
gtggtggcca aagtggaaaa gggcaagtcc aagaaactga agagtgtgaa agagctgctg   3960
gggatcacca tcatggaaag aagcagcttc gagaagaatc catcgactt tctggaagcc   4020
aagggctaca aagaagtgaa aaaggacctg atcatcaagc tgcctaagta ctccctgttc   4080
gagctggaaa acggccggaa gagaatgctg gcctctgccg gcgaactgca gaagggaaac   4140
gaactggccc tgccctccaa atatgtgaac ttcctgtacc tggccagcca ctatgagaag   4200
ctgaagggct cccccgagga taatgagcag aaacagctgt tgtgaaca gcacaagcac   4260
tacctggacg agatcatcga gcagatcagc gagttctcg gaggatctag cggtggttcc   4320
tctggaagcg agacaccagg cacaagcgag tccgccacac cagagagctc cggcggctcc   4380
tccgaggat cctctgaggt ggagtttttcc cacgagtact ggatgagaca tgccctgacc   4440
ctggccaaga gggcatggga tgaaaagaaa gtccccgtgg cgccgtgct ggtgcacaac   4500
aatagagtga tcggagaggg atggaacagg ccaatcggcc gccacgaccc taccgccac   4560
gcagagatca tggcactgag gcagggaggc ctggtcatgc agaattaccg cctgatcgat   4620
gccaccctgt atgtgacact ggagccatgc gtgatgtgcg caggagcaat gatccacagc   4680
aggatcggaa gagtggtgtt cggagcacgg gacgccaaga ccggcgcagc aggctccctg   4740
atggatgtgc tgcaccaccc cggcatgaac caccgggtgg agatcacaga gggaatcctg   4800
gcagacgagt gcgccgccct gctgagcgat ttcttagaa tgcggagaca ggagatcaag   4860
gcccagaaga aggcacagag ctccaccgac tctggaggat ctagcggcgg atcctctgga   4920
agcgagacac aggcacaag cgagtccgcc acaccagaga gctccggcgg ctcctccgga   4980
ggatcctcg aggtggagtt ttcccacgag tactggatga gacatgcct ggcccctggc   5040
aagagggcac gcgatgagag ggaggtgcct gtgggagccg tgctggtgct gaacaataga   5100
gtgatcggcg agggctggaa cagagccatc ggcctgcacg acccaacagc ccatgccgaa   5160
attatgcc tgacagggg cggcctggtc atgcagaact acagactgat tgacgccacc   5220
ctgtacgtga cattcgagcc ttgcgtgatg tgccgcggcc ccatgatcca ctctaggatc   5280
ggccgcgtg tgtttggcgt gaggaacgca aaaaccggcg ccgcaggctc cctgatggac   5340
gtgctgcact accccggcat gaatcaccgc gtcgaaatta ccgagggaat cctggcagat   5400
gaatgtgccg ccctgctgtg ctattctttt cggatgccta gacaggtgtt caatgctcag   5460
aagaaggccc agagctccac cgactccgga ggatctagcg gaggctcctc tggctctgag   5520
acacctggca caagcgagag cgcaacacct aaagcagcag cggggggtca tccaagagag   5580
tgatcctggc cgacgctaat ctggacaaag tgctgtccgc ctacaacaag   5640
caccgggata agcccatcag agagcaggcc gagaatatca tccacctgtt taccctgacc   5700
aatctgggag cccctgccgc cttcaagtac tttgacacca ccatcgaccg gaagaggtac   5760
accagcacca aagaggtgct ggacgccacc ctgatccacc agagcatcac cggcctgtac   5820
gagacacgtga tcgacctgtc tcagctggga ggtgactctg gcggctcaaa aagaaccgcc   5880
gacggcagcg aattcgagcc caagaagaag aggaaagtct aaccggtcat catcaccatc   5940
accattgagt ttaaacccgc tgatcagcct cgactgtgcc ttctagttgc cagccatctg   6000
ttgtttgccc ctccccgtg ccttccttga ccctggaagg tgccactccc actgtccttt   6060
cctaataaaa tgaggaaatt gcatcgcatt gtctgagtag tgtcattct attctggggg   6120
gtggggtggg gcaggacagc aagggggagg attgggaaga caatagcagg catgctgggg   6180
atgcggtggg ctctatggct tctgaggcgg aaagaaccag ctgggctcg ataccgtcga   6240
cctctagcta gagcttggcg taatcatggt catagctgtt tcctgtgtga aattgttatc   6300
cgctcacaat tccacacaac atacgagccg gaagcataaa gtgtaaagcc tagggtgcct   6360
aatgagtgag ctaactcaca ttaattgcgt tgcgctcact gcccgctttc cagtcgggaa   6420
acctgtcgtg ccagctgcat taatgaatcg gccaacgcgc ggggagaggc ggtttgcgta   6480
```

```
ttgggcgctc ttccgcttcc tcgctcactg actcgctgcg ctcggtcgtt cggctgcggc   6540
gagcggtatc agctcactca aaggcggtaa tacggttatc cacagaatca ggggataacg   6600
caggaaagaa catgtgagca aaaggccagc aaaaggccag gaaccgtaaa aaggccgcgt   6660
tgctggcgtt tttccatagg ctccgccccc ctgacgagca tcacaaaaat cgacgctcaa   6720
gtcagaggtg gcgaaacccg acaggactat aaagatacca ggcgtttccc cctggaagct   6780
ccctcgtgcg ctctcctgtt ccgaccctgc cgcttaccgg atacctgtcc gcctttctcc   6840
cttcgggaag cgtggcgctt tctcatagct cacgctgtag gtatctcagt tcggtgtagg   6900
tcgttcgctc caagctgggc tgtgtgcacg aaccccccgt tcagcccgac cgctgcgcct   6960
tatccggtaa ctatcgtctt gagtccaacc cggtaagaca cgacttatcg ccactggcag   7020
cagccactgg taacaggatt agcagagcga ggtatgtagg cggtgctaca gagttcttga   7080
agtggtggcc taactacggc tacactagaa gaacagtatt tggtatctgc gctctgctga   7140
agccagttac cttcggaaaa agagttggta gctcttgatc cggcaaacaa accaccgctg   7200
gtagcggtgg ttttttgtt tgcaagcagc agattacgcg cagaaaaaaa ggatctcaag   7260
aagatccttt gatcttttct acggggtctg acactcagtg gaacgaaaac tcacgttaag   7320
ggattttggt catgagatta tcaaaaagga tcttcaccta gatcctttta aattaaaaat   7380
gaagttttaa atcaatctaa agtatatatg agtaaacttg gtctgacagt taccaatgct   7440
taatcagtga ggcacctatc tcagcgatct gtctatttcg ttcatccata gttgcctgac   7500
tccccgtcgt gtagataact acgatacggg agggcttacc atctggcccc agtgctgcaa   7560
tgataccgcg agacccacgc tcaccggctc cagatttatc agcaataaac cagccagccg   7620
gaagggccga gcgcagaagt ggtcctgcaa ctttatccgc ctccatccag tctattaatt   7680
gttgccggga agctagagta gtagttcgc cagttaatag tttgcgcaac gttgttgcca   7740
ttgctacagg catcgtggtg tcacgctcgt cgtttggtat ggcttcattc agctccggtt   7800
cccaacgatc aaggcgagtt acatgatccc ccatgttgtg caaaaaagcg gttagctcct   7860
tcggtcctcc gatcgttgtc agaagtaagt tggccgcagt gttatcactc atggttatgg   7920
cagcactgca taattctctt actgtcatgc catccgtaag atgcttttct gtgactggtg   7980
agtactcaac caagtcattc tgagaatagt gtatgcggcg accgagttgc tcttgcccgg   8040
cgtcaatacg ggataatacc gcgccacata gcagaacttt aaaagtgctc atcattggaa   8100
aacgttcttc gggcgaaaa ctctcaagga tcttaccgct gttgagatcc agttcgatgt   8160
aacccactcg tgcacccaac tgatcttcag catcttttac tttcaccagc gtttctgggt   8220
gagcaaaaac aggaaggcaa aatgccgcaa aaaagggaat aagggcgaca cggaaatgtt   8280
gaatactcat actcttcctt tttcaatatt attgaagcat ttatcagggt tattgtctca   8340
tgagcggata catatttgaa tgtatttaga aaaataaaca aataggggtt ccgcgcacat   8400
ttccccgaaa agtgccacct gacgtcgacg gatcgggaga tcgatctccc gatccctag   8460
ggtcgactct cagtacaatc tgctctgatg ccgcatagtt aagccagtat ctgctccctg   8520
cttgtgtgtt ggaggtcgct gagtagtgcg cgagcaaaat ttaagctaca caaggcaag   8580
gcttgaccga caattgcatg aagaatctgc ttagggttag gcgttttgcg ctgcttcgcg   8640
atgtacgggc cagatatacg cgttgacatt gattattgac tagttattaa tagtaatcaa   8700
ttacggggtc attagttcat agcccatata tggagttccg cgttacataa cttacggtaa   8760
atggcccgcc tggctgaccg cccaacgacc cccgcccatt gacgtcaata atgacgtatg   8820
ttcccatagt aacgccaata gggactttcc attgacgtca atgggtggag tatttacggt   8880
aaactgccca cttggcagta catcaagtgt atc                                8913

SEQ ID NO: 55          moltype = DNA  length = 8913
FEATURE                Location/Qualifiers
source                 1..8913
                       mol_type = other DNA
                       organism = Synthetic construct
SEQUENCE: 55
atatgccaag tacgcccct attgacgtca atgacggtaa atggcccgcc tggcattatg     60
cccagtacat gaccttatgg gactttccta cttggcagta catctacgta ttagtcatcg    120
ctattaccat ggtgatgcgg ttttggcagt acatcaatgg gcgtggatag cggtttgact    180
cacggggatt tccaagtctc caccccattg acgtcaatgg gagtttgttt tggcaccaaa    240
atcaacggga ctttccaaaa tgtcgtaaca actccgcccc attgacgcaa atgggcggta    300
ggcgtgtacg gtgggaggtc tatataagca gagctggttt agtgaaccgt cagatccgct    360
agagatcccg ggccgctaat acgactcact ataggggaga ccgccaccat gaaacggaca    420
gccgacggaa gcgagttcga gtcaccaaag aagaagcgga agtcagcag tgacaagaag    480
tacagcatcg gcctggccat cggcaccaac tctgtgggct gggccgtgat caccgacgag    540
tacaaggtgc ccagcaagaa attcaaggtg ctgggcaaca ccgaccggca cagcatcaag    600
aagaacctga tcggagccct gctgttcgac agcggcgagg cagccggctg cagccggctg    660
aagagaaccg ccagaagaag atacaccaga cggaagaacc ggatctgcta tctgcagaag    720
atcttcagca acgagatggc caaggtggac gacagcttct tccacagact ggaagagtcc    780
ttcctggtgg aagaggataa gaagcacgag cggcacccca tcttcggcaa catcgtggac    840
gaggtggcct accacgagaa gtaccccacc atctaccacc tgagaaagaa actggtggac    900
agcaccgaca aggccgacct gcggctgatc tatctggccc tggcccacat gatcaagttc    960
cggggccact tcctgatcga gggcgacctg aaccccgaca acagcgacgt ggacaagctg    1020
ttcatccagc tggtgcagac ctacaaccag ctgttcgaga aaaaacccat caacgccagc    1080
ggcgtggacg ccaaggccat cctgtctgcc agactgagca gagcagacg gctggaaaat    1140
ctgatcgccc agctgcccgg cgagaagaag aatggcctgt tcggaaacct gattgccctg    1200
agcctgggcc tgacccccaa cttcaagagc aacttcgacc tggccgagga tgccaaactg    1260
cagctgagca aggacaccta cgacgacgac ctggacaacc tgctggccca gatcggcgac    1320
cagtacgccg acctgtttct ggccgccaag aacctgtccg acgccatcct gctgagcgac    1380
atcctgagag tgaacaccga gatcaccaag gccccctga gcgcctctat gatcaagaga    1440
tacgacgagc accaccagga cctgaccctg ctgaaagctc tcgtgcggca gcagctgcct    1500
gagaagtaca aagagatttt cttcgaccag agcaagaacg gctacgccgg ctacattgac    1560
ggcggagcca gccaggaaga gttctacaag ttcatcaagc ccatcctgga aaagatggac    1620
ggcaccgagg aactgctcgt gaagctgaac agagaggacc tgctgcggaa gcagcggacc    1680
ttcgacaacg gcagcatccc ccaccagatc cacctgggag agctgcacgc cattctgcgg    1740
cggcaggaag atttttaccc attcctgaag gacaaccggg aaaagatcga aaagatcctg    1800
accttccgca tccctactac cgtgggccct ctggccaggg gaaacagcag attcgcctgg    1860
```

```
atgaccagaa agagcgagga aaccatcacc ccctggaact tcgaggaagt ggtggacaag  1920
ggcgcttccg cccagagctt catcgagcgg atgaccaact tcgataagaa cctgcccaac  1980
gagaaggtgc tgcccaagca cagcctgctg tacgagtact tcaccgtgta taacgagctg  2040
accaaagtga aatacgtgac cgagggaatg agaaagcccg ccttcctgag cggcgagcag  2100
aaaaaggcca tcgtggacct gctgttcaag accaaccgga aagtgaccgt gaagcagctg  2160
aaagaggact acttcaagaa aatcgagtgc ttcgactccg tggaaatctc cggcgtggaa  2220
gatcggttca acgcctccct gggcacatac cacgatctgc tgaaaattat caaggacaag  2280
gacttcctgg acaatgagga aaacgaggac attctggaag atatcgtgct gaccctgaca  2340
ctgtttgagg acagagagat gatcgaggaa cggctgaaaa cctatgccca cctgttcgac  2400
gacaaagtga tgaagcagct gaagcggcgg agatacaccg gctgggcag gctgagccgg  2460
aagctgatca acggcatccg ggacaagcag tccggcaaga caatcctgga tttcctgaag  2520
tccgacggct cgccaacag aaacttcatg cagctgatcc acgacgacag cctgaccttt  2580
aaagaggaca tccagaaagc ccaggtgtcc ggccagggcg atagcctgca cgagcacatt  2640
gccaatctgg ccggcagccc cgccattaag aagggcatcc tgcagacagt gaaggtggtg  2700
gacgagctcg tgaaagtgat gggccggcac aagcccgaga acatcgtgat cgaaatggcc  2760
agagagaacc agaccaccca gaagggacag aagaacagcc gcgagagaat gaagcggatc  2820
gaagagggca tcaaagagct gggcagccag atcctgaaag aacaccccgt ggaaaacacc  2880
cagctgcaga acgagaagct gtacctgtac tacctgcaga atgggcggga tatgtacgtg  2940
gaccaggaac tggacatcaa ccggctgtcc gactacgatg tggaccatat cgtgcctcag  3000
agctttctga aggacgactc catcgacaac aaggtgctga ccagaagcga caagaaccgg  3060
ggcaagagcg acaacgtgcc ctccgaagag gtcgtgaaga gatgaagaa ctactggcgg  3120
cagctgctga acgccaagct gattacccag agaaagttcg acaatctgac caaggccgaa  3180
agaggcggcc tgagcgaact ggataaggcc ggcttcatca agagacagct ggtggaaacc  3240
cggcagatca caaagcacgt ggcacagatc ctggactccc ggatgaacac taagtacgac  3300
gagaatgaca agctgatccg ggaagtgaaa gtgatcaccc tgaagtccaa gctggtgtcc  3360
gatttccgga aggatttcca gttttacaaa gtgcgcgaga tcaacaacta ccaccacgcc  3420
cacgacgcct acctgaacgc cgtcgtggga accgccctga tcaaaagta ccctaagctg  3480
gaaagcgagt tcgtgtacgg cgactacaag gtgtacgacg tgcggaagat gatcgccaag  3540
agcgagcagg aaatcggcaa ggctaccgcc aagtacttct tctacagcaa catcatgaac  3600
ttttcaaga ccgagattac cctggccaac ggcgagatcc ggaagcggcc tctgatcgag  3660
acaaacggcg aaaccgggga gatcgtgtgg gataagggcc gggattttgc caccgtgcgg  3720
aaagtgctga gcatgcccca agtgaatatc gtgaaaaaga ccgaggtgca gacaggcggc  3780
ttcagcaaag agtctatcct gcccaagagg aacagcgata agctgatcgc cagaaagaag  3840
gactgggacc ctaagaagta cggcggcttc gacagcccca ccgtggccta ttctgtgctg  3900
gtggtggcca aagtggaaaa gggcaagtcc aagaaactga agagtgtgaa agagctgctg  3960
gggatcacca tcatggaaag aagcagcttc gagaagaatc catcgacttt tctggaagcc  4020
aagggctaca aagaagtgaa aaaggacctg atcatcaagc tgcctaagta ctccctgttc  4080
gagctggaaa acggccggaa gagaatgctg gcctctgccg gcgaactgca gaagggaaac  4140
gaactggccc tgccctccaa atatgtgaac ttcctgtacc tggccagcca ctatgagaag  4200
ctgaagggct cccccgagga taatgagcag aaacagctgt tgtggaaca gcacaagcac  4260
tacctggacg agatcatcga gcagatcagc gagttctcca agagagtgat cctgccgac  4320
gctaatctgg acaaagtgct gtccgcctac aacaagcacc gggataagcc catctctgga  4380
ggatcgcacg gtggttcctc tggaagcgag acaccaggca agcgagtc cgccacacca  4440
gagagctccg gcggcctc cggaggatcc tctgaggtgg agttttccca cgagtactgg  4500
atgagacatg ccctgacct ggccaagagg gcatgggatg aaagagaagt ccccgtgggc  4560
gccgtgctgg tgcacaacaa tagagtgatc ggagagggat ggaacaggcc aatcggccgc  4620
cacgacccta ccgcacacgc agagatcatg gcactgagga gggaggcct ggtcatgcag  4680
aattaccgcc tgatcgatgc caccctgtat gtgacactgg agccatgcgt gatgtgcgca  4740
ggagcaatga tccacagcag gatcggaaga gtggtgttcg gagcacggga cgccaagacc  4800
ggcgcagcag gctccctgat ggatgtgctg caccacccg gcatgaacca ccgggtggag  4860
atcacagagg gaatcctggc agacgatgc gccgccctgc tgagcgattt ctttagaatg  4920
cggagacagg agatcaaggc ccagaagaag gcacagagct ccaccgactc tggaggatct  4980
agcggcggat cctctggaag cgagacacca ggcacaagcg agtccgccac accagagagc  5040
tccggcggct cctccggagg atcctctgag gtggagtttt cccacgagta ctggatgaga  5100
catgccctga ccctggccaa gagggcacgc gatgagaggg aggtgcctgt gggagccgtg  5160
ctggtgctga acaatagagt gatcggcgag ggctggaaca gagccatcgg cctgcacgac  5220
ccaacagccc atgccgaaat tatgccctg acaggggcg gcctggtcat gcagaactac  5280
agactgattg acgccaccct gtacgtgaca ttcgagcctt gcgtgatgtg cgccggcgcc  5340
atgatccact ctaggatcgg ccgctgtggt tttggcgtga ggaacgcaaa aaccggcgcc  5400
gcaggctccc tgatggacgt gctgcactac cccggatga tcaccgcgt cgaaattacc  5460
gagggaatcc tggcagatga atgtgccgcc ctgctgtgct atttctttcg gatgcctaga  5520
caggtgttca atgctcagaa gaaggcccag agctccaccg actccggagg atctagcgga  5580
ggctcctctg gctctgagac cctggcaca agcgagagcc aaacctga agcagcggg  5640
ggcagcagcg gggtcaag agagcagcc gagaatatca tccacctgtt taccctgacc  5700
aatctgggag ccctgccgc cttcaagtac tttgacacca ccatcgaccg gaagaggtac  5760
accagcacca aagaggtgct ggacgccacc ctgatccacc agagcatcac cggcctgtac  5820
gagacacgga tcgacctgtc tcagctggga ggtgactctg gcggctcaaa aagaaccgcc  5880
gacggcagcg aattcgagcc caagaagaag aggaaagtct aaccggtcat catcaccatc  5940
accattgagt ttaaacccgc tgatcagcct cgactgtgcc ttctagttgc cagccatctg  6000
ttgtttgccc ctccccgtg ccttccttga ccctggaagg tgccactccc actgtccttt  6060
cctaataaaa tgaggaaatt gcatcgcatt gtctgagtag gtgtcattct attctggggg  6120
gtggggtggg gcaggacagc aagggggagg attgggaaga caatagcagg catgctgggg  6180
atgcggtggg ctctatggct tctgaggcgg aaagaaccag ctgggctcg ataccgtcga  6240
cctctagcta gagcttgcg taatcatggt catagctgtt tcctgtgtga aattgttatc  6300
cgctcacaat tccacacaac atacgagccg aagcataaa gtgtaaagcc tagggtgcct  6360
aatgagtgag ctaactcaca ttaattgcgt tgcgctcact gcccgctttc cagtcgggaa  6420
acctgtcgtg ccagctgcat taatgaatcg gccaacgcgc ggggagaggc ggtttgcgta  6480
ttgggcgctc ttccgcttcc tcgctcactg actcgctgcg ctcggtcgtt cggctgcggc  6540
gagcggtatc agctcactca aaggcggtaa tacggttatc cacagaatca ggggataacg  6600
```

```
caggaaagaa catgtgagca aaaggccagc aaaaggccag gaaccgtaaa aaggccgcgt   6660
tgctggcgtt tttccatagg ctccgccccc ctgacgagca tcacaaaaat cgacgctcaa   6720
gtcagaggtg gcgaaacccg acaggactat aaagatacca ggcgtttccc cctggaagct   6780
ccctcgtgcg ctctcctgtt ccgaccctgc cgcttaccgg atacctgtcc gcctttctcc   6840
cttcgggaag cgtggcgctt tctcatagct cacgctgtag gtatctcagt tcggtgtagg   6900
tcgttcgctc caagctgggc tgtgtgcacg aaccccccgt tcagcccgac cgctgcgcct   6960
tatccggtaa ctatcgtctt gagtccaacc cggtaagaca cgacttatcg ccactggcag   7020
cagccactgg taacaggatt agcagagcga ggtatgtagg cggtgctaca gagttcttga   7080
agtggtggcc taactacggc tacactagaa gaacagtatt tggtatctgc gctctgctga   7140
agccagttac cttcggaaaa agagttggta gctcttgatc cggcaaacaa accaccgctg   7200
gtagcggtgg tttttttgtt tgcaagcagc agattacgcg cagaaaaaaa ggatctcaag   7260
aagatccttt gatcttttct acggggtctg acactcagtg gaacgaaaac tcacgttaag   7320
ggattttggt catgagatta tcaaaaagga tcttcaccta gatcctttta aattaaaaat   7380
gaagttttaa atcaatctaa agtatatatg agtaaacttg gtctgacagt taccaatgct   7440
taatcagtga ggcacctatc tcagcgatct gtctatttcg ttcatccata gttgcctgac   7500
tccccgtcgt gtagataact acgatacggg agggcttacc atctggcccc agtgctgcaa   7560
tgataccgcg agacccacgc tcaccggctc cagatttatc agcaataaac cagccagccg   7620
gaagggccga gcgcagaagt ggtcctgcaa ctttatccgc ctccatccag tctattaatt   7680
gttgccggga agctagagta agtagttcgc cagttaatag tttgcgcaac gttgttgcca   7740
ttgctacagg catcgtggtg tcacgctcgt cgtttggtat ggcttcattc agctccggtt   7800
cccaacgatc aaggcgagtt acatgatccc ccatgttgtg caaaaaagcg gttagctcct   7860
tcggtcctcc gatcgttgtc agaagtaagt tggccgcagt gttatcactc atggttatgg   7920
cagcactgca taattctctt actgtcatgc catccgtaag atgcttttct gtgactggtg   7980
agtactcaac caagtcattc tgagaatagt gtatgcggcg accgagttgc tcttgcccgg   8040
cgtcaatacg ggataatacc gcgccacata gcagaacttt aaaagtgctc atcattggaa   8100
aacgttcttc ggggcgaaaa ctctcaagga tcttaccgct gttgagatcc agttcgatgt   8160
aacccactcg tgcacccaac tgatcttcag catctttac tttcaccagc gtttctgggt   8220
gagcaaaaac aggaaggcaa aatgccgcaa aaaagggaat aagggcgaca cggaaatgtt   8280
gaatactcat actcttcctt tttcaatatt attgaagcat ttatcagggt tattgtctca   8340
tgagcggata catatttgaa tgtatttaga aaaataaaca aataggggtt ccgcgcacat   8400
ttccccgaaa agtgccacct gacgtcgacg gatcgggaga tcgatctccc gatccctag   8460
ggtcgactct cagtacaatc tgctctgatg ccgcatagtt aagccagtat ctgctccctg   8520
cttgtgtgtt ggaggtcgct gagtagtgcg cgagcaaaat ttaagctaca caaggcaag   8580
gcttgaccga caattgcatg aagaatctgc ttagggttag gcgttttgcg ctgcttcgcg   8640
atgtacgggc cagatatacg cgttgacatt gattattgac tagttattaa tagtaatcaa   8700
ttacggggtc attagttcat agcccatata tggagttccg cgttacataa cttacgtaa   8760
atggcccgcc tggctgaccg cccaacgacc cccgcccatt gacgtcaata atgacgtatg   8820
ttcccatagt aacgccaata gggactttcc attgacgtca atgggtggag tatttacggt   8880
aaactgccca cttggcagta catcaagtgt atc                               8913

SEQ ID NO: 56           moltype = DNA   length = 8924
FEATURE                 Location/Qualifiers
source                  1..8924
                        mol_type = other DNA
                        organism = Synthetic construct
SEQUENCE: 56
atatgccaag tacgccccct attgacgtca atgacggtaa atggcccgcc tggcattatg     60
cccagtacat gaccttatgg gactttccta ctggcagtac atctacgtat tagtcatcgc    120
tattaccatg gtgatgcggt tttggcagta catcaatggg cgtggatagc ggtttgactc    180
acggggattt ccaagtctcc accccattga cgtcaatggg agtttgtttt ggcaccaaaa    240
tcaacggggc tttccaaaat gtcgtaacaa ctccgcccca ttgacgcaaa tgggcggtag    300
gcgtgtacgg tgggaggtct atataagcag agctggttta gtgaaccgtc agatccgcta    360
gagatccgcg gccgctaata cgactcacta tagggagagc cgccaccatg aaacggacag    420
ccgacgaagc gagttcgag tcaccaaaga gaagcggaaa agtcagcagt gacaagaagt    480
acagcatcgg cctggcatc ggcaccaact ctgtgggctg gccgtgatc accgacgagt    540
acaaggtgcc cagcaagaaa ttcaaggtgc tgggcaacac cgaccggcac agcatcaaga    600
agaacctgat cggagccctg ctgttcgaca gcggcgaaac agccgaggcc acccggctga    660
agagaaccgc cagaagaaga taccagac ggaagaaccg gatctgctat ctgcaagaga    720
tcttcagcaa cgagatggcc aaggtggacg acagcttcct ccacagactg gaagagtcct    780
tcctggtgga agaggataag aagcacgagc ggcaccccat cttcggcaac atcgtggacg    840
aggtggccta ccacgagaag taccccacca tctaccacct gagaaagaaa ctggtggaca    900
gcaccgacaa ggccgacctg cggctgatct atctggccct ggcccacatg atcaagttcc    960
ggggccactt cctgatcgag ggcgacctga accccgacaa cagcgacgtg gacaagctgt   1020
tcatccagct ggtgcagacc tacaaccagc tgttcgagga aaacccat acgcgcagtg   1080
gcgtggacgc caaggccatc ctgtctgcca gactgagcaa gagcagacgg ctggaaaatc   1140
tgatcgccca gctgcccggc gagaagaaga atggcctgtt cggaaacctg attgccctga   1200
gcctgggcct gaccccaac ttcaagagca acttcgacct ggccgaggat gccaaactgc   1260
agctgagcaa ggacacctac gacgacgacc tggacaacct gctggccag atcgcgacc   1320
agtaccgcga cctgtttctg gccgccaaga acctgtccga cgccatcctg ctgagcgaca   1380
tcctgagagt gaacaccgag atcaccaagg cccccctgag cgcctctatg atcaagagat   1440
acgacgagca ccaccaggac ctgaccctgc tgaaagctct cgtgcggcag cagctgcctg   1500
agaagtacaa agagattttc ttcgaccaga gcaagaacgg ctacgccggc tacattgacg   1560
gcggagccag ccaggaagag ttctacaagt tcatcaagcc catcctggaa aagatggacg   1620
gcaccgagga actgctcgtg aagctgaaca gagaggacct gcgggaaacct   1680
tcgacaacgg cagcatcccc caccagatcc acctgggaga gctgcacgcc attctgcggc   1740
ggcaggaaga ttttttaccca ttcctgaagg acaaccggga aaagatcgag aagatcctga   1800
ccttccgcat ccctactac gtgggcccc tggccagggg aaacagcaga ttcgcctgga   1860
tgaccagaaa gagcgaggaa accatcaccc cctggaactt cgaggaagtg gtggacaagg   1920
gcgcttccgc ccagagcttc atcgagcgga tgaccaactt cgataagaac ctgccaacg   1980
```

```
agaaggtgct gcccaagcac agcctgctgt acgagtactt caccgtgtat aacgagctga  2040
ccaaagtgaa atacgtgacc gagggaatga gaaagcccgc cttcctgagc ggcgagcaga  2100
aaaaggccat cgtggacctg ctgttcaaga ccaaccggaa agtgaccgtg aagcagctga  2160
aagaggacta cttcaagaaa atcgagtgct tcgactccgt ggaaatctcc ggcgtggaag  2220
atcggttcaa cgcctccctg ggcacatacc acgatctgct gaaaatttat aaggacaagg  2280
acttcctgga caatgaggaa aacgaggaca ttctggaaga tatcgtgctg accctgacac  2340
tgtttgagga cagagagatg atcgaggaac ggctgaaaac ctatgccac ctgttcgacg  2400
acaaagtgat gaagcagctg aagcggcgga gatacaccgg ctgggcagg ctgagccgga  2460
agctgatcaa cggcatccgg gacaagcagt ccggcaagac aatcctggat ttcctgaagt  2520
ccgacggctt cgccaacaga aacttcatgc agctgatcca cgacgacagc ctgaccttta  2580
aagaggacat ccagaaagcc caggtgtccg gccagggcga tagcctgcac gagcacattg  2640
ccaatctggc cggcagcccc gccattaaga agggcatcct gcagacagtg aaggtggtgg  2700
acgagctcgt gaaagtgatg ggccggcaca agcccgagaa catcgtgatc gaaatggcca  2760
gagagaacca gaccacccag aagggacaga agaacagccc cgagagaatg aagcggatcg  2820
aagagggcat caaagagctg ggcagccaga tcctgaaaga acaccccgtg aaaacaccc  2880
agctgcagaa cgagaagctg tacctgtact acctgcagaa tgggcgggat atgtacgtgg  2940
accaggaact ggacatcaac cggctgtccg actacgatgt ggaccatatc gtgcctcaga  3000
gctttctgaa ggacgactcc atcgacaaca aggtgctgac cagaagcgac aagaaccggg  3060
gcaagagcga caacgtgccc tccgaagagg tcgtgaagaa gatgaagaac tactggcggc  3120
agctgctgaa cgccaagctg attcccaga gaaagttcga caatctgacc aaggccgaga  3180
gaggcggcct gagcgaactg gataaggcg gcttcatcaa gagacagctg gtggaaaccc  3240
ggcagatcac aaagcacgtg gcacagatcc tggactccga tgaacact aagtacgacg  3300
agaatgacaa gctgatccgg gaagtgaaag tgatcaccct gaagtccaag ctggtgtccg  3360
atttccggaa ggatttccag ttttacaaag tgcgcgagat caacaactac caccacgccc  3420
acgacgccta ccctaaacgcc gtcgtgggaa ccgccctgat caaaaagtac cctaagctgg  3480
aaagcgagtt cgtgtacggc gactacaagg tgtacgacgt gcggaagatg atcgccaaga  3540
gcgagcagga aatcggcaag gctaccgcca agtacttctt ctacagcaac atcatgaact  3600
tttcaagtc cggatccgag accccaggca cctccgagtc tgccacacct gagagcggaa  3660
gcgaaaccgg accagtggca gtggacccaa ccctgaggag acggattgag ccccatgaat  3720
ttgaagtgtt cttgaccca aggagctga ggaaggagac atgcctgctg tacgagatca  3780
agtgggcac aagccacaag atctggctgcc acagctccaa gaacaccaca aagcacgtgg  3840
aagtgaattt catcgagaag tttacctccg agcggcactt ctgcccctct accagctgtt  3900
ccatcacatg gtttctgtct tggagccctt gcggcgagtg ttccaaggcc atcaccgagt  3960
tcctgtctca gcaccctaac gtgaccctgg tcatctacgt ggcccggctg tatcaccaca  4020
tggaccagca gaacaggcag ggcctgcgcg atctggtgga tttctggctg accatccaga  4080
tcatgacagc cccagagtac gactattgct ggcggaactt cgtgaattat ccacctggca  4140
aggaggcaca ctggccaaga tacccacccc tgtggatgaa gctgtatgca ctggagctgc  4200
acgcaggaat cctgggcctg cctccatgtc tgaatatcct gcggagaaag cagccccagc  4260
tgcatttttt caccattgct ctgcagtctt gtcactatca gcggctgcct cctcatattc  4320
tgtgggctac aggcctgaag tctgatctg cagcgagac accaggaaca agcgagtcag  4380
caacaccaga gagcgagaca aacggcgaaa ccggggagat cgtgtgggat aagggccggg  4440
attttgccac cgtgcgcgaaa gtgctgagca tgccccaagt gaatatcgtg aaaaagaccg  4500
aggtgcgaac aggcggcttc agcaaagagt ctatcctgcc caagaggaac agcgataagc  4560
tgatcgccag aaaaaggac tgggaccta agaagtacgg cggcttcgac agccccaccg  4620
tggcctattc tgtgctggtg gtggccaaag tggaaagggg caagtccaag aaactgaaga  4680
gtgtgaaaga gctgctgggg atcaccatca tggaaagaag cagcttcgag aagaatccca  4740
tcgactttct ggaagccaag ggctacaaag aagtgaaaaa ggacctgatc atcaagctgc  4800
ctaagtactc cctgttcgag ctggaaaacg gccggaagag aatgctggcc tctgccggcg  4860
aactgcagaa gggaaacgaa ctggcccgtgc cctccaaata tgtgaacttc ctgtacctgg  4920
ccagccacta tgagaagctg aagggctccc ccgaggataa tgagcagaaa cagctgtttg  4980
tggaacagca caagcactac ctggacgaga tcatcgaaca gatcagcgag ttctccaagg  5040
gagtgatcct ggccgacgct aatctggaca aagtgctgtc cgcctacaac aagcaccggg  5100
ataagccat cagagagcag gccgagaata tcatccacct gttacccctg accaatctgg  5160
gagccctgc cgccttcaag tactttgaca ccaccatcga ccggaagagg tacaccagca  5220
ccaaagaggt gctggacgcc accctgatcc accagagcat cacccgcctg tacgagacac  5280
ggatcgacct gtctcagctg ggaggtgaca gcggcgggag cggcggagc gggggagca  5340
ctaatctgag cgacatcatt gagaaggaga ctgggaaaca gctggtcatt caggagtcca  5400
tcctgatgct gcctgaggag gtggaggaag tgatcggcaa caagccagag tctgacatcc  5460
tggtgcacac cgcctacgac gagtccacag atgagaatgt gatgctgctg acctctgacg  5520
cccccgagta taagcttgg gccctggtca tccaggattc taacggcgag aataagatca  5580
agatgctgag cggaggatcc ggaggatctg gaggcagcac caacctgtct gacatcatcg  5640
agaaggagac aggcaagcag ctggtcatcc aggagagcat cctgatgctg cccgaagaag  5700
tcgaagaagt gatcggaaac aagcctgaga gcgatatcct ggtccatacc gcctacgacg  5760
agagtaccga cgaaaatgtg atgctgctga catccgacgc tccagagtat aagccgatca  5820
ctctggtcat ccaggattcc aacggagaga acaaaatcaa aatgctgtct ggcggctcaa  5880
aaagaaccgc cgacggcagc gaattcgagc ccaagaagaa gaggaaagtc taaccggtca  5940
tcatcaccat caccattgag tttaaacccg ctgatcagcc tcgactgtgc cttctagttg  6000
ccagccatct gttgtttgcc cctccccgt gccttccttg acctggaag gtgccactcc  6060
cactgtcctt tcctaataaa atgaggaaat tgcatcgcat tgtctgagta ggtgtcattc  6120
tattctgggg ggtggggtgg ggcaggacag caagggggag gattgggaag acaatagcag  6180
gcatgctggg gatgcggtgg gctctatggc ttctgaggcg gaaagaacca gctgggctc  6240
gataccgtcg acctctagct agagcttggc gtaatcatgg tcatagctgt ttcctgtgtg  6300
aaattgttat ccgctcacaa ttccacacaa catacgagcc ggaagcataa agtgtaaagc  6360
ctaggatgcc taatgagtga gctaactcac attaattgcg ttgcgctcac tgcccgcttt  6420
ccagtcggga aacctgtcgt gccagctgca ttaatgaatc ggccaacgcg cggggagagg  6480
cggtttgcgt attgggcgct cttccgcttc ctcgctcact gactcgctgc gctcggtcgt  6540
tcggctgcgg cgagcggtat cagctcactc aaaggcggta atacggttat ccacagaatc  6600
aggggataac gcaggaaaga acatgtgagc aaaaggccag caaaaggcca ggaaccgtaa  6660
aaaggccgcg ttgctggcgt ttttccatag gctccgcccc cctgacgagc atcacaaaaa  6720
```

```
tcgacgctca agtcagaggt ggcgaaaccc gacaggacta taaagatacc aggcgtttcc   6780
ccctggaagc tccctcgtgc gctctcctgt tccgaccctg ccgcttaccg gatacctgtc   6840
cgcctttctc ccttcgggaa gcgtggcgct ttctcatagc tcacgctgta ggtatctcag   6900
ttcggtgtag gtcgttcgct ccaagctggg ctgtgtgcac gaaccccccg ttcagcccga   6960
ccgctgcgcc ttatccggta actatcgtct tgagtccaac ccggtaagac acgacttatc   7020
gccactggca gcagccactg gtaacaggat tagcagagcg aggtatgtag gcggtgctac   7080
agagttcttg aagtggtggc ctaactacgg ctacactaga agaacagtat ttggtatctg   7140
cgctctgctg aagccagtta ccttcggaaa aagagttggt agctcttgat ccggcaaaca   7200
aaccaccgct ggtagcggtg gtttttttgt ttgcaagcag cagattacgc gcagaaaaaa   7260
aggatctcaa gaagatcctt tgatcttttc tacggggtct gacactcagt ggaacgaaaa   7320
ctcacgttaa gggattttgg tcatgagatt atcaaaaagg atcttcacct agatcctttt   7380
aaattaaaaa tgaagtttta atcaatcta  agtatatat gagtaaactt ggtctgacag   7440
ttaccaatgc ttaatcagtg aggcacctat ctcagcgatc tgtctatttc gttcatccat   7500
agttgcctga ctccccgtcg tgtagataac tacgatacgg gagggcttac catctggccc   7560
cagtgctgca atgataccgc gagacccacg ctcaccggct ccagatttat cagcaataaa   7620
ccagccagcc ggaagggccg agcgcagaag tggtcctgca actttatccg cctccatcca   7680
gtctattaat tgttgccggg aagctagagt aagtagttcg ccagttaata gtttgcgcaa   7740
cgttgttgcc attgctacag gcatcgtggt gtcacgctcg tcgtttggta tggcttcatt   7800
cagctccggt tcccaacgat caaggcgagt tacatgatcc cccatgttgt gcaaaaaagc   7860
ggttagctcc ttcggtcctc cgatcgttgt cagaagtaag ttggccgcag tgttatcact   7920
catggttatg gcagcactgc ataattctct tactgtcatg ccatccgtaa gatgcttttc   7980
tgtgactggt gagtactcaa ccaagtcatt ctgagaatag tgtatgcggc gaccgagttg   8040
ctcttgcccg gcgtcaatac gggataatac cgcgccacat agcagaactt taaaagtgct   8100
catcattgga aaacgttctt cggggcgaaa actctcaagg atcttaccgc tgttgagatc   8160
cagttcgatg taacccactc gtgcacccaa ctgatcttca gcatctttta ctttcaccag   8220
cgtttctggg tgagcaaaaa caggaaggca aaatgccgca aaaaagggaa taagggcgac   8280
acggaaatgt tgaatactca tactcttcct ttttcaatat tattgaagca tttatcaggg   8340
ttattgtctc atgagcggat acatatttga atgtatttag aaaaataaac aataggggt    8400
tccgcgcaca tttccccgaa aagtgccacc tgacgtcgac ggatcgggag atcgatctcc   8460
cgatccccta gggtcgactc tcagtacaat ctgctcgat gccgcatagt taagccagta   8520
tctgctccct gcttgtgtgt tggaggtcgc tgagtagtgc gcgagcaaaa tttaagctac   8580
aacaaggcaa ggcttgaccg acaattgcat gaagaatctg cttagggtta ggcgttttgc   8640
gctgcttcgc gatgtacggg ccagatatac gcgttgacat tgattattga ctagttatta   8700
atagtaatca attacgggt cattagttca tagcccatat atggagttcc gcgttacata   8760
acttacggta aatggcccgc ctggctgacc gcccaacgac ccccgcccat tgacgtcaat   8820
aatgacgtat gttcccatag taacgccaat agggactttc cattgacgtc aatgggtgga   8880
gtatttacgg taaactgccc acttggcagt acatcaagtg tatc                    8924
```

```
SEQ ID NO: 57           moltype = DNA   length = 23
FEATURE                 Location/Qualifiers
source                  1..23
                        mol_type = other DNA
                        organism = Synthetic construct
SEQUENCE: 57
ccttcccaga aaacctacca ggg                                              23

SEQ ID NO: 58           moltype = DNA   length = 23
FEATURE                 Location/Qualifiers
source                  1..23
                        mol_type = other DNA
                        organism = Synthetic construct
SEQUENCE: 58
caaccccag agcacggtgg tgg                                               23

SEQ ID NO: 59           moltype = DNA   length = 23
FEATURE                 Location/Qualifiers
source                  1..23
                        mol_type = other DNA
                        organism = Synthetic construct
SEQUENCE: 59
caaatctgtc acattgggta agg                                              23

SEQ ID NO: 60           moltype = DNA   length = 23
FEATURE                 Location/Qualifiers
source                  1..23
                        mol_type = other DNA
                        organism = Synthetic construct
SEQUENCE: 60
acagctgcag agagccctgc agg                                              23

SEQ ID NO: 61           moltype = DNA   length = 23
FEATURE                 Location/Qualifiers
source                  1..23
                        mol_type = other DNA
                        organism = Synthetic construct
SEQUENCE: 61
ttccgcctcc gacctgtggc tgg                                              23

SEQ ID NO: 62           moltype = DNA   length = 23
```

```
FEATURE                 Location/Qualifiers
source                  1..23
                        mol_type = other DNA
                        organism = Synthetic construct
SEQUENCE: 62
ttccttcagg ctctgaatct tgg                                              23

SEQ ID NO: 63           moltype = DNA   length = 23
FEATURE                 Location/Qualifiers
source                  1..23
                        mol_type = other DNA
                        organism = Synthetic construct
SEQUENCE: 63
aggccgggag ctggaggagc tgg                                              23

SEQ ID NO: 64           moltype = DNA   length = 23
FEATURE                 Location/Qualifiers
source                  1..23
                        mol_type = other DNA
                        organism = Synthetic construct
SEQUENCE: 64
agagcccccc ctcaaagaga ggg                                              23

SEQ ID NO: 65           moltype = DNA   length = 23
FEATURE                 Location/Qualifiers
source                  1..23
                        mol_type = other DNA
                        organism = Synthetic construct
SEQUENCE: 65
ggagccacag gagccgctgc agg                                              23

SEQ ID NO: 66           moltype = DNA   length = 23
FEATURE                 Location/Qualifiers
source                  1..23
                        mol_type = other DNA
                        organism = Synthetic construct
SEQUENCE: 66
tactcccagg tcctcttcaa ggg                                              23

SEQ ID NO: 67           moltype = DNA   length = 23
FEATURE                 Location/Qualifiers
source                  1..23
                        mol_type = other DNA
                        organism = Synthetic construct
SEQUENCE: 67
ggcccagact gagcacgtga tgg                                              23

SEQ ID NO: 68           moltype = DNA   length = 678
FEATURE                 Location/Qualifiers
source                  1..678
                        mol_type = other DNA
                        organism = Synthetic construct
SEQUENCE: 68
gaaaccggac cagtggcagt ggacccaacc ctgaggagac ggattgagcc ccatgaattt       60
gaagtgttct ttgacccaag ggagctgagg aaggagacat gcctgctgta cgagatcaag      120
tggggcacaa gccacaagat ctggcgccac agctccaaga acaccacaaa gcacgtggaa      180
gtgaatttca tcgagaagtt tacctccgag cggcacttct gccctctac cagctgttcc       240
atcacatggt ttctgtcttg gagcccttgc ggcgagtgtt ccaaggccat caccgagttc      300
ctgtctcagc accctaacgt gaccctggtc atctacgtgg cccggctgta tcaccacatg      360
gaccagcaga acaggcaggg cctgcgcgat ctggtgaatt ctggcgtgac catccagatc      420
atgcagcccc agagtacgga ctattgctgg cggaacttcg tgaattatcc acctggcaag      480
gaggcacact ggccaagata cccaccctg tggatgaagc tgtatgcact ggagctgcac       540
gcaggaatcc tgggcctgcc tccatgtctg aatatcctgc ggagaaagca gccccagctg      600
acatttttca ccattgctct gcagtcttgt cactatcagc ggctgcctcc tcatattctg      660
tgggctacag gcctgaag                                                    678

SEQ ID NO: 69           moltype = DNA   length = 609
FEATURE                 Location/Qualifiers
source                  1..609
                        mol_type = other DNA
                        organism = Synthetic construct
SEQUENCE: 69
atggaagcca gcccagcatc cgggcccaga cacttgatgg atccacacat attcacttcc       60
aactttaaca atggcattgg aaggcataag acctacctgt gctacgaagt ggagcgcctg      120
gacaatggca cctcggtcaa gatgaccag cacagggct ttctacacaa ccaggctaag        180
aatcttctct gtggctttta cggccgccat gcggagctgc gcttcttgga cctggttcct      240
tctttgcagt tggaccccgc ccagatctac agggtcactt ggttcatctc ctggagcccc      300
tgcttctcct ggggctgtgc cggggaagtg cgtgcgttcc ttcaggagaa cacacacgtg      360
agactgcgta tcttcgctgc ccgcatcttt gattacgacc ccctatataa ggaggcactg      420
```

```
caaatgctgc gggatgctgg ggcccaagtc tccatcatga cctacgatga atttaagcac   480
tgctgggaca cctttgtgga ccaccaggga tgtcccttcc agccctggga tggactagat   540
gagcacagcc aagccctgag tgggaggctg cgggccattc tccagaatca gggaaacagc   600
ggcagcgag                                                           609
```

| SEQ ID NO: 70 | moltype = DNA length = 8855 |
|---|---|
| FEATURE | Location/Qualifiers |
| source | 1..8855 |
| | mol_type = other DNA |
| | organism = Synthetic construct |

SEQUENCE: 70

```
atatgccaag tacgccccct attgacgtca atgacggtaa atggcccgcc tggcattatg   60
cccagtacat gaccttatgg gactttccta ctggcagtac atctacgtat tagtcatcgc   120
tattaccatg gtgatgcggt tttggcagta catcaatggg cgtggatagc ggtttgactc   180
acggggattt ccaagtctcc accccattga cgtcaatggg agtttgtttt ggcaccaaaa   240
tcaacgggac tttccaaaat gtcgtaacaa ctccgcccca ttgacgcaaa tgggcggtag   300
gcgtgtacgg tgggaggtct atataagcag agctggttta gtgaaccgtc agatccgcta   360
gagatccgcg gccgctaata cgactcacta tagggagagc cgccaccatg aaacggacag   420
ccgacggaag cgagttcgag tcaccaaaga agaagcggaa agtcagcagt gacaagaagt   480
acagcatcgg cctggccatc ggcaccaact ctgtgggctg gccgtgatc accgacagt   540
acaaggtgcc cagcaagaaa ttcaaggtgc tgggcaacac cgaccggcac agcatcaaga   600
agaacctgat cggagccctg ctgttcgaca gcggcgaaac agccgaggcc acccggctga   660
agagaaccgc cagaagaaga taccccagac ggaagaaccg gatctgctat ctgcaagaga   720
tcttcagcaa cgagatggcc aaggtggacg acagcttctt ccacagactg aagagtcct   780
tcctggtgga agaggataag aagcacgagc ggcaccccat cttcggcaac atcgtggacg   840
aggtggccta ccacgagaag taccccacca tctaccacct gagaaagaaa ctggtggaca   900
gcaccgacaa ggccgacctg cggctgatct atctggccct ggcccacatg atcaagttc   960
ggggccactt cctgatcgag ggcgacctga accccgacaa cagcgacgtg gacaagctgt  1020
tcatccagct ggtgcagacc tacaaccagc tgttcgagga aaaccccatc aacgccagcg  1080
gcgtggacgc caaggccatc ctgtctgcca gactgagcaa gagcagacgt ctggaaatc  1140
tgatcgccca gctgcccggc gagaagaaga atggcctgtt cggaaacctg attgccctga  1200
gcctgggcct gaccccaac ttcaagagca acttcgacct ggccgaggat gccaaactgc  1260
agctgagcaa ggacacctac gacgacgacc tggacaacct gctggcccag atcggcgacc  1320
agtacgccga cctgtttctg gccgccaaga acctgtccga cgccatcctg ctgagcgaca  1380
tcctgagagt gaacaccgag atcaccaagg cccccctgag cgcctctatg atcaagagat  1440
acgacgagca ccaccaggac ctgaccctgc tgaaagctct cgtgcggcag cagctgcctg  1500
agaagtacaa agagattttc ttcgaccaga gcaagaacgg ctacgccggc tacattgacg  1560
gcggagccaa ccaggaagag ttctacaagt tcatcaagcc catcctggaa aagatggacg  1620
gcaccgagga actgctcgtg aagctgaaca gagaggacct gctgcggaag cagcggacct  1680
tcgacaacgg cagcatcccc caccagatcc acctgggaga gctgcacgcc attctgcgc  1740
ggcaggaaga ttttttaccca ttcctgaagg acaaccggga aaagatcgag aagatcctga  1800
ccttccgcat cccctactac gtgggccctc tggccagggg aaacagcaga ttcgcctgga  1860
tgaccagaaa gagcgaggaa accatcaccc cctggaactt cgaggaagtg gtggacaagg  1920
gcgcttccgc ccagagcttc atcgagcgga tgaccaactt cgataagaac ctgcccaacg  1980
agaaggtgct gcccaagcac agcctgctgt acgagtactt caccgtgtat aacgagctga  2040
ccaaagtgaa atacgtgacc gagggaatga gaaagccccg cttcctgagc ggcgagcaga  2100
aaaaggccat cgtggacctg ctgttcaaga ccaaccgcaa agtgaccgtg aagcagctga  2160
aagaggacta cttcaagaaa atcgagtgct tcgactccgt ggaaatctcc ggcgtggaag  2220
atcggttcaa cgcctccctg ggcacatacc acgatctgct gaaaattatc aaggacaagg  2280
acttcctgga caatgaggaa aacgaggaca ttctggaaga tatcgtgctg accctgacac  2340
tgtttgagga cagagagatg atcgaggaac ggctgaaaac ctatgcccac ctgttcgacg  2400
acaaagtgat gaagcagctg aagcggcgga gatacaccgg ctggggcagg ctgagccgga  2460
agctgatcaa cggcatccgg gacaagcagt ccggcaagac aatcctggat ttcctgaagt  2520
ccgacggctt cgccaacaga aacttcatgc agctgatcca cgacgacagc ctgacctta  2580
aagaggacat ccagaaagcc caggtgtccg gccagggcca tagcctgcac gagcacattg  2640
ccaatctggc cggcagcccc gccattaaga agggcatcct gcagacagtg aaggtggtgg  2700
acgagctcgt gaaagtgatg ggccggcaca gcccgagaa catcgtgatc gaaatggcca  2760
gagagaacca gaccacccag aagggacaga gaacagccg cgagagaatg aagcggatcg  2820
aagagggcat caaagagctg ggcagccaga tcctgaaaga acaccccgtg gaaaacaccc  2880
agctccagaa cgagaagctg tacctgtact acctgcagaa tgggcgggat atgtacgtgg  2940
accaggaact ggacatcaac cggctgtccg actacgatgt ggaccatatc gtgcctcaga  3000
gctttctgaa ggacgactcc atcgacaaca aggtgctgac cagaagcgac aagaaccggg  3060
gcaagagcga caacgtgccc tccgaagagg tcgtgaagaa gatgaagaac tactggcggc  3120
agctgctgaa cgccaagctg attacccaga gaaagttcga caatctgacc aaggccgaga  3180
ggggcggcct gagcgaactg gataaggccg gcttcatcaa gagacagctg gtggaaaccc  3240
ggcagatcac aaagcacgtg gcacagatcc tggactcccg gatgaacact aagtacgacg  3300
agaatgacaa gctgatccgg gaagtgaaag tgatcaccct gaagtccaag ctggtgtccg  3360
atttccggaa ggatttccag tttttacaaag tgcgcgagat caacaactac caccacgccc  3420
acgacgccta cctaaacgcc gtcgtgggaa ccgccctgat caaaaagtac cctaagctga  3480
aaagcgagtt cgtgtacggc gactacaagg tgtacgacgt gcggaagatg atcgccaaga  3540
gcgagcagga aatcggcaag gctaccgcca gtacttctt ctacagcaac atcatgaact  3600
tttttcaagtc cggatccgag acccaggca cctccgagtc tgccacacct gagagcgaa  3660
gcatggaagc cagcccagca tccgggccca gacttgat ggatccacac atattcactt  3720
ccaactttaa caatggcatt ggaaggcata agcctactgc tgtctacgga gtgagcgcc  3780
tggacaatgg cacctcggtc aagatggacc agcacagggg cttctctaca accaggcta  3840
agaatcttct ctgtgctttt acggccgcc atgcgggct gcgcttcttg acctggttc  3900
cttctttgca gttggacccg gcccagatct acagggtcac ttggttcatc tcctggagcc  3960
cctgcttctc ctggggctgt gccggggaag tgcgtgcgtt ccttcaggag aacacacacg  4020
tgagactgcg tatcttcgct gcccgcatct ttgattacga cccctatat aaggaggcac  4080
```

```
tgcaaatgct gcgggatgct ggggcccaag tctccatcat gacctacgat gaatttaagc   4140
actgctggga cacctttgtg gaccaccagg gatgtccctt ccagccctgg gatggactag   4200
atgagcacag ccaagccctg agtgggaggc tgcgggccat tctccagaat cagggaaaca   4260
gcggcagcga gtctggatct ggcagcgaga caccaggaac aagcgagtca gcaacaccag   4320
agagcgagac aaacggcgaa accgggagga tcgtgtggga taagggccgg gattttgcca   4380
ccgtgcggaa agtgctgagc atgcccaag tgaatatcgt gaaaaagacc gaggtgcaga   4440
caggcggctt cagcaaagag tctatcctgc caagaggaa cagcgataag ctgatcgcca   4500
gaaagaagga ctgggaccct aagaagtacg gcggcttcga cagccccacc gtggcctatt   4560
ctgtgctggt ggtggccaaa gtggaaaagg gcaagtccaa gaaactgaag agtgtgaaag   4620
agctgctggg gatcaccatc atggaaagaa gcagcttcga gaagaatccc atcgactttc   4680
tggaagccaa gggctacaaa gaagtgaaaa aggacctgat catcaagctg cctaagtact   4740
ccctgttcga gctggaaaac ggccggaaga gaatgctggc ctctgccggc gaactgcaga   4800
agggaaacga actgggccctg ccctccaaat atgtgaactt cctgtacctg gccagccact   4860
atgagaagct gaagggctcc cccgaggata atgagcagaa acagctgttt gtggaacagc   4920
acaagcacta cctggacgag atcatcgagc agatcagcga gttctccaag agagtgatcc   4980
tggccgacgc taatctggac aaagtgctgt ccgcctacaa caagcaccgg gataagccca   5040
tcagagagca ggccgagaat atcatccacc tgtttaccct gaccaatctg ggagcccctg   5100
ccgccttcaa gtactttgac atacaccgg accggaagag gtacaccagc accaaagagg   5160
tgctggacgc caccctgatc caccagagca tcaccggcct gtacgagaca cggatcgacc   5220
tgtctcagct gggaggtgac agcggcggga gcggcgggag cggggggagc actaatctga   5280
gcgacatcat tgaagaggag actgggaaac agctggtcat tcaggagtcc atcctgatgc   5340
tgcctgagga ggtggaggaa gtgatcgaca acaagccaga gtctgacatc ctggtgcaca   5400
ccgcctacga cgagtccaca gatgagaatg tgatgctgct gacctctgac gcccccgagt   5460
ataagccttg ggccctggtc atccaggatt ctaacggcga gaataagatc aagatgctga   5520
gcggaggatc cggaggatct ggaggcagca ccaacctgtc tgacatcatc gagaaggaga   5580
caggcaagca gctggtcatc caggagagca tcctgatgct gcccgaagaa gtcgaagaag   5640
tgatcggaaa caagcctgag agcgatatcc tggtccatac cgcctacgac gagagtaccg   5700
acgaaaatgt gatgctgctg acatccgacg ccccagagta taagccctgg gctctggtca   5760
tccaggattc caacggagag aacaaaatca aaatgctgtc tggcggctca aaaagaaccg   5820
ccgacggcag cgaattcgag cccaagaaga agaggaaagt ctaaccggtc atcatcacca   5880
tcaccattga gtttaaaccc gctgatcagc ctcgactgtg ccttctagtt gccagccatc   5940
tgttgtttgc ccctccccg tgccttcctt gaccctggaa ggtgccactc ccactgtcct   6000
ttcctaataa aatgaggaaa ttgcatcgca ttgtctgagt aggtgtcatt ctattctggg   6060
gggtggggtg gggcaggaca gcaaggggga ggattgggaa gacaatagca ggcatgctgg   6120
ggatgcggtg ggctctatgg cttctgaggc ggaaagaacc agctggggct cgataccgtc   6180
gacctctagc tagagcttgg cgtaatcatg gtcatagctg tttcctgtgt gaaattgtta   6240
tccgctcaca attccacaca acatacgagc cggaagcata aagtgtaaag cctaggatgc   6300
ctaatgagtg agctaactca cattaattgc gttgcgctca ctgcccgctt tccagtcggg   6360
aaacctgtcg tgccagctgc attaatgaat cggccaacgc gcggggagag gcggtttgcg   6420
tattgggcgc tcttccgctt cctcgctcac tgactcgctg cgctcggtcg ttcggctgcg   6480
gcgagcggta tcagctcact caaaggcggt aatacggtta tccacagaat caggggataa   6540
cgcaggaaag aacatgtgag caaaaggcca gcaaaaggcc aggaaccgta aaaaggccgc   6600
gttgctgcgg tttttccata ggctccgccc ccctgacgag catcacaaaa atcgacgctc   6660
aagtcagagg tggcgaaacc cgacaggact ataaagatac caggcgtttc ccctgaag   6720
ctccctcgtg cgctctcctg ttccgaccct gccgcttacc ggatacctgt ccgcctttct   6780
cccttcggga agcgtggcgc tttctcatag ctcacgctgt aggtatctca gttcggtgta   6840
ggtcgttcgc tccaagctgg gctgtgtgca cgaaccccc gttcagccca accgctgcgc   6900
cttatccggt aactatcgtc ttgagtccaa cccggtaaga cacgacttat cgccactggc   6960
agcagccact ggtaacagga ttagcagagc gaggtatgta ggcggtgcta cagagttctt   7020
gaagtggtgg cctaactacg gctacactag aagaacagta tttggtatct gcgctctgct   7080
gaagccagtt accttcggaa aaagagttgg tagctcttga tccggcaaac aaaccaccgc   7140
tggtagcggt ggtttttttg tttgcaagca gcagattacg cgcagaaaaa aaggatctca   7200
agaagatcct ttgatctttt ctacggggtc tgacactcag tggaacgaaa actcacgtta   7260
agggattttg gtcatgagat tatcaaaaag gatcttcacc tagatccttt taaattaaaa   7320
atgaagtttt aaatcaatct aaagtatata tgagtaaact tggtctgaca gttaccaatg   7380
cttaatcagt gaggcaccta tctcagcgat ctgtctattt cgttcatcca tagttgcctg   7440
actccccgtc gtgtagataa ctacgatacg ggagggctta ccatctggcc ccagtgctgc   7500
aatgataccg cgagacccac gctcaccggc tccagattta tcagcaataa accagccagc   7560
cggaagggcc gagcgcagaa gtggtcctgc aactttatcc gcctccatcc agtctattaa   7620
ttgttgccgg gaagctagag taagtagttc gccagttaat agtttgcgca acgttgttgc   7680
cattgctaca ggcatcgtgg tgtcacgctc gtcgtttggt atggcttcat tcagctccgg   7740
ttcccaacga tcaaggcgag ttacatgatc cccatgttg tgcaaaaaag cggttagctc   7800
cttcggtcct ccgatcgttg tcagaagtaa gttggccgca gtgttatcac tcatggttat   7860
ggcagcactg cataattctc ttactgtcat gccatccgta agatgctttt ctgtgactgg   7920
tgagtactca accaagtcat tctgagaata gtgtatgcgg cgaccgagtt gctcttgccc   7980
ggcgtcaata cgggataata ccgcgccaca tagcagaact ttaaaagtgc tcatcattgg   8040
aaaacgttct cggggcgaaa actctcaag gatcttaccg ctgttgagat ccagttcgat   8100
gtaacccact cgtgcaccca actgatcttc agcatctttt actttcacca gcgtttctgg   8160
gtgagcaaaa acaggaaggc aaaatgccgc aaaaaaggga ataagggcga cacggaaatg   8220
ttgaatactc atactcttcc tttttcaata ttattgaagc atttatcagg gttattgtct   8280
catgagcgga tacatatttg aatgtattta gaaaaataaa caataggggt tccgcgcac   8340
atttccccga aaagtgccac ctgacgtcga cggatcggga gatcgatctc ccgatcccct   8400
agggtcgact ctcagtacaa tctgctctga tgccgcatag ttaagccagt atctgctccc   8460
tgcttgtgtg ttggaggtcg ctgagtagtg cgcgagcaaa atttaagcta caaaggca   8520
aggcttgacc gacaattgca tgaagaatct gcttagggtt aggcgttttg cgctgcttcg   8580
cgatgtacgg gccagatata cgcgttgaca ttgattattg actagttatt aatagtaatc   8640
aattacgggg tcattagttc atagcccata tatggagttc cgcgttacat aacttacggt   8700
aaatggcccg cctggctgac cgcccaacga cccccgccca ttgacgtcaa taatgacgta   8760
tgttcccata gtaacgccaa taggactttt ccattgacgt caatgggtgg agtatttacg   8820
```

```
gtaaactgcc cacttggcag tacatcaagt gtatc                                8855

SEQ ID NO: 71          moltype = DNA   length = 22
FEATURE                Location/Qualifiers
source                 1..22
                       mol_type = other DNA
                       organism = Synthetic construct
SEQUENCE: 71
ggtctctgat ccggcgcacg aa                                              22

SEQ ID NO: 72          moltype = DNA   length = 22
FEATURE                Location/Qualifiers
source                 1..22
                       mol_type = other DNA
                       organism = Synthetic construct
SEQUENCE: 72
ggtctctgat ccggcgcacg aa                                              22

SEQ ID NO: 73          moltype = DNA   length = 22
FEATURE                Location/Qualifiers
source                 1..22
                       mol_type = other DNA
                       organism = Synthetic construct
SEQUENCE: 73
gacaagaagt acagcatcgg cc                                              22

SEQ ID NO: 74          moltype = DNA   length = 37
FEATURE                Location/Qualifiers
source                 1..37
                       mol_type = other DNA
                       organism = Synthetic construct
SEQUENCE: 74
gctgtacttc ttgtcactgc tgactttccg cttcttc                              37

SEQ ID NO: 75          moltype = DNA   length = 36
FEATURE                Location/Qualifiers
source                 1..36
                       mol_type = other DNA
                       organism = Synthetic construct
SEQUENCE: 75
gaagaagcgg aaagtcgaca agaagtacag catcgg                               36

SEQ ID NO: 76          moltype = DNA   length = 42
FEATURE                Location/Qualifiers
source                 1..42
                       mol_type = other DNA
                       organism = Synthetic construct
SEQUENCE: 76
ctcactgatt aagcattggt aagcgcggaa cccctatttg tt                        42

SEQ ID NO: 77          moltype = DNA   length = 48
FEATURE                Location/Qualifiers
source                 1..48
                       mol_type = other DNA
                       organism = Synthetic construct
SEQUENCE: 77
ccgtttcatg gtggcatgta tatctccttc ttaaagttaa acaaaatt                  48

SEQ ID NO: 78          moltype = DNA   length = 59
FEATURE                Location/Qualifiers
source                 1..59
                       mol_type = other DNA
                       organism = Synthetic construct
SEQUENCE: 78
gtataatact agtgctcttg cccggcgtca atacgtttta gagctagaaa tagcaagtt      59

SEQ ID NO: 79          moltype = DNA   length = 34
FEATURE                Location/Qualifiers
source                 1..34
                       mol_type = other DNA
                       organism = Synthetic construct
SEQUENCE: 79
gttagcagcc ggatcaaaaa aagcaccgac tcgg                                 34

SEQ ID NO: 80          moltype = DNA   length = 44
FEATURE                Location/Qualifiers
source                 1..44
                       mol_type = other DNA
                       organism = Synthetic construct
```

```
SEQUENCE: 80
ttgacagcta gctcagtcct aggtataata ctagtgctct tgcc                      44

SEQ ID NO: 81          moltype = DNA   length = 34
FEATURE                Location/Qualifiers
source                 1..34
                       mol_type = other DNA
                       organism = Synthetic construct
SEQUENCE: 81
gttagcagcc ggatcaaaaa aagcaccgac tcgg                                 34

SEQ ID NO: 82          moltype = DNA   length = 35
FEATURE                Location/Qualifiers
source                 1..35
                       mol_type = other DNA
                       organism = Synthetic construct
SEQUENCE: 82
cttttcgggg aaatgtggga aatgtgcgcg gaacc                                35

SEQ ID NO: 83          moltype = DNA   length = 20
FEATURE                Location/Qualifiers
source                 1..20
                       mol_type = other DNA
                       organism = Synthetic construct
SEQUENCE: 83
cccggcgtca atacgggata                                                 20

SEQ ID NO: 84          moltype = DNA   length = 35
FEATURE                Location/Qualifiers
source                 1..35
                       mol_type = other DNA
                       organism = Synthetic construct
SEQUENCE: 84
gtattgacgc cgggtaagag caactcggtc gccgc                                35

SEQ ID NO: 85          moltype = DNA   length = 27
FEATURE                Location/Qualifiers
source                 1..27
                       mol_type = other DNA
                       organism = Synthetic construct
SEQUENCE: 85
ttaccaatgc ttaatcagtg aggcacc                                         27

SEQ ID NO: 86          moltype = DNA   length = 35
FEATURE                Location/Qualifiers
source                 1..35
                       mol_type = other DNA
                       organism = Synthetic construct
SEQUENCE: 86
cttttcgggg aaatgtggga aatgtgcgcg gaacc                                35

SEQ ID NO: 87          moltype = DNA   length = 23
FEATURE                Location/Qualifiers
source                 1..23
                       mol_type = other DNA
                       organism = Synthetic construct
SEQUENCE: 87
cggatgccta gacaggtgtt caa                                             23

SEQ ID NO: 88          moltype = DNA   length = 34
FEATURE                Location/Qualifiers
source                 1..34
                       mol_type = other DNA
                       organism = Synthetic construct
SEQUENCE: 88
agggagagcc gccaccatga aacggacagc cgac                                 34

SEQ ID NO: 89          moltype = DNA   length = 37
FEATURE                Location/Qualifiers
source                 1..37
                       mol_type = other DNA
                       organism = Synthetic construct
SEQUENCE: 89
tcctcttctt cttgggctcg aattcgctgc cgtcggc                              37

SEQ ID NO: 90          moltype = DNA   length = 26
FEATURE                Location/Qualifiers
source                 1..26
                       mol_type = other DNA
```

-continued

```
                            organism = Synthetic construct
SEQUENCE: 90
ggtggcggct ctccctatag tgagtc                                                26

SEQ ID NO: 91              moltype = DNA   length = 26
FEATURE                    Location/Qualifiers
source                     1..26
                           mol_type = other DNA
                           organism = Synthetic construct
SEQUENCE: 91
cccaagaaga agaggaaagt ctaacc                                                26

SEQ ID NO: 92              moltype = DNA   length = 37
FEATURE                    Location/Qualifiers
source                     1..37
                           mol_type = other DNA
                           organism = Synthetic construct
SEQUENCE: 92
catgaacttt ttcaagtccg gatccgagac cccaggc                                    37

SEQ ID NO: 93              moltype = DNA   length = 35
FEATURE                    Location/Qualifiers
source                     1..35
                           mol_type = other DNA
                           organism = Synthetic construct
SEQUENCE: 93
tttcgccgtt tgtctcgctc tctggtgttg ctgac                                      35

SEQ ID NO: 94              moltype = DNA   length = 35
FEATURE                    Location/Qualifiers
source                     1..35
                           mol_type = other DNA
                           organism = Synthetic construct
SEQUENCE: 94
tttcgccgtt tgtctcgctc tctggtgttg ctgac                                      35

SEQ ID NO: 95              moltype = DNA   length = 37
FEATURE                    Location/Qualifiers
source                     1..37
                           mol_type = other DNA
                           organism = Synthetic construct
SEQUENCE: 95
catgaacttt ttcaagtccg gatccgagac cccaggc                                    37

SEQ ID NO: 96              moltype = DNA   length = 35
FEATURE                    Location/Qualifiers
source                     1..35
                           mol_type = other DNA
                           organism = Synthetic construct
SEQUENCE: 96
tttcgccgtt tgtctcgctc tctggtgttg ctgac                                      35

SEQ ID NO: 97              moltype = DNA   length = 27
FEATURE                    Location/Qualifiers
source                     1..27
                           mol_type = other DNA
                           organism = Synthetic construct
SEQUENCE: 97
gagacaaacg gcgaaaccgg ggagatc                                               27

SEQ ID NO: 98              moltype = DNA   length = 23
FEATURE                    Location/Qualifiers
source                     1..23
                           mol_type = other DNA
                           organism = Synthetic construct
SEQUENCE: 98
cttgaaaaag ttcatgatgt tgc                                                   23

SEQ ID NO: 99              moltype = DNA   length = 22
FEATURE                    Location/Qualifiers
source                     1..22
                           mol_type = other DNA
                           organism = Synthetic construct
SEQUENCE: 99
atgcctgcta ttgtcttccc aa                                                    22

SEQ ID NO: 100             moltype = DNA   length = 21
FEATURE                    Location/Qualifiers
source                     1..21
```

```
                              mol_type = other DNA
                              organism = Synthetic construct
SEQUENCE: 100
aacgggactt ccaaaatgt c                                              21

SEQ ID NO: 101                moltype = DNA   length = 24
FEATURE                       Location/Qualifiers
source                        1..24
                              mol_type = other DNA
                              organism = Synthetic construct
SEQUENCE: 101
tctcgcgcgt ttcggtgatg acgg                                          24

SEQ ID NO: 102                moltype = DNA   length = 25
FEATURE                       Location/Qualifiers
source                        1..25
                              mol_type = other DNA
                              organism = Synthetic construct
SEQUENCE: 102
aaaaaaatct cgccaacaag ttgac                                         25

SEQ ID NO: 103                moltype = DNA   length = 23
FEATURE                       Location/Qualifiers
source                        1..23
                              mol_type = other DNA
                              organism = Synthetic construct
SEQUENCE: 103
aaagatcttc acaggctacc ccc                                           23

SEQ ID NO: 104                moltype = DNA   length = 22
FEATURE                       Location/Qualifiers
source                        1..22
                              mol_type = other DNA
                              organism = Synthetic construct
SEQUENCE: 104
aatccacagc aacacctct cc                                             22

SEQ ID NO: 105                moltype = DNA   length = 45
FEATURE                       Location/Qualifiers
source                        1..45
                              mol_type = other DNA
                              organism = Synthetic construct
SEQUENCE: 105
gcgcggtatt atcccgtatt gacgccgggt aagagcaact cggtc                   45

SEQ ID NO: 106                moltype = AA    length = 57
FEATURE                       Location/Qualifiers
source                        1..57
                              mol_type = protein
                              organism = Streptococcus agalactiae
SEQUENCE: 106
YSNIMNFFTK VTLADGTVVV KDDIEVNNDT GEIVWDKKKH FATVRKVLSY PQVNIVK      57

SEQ ID NO: 107                moltype = AA    length = 58
FEATURE                       Location/Qualifiers
source                        1..58
                              mol_type = protein
                              organism = Streptococcus mitis
SEQUENCE: 107
YSNLLNFFKE EVHYADGTIV KRENIEYSKD TGEIAWNKEK DFATIKKVLS FPQVNIVK     58

SEQ ID NO: 108                moltype = AA    length = 58
FEATURE                       Location/Qualifiers
source                        1..58
                              mol_type = protein
                              organism = Streptococcus pseudopneumoniae
SEQUENCE: 108
YSNLLNFFKE EVHYADGTIV KRENIEYSKD TGEIAWNKEK DFATIKKVLS FPQVNIVK     58

SEQ ID NO: 109                moltype = AA    length = 58
FEATURE                       Location/Qualifiers
source                        1..58
                              mol_type = protein
                              organism = Streptococcus oralis
SEQUENCE: 109
YSNLLNFFKE EVHYADGTIV KRENIEYSKD TGEIAWNKEK DFATIKKVLS FPQVNIVK     58

SEQ ID NO: 110                moltype = AA    length = 58
FEATURE                       Location/Qualifiers
```

```
source                        1..58
                              mol_type = protein
                              organism = Streptococcus sanguinis
SEQUENCE: 110
YSNLLNFFKE KVRYADGTIK KRENIEYSND TGEIAWNKEK DFATIKKVLS LPQVNIVK      58

SEQ ID NO: 111                moltype = AA  length = 58
FEATURE                       Location/Qualifiers
source                        1..58
                              mol_type = protein
                              organism = Streptococcus gordonii
SEQUENCE: 111
YSNLLNFFKE EVHYADGTIV KRENIEYSKD TGEIAWNKEK DFAIIKKVLS LPQVNIVK      58

SEQ ID NO: 112                moltype = AA  length = 58
FEATURE                       Location/Qualifiers
source                        1..58
                              mol_type = protein
                              organism = Streptococcus cristatus
SEQUENCE: 112
YSNLLNFFKE EVHYADGTIV KRENIEYSKD TGEIAWNKEK DFATIKKVLA YPQVNIVK      58

SEQ ID NO: 113                moltype = AA  length = 59
FEATURE                       Location/Qualifiers
source                        1..59
                              mol_type = protein
                              organism = Streptococcus uberis
SEQUENCE: 113
YSNLMNFFKK EVRLSDGTVI TRPQIETSSD DTGEIVWDKV KDIKTIRKVL SMPQINVVK     59

SEQ ID NO: 114                moltype = AA  length = 58
FEATURE                       Location/Qualifiers
source                        1..58
                              mol_type = protein
                              organism = Streptococcus iniae
SEQUENCE: 114
YSNLMNFFKK EIKLADDTIF TRPQIEVNTE TGEIVWDKVK DMQTIRKVMS YPQVNIVM      58

SEQ ID NO: 115                moltype = AA  length = 58
FEATURE                       Location/Qualifiers
source                        1..58
                              mol_type = protein
                              organism = Streptococcus phocae
SEQUENCE: 115
YSNLMNFFKS EVKLANGNII KRSPIEVNEE TGEIVWDKTK DFGTVRKVLS APQVNIVK      58

SEQ ID NO: 116                moltype = AA  length = 58
FEATURE                       Location/Qualifiers
source                        1..58
                              mol_type = protein
                              organism = Streptococcus canis
SEQUENCE: 116
YSNIMNFFKT EVKLANGEIR KRPLIETNGE TGEVVWNKEK DFATVRKVLA MPQVNIVK      58

SEQ ID NO: 117                moltype = AA  length = 58
FEATURE                       Location/Qualifiers
source                        1..58
                              mol_type = protein
                              organism = Streptococcus dysgalactiae
SEQUENCE: 117
YSNIMNFFKT EITLANGEIR KRPLIETNEE TGEIVWDKGR DFATVRKVLS MPQVNIVK      58

SEQ ID NO: 118                moltype = AA  length = 58
FEATURE                       Location/Qualifiers
source                        1..58
                              mol_type = protein
                              organism = synthetic construct
SEQUENCE: 118
YSNIMNFFKT EITLANGEIR KRPLIETNGE TGEIVWDKGR DFATVRKVLS MPQVNIVK      58

SEQ ID NO: 119                moltype = AA  length = 58
FEATURE                       Location/Qualifiers
source                        1..58
                              mol_type = protein
                              organism = Streptococcus pyogenes
SEQUENCE: 119
YSNIMNFFKT EITLANGEIR KRPLIETNGE TGEIVWDKGR DFATVRKVLS MPQVNIVK      58

SEQ ID NO: 120                moltype = AA  length = 58
```

```
FEATURE             Location/Qualifiers
source              1..58
                    mol_type = protein
                    organism = Streptococcus thermophilus
SEQUENCE: 120
YSNIMNIFKK SISLADGRVI ERPLIEVNEE TGESVWNKES DLATVRRVLS YPQVNVVK      58

SEQ ID NO: 121      moltype = AA  length = 58
FEATURE             Location/Qualifiers
source              1..58
                    mol_type = protein
                    organism = Streptococcus salivarius
SEQUENCE: 121
YSNIMNIFKK FISLADGTVI ERPLIEVNEE TGESVNWKVA DLNTVRKVLS YSQVNIVK      58

SEQ ID NO: 122      moltype = AA  length = 58
FEATURE             Location/Qualifiers
source              1..58
                    mol_type = protein
                    organism = Streptococcus mutans
SEQUENCE: 122
YSNIMNMFKS KVKLADDQIV ERPMIEVNDE TGEIAWDKTK HITTVKKVLS YPQVNIVK      58

SEQ ID NO: 123      moltype = AA  length = 59
FEATURE             Location/Qualifiers
source              1..59
                    mol_type = protein
                    organism = Streptococcus suis
SEQUENCE: 123
YSNIMNFFKR VVKSSKTGTV KIRPIIEVNK ETGEIVWDKK SDFRTVRKVL SYPQVNVVK     59

SEQ ID NO: 124      moltype = AA  length = 58
FEATURE             Location/Qualifiers
source              1..58
                    mol_type = protein
                    organism = Streptococcus respiraculi
SEQUENCE: 124
YSNLLNFFKT KIKLADGSEI KQATVEVYSE TGEIIWNKKK DFATIRKVLA YPQVNVVK      58

SEQ ID NO: 125      moltype = AA  length = 45
FEATURE             Location/Qualifiers
source              1..45
                    mol_type = protein
                    organism = Streptococcus intermedius
SEQUENCE: 125
YSNIMNFFKK DDVRTDKNGE IIWKKDEHIS NIKKVLSYPQ VNIVK                    45

SEQ ID NO: 126      moltype = AA  length = 45
FEATURE             Location/Qualifiers
source              1..45
                    mol_type = protein
                    organism = Streptococcus orisasini
SEQUENCE: 126
YSNIMNFFKK DDVRTDENGE IIWKKDEHIS NIKKVLSYPQ VNIVK                    45

SEQ ID NO: 127      moltype = AA  length = 57
FEATURE             Location/Qualifiers
source              1..57
                    mol_type = protein
                    organism = Streptococcus anginosus
SEQUENCE: 127
YSNLMNFFKK EVKFADGTVV ERPDIETSED GEIAWNKQTD FKIVRKVLSY PQVNIVK       57

SEQ ID NO: 128      moltype = AA  length = 57
FEATURE             Location/Qualifiers
source              1..57
                    mol_type = protein
                    organism = Streptococcus milleri
SEQUENCE: 128
YSNLMNFFKK EVKFADGTVV ERPDIETSED GEIAWNKQTD FKIVRKVLSY PQVNIVK       57

SEQ ID NO: 129      moltype = AA  length = 45
FEATURE             Location/Qualifiers
source              1..45
                    mol_type = protein
                    organism = Streptococcus viridans
SEQUENCE: 129
YSNILRFFKK EDIQTNEDGE IAWNKEKHIK ILRKVLSYPQ VNIVK                    45
```

```
SEQ ID NO: 130         moltype = AA  length = 57
FEATURE                Location/Qualifiers
source                 1..57
                       mol_type = protein
                       organism = Streptococcus lutetiensis
SEQUENCE: 130
YSNLMNFFKT EVKYADGRVF ERPDIETNAD GEVVWNKQKD FEIIRKVLSY PQVNIVK       57

SEQ ID NO: 131         moltype = AA  length = 57
FEATURE                Location/Qualifiers
source                 1..57
                       mol_type = protein
                       organism = Streptococcus  macedonicus
SEQUENCE: 131
YSNLMNFFKT EVKYADGRVF ERPDIETNAD GEVVWNKQKD FDIVRKVLSY PQVNIVK       57

SEQ ID NO: 132         moltype = AA  length = 58
FEATURE                Location/Qualifiers
source                 1..58
                       mol_type = protein
                       organism = Streptococcus pantholopis
SEQUENCE: 132
YSNLMNFFKR VVRYSNGRVI VRPVIEYSKD TGEIVWNKET DFRTICKVLS YPQVNIVK      58

SEQ ID NO: 133         moltype = AA  length = 58
FEATURE                Location/Qualifiers
source                 1..58
                       mol_type = protein
                       organism = Streptococcus gallolyticus
SEQUENCE: 133
YSNLMNFFKR VIRYSNGKVV VRPVIECSKD TGEIAWNKQT DFEKVRRVLS YPQVNIVK      58

SEQ ID NO: 134         moltype = AA  length = 58
FEATURE                Location/Qualifiers
source                 1..58
                       mol_type = protein
                       organism = Streptococcus equinus
SEQUENCE: 134
YSNLMNFFKR IIRYSNGKVV VRPVIECSKD TGEIAWNKQT DFEKVRMVLS YPQVNIVK      58
```